(12) United States Patent
Sanghani et al.

(10) Patent No.: US 10,260,060 B2
(45) Date of Patent: Apr. 16, 2019

(54) GENETICALLY MODIFIED PHENYLPYRUVATE DECARBOXYLASE, PROCESSES TO PREPARE, AND USES THEREOF

(71) Applicant: Dow Global Technologies LLC, Midland, MI (US)

(72) Inventors: Paresh C. Sanghani, Indianapolis, IN (US); Christopher C. Stowers, Indianapolis, IN (US); Brandon A. Rodriguez, Freeport, TX (US); Eric C. Shiue, Indianapolis, IN (US); Scott A. Greenwalt, Indianapolis, IN (US)

(73) Assignee: Dow Global Technologies LLC, Midland, MI (US)

(*) Notice: Subject to any disclaimer, the term of this patent is extended or adjusted under 35 U.S.C. 154(b) by 0 days.

(21) Appl. No.: 15/533,390

(22) PCT Filed: Dec. 10, 2015

(86) PCT No.: PCT/US2015/064879

§ 371 (c)(1),
(2) Date: Jun. 6, 2017

(87) PCT Pub. No.: WO2016/094604

PCT Pub. Date: Jun. 16, 2016

(65) Prior Publication Data

US 2017/0369863 A1   Dec. 28, 2017

Related U.S. Application Data

(60) Provisional application No. 62/089,912, filed on Dec. 10, 2014.

(51) Int. Cl.
*C12N 9/88* (2006.01)
*C12P 5/02* (2006.01)
(Continued)

(52) U.S. Cl.
CPC .................. *C12N 9/88* (2013.01); *C12P 5/02* (2013.01); *C12P 7/04* (2013.01); *C12P 7/24* (2013.01);
(Continued)

(58) Field of Classification Search
None
See application file for complete search history.

(56) References Cited

U.S. PATENT DOCUMENTS 8,232,089 B2   7/2012   Urano et al.
8,298,798 B2  10/2012   Liao et al.
(Continued)

FOREIGN PATENT DOCUMENTS

WO   2009046375 A2   4/2009
WO   2009096370 A1   8/2009
(Continued)

OTHER PUBLICATIONS

Atsumi et al., "Non-Fermentative Pathways for Synthesis of Branched-Chain Higher Alcohols as Biofuels", Nature, 2008, vol. 451, 86-90, Nature Publishing Group.
(Continued)

*Primary Examiner* — Richard C Ekstrom
(74) *Attorney, Agent, or Firm* — Dinsmore & Shohl LLP

(57) ABSTRACT

Modification of the amino acid sequence of a phenylpyruvate decarboxylase from *Azospirillum brasilense* produces a novel group of phenylpyruvate decarboxylases with improved specificity to certain substrates, including in particular C7-C11 2-ketoacids such as, for example, 2-ketononanoate and 2-keto-octanoate. This specificity enables effective use of the phenylpyruvate decarboxylase in, for example, an in vivo process wherein 2-ketobutyrate or 2-ketoisovalerate are converted to C7-C11 2-ketoacids, and the novel phenylpyruvate decarboxylase converts the C7-C11 2-ketoacid to a C6-C10 aldehyde having one less carbon than the 2-ketoacid. Ultimately, through contact with additional enzymes, such C6-C10 aldehydes may be converted to, for example, C6-C10 alcohols, C6-C10 carboxylic acids, C6-C10 alkanes, and other derivatives. Use of the novel genetically modified phenylpyruvate decarboxylases
(Continued)

The mean alcohol distributions for serum bottle fermentations of *E. coli* containing the "+1 pathway" enzymes in combination with AbPPDC WT, AbPPDC variants, KIVD wild type (*Lactococcus lactis* keto-isovalerate decarboxylase), and no decarboxylase. ADH6 was also included in all strain constructs. The 1-octanol titers have been multiplied by ten so that they can be plotted on the same scale as the 1-heptanol, 1-hexanol and 1-pentanol titers. Titers were measured at 24 hours after induction. The "none" column represents the strain with no decarboxylase gene.

US 10,260,060 B2
Page 2 may represent a lower cost alternative to non-biobased approaches.

17 Claims, 5 Drawing Sheets

Specification includes a Sequence Listing.

(51) Int. Cl.
| | | |
|---|---|---|
| C12P 7/04 | (2006.01) | |
| C12P 7/24 | (2006.01) | |
| C12P 7/40 | (2006.01) | |
| C12P 7/64 | (2006.01) | |
| C10L 1/02 | (2006.01) | |
| C10L 1/04 | (2006.01) | |
| C10L 1/14 | (2006.01) | |

(52) U.S. Cl.
CPC .............. *C12P 7/40* (2013.01); *C12P 7/6409* (2013.01); *C12Y 401/01043* (2013.01); *C10L 1/02* (2013.01); *C10L 1/04* (2013.01); *C10L 1/14* (2013.01)

(56) References Cited

U.S. PATENT DOCUMENTS

| | | | |
|---|---|---|---|
| 2011/0201083 A1 | 8/2011 | Liao et al. | |
| 2012/0070868 A1 | 3/2012 | Lee et al. | |
| 2014/0377857 A1 | 12/2014 | Liao et al. | |
| 2015/0259710 A1* | 9/2015 | Dundon ................... | C12N 9/88 435/160 |
| 2016/0355850 A1* | 12/2016 | Sanghani ................... | C12P 7/24 |
| 2017/0232043 A1* | 8/2017 | Falb ........................ | A61K 35/74 424/93.2 |
| 2017/0369863 A1* | 12/2017 | Sanghani ................. | C12N 9/88 |

FOREIGN PATENT DOCUMENTS

| | | |
|---|---|---|
| WO | 2010045629 A2 | 4/2010 |
| WO | 2012135731 A2 | 10/2012 |
| WO | 2015089127 A1 | 6/2015 |

OTHER PUBLICATIONS

Becker et al., "Bio-Based Production of Chemicals, Materials and Fuels—Corynebacterium Glutamicum as Versatile Cell Factory", Current Opinion in Biotechnology, 2012, 23, 631-640, Elsevier.
Becker et al., "Systems and Synthetic Metabolic Engineering for Amino Acid Production—The Heartbeat of Industrial Strain Development", Current Opinion in Biotechnology, 2012, 23, 718-726, Elsevier.
Choi et al., "Microbial Production of Short-Chain Alkanes", Nature, 2013, 502, 571-576, Macmillan Publishers.
Datsenko et al., "One-Step Inactivation of Chromosomal Genes in *Escherichia coli* K-12 Using PCR Products", Proc. Natl. Acad. Sci. USA, 2000, 97:12, 6640-6645.
Gronenberg et al., "Next Generation Biofuel Engineering in Prokaryotes", Current Opinion in Biotechnology, 2013, 17, 462-471, Elsevier.
Holton et al., "Structural Characterization of a D-Isomer Specific 2-Hydroxyacid Dehydrogenase from Lactobacillus Delbrueckii ssp. Bulgaricus", Journal of Structural Biology, 2013, 181, 179-184, Elsevier Inc.
Hummel, Werner, "Large-Scale Applications of NAD(P)-Dependent Oxidoreductases: Recent Developments", Tibtech, 1999, 17, 487-492, Elsevier Science Ltd.
Koon et al., "Crystal Structure of LeuA from *Mycobacterium tuberculosis*, a Key Enzyme in Leucine Biosynthesis", Proc. Natl. Acad. Sci. USA, 2004, 101:22, 8295-8300.

Manikandan et al., "Structural Studies on the Enzyme Complex Isopropylmalate Isomerase [LeuCD] from *Mycobacterium tuberculosis*", Proteins, 2010, 35-49, Wiley-Liss, Inc.
Spaepen et al., "Characterization of Phenylpyruvate Decarboxylase, Involved in Auxin Production of Azospirillum Brasilense", Journal of Bacteriology, 2007, 189:21, 7626-7633.
Vedha-Peters et al., "Creation of a Broad-Range and Highly Stereoselective D-Amino Acid Dehydrogenase for the One-Step Synthesis of D-Amino Acids", J. Am. Chem. Soc., 2006, 128, 10923-10929, American Chemical Society.
Versees et al., "The Crystal Structure of Phenylpyruvate Decarboxylase from Azospirillum Brasilense at 1.5 A Resolution Implications for its Catalytic and Regulatory Mechanism", The FEBS Journal, 2007, 274, 2363-2375, The Authors Journal compilation.
Xiong et al., "A Bio-Catalytic Approach to Aliphatic Ketones", Scientific Reports, 2:311, doi: 10.1035/srep0311 (Mar. 13 , 2012).
Zhang et al., "A Synthetic Metabolic Pathway for Production of the Platform Chemical Isobutyric Acid", ChemSusChem, 2011, 4, 1068-1070 Wiley-VCH Verlag GmbH & Co.
International Search Report and Written Opinion pertaining to PCT/US2015/064879 dated Mar. 22, 2016.
International Search Report and Written Opinion pertaining to PCT/US2016/069430 dated Jul. 4, 2017.
International Search Report and Written Opinion pertaining to PCT/US2016/069476 dated Jul. 4, 2017.
Felnagle et al., "Engineering Synthetic Recursive Pathways to Generate Non-Natural Small Molecules", Nature Chemical Biology, Jun. 2012, 518-526, vol. 8, Nature America, Inc.
Han et al., "Sites and Mechanisms of Aconitase Inactivation by Peroxynitrite: Modulation by Citrate and Glutathione", Biochemistry, 2005, 11986-11996, 44, American Chemical Society.
Hsu et al., "Leucine Biosynthesis in *Saccharomyces cerevisiae*, Purification and Characterization of b-Isopropylmalate Dehydrogenase", The Journal of Biological Chemistry, 1980, 7255-7260, vol. 255 No. 15.
Imada et al., "Structure of 3-Isopropylmalate Dehydrogenase in Complex with 3-Isopropylmalate at 2.0 A Resolution: the Role of Glu88 in the Unique Substrate-Recognition Mechanism", Structure, Aug. 1998, 971-982, 6, Current Biology Publications ISSN 0969-2126.
International Search Report and Written Opinion dated Mar. 18, 2015 pertaining to International Application No. PCT/US2014/069438.
Lee et al., "Metabolic Engineering of Clostridium Acetobutylicum M5 for Highly Selective Butanol Production", Biotechnology Journal, 2009, 1432-1440, 4, Wiley-VCH Verlag GmbH & Co.
Marcheschi et al., "A Synthetic Recursive '+1' Pathway for Carbon Chain Elongation", ACS Chemical Biology, 2012, 689-697, 7, American Chemical Society.
Sanghani et al., "Kinetic Mechanism of Human Glutathione-Dependent Formaldehyde Dehydrogenase", Biochemistry, 2000, 10720-10729, 39, American Chemical Society.
Shen et al., "A Synthetic Iterative Pathway for Ketoacid Elongation", Methods in Enzymology, 2011, 469-481, 497, Elsevier Inc.
Wang et al., "Optimization of Butanol Production from Tropical Maize Stalk Juice by Fermentation with Clostridium Beijerinckii NCIMB 8052", Bioresource Technology, 2011, 9985-9990, 102, Elsevier Ltd.
Zhang et al., "Expanding Metabolism for Biosynthesis of Non-natural Alcohols", PNAS, Dec. 2008, 20653-20658, vol. 105 No. 52, The National Academy of Science of the USA.
Rude et al., "New Microbial Fuels: A Biotech Perspective", Current Opinion in Microbiology, 2009, 274-281.
Zhang et al., "Subdomain II of alpha-isopropylmalate synthase is essential for activity: inferring a mechanism of feedback inhibition", The Journal of biological chemistry 2014, 289, 27966-27978.
Office Action pertaining to U.S. Appl. No. 15/030,616 dated Sep. 13, 2017.

* cited by examiner

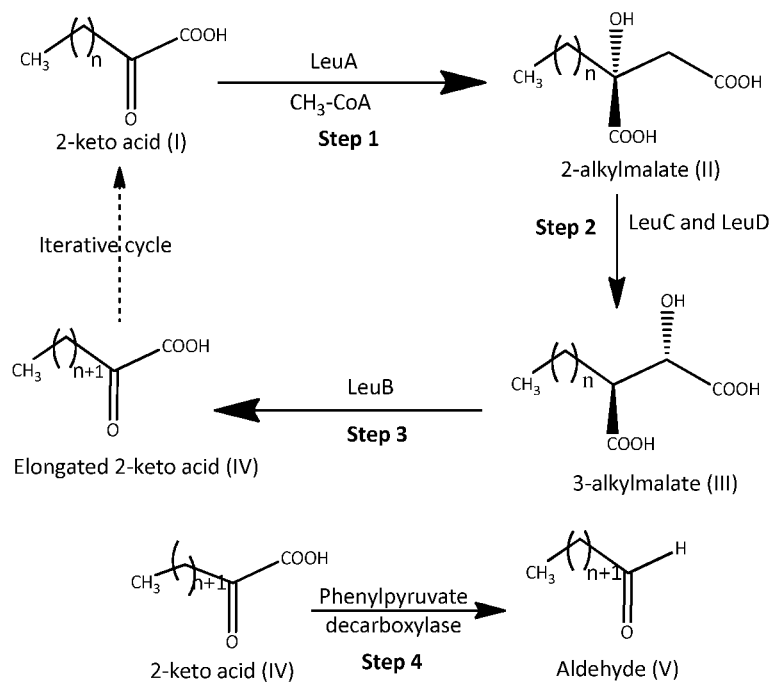

FIGURE 1

Elongated 2-ketoacids would be produced by the recursive activities of Isopropylmalate synthase (LeuA in *E. coli*), isopropylmalate isomerase (LeuC and LeuD in E.coli), and isopropylmalate dehydrogenase (LeuB in E.coli) (steps 1-3) that lengthen the 2-ketoacid by one carbon in each iteration. Phenylpyruvate decarboxylase specific for a particular elongated 2-ketoacid would decarboxylate it to an aldehyde that is one carbon shorter (step 4).

Linear C5-C8 alcohol production from 2-ketobutyrate *in vitro* using a combination of isopropylmalate synthase, isopropylmalate isomerase, isopropylmalate dehydrogenase, and alcohol dehydrogenase (ADH6) in combination with the F385L variant of AbPPDC (SEQ ID 8).

Branched C5-C8 alcohol production from 2-ketoisovalerate *in vitro* using a combination of isopropylmalate synthase, isopropylmalate isomerase, isopropylmalate dehydrogenase, and alcohol dehydrogenase (ADH6) in combination with the F385L variant of AbPPDC (SEQ ID 8).

Branched C5-C8 alcohol production from 3-methyl-2-ketopentanoate *in vitro* using a combination of isopropylmalate synthase, isopropylmalate isomerase, isopropylmalate dehydrogenase, and alcohol dehydrogenase (ADH6) in combination with the F385L variant of AbPPDC (SEQ ID 8).

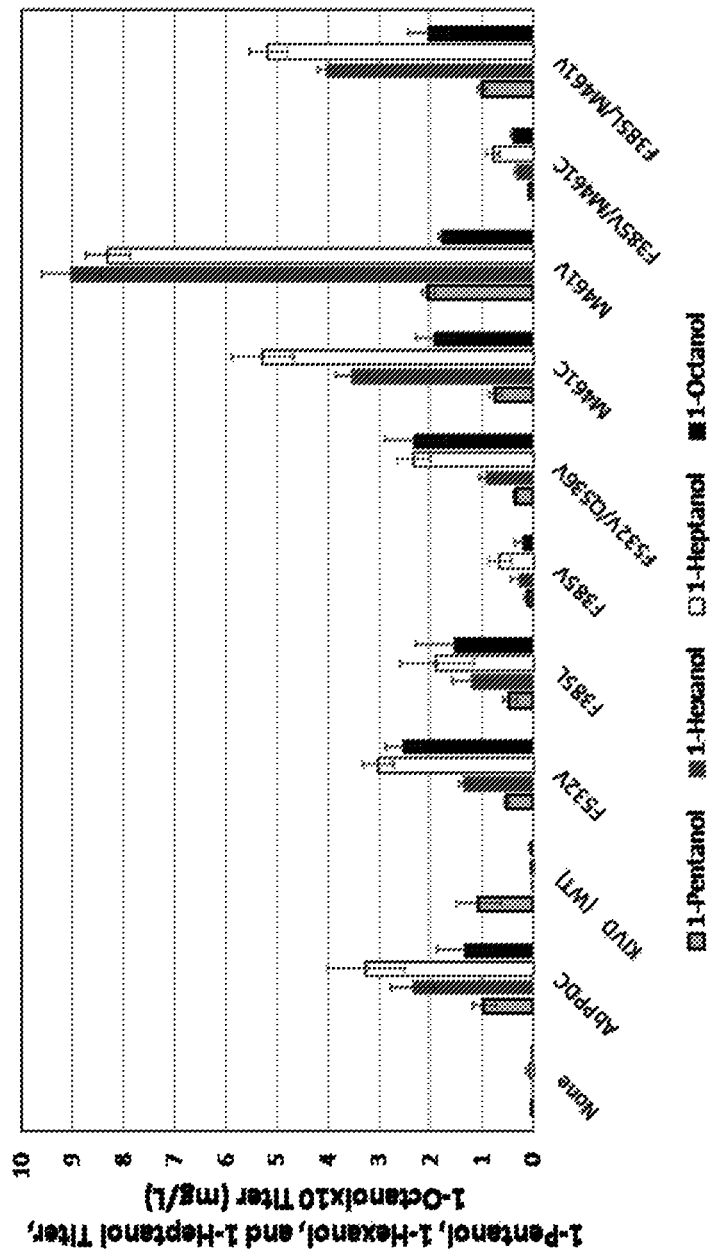

FIGURE 5

The mean alcohol distributions for serum bottle fermentations of E. coli containing the "+1 pathway" enzymes in combination with AbPPDC WT, AbPPDC variants, KIVD wild type (Lactococcus lactis keto-isovalerate decarboxylase), and no decarboxylase. ADH6 was also included in all strain constructs. The 1-octanol titers have been multiplied by ten so that they can be plotted on the same scale as the 1-heptanol, 1-hexanol and 1-pentanol titers. Titers were measured at 24 hours after induction. The "none" column represents the strain with no decarboxylase gene.

GENETICALLY MODIFIED PHENYLPYRUVATE DECARBOXYLASE, PROCESSES TO PREPARE, AND USES THEREOF

This patent application claims the benefit of U.S. Patent Application Ser. No. 62/089,912, filed Dec. 10, 2014, entitled "Genetically Modified Phenylpyruvate Decarboxylase, Processes to Prepare, and Uses Thereof," which is incorporated herein by reference in its entirety.

The invention relates to the field of using biological enzymes to produce C6-C10 compounds such as alcohols, carboxylic acids and alkanes in microbial organisms. More particularly, it relates to the field of using one or more engineered thiamin dependent decarboxylase enzymes to convert a given 2-keto-acid substrate.

Samples of microorganisms expressing one particular embodiment of the genetically modified decarboxylase of the invention representing the M461V variant, as described hereinbelow, have been deposited at the American Tissue Type Collection (ATCC) Patent Repository, 10801 University Blvd., Manassas, Va. 20110, on Dec. 9, 2015.

Geopolitical and environmental concerns have sparked researchers around the world in the pursuit of producing petrochemical based products using renewable avenues, including but not limited to fermentation using microorganisms. However, because microorganisms often fail to produce many of the petrochemical based products at economically viable rates or yields, metabolic engineering has been extensively employed, either to build pathways and/or to channel metabolites toward the pathway of interest. Currently, ethanol is the most common biochemical made using microorganisms. However, economically viable methods for producing longer chain alcohols and carboxylic acids are being actively pursued in both the biofuel and chemical industries.

The success in the production of natural amino acids by microbial fermentation has generated significant interest specifically in utilizing the amino acid biosynthetic pathways for producing chemicals of interest, including the longer chain alcohols and carboxylic acids. See, e.g., Becker, J.; Wittmann, C. "Systems and synthetic metabolic engineering for amino acid production—the heartbeat of industrial strain development," *Curr. Opin Biotechnol.*, 2012, 23:718-726; and Becker, J.; Wittmann, C. "Bio-based production of chemicals, materials and fuels—*Corynebacterium glutamicum* as versatile cell factory," *Curr. Opin. Biotechnol.*, 2012, 23:631-640. The 2-ketoacids, which are key intermediates during amino acid biosynthesis, are amenable to different types of modifications that can be exploited for the biosynthesis of chemicals inside the cells. See, e.g., Gronenberg, L. S.; Marcheschi, R. J.; Liao, J. C. "Next generation biofuel engineering in prokaryotes," *Curr. Opin. Chem. Biol.*, 2013, 17:462-471.

In one example, U.S. Pat. No. 8,232,089 describes a recombinant yeast that expresses an isobutanol-producing metabolic pathway including an *Azospirillum brasilense* decarboxylase that, when coexpressed with isobutanol producing genes, converts 2-ketoisovalerate to isobutyraldehyde.

In another example, U.S. Pat. No. 8,298,798 describes production of both linear and branched chain alcohols in *Escherichia coli* (*E. coli*) cells through the decarboxylation of 2-ketoacids, followed by reduction of the generated aldehyde through expression of *Lactobacillus lactis* (*L. lactis*) keto-isovalerate decarboxylase and yeast alcohol dehydrogenase, ADH6. See also, Atsumi, S.; Hanai, T.; Liao, J. C. "Non-fermentative pathways for synthesis of branched-chain higher alcohols as biofuels" *Nature*, 2008, 451:86-89; Marcheschi, R. J.; Li, H.; Zhang, K.; Noey, E. L.; Kim, S.; Chaubey, A.; Houk, K. N.; Liao, J. C. "Synthetic recursive "+1" pathway for carbon chain elongation," *ACS Chem. Biol.*, 2012, 7:689-697; and Zhang, K.; Sawaya, M. R.; Eisenberg, D. S.; Liao, J. C. "Expanding metabolism for biosynthesis of nonnatural alcohols," *Proc. Natl. Acad. Sci. USA*, 2008, 105:20653-20658. The conversion of 2-ketoacid intermediates to carboxylic acids inside cells has been demonstrated via expression of decarboxylase and an aldehyde dehydrogenase. See, e.g., Xiong, M.; Deng, J.; Woodruff, A. P.; Zhu, M.; Zhou, J.; Park, S. W.; Li, H.; Yao, F. "A bio-catalytic approach to aliphatic ketones," 2012, *Sci. Rep.* 2:311; and Zhang, K.; Woodruff, A. P.; Xiong, M.; Zhou, J.; Dhande, K. "A synthetic metabolic pathway for production of the platform chemical isobutyric acid," *ChemSusChem*, 2011, 4:1068-1070.

The feasibility of extending the length of 2-ketoacids inside the cell via engineering of the LeuA gene product of *E. coli* has also expanded the range of biochemicals that can be produced from 2-ketoacids. See, e.g., Atsumi, S., ibid., and Zhang, K., ibid. In *E. coli*, LeuABCD genes extend the length of 2-ketoacids by one carbon unit, as observed during leucine biosynthesis, in which they work together to convert 2-ketoisovalerate (a 5-carbon acid) to 2-ketoisocaproate (a 6-carbon acid). Marcheschi, et al. *ACS Chem. Biol.*, 2012, 7:689-697, describes the expansion of the active site of LeuA and extension of the C4 ketoacid, 2-ketobutyric acid [2-ketobutyrate], to a C9 ketoacid, 2-ketononanoic acid [2-ketononanoate].

While it is possible to produce alcohols and carboxylic acids of varied lengths in microorganisms using metabolic engineering, production of a particular C6-C8 alcohol or acid, preferably, in an amount of greater than 20 weight percent (wt %), more preferably greater than 30 wt %, based on total alcohols product, has not been demonstrated to date. Several factors appear to determine the specificity of the alcohol/acid produced from the 2-ketoacids inside the cells. The promiscuity of the decarboxylase in accepting 2-ketoacids of varied lengths leads to aldehydes of varied lengths, which are then oxidized or reduced by the respective coexpressed aldehyde or alcohol dehydrogenase. Thus, higher levels of promiscuity, i.e., lower levels of specificity, lead to higher numbers of products. This, in turn, may mean lower yields of particularly desired, specific products.

Specific production of an alcohol or carboxylic acid via 2-ketoacids may also be unfavorably affected by the level of expression of a decarboxylase with respect to the LeuABCD gene products. Higher levels of a decarboxylase having a broad substrate specificity tend to compete with the LeuA gene product for the 2-ketoacid intermediate and thereby limit the pathway's ability to elongate 2-ketoacids. This may result in formation of a shorter alcohol or carboxylic acid than may be desired, again resulting in an undesirable product and/or product mix.

In general, methods for the improvement of industrial microbial organisms range from the random approach of classical strain improvement (CSI) to the highly rational methods of metabolic engineering. CSI is generally effective for alleviating product inhibition or improving productivity, but is a far less effective approach at generating strains capable of producing entirely new products. Furthermore, CSI is intensive as to both time and resources. To obtain strains with high tolerance to inhibitory fermentation products, it is necessary to continuously screen and select mutants by successively culturing the strain in the media in the presence of increasing inhibitor concentrations. This is usually carried out in conjunction with induced mutagenesis using chemical mutagens and/or ultraviolet (UV) radiation. However, the conventional culture screening process is tedious, time-consuming, and often fruitless.

Metabolic modifications are generally more effective at creating strains that produce new products. This is because genes, and in some cases even entire pathways, can be transferred between organisms (recombinant methods) and/or enzymes can be modified (engineered methods). These methods avoid some of the disadvantages of CSI. Metabolic engineering, a term comprehending both recombinant and engineered methods, is a targeted and often faster approach that is widely used to design strains to achieve higher efficiencies in metabolite overproduction, through alterations in the metabolic flux distribution. Most of this work to date is related to the production of secondary metabolites (such as antibiotics), amino acids (e.g., lysine), and heterologous proteins using organisms with well-studied genetics and physiology (e.g., *Escherichia coli*, yeast, and hybridoma cells). Stoichiometric analysis of metabolic flux distributions provides a guide to appropriate metabolic modification, optimal medium formulation and feeding strategies, and bioprocess optimization. However, this approach still requires in-depth knowledge of the metabolic and regulatory networks in the fermentation cells. Although these rational approaches have been successful in cases involving single gene or a few genes within a single gene cluster, they have often been ineffective in cases involving more complex or largely unknown metabolic pathways. This is because such usually target one gene at a time, and thus fail to predict complex interactions among multiple genes in a given pathway.

Enzyme modification is performed by modifying that portion of the genetic code, i.e., the organism's DNA, which corresponds to the expression of that enzyme. Modification of enzymes can lead to entirely new functionality or may be used to improve the specificity or efficiency of desired intermediates or products. Additionally, certain enzymes are known to be promiscuous and may be found performing tasks beyond their known natural roles. Such enzymes may also be modified to perform novel conversions, but to date the success of this approach has been frequently limited to product yields that are not commercially viable. See, e.g., Zhang, K., ibid. Modifying multiple enzymes in a pathway may theoretically be used as a technique to maximize specificity and/or catalytic efficiency.

One example of an organism known to produce octanol under certain conditions is *Clostridium*. Various species of *Clostridium* (e.g., *C. acetobutylicum, difficile,* and *kluyveri*) are employed in WO 2012135731. That publication describes production of a small amount of n-octanol, along with other products, by an engineered *Clostridium* species, and ascribes the poor specificity to n-octanol to the organism's ability to express or overexpress beta-ketothiolase (e.g., BktB), acetyl CoA acetyltransferase (e.g., AtoB), 3-hydroxybutyryl-CoA dehydrogenase (e.g., Hbd, from the *Clostridium,* or PaaHl), crotonase (e.g., Crt), and trans-enoyl-CoA reductase (e.g., Ter). In general, the engineered modifications are to the organism's CoA pathway for the production of higher alcohols, and this pathway avoids the butanol production pathway, found in many species of *Clostridium*, involving oxygen-sensitive enzymes and intermediates. The amount of n-octanol shown to have been produced via this invention is too small to be commercially viable. See also, e.g., Lee, J. Y.; Jang, Y. S.; Lee, J.; Papoutsakis, E. T.; Lee, S. Y. "Metabolic engineering of *Clostridium acetobutylicum* M5 for highly selective butanol production," *Biotechnol.* 2009, 4:1432-1440; and Wang, Y.; Blaschek, H. P. "Optimization of butanol production from tropical maize stalk juice by fermentation with *Clostridium beijerinckii,*" *Bioresour. Technol.,* 2011, 102:9985-9990.

One application of genetic engineering currently being explored is in the energy field. Concerns about the future scarcity, cost, and environmental impact of obtaining and using fossil fuels have stimulated interest in the exploitation of cheap, renewable biomass as alternative sources for both fuels and chemicals made from them. As crude oil prices have become more volatile, bio-based chemicals and industrial products have become attractive alternatives to their petroleum-derived counterparts. Fermentation processes using anaerobic microbial organisms offer a promising path for converting biomass and agricultural wastes into useful products, while at the same time remediating problems that may be encountered in disposal of low-value agricultural commodities and food processing byproducts/wastes. Some of the useful products that can be prepared from low-cost biomass feedstocks are organic acids and alcohols, including octanol. C6-C10 alcohols find particular use as a lower-cost starting material to prepare alkanes, alkenes and aldehydes which are highly desirable feedstock chemicals in a number of industries. These industries include uses as co-monomers for solution polymerizations, and the detergent industry, which uses these precursors to alkylate phenols to produce detergent precursors. These alcohols can also be used as surfactants; as emollients; as thickeners in the cosmetic and food industries; as pesticides; and in a variety of other applications.

In one embodiment the invention provides a process for genetically modifying a microorganism comprising (A) selecting a microorganism that produces a C7-C11 2-ketoacid; and (B) inserting a non-native nucleic acid sequence that encodes an amino acid sequence corresponding to SEQ ID 4, 8, 14, 16, 18, 28, 30, 32, 34, 36, 38, 40, 42, 46, 52, 54, 56, 62, 64, 66, 68, or 76, or an amino acid sequence that is at least 90 percent homologous thereto; such that a non-native phenylpyruvate decarboxylase is expressed in the microorganism.

In another embodiment, the invention provides the genetically modified microorganism.

In yet another embodiment, the invention provides a process to prepare a C6-C10 aldehyde, a C6-C10 alcohol, a C6-C10 carboxylic acid, or a C6-C10 alkane, comprising the steps of (A) contacting 2-ketobutyrate or 2-ketoisovalerate, isopropylmalate synthase, isopropylmalate isomerase, and isopropylmalate dehydrogenase, under conditions such that the 2-ketobutyrate or 2-ketoisovalerate is converted to a C7-C11 2-ketoacid; (B) contacting the C7-C11 2-ketoacid and a phenylpyruvate decarboxylase which is expressed by a non-native nucleic acid sequence that encodes an amino acid sequence corresponding to SEQ ID 4, 8, 14, 16, 18, 28, 30, 32, 34, 36, 38, 40, 42, 46, 52, 54, 56, 62, 64, 66, 68, or 76, or an amino acid sequence that is at least 90 percent homologous thereto; under conditions such that the C7-C11 2-ketoacid is converted to a C6-C10 aldehyde having one less carbon atom than the C7-C11 2-ketoacid being converted; and (C) optionally, contacting the C6-C10 aldehyde and (1) an alcohol dehydrogenase under conditions to form a C6-C10 alcohol; or (2) an aldehyde dehydrogenase under conditions to form a C6-C10 carboxylic acid; or (3) a fatty aldehyde decarbonylase under conditions to form a C6-C10 alkane; the process being carried out such that each step and substep occurs independently within or outside of a microbial organism and under aerobic or anaerobic conditions.

In still another embodiment, the invention provides a polypeptide comprising, consisting essentially of, or consisting of an amino acid sequence corresponding to SEQ ID 8, 14, 16, 18, 28, 30, 32, 34, 36, 38, 40, 42, 46, 52, 54, 56, 62, 64, 66, 68, or 76, or at least 90 percent homologous thereto.

In still another embodiment the invention provides a genetically-modified microorganism comprising (A) a source of a 2-ketoacid; (B) a wild type metabolic pathway that converts the 2-ketoacid to a C7-C11 aldehyde; and (C) a non-native phenylpyruvate decarboxylase represented by a nucleic acid sequence encoding an amino acid sequence corresponding with GenBank: Accession No. L26240, or an amino acid sequence that is at least 80 percent homologous thereto; such sequence having been optionally modified by (1) substituting Met-380 with valine; or (2) substituting Phe-385 with valine, leucine or isoleucine; or (3) substituting Met-461 with valine, leucine, alanine or, cysteine; or (4) substituting Phe-465 with valine or leucine; or (5) substituting Phe-532 with glycine, alanine, valine, or leucine; or (6) substituting Gln-536 with valine, leucine, isoleucine, alanine, or glycine; or (7) any combination of two or three substitutions as described in (1)-(6)

For the sequences described hereinafter, each odd-numbered sequence identification number (SEQ ID) shows the nucleotide, or nucleic acid, sequence, and each even-numbered SEQ ID shows the corresponding coded amino acid sequence. The nucleic acid sequence encodes the amino acid sequence, with the term "amino acid sequence" being equivalent to "polypeptide" or "protein." All references to the protein (even-numbered) SEQ IDs acknowledge the fact that it is possible to produce a given amino acid sequence using alternative codons.

SEQ IDs 1 and 2 represents the 13-amino acid histidine tag that is attached at the beginning of the amino acid sequences.

SEQ IDs 3 and 4 represent the wild type *Azospirillum brasilense* phenylpyruvate decarboxylase gene corresponding to GenBank: Accession No. L26240.

SEQ ID 5 and 6 represent the gene sequence of SEQ ID 3 and 4, but the Met-380 in AbPPDC is replaced with valine at position 380 (based on the amino acid sequence without the his-tag; with the 13-amino acid his-tag, this would be position 393). The modification carries the denomination M380V, therefore adhering to industry standard wherein amino acid modifications are defined as the original single letter amino acid code, followed by the amino acid position, followed by the new amino acid single letter code.

SEQ ID 7 and 8 represent F385L.
SEQ ID 9 and 10 represent F385V.
SEQ ID 11 and 12 represent F385I.
SEQ ID 13 and 14 represent M461C.
SEQ ID 15 and 16 represent M461V.
SEQ ID 17 and 18 represent M461L.
SEQ ID 19 and 20 represent M461A.
SEQ ID 21 and 22 represent F465L.
SEQ ID 23 and 24 represent F532A.
SEQ ID 25 and 26 represent F532G.
SEQ ID 27 and 28 represent F532V.
SEQ ID 29 and 30 represent F532L.
SEQ ID 31 and 32 represent Q536G.
SEQ ID 33 and 34 represent Q536A.
SEQ ID 35 and 36 represent Q536L.
SEQ ID 37 and 38 represent Q536I.
SEQ ID 39 and 40 represent Q536V.
SEQ ID 41 and 42 represent F532V/Q536V.
SEQ ID 43 and 44 represent M380L/M461V.
SEQ ID 45 and 46 represent M380V/M461V.
SEQ ID 47 and 48 represent F385V/M461V.
SEQ ID 49 and 50 represent F385L/M461V.
SEQ ID 51 and 52 represent F532A/Q536V.
SEQ ID 53 and 54 represent F532V/Q536A.
SEQ ID 55 and 56 represent F385L/Q536V.
SEQ ID 57 and 58 represent F385V/Q536V.
SEQ ID 59 and 60 represent M461V/Q536V.
SEQ ID 61 and 62 represent M461L/Q536V.
SEQ ID 63 and 64 represent M461A/Q536V.
SEQ ID 65 and 66 represent M461V/F532V.
SEQ ID 67 and 68 represent F465L/Q536V.
SEQ ID 69 and 70 represent F465V/Q536V.
SEQ ID 71 and 72 represent F465L/F532V.
SEQ ID 73 and 74 represent F532A/Q536A.
SEQ ID 75 and 76 represent M461V/F532V/Q536V.
SEQ ID 77 and 78 represent M380V/M461V/Q536V.
SEQ ID 79 and 80 represent F385L/M461L/Q536V.
SEQ ID 81 and 82 represent M380V/F385V/M461V.

FIG. 1 illustrates chain elongation by recursive (iterative) activity followed by decarboxylation to an aldehyde that is one carbon atom shorter than the 2-ketoacid preceding it in the iterative pathway.

FIG. 5 illustrates the mean alcohol distributions for serum bottle fermentations of *E. coli* containing the "+1 pathway" enzymes in combination with AbPPDC wild type (WT), AbPPDC variants, KIVD WT (*Lactococcus lactis* keto-isovalerate decarboxylase), and no decarboxylase. ADH6 is also included in all strain constructs.

Figure 2:
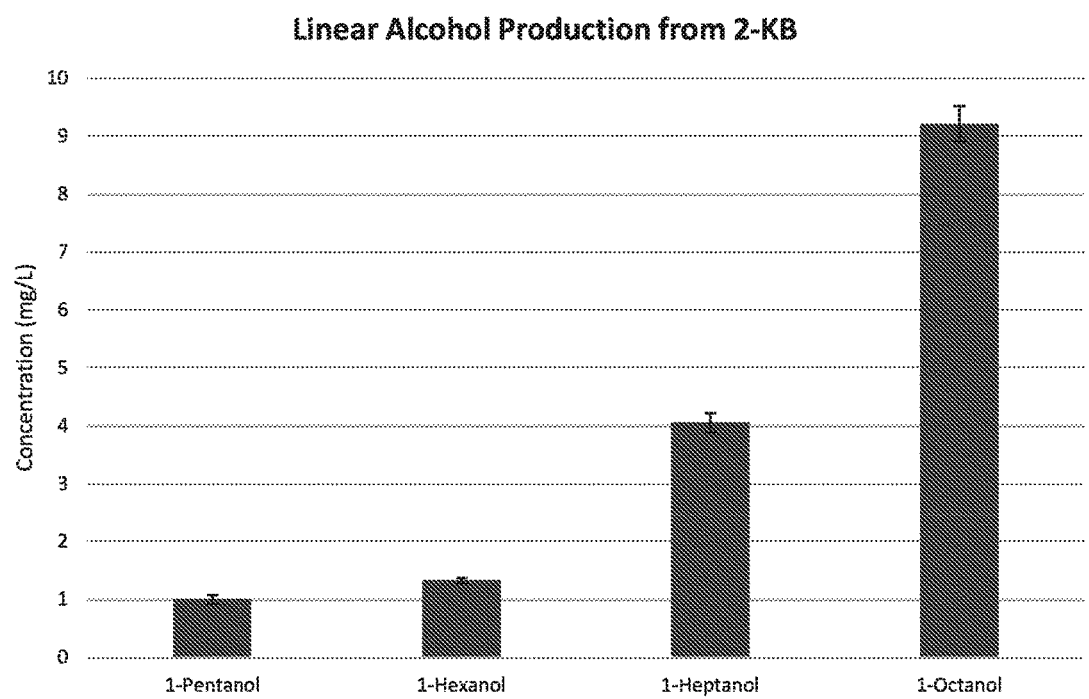
FIG. 2 illustrates linear C5-C8 alcohol production from 2-ketobutyrate in vitro using a combination of isopropylmalate synthase, isopropylmalate isomerase, isopropylmalate dehydrogenase, and alcohol dehydrogenase (ADH6) in combination with the F385L variant of AbPPDC (SEQ ID 8).

In general the present invention includes, among other things, two specific embodiments of a novel phenylpyruvate decarboxylase that may be, in the first embodiment, the expression of an amino acid sequence that is obtained from *Azospirillum brasilense* (*A. brasilense*), corresponding to GenBank: Accession No. L26240, or is at least 80 percent (%) homologous thereto. In a second embodiment, the present invention includes the previously defined genetically modified phenylpyruvate decarboxylase, but with further intentional genetic engineering to insert one, two or three modifications of specific amino acids within the sequence, which again serve to modify the catalytic efficiency of the phenylpyruvate decarboxylase in ways that are in many cases advantageous in carrying out a variety of biosyntheses wherein the phenylpyruvate decarboxylase participates. In particular, either the wild type or the nucleic acid-modified *Azospirillum brasilense* phenylpyruvate decarboxylase enzymes can be used in combination with isopropylmalate synthase, isopropylmalate isomerase and isopropylmalate dehydrogenase enzymes to produce alcohols, carboxylic acids or alkanes.

As will be shown herein, novel phenylpyruvate decarboxylase enzymes with improved properties over the wild type enzyme of a selected host microorganism were created through genetic modification in one of a variety of ways that are described herein; or is an enzyme represented by an amino acid sequence that is at least 80% homologous to the A. brasilense phenylpyruvate decarboxylase and includes the same modifications; processes to make it via recombinant, engineered, or technology combining both recombinant and engineered approaches; processes to make C6-C10 alcohols, carboxylic acids and alkanes using the wild type or novel phenylpyruvate decarboxylase; and a genetically modified microbial organism that can express or overexpress this enzyme and can be used to produce C6-C10 alcohols, carboxylic acids and alkanes. As the term is used herein, homology refers to identical or functional correspondence of 80 percent, or more, of the amino acids listed in the sequence, in their given positions.

The novel phenylpyruvate decarboxylase may be used or expressed as part of, in certain particular embodiments, a metabolic pathway that produces acetyl co-A via either an anabolic (e.g., Wood-Ljundahl) or catabolic (e.g., glycolysis, or a pentose phosphate pathway) route, and ultimately takes part in conversion of a C7-C11 2-ketoacid to form the corresponding C6-10 aldehyde having one less carbon. In some embodiments the C6-C10 aldehyde may be further reacted to form a C6-C10 alcohol, carboxylic acid or alkane. Because of the specific alterations in its amino acid sequence that are described herein, the genetically modified phenylpyruvate decarboxylases of the invention offer some significant differences in specificity to various substrates, and this alteration in specificity offers important advantages in terms of product yields and the reduction or elimination of undesirable and/or competing side products.

The invention includes a number of altered amino acid sequences of A. brasilense phenylpyruvate decarboxylase that have been identified as exhibiting improved decarboxylations of C7-C11 2-ketoacids in comparison with the wild type A. brasilense amino acid sequence corresponding to GenBank: Accession No. L26240, which is shown in SEQ ID 4. Six sites within the wild type sequence have been identified as key to obtaining the improvements. These are: Met-380, Phe-385, Met-461, Phe-465, Phe-532, Gln-536, and combinations thereof. In each alteration changes are made wherein either valine, leucine, alanine, glycine, or isoleucine are substituted at the identified site(s) for the wild type amino acid, with substitutions varying from single-site (i.e., single amino acid constituting three base pairs) substitution, to a wide variety of multiple-site (from 2 to 5 sites) substitutions defined as "combinations" of the identified sites, preferably from 2 to 3. SEQ ID 3-82 show amino acid sequences for the many variations produced that include one or more of the substitutions as specified. The substitutions can be summarized as follows: (1) substituting Met-380 with valine; or (2) substituting Phe-385 with valine, leucine or isoleucine; or (3) substituting Met-461 with valine, leucine, alanine, or cysteine; or (4) substituting Phe-465 with valine or leucine; or (5) substituting Phe-532 with glycine, alanine, valine, or leucine; or (6) substituting Gln-536 with valine, leucine, isoleucine, alanine, or glycine; or (7) any combination of three substitutions as described in (1)-(6);

It will be understood by those skilled in the art that the inventive genetically modified phenylpyruvate decarboxylases may be used either in vivo, i.e., by a genetically modified microorganism, or in vitro. In view of this, the terms "genetically modified," or "modified," as used herein, refer to the group of inventive phenylpyruvate decarboxylases having an intentionally altered amino acid sequence, i.e., a "non-wild type" amino acid sequence, or a microbial organism (depending upon placement of either term as an adjective) having a genome that has been intentionally altered as to (at least) the specific, modified decarboxylase(s) described and defined as inventive herein. Such alteration may have been accomplished via recombinant technology, where one or more genes is transferred from a second, different microbial organism into a target microbial organism; or engineered technology, wherein the nucleic acids within the target microbial organism are altered, generally via site-directed mutagenesis, resulting in the conversion of at least one nucleic acid to a different nucleic acid and therefore modification of one or more enzymes. With today's DNA synthesis technologies, recombinant technology can also be accomplished using fully synthetic DNA that is transferred to the target microorganism using conventional methods. Combinations of any of the above methods may also be employed.

The invention further includes a process to prepare C6-C10 aldehydes, C6-C10 carboxylic acids, C6-C10 alkanes, and C6-10 alcohols such as hexanol, heptanol and/or 1-octanol, via contact between a starting substrate and a series of enzymes that include one or more of the genetically-modified phenylpyruvate decarboxylases of the invention to ultimately convert that substrate, using additional enzymes and steps, to the desired C6-C10 aldehyde, alcohol, carboxylic acid, or alkane. This process may be carried out biosynthetically, in one of the described embodiments of a non-naturally occurring, i.e., genetically engineered, cell, i.e., in a non-naturally occurring microbial organism; or production of the C6-C10 alcohol(s), carboxylic acid(s), or alkane(s), may be carried out via in vitro methodology, typically beginning from a starting point that does not include a microbial organism.

In order to obtain the group of modified phenylpyruvate decarboxylases of the invention, it is desirable, in one embodiment, to perform a protocol similar to that described hereunder. In general the examples show genetic modification involving engineering to alter one or more nucleic acid base(s) in a given codon in order to alter the enzyme of which the nucleic acid base(s) is/are a part. Such may be used simply to produce altered enzyme for, e.g., in vitro assay purposes. In contrast, the genome of a host microbial organism may be preferably altered for a larger scale production strain.

The following methodology, designed for in vitro enzyme production, may be carried out as is generally understood by those skilled in the art. In general, a suitable database, such as GenBank, is used to obtain the genetic codes for the wild type enzyme(s), followed by identification of the codons suitable for modification. This identification may be used as the basis for art-known methods of protein engineering, wherein computer molecular modeling identifies and also enables differentiation of structural locations at which modifications of enzyme/substrate interfaces may be effectively employed. A given desirable modification is then performed, using a molecular biology technique wherein the alteration(s) of the nucleic acid base(s) is/are done via site-directed mutagenesis. The variant-type enzymes must then be subjected to purification to separate out non-targeted proteins, leaving a purified enzyme that will exhibit a higher-than-wild type catalytic efficiency. This can be appropriately assayed in vitro, according to the methodology most suitable for the given particular enzyme. An assayed enzyme that is shown to have a desirable level of catalytic efficiency is thereby confirmed to be the product of a desirable genetic modification, and may be used for in vitro production methods, such as for the in vitro conversion of a C7-C11 2-ketoacid to the corresponding C6-C10 aldehyde having one less carbon (e.g., converting 2-ketononanoate to octanal, or 2-ketooctanoate to heptanal) which can then be reduced, in one embodiment, by contact with an appropriate wild type or non-wild type alcohol dehydrogenase, to form the corresponding C6-C10 alcohol.

As noted hereinabove, the invention may be carried out either in vivo or in vitro. An in vivo approach may be preferred for commercial scale production, although in some cases an in vitro approach may be suitable for commercial scale production. Frequently, an in vitro approach may be particularly convenient for laboratory and general research purposes, such as to carry out enzymatic assays. For example, desirable microbial organism, useful for large or commercial scale fermentative production of an enzyme-facilitated product, such as, in certain particular embodiments, a C6-C10 alcohol or combination of C6-C10 alcohols, may be prepared. Such preparation may be carried out by inserting the DNA, or pieces of DNA, which encode for the desired improved enzyme, from a first microbial organism into the genome of a second, "host" microbial organism known or believed to possess one or more desired metabolic pathways and/other desired features, such as inhibition-resistant fermentative capability, using recombinant technology. In general the in vivo approach employs such a microbial organism's wild type metabolic pathway(s), first to convert a suitable carbon-containing substrate to pyruvate, and then to convert the pyruvate to 2-ketobutyrate or, alternatively, to 2-ketoisovalerate, in a varying number of steps.

For example, in one embodiment a suitable carbon-containing substrate, such as a C5 or C6 sugar (e.g., glucose, sucrose, pentose, or a combination thereof), may be converted directly to pyruvate via one of the catabolic or anabolic pathways, such as a glycolysis or pentose phosphate pathway. Thereafter the pyruvate may be converted first to L-threonine, via PC (pyruvate carboxylase); AAT (aspartate aminotransferase); ThrABC (ThrA, which is a bifunctional aspartokinase/homoserine dehydrogenase; ThrB, which is homoserine kinase; ThrC, which is threonine synthase; and ASD, which is aspartate semialdehyde dehydrogenase). The L-threonine is then converted to 2-ketobutyrate via Ilva (threonine dehydratase). In an alternative embodiment, the pyruvate may be converted to 2-ketoisovalerate via the activities of IlvBN/IlvGM, IlvC, and IlvD in leucine biosynthesis. See, also, Zhang, K.; Sawaya, M. R.; et al., ibid.

From this point a wild type or genetically modified form of one or more of the three enzymes within the leucine biosynthetic pathway, that are involved in elongating 2-ketoacids, operate to convert the 2-ketobutyrate or 2-ketoisovalerate to a C7-C11 2-ketoacid. These enzymes are generally referred to, without reference to any specific microbial organism, as isopropylmalate synthase, isopropylmalate isomerase, and isopropylmalate dehydrogenase. However, in E. coli specifically, they are referred to as LeuA (GenBank: Accession No. NC 000913.3 Gene ID: 947465), LeuB (GenBank: Accession No. NC 000913.3 Gene ID: 944798), and LeuCD (GenBank: Accession No. NC 000913.3 Gene ID: 945076 and Gene ID: 945642), respectively. One example of this chain elongation is shown in FIG. 1, wherein 2-ketobutyrate is converted, via a number of steps termed a "+1 pathway," to the C7-C11 2-ketoacid 2-ketononanoate.

In certain particular embodiments the wild type enzymes of leucine biosynthetic pathway involved in extending 2-ketoacids may be modified, in particular by inclusion of at least one exogenous enzyme, enzyme complex, or combination thereof, to convert 2-ketobutyrate first to 2-ketovalerate, then to 2-ketocaproate, then to 2-ketoheptanoate and continuing, if desired, to another elongated 2-ketoacid up to 2-ketoundecanoate, i.e., a desired C7-C11 2-ketoacid, as chain-lengthening occurs. However, it is optionally possible to modify only one or two of the enzymes, enzyme complex, or combination thereof, in order to obtain acceptable or desirable production of the C7-C11 2-ketoacid. These enzymes may include LeuA, LeuB and/or LeuCD, as mentioned hereinabove.

Particularly applicable to modification of this portion of the pathway is the disclosure of co-pending International Patent Application Serial No. PCT/US14/69438, filed Dec. 10, 2014, claiming the benefit of U.S. Provisional Patent Application No. 61/915,040, filed Dec. 12, 2013, which are both incorporated herein in their entireties by reference. In certain embodiments, at least a modified isopropylmalate dehydrogenase variant (which is the product of the LeuB gene in E. coli) is selected, or in other embodiments at least a modified LeuA (LeuA') and LeuB' variant is included, preferably, but not necessarily, as described in one or both of the referenced patent applications. It is also preferable to employ other combinations of the LeuA', LeuB' and modified LeuCD (LeuCD') enzymes/enzyme complex. Again, it should be noted that the "Leu"+letter (A, B, CD) designations are specific names for the leucine pathway enzymes of isopropylmalate synthase, isopropylmalate isomerase, and isopropylmalate dehydrogenase in E. coli, while the same or equivalent enzymes in the leucine pathway of other organisms may have different names.

Finally, the inventive genetically modified phenylpyruvate decarboxylase may, in this particular embodiment, serve to convert the C7-C11 2-ketoacid to an aldehyde having one less carbon than the substrate 2-ketoacid. In various embodiments, the resulting C6-C10 aldehyde may find a wide variety of uses, as a product in itself or as a starting or intermediate product for the production of products including the C6-C10 alcohols. Preparation of C6-C10 alcohols may be accomplished via conversion of the C6-C10 aldehyde by an appropriate wild type or genetically modified alcohol dehydrogenase, but other products, such as C6-C10 alkanes, may also be prepared, via the action or expression of a fatty aldehyde decarbonylase, or C6-10 carboxylic acids may be prepared by the action or expression of an aldehyde dehydrogenase. See, e.g., Choi, Y. J.; Lee, S. Y. "Microbial production of short-chain alkanes," *Nature,* 2013, 502:571-574. Thus, the C6-10 aldehydes are industrially highly useful as excellent intermediate products for preparing a wide variety of other products.

Accordingly, it is anticipated that the inventive family of genetically modified phenylpyruvate decarboxylases will be applicable in a wide variety of industries. Such industries may include, for example, use in fuels, plastics, food, packaging, cosmetics, perfumes, pharmaceuticals, cleaning materials, pollution control, perfumes, drugs, and many others. While there are a number of possible amino acid sequences falling fully within the scope of the claims of the present invention, it is noted that certain amino acid sequences, identified by their sequence identification numbers (SEQ ID) as selected from SEQ ID 34, 36, 38, 40, 42, 46, 62, 68, and 76, are particularly well-suited and preferred for decarboxylating the C7-C11 2-ketoacids.

EXAMPLE 1

Design of *A. brasilense* Phenylpyruvate Decaroxylase (AbPPDC) Variants with Higher Catalytic Efficiency for 2-Ketononanoic Acid Decarboxylation A crystal structure model of the ternary complex of AbPPDC with 3-deaza-thiamine diphosphate and 5-phenyl-2-oxovaleric acid (PDB ID Code 2Q5Q) is used to identify residues lining the 2-ketoacid binding pocket within the active site of AbPPDC. See, e.g., Versees, W.; Spaepen, S.; Wood, M. D.; Leeper, F. J.; Vanderleyden, J.; Steyaert, J. "Molecular mechanism of allosteric substrate activation in a thiamine diphosphate-dependent decarboxylase," *J. Biol. Chem.*, 2007, 282:35269-35278. The amino acid sites denominated as Met-380, Met-461, Phe-385, Phe-465, Gln-536 and Phe-532 are selected for substitution experimentation based on their relationship with 5-phenyl-2-oxovaleric acid. Substitutions of one or more sites are made as listed in Table 1 and the variants prepared.

Enzyme F532V replaces Phe-532 in AbPPDC with valine, while enzyme F532L replaces Phe-532 with leucine. Enzyme F385L/M461V replaces Phe-385 with leucine and Met-461 with valine. The remaining *A. brasilense* phenylpyruvate decarboxylase (AbPPDC) variants in the Table 1 are named according to the amino acid (first letter, with "F" representing "phenylalanine [Phe];" "M" representing "methionine" [Met]; and "Q" representing "glutamine" [Gln]), its position in the amino acid sequence (the number), and the amino acid used as a replacement (last letter, with "L" representing "leucine;" "V" representing "valine;" "A" representing "alanine"; "C" representing "cysteine"; "I" representing "isoleucine"; and "G" representing "glycine.")

Each of the modified AbPPDC variants is expressed and purified, and then tested for activity against the three substrates, which are 2-ketohexanoate (2-KH), 2-ketooctanoate (2-KO) and 2-ketononanoate (2-KN). The 2-KH, 2-KO and 2-KN would be anticipated to form pentanal, heptanal and octanal, respectively, upon decarboxylation by AbPPDC.

The evaluation of the AbPPDC variants is performed in two steps using the high-throughput enzyme assay described hereinbelow. Initially, all the variants are tested for activity against a single high concentration (2 mM) of 2-KH and 2-KN (as shown in Table 1). Following the initial evaluation, detailed kinetic analysis is performed on a select number of variants to determine the maximal rate ($k_{cat}$), substrate concentration yielding half maximal rate ($K_{0.5}$, equivalent of $K_M$ for enzymes following Michaelis-Menten kinetics), and the catalytic efficiency of the enzyme ($k_{cat}/K_{0.5}$) against 2-KO and 2-KN (as shown in Table 2). AbPPDC variants, having higher specificity (higher $k_{cat}/K_{0.5}$) for 2-KN, will be efficient in producing octanal and chemicals derived from it inside the cells.

TABLE 1

Sequence listings and activity of AbPPDC variants

| Enzyme | SEQ ID | Activity, nmol · min⁻¹ · mg⁻¹ 2-KH | Activity, nmol · min⁻¹ · mg⁻¹ 2-KN |
| --- | --- | --- | --- |
| AbPPDC | 4 | 4.5 ± 2.7 | 199 ± 18 |
| M380V | 6 | 9.4 ± 0.6 | 178 ± 17 |
| F385L | 8 | 11.9 ± 2.6 | 78 ± 2 |
| F385V | 10 | 9.6 ± 0.4 | 145 ± 3 |

TABLE 1-continued

Sequence listings and activity of AbPPDC variants

| Enzyme | SEQ ID | Activity, nmol · min⁻¹ · mg⁻¹ 2-KH | Activity, nmol · min⁻¹ · mg⁻¹ 2-KN |
| --- | --- | --- | --- |
| F385I | 12 | 0.8 ± 0.0 | 25 ± 0 |
| M461C | 14 | 17.7 ± 12 | 241 ± 14 |
| M461V | 16 | 9.6 ± 0.2 | 332 ± 22 |
| M461L | 18 | 2 ± 0.8 | 293 ± 3 |
| M461A | 20 | 1.2 ± 0.1 | 40 ± 2 |
| F465L | 22 | 1.8 ± 6.3 | 99 ± 2 |
| F532A | 24 | 0.6 ± 0.1 | 6 ± 0 |
| F532G | 26 | 0.4 ± 0.1 | 106 ± 0 |
| F532V | 28 | 0.0 | 209 ± 3 |
| F532L | 30 | 0.0 | 309 ± 8 |
| Q536G | 32 | 1.1 ± 0.3 | 251 ± 1 |
| Q536A | 34 | 4.7 ± 0.9 | 396 ± 1 |
| Q536L | 36 | 53 ± 1 | 497 ± 7 |
| Q536I | 38 | 136 ± 2 | 715 ± 57 |
| Q536V | 40 | 57 ± 1 | 779 ± 16 |
| F532V/Q536V | 42 | 16 ± 0.1 | 307 ± 10 |
| M380L/M461V | 44 | 2.8 ± 1.4 | 156 ± 8 |
| M380V/M461V | 46 | 4 ± 0.9 | 196 ± 8 |
| F385V/M461V | 48 | 5.9 ± 2 | 100 ± 15 |
| F385L/M461V | 50 | 8.1 ± 1.5 | 78 ± 1 |
| F532A/Q536V | 52 | 1.6 ± 0.2 | 238 ± 1 |
| F532V/Q536A | 54 | 1 ± 3 | 242 ± 0 |
| F385L/Q536V | 56 | 1.8 ± 0.4 | 164 ± 2 |
| F385V/Q536V | 58 | 3.5 ± 0.5 | 219 ± 0.5 |
| M461V/Q536V | 60 | 11.8 ± 0.1 | 312 ± 2 |
| M461L/Q536V | 62 | 0 | 644 ± 5 |
| M461A/Q536V | 64 | 1.7 ± 0.1 | 272 ± 7 |
| M461V/F532V | 66 | 1.3 ± 0.3 | 260 ± 3 |
| F465L/Q536V | 68 | 2.6 ± 0.5 | 327 ± 1 |
| F465V/Q536V | 70 | 0.9 ± 0.1 | 201 ± 1 |
| F465L/F532V | 72 | 6.2 ± 0.4 | 393 ± 40 |
| F532A/Q536A | 74 | 1.4 ± 0.8 | 57 ± 6 |
| M461V/F532V/Q536V | 76 | 1.6 ± 2.5 | 494 ± 28 |
| M380V/M461V/Q536V | 78 | 0.0 | 195 ± 7 |
| F385L/M461L/Q536V | 80 | 1.4 ± 0.8 | 129 ± 1 |
| M380V/F385V/M461V | 82 | 6.7 ± 0.5 | 87 ± 7 |

SEQ ID 4 is the amino acid sequence of *A. brasilense* phenylpyruvate decarboxylase (GenBank: Accession No. L26240). SEQ ID 6-82 are sequences of proteins designed and expressed in this invention. All the proteins expressed in this invention have 13 additional amino acids at the N-terminus, added as the histidine-tag (shown in SEQ ID 2).

EXAMPLE 2

A. Heterologous Expression of *Azospirillum brasilense* Phenylpyruvate Decarboxylase (AbPPDC) and its Engineered Variants in *E. coli*

To evaluate the substrate specificity of the wild type AbPPDC and its variants listed in Table 1, genes of all the proteins are expressed in *E. coli* cells separately and the protein products are isolated from the cells. The gene sequence of the *Azospirillum brasilense* phenylpyruvate decarboxylase (GenBank: Accession no. L26240) is downloaded from the NCBI database. Codons of 13 additional amino acids that include six (6) histidines (his) are added upstream of the Met-1 codon of the AbPPDC gene sequence. Such a modification allows expression of a Histidine-tagged AbPPDC having 13 additional amino acids on the N-terminus. The additional amino acids are attached as an aid for purifying the protein in a single step using Ni-NTA chromatography. The entire AbPPDC sequence with 13 additional amino acids (SEQ ID 2) is chemically synthesized and then cloned into the pRSFDuet-1 vector (EMD Biosciences) downstream of the T7 polymerase promoter by Synthetic Genomics, Inc. (San Diego, Calif.). The final vector is sequenced by Synthetic Genomics, Inc. before shipping.

Genes of the AbPPDC variants listed in Table 1 are either chemically synthesized or generated using New England Biolab's Q5 Site-directed Mutagenesis Kit (cat. no. E0554S) and cloned into the pRSFDuet-1 vector. The pRSFDuet-1 vector containing AbPPDC or the AbPPDC variant gene is transformed into *E. coli*, AbPPDC or its variant, then expressed and eventually purified, as described below.

*E. coli* expression studies are then conducted using the competent BL21(DE3) cells acquired from EMD Biosciences. Transformations are performed as per the kit instructions and involve mixing a 50 microliter (μL) aliquot of competent cells with 1 μL of the vector. Cells harboring the AbPPDC expression vector are selected using kanamycin as the marker in the growth medium.

*E. coli* transformants harboring the AbPPDC or AbPPDC variant expression vector are then selected on Luria-Bertani (LB) broth agar plates containing 50 micrograms per milliliter (μg/mL) of kanamycin. The plates are incubated at 37 degrees Celsius (° C.) for 16 hours (h). A starter culture is started by transferring a single colony of transformant into 50 milliliters (mL) of LB medium containing 50 ug/mL of kanamycin and incubated at 37° C. with shaking at 220 revolutions per minute (rpm) overnight. On the next day, 7 mL of starter culture is inoculated into 800 mL of Terrific Broth (TB) and the culture is incubated at 37° C. until the culture reaches an optical density at 600 nanometers ($OD_{600\ nm}$) of 0.5. Isopropyl β-D-1-thiogalactopyranoside (IPTG) at a final concentration of 1 mM is added to induce the expression of the AbPPDC or AbPPDC variant genes and the culture is transferred to a 15° C. incubator for 16 hours (h). At the end of 16 h, the culture is centrifuged at 8000 revolutions per minute (rpm) to pelletize the cells. The cell pellet is divided into two aliquots and stored at −80° C. overnight before purification.

An *E. coli* cell pellet taken from 400 mL of expression culture is suspended in B-PER reagent (Thermo Fisher Scientific, Inc., Rockford, Ill.) containing 1 μg/mL of DNAse (Thermo Fisher Scientific, Inc., Rockford, Ill.), 1 μg/mL of lysozyme (Thermo Fisher Scientific, Inc., Rockford, Ill.), 1 millimolar (mM) of dithiothreitol, and protease inhibitor cocktail (RPI Corp., Mount Prospect, Ill.). The suspension is rocked gently for 30 minutes (min) at room temperature and centrifuged at 15,000 times gravity (×g) for 20 min to pelletize cell debris. The supernatant is separated and incubated with 5 mL of Co-NTA resin (Thermo Fisher Scientific, Inc., Rockford, Ill.) that has been pre-equilibrated with an equilibration buffer (50 mM sodium phosphate, pH 8.0, containing 300 mM sodium chloride, 20 mM imidazole, 50 μL protease inhibitor cocktail, and 15% glycerol). Following an incubation period of 1 h at 4° C., the enzyme bound resin is washed with 5 volumes of equilibration buffer. AbPPDC or its variants are eluted from the Co-NTA resin with equilibration buffer containing 200 mM imidazole. The eluted proteins are dialyzed against phosphate buffered saline and stored as a 20% glycerol solution at −20° C.

B. Determination of the Substrate Specificity of AbPPDC and AbPPDC Variants

The evaluation of the substrate specificities of AbPPDC variants is performed using the methods as described in detail in Example 1.

A high-throughput AbPPDC coupled enzyme assay is developed for evaluating the substrate specificity of AbP-PDC variants. The assay involves reducing the aldehyde produced from AbPPDC mediated 2-ketoacid decarboxylation, using an alcohol dehydrogenase (ADH6, GenBank: Accession No. NP 014051.3). The initial velocities of the AbPPDC catalyzed reactions are determined from the rates of oxidation of reduced nicotinamide adenine dinucleotide phosphate (NADPH) occurring during the ADH6 catalyzed reduction of aldehyde.

The HTP screening assay involves incubating 2 mM 2-KH or 2 mM 2-KN with 0.5 mM thiamine diphosphate, 0.35 mM NADPH, 4.7 micrograms (μg) of yeast ADH6 (GenBank: Accession No. NP 014051.3) and 0.3 milligrams per milliliter (mg/mL) bovine serum albumin (BSA) in AbPPDC assay buffer (50 mM 3-(N-morpholino)propanesulfonic acid, pH 6.8, containing 2.5 mM magnesium chloride ($MgCl_2$)) at 30° C. The reaction is started by addition at 30° C. of working enzyme stock containing from 0.5 μg to 3.5 μg of AbPPDC variant diluted in AbPPDC assay buffer containing 1 mg/mL BSA. The plate containing the 200 μL of reaction mixture is centrifuged at 2500×g for 15 sec and the absorbance change of the reaction mixture followed spectrophotometrically at 340 nm on a BioTek™ plate reader, pre-equilibrated at 30° C. Initial velocity of the enzyme reaction is calculated using the rate of NADPH consumption at 340 nm and the extinction coefficient of NADPH (6.22 $mM^{-1}\ cm^{-1}$). The activity of all the variants is normalized with the amount of enzyme present in the reaction mixture and expressed as nanomoles per minute per milligram ($nmol \cdot min^{-1} \cdot mg^{-1}$). Protein concentrations for normalizing the activities are determined using the 660 nm total protein assay kit from Pierce Biotechnology Inc., available from Thermo Fisher Scientific, Inc., using BSA as the standard.

The kinetic parameters of the decarboxylation of 2-ketooctanoate (2-KO) and 2-ketononanoate (2-KN) by AbPPDC and its variants are also determined using the same HTP AbPPDC coupled enzyme assay, except that the concentrations of 2-KO or 2-KN are varied from 0 to 4 mM.

For AbPPDC variants exhibiting substrate activation, as evident from a sigmoidal plot of initial velocities versus substrate concentration plot, the kinetic parameters ($k_{cat}$, $K_{0.5}$, and $k_{cat}/K_{0.5}$) of 2-keto-acid decarboxylation are obtained by fitting the data to the Hill equation (shown in the legend of Table 2) using nonlinear regression. For variants following normal saturation kinetics, the kinetic parameters ($k_{cat}$, $K_M$, and $k_{cat}/K_M$) are obtained by fitting initial velocities to the Michaelis-Menten equation using nonlinear regression. Nonlinear regression is performed using the GraphPad Prism™ software. Table 2 lists the kinetic parameters of 2-KO and 2-KN decarboxylation by AbPPDC and its variants. The amount of enzyme in the reaction mixture is determined using the Pierce Biotechnology Inc.™ 660 nm total protein assay kit and using BSA as the standard.

Narrowing the substrate specificity of AbPPDC is expected to improve the accumulation of a specific aldehyde and its downstream products. In general AbPPDC prefers bulkier 2-ketoacids, such as 5-phenyl-2-ketopentanoate and phenylpyruvic acid, as evidenced by high catalytic efficiencies with respect to those substrates (See, e.g., Spaepen, S.; Versees, W.; Gocke, D.; Pohl, M.; Steyaert, J.; Vanderleyden, J. "Characterization of phenylpyruvate decarboxylase, involved in auxin production of *Azospirillum brasilense*," J. Bacteriol., 2007, 189:7626-7633).

AbPPDC and the variants listed in Table 1 are screened for activity against 2 mM 2-ketohexanoate (2-KH) and 2 mM 2-ketononanoate (2-KN) as substrates. That screening reveals that the wild type AbPPDC catalyzes the decarboxylation of 2-KN, but exhibits poor activity against 2-KH under the assay conditions. All of the AbPPDC variants, also catalyze the decarboxylation of 2-KN, and exhibit relatively low activity against 2-KH (Table 1). Substitution of Gln-536 with alanine, valine, isoleucine or leucine increases the 2-KN decarboxylating activity over that of the wild type enzyme, but also improves activity against 2-KH as a substrate. These results suggest that all of the AbPPDC variants listed in Table 1 can be expressed in an active form in heterologous systems. Furthermore, all of them have significantly higher activity against 2-KN than 2-KH, suggesting that AbPPDC and the variants described herein prefer >C6 2-ketoacids.

Detailed steady state kinetic analysis is performed on all the enzymes to determine the maximal rate and the catalytic efficiency of decarboxylating 2-ketooctanoate (2-KO) and 2-ketononanoate (2-KN). Both the substrates exhibit hyperbolic and non-hyperbolic kinetics as evident from Table 2. For AbPPDC variants showing non-hyperbolic kinetics, initial velocities of the decarboxylations of 2-KO and 2-KN are fitted to the Hill equation (Table 2 legend) and the maximal rate and the catalytic efficiencies ($k_{cat}/K_{0.5}$) calculated as shown in Table 2. A Hill coefficient greater than 1 suggests presence of substrate activation with 2-KO and 2-KN. Substrate activations have been reported with AbPPDC and with other decarboxylases. See, also, Spaepen, S., Ibid.

As evident from Table 2, the amino acid substitutions affect the catalytic efficiency of the variants in capturing 2-KO and 2-KN for catalysis in different ways. For some variants, for example, F532V, the catalytic efficiency of decarboxylation of 2-KN and 2-KO is 180% and 45%, respectively, in comparison with that of the wild type AbPPDC. This suggests that F532V substitution increases the substrate specificity for 2-KN while decreasing it for 2-KO. The preference of the AbPPDC variants for 2-KN over 2-KO is calculated by taking the ratio of the variant's catalytic efficiencies and is shown in Table 2. As evidenced in Table 2, the specificities of AbPPDC and F532V are 1.8 and 5.6, respectively, indicating that their catalytic efficiency of decarboxylating 2-KN is 1.8 and 5.6 times higher than that of decarboxylating 2-KO. This also indicates that the F532V variant is 3-fold more specific than AbPPDC in preferring 2-KN over 2-KO. Similarly, the preference of F385L for 2-KN over 2-KO is 5-fold higher than that of AbPPDC. This data suggests that the F385L and F532V substitutions improve the substrate specificity for a longer 2-ketoacid (for example 2-KN) over shorter one (for example 2-KO). Thus, the F385L and F532V variants would improve the accumulation of longer (C7-C10) aldehyde based products when 2-ketoacids are being elongated using the "+1 pathway" (FIG. 1).

Similarly, the specificities of the M461L, F532L, Q536G, Q536L, F532V/Q536V, M380V/M461V, F532A/Q536V, F532V/Q536A, F385L/Q536V, M461V/F532V and M461V/F532V/Q536V variants for 2-KN, in comparison with the specificity of each variant for 2-KO, are 3.3, 4.3, 4.8, 2.7, 3.6, 2.7, 6.8, 4.6, 4.3, 5.4, and 2.1, respectively. This suggests that all of these variants are more specific than AbPPDC in capturing 2-KN for catalysis.

In addition to the specificity of the AbPPDC variant for 2-KN, maximal accumulation of octanal and biochemicals derived from it will also be dependent on the relative efficiencies of the 2-KN producing pathways versus that of the AbPPDC variant. For example, where the efficiency of the engineered 2-ketoacid chain extension pathway (involving the three enzymes, isopropylmalate synthase, isopropylmalate isomerase and isopropylmalate dehydrogenase) in producing 2-KN is relatively low compared to that for producing 2-KO, heptanal formation would result, due to the decarboxylation of 2-KO by AbPPDC variants in combination with reduction in the accumulation of octanal based chemicals inside the cells. Under such circumstances, AbPPDC variant such as F385L would be preferred decarboxylase based upon its relatively high specificity (9.1), coupled with its reduced efficiency as 2-KN decarboxylating catalyst (Table 2).

The results also show that substituting Gln-536 with a hydrophobic amino acid (i.e., glycine, alanine, valine, leucine, or isoleucine) improves the catalytic efficiency of AbPPDC and other specificity enhancing substitutions as shown in Table 2. The Q536V variant is 8- and 5.7-fold more efficient than the wild type enzyme in decarboxylating 2-KO and 2-KN, respectively (Table 2). Similarly, the M461V/F532V/Q536V variant is 27- and 10-fold more efficient than M461V/F532V variant in decarboxylating 2-KO and 2-KN, respectively (Table 2). The M461V/F532V/Q536V variant is about 17- and 20-fold more efficient enzyme than the wild type enzyme in decarboxylating 2-KO and 2-KN, respectively (Table 2). The higher catalytic efficiency of the M461V/F532V/Q536V variant allows effective decarboxylation of 2-KO at 17-fold lower intracellular levels than the wild type enzyme and promotes accumulation of heptanal-derived chemicals, such as heptanol (through coexpression with an alcohol dehydrogenase) or heptanoate (through coexpression of an aldehyde dehydrogenase) inside the cells.

Other substitutions of Gln-536, such as with glycine, alanine, leucine or isoleucine, which also improve the catalytic efficiency of decarboxylation, will also improve the catalytic efficiencies of specificity-enhancing substitutions. This is exhibited by Q536A substitution, which, when added into a F532V variant (with $k_{cat}/K_{0.5}$=4.8 mM$^{-1}$ min$^{-1}$ for 2-KO and $k_{cat}/K_{0.5}$=27 mM$^{-1}$ min$^{-1}$ for 2-KN), gives rise to a F532V/Q536A variant (with $k_{cat}/K_{0.5}$=8.3 mM$^{-1}$ min$^{-1}$ for 2-KO and $k_{cat}/K_{0.5}$=38 mM$^{-1}$ min$^{-1}$ for 2-KN) having 72% and 40% higher catalytic efficiencies, respectively, against 2-KO and 2-KN.

In summary, results suggest that the expression of AbPPDC and its genetically modified variants allow efficient decarboxylation of C7-C11, and particularly C7-C9 in this example, 2-ketoacids in vivo, and thereby allow accumulation of, for example, chemicals derived from aldehydes such as hexanal, heptanal, and/or octanal, inside the cells. Furthermore, modifications of F532, F385, Q536, M380, M461, F465 either alone or in combination, may give rise to microbial organisms that exhibit specifically improved accumulation of, for example, similarly-derived chemicals inside the cells.

TABLE 2

Kinetic characterization of AbPPDC and its variants*

| | 2-ketooctanoate (2-KO) | | | | 2-ketononanoate (2-KN) | | | | |
|---|---|---|---|---|---|---|---|---|---|
| Description | $k_{cat}$, min$^{-1}$ | $k_{0.5}$ or $K_M$, mM | h | $k_{cat}/K_{0.5}$, mM$^{-1}\cdot$min$^{-1}$ | kcat, min-1 | $K_{0.5}$ or $K_M$, mM | h | $k_{cat}/K_{0.5}$, mM$^{-1}\cdot$min$^{-1}$ | Spec |
| AbPPDC | 15 ± 0.7 | 1.7 ± 0.1 | 2.4 ± 0.1 | 9.0 ± 0.7 | 20 ± 0 | 1.23 ± 0.02 | 2.1 ± 0.1 | 16.2 ± 0.4 | 1.8 |
| [1]F385L | 1.7 ± 0.3 | 2.3 ± 0.5 | 2.3 ± 0.8 | 0.8 ± 0.2 | 17 ± 1 | 2.39 ± 0.26 | 2.7 ± 0.4 | 7.0 ± 1.0 | 9.1 |
| M461L | 12 ± 0.5 | 1.4 ± 0.1 | 2.6 ± 0.4 | 8.9 ± 0.7 | 28 ± 1 | 0.97 ± 0.04 | 2.1 ± 0.1 | 29 ± 1.4 | 3.3 |
| F532V | 9.8 ± 0.2 | 2.0 ± 0.1 | 3.4 ± 0.3 | 4.8 ± 0.2 | 23 ± 2 | 0.89 ± 0.15 | 1.8 ± 0.4 | 27 ± 5 | 5.6 |
| F532L | 13 ± 0.3 | 1.6 ± 0.1 | 2.5 ± 0.2 | 8.2 ± 0.3 | 30 ± 5 | 0.94 ± 0.27 | 1.4 ± 0.3 | 35 ± 12 | 4.3 |
| Q536G | 11 ± 0.8 | 1.9 ± 0.2 | 2.2 ± 0.2 | 5.8 ± 0.6 | 21 ± 0 | 0.76 ± 0.02 | 2.7 ± 0.2 | 28 ± 1 | 4.8 |
| Q536A | 20 ± 0.2 | 0.72 ± 0.02 | 2.1 ± 0.1 | 27 ± 1 | 30 ± 1 | 0.52 ± 0.03 | 1.6 ± 0.1 | 58 ± 4 | 2.1 |
| Q536L[§] | 27 ± 1.7 | 1.34 ± 0.23 | — | 21 ± 4 | 83 ± 6 | 1.51 ± 0.26 | — | 56 ± 11 | 2.7 |
| Q536I[§] | 32 ± 1.1 | 0.71 ± 0.07 | — | 45 ± 5 | 63 ± 3 | 0.69 ± 0.09 | — | 92 ± 13 | 2.0 |
| Q536V | 39 ± 1.3 | 0.55 ± 0.05 | 1.3 ± 0.2 | 72 ± 6 | 41 ± 3 | 0.45 ± 0.08 | 1.2 ± 0.3 | 93 ± 18 | 1.3 |
| F532V/Q536V | 16 ± 0.3 | 0.42 ± 0.01 | 4.3 ± 0.4 | 39 ± 1 | 21 ± 1 | 0.15 ± 0.01 | 5.3 ± 0.8 | 141 ± 7 | 3.6 |
| M380V/M461V[§] | 3.1 ± 0.1 | 0.18 ± 0.02 | — | 17 ± 2 | 6 ± 0.1 | 0.13 ± 0.02 | — | 46 ± 6 | 2.7 |
| F385L/M461V[§] | 2.8 ± 0.1 | 0.61 ± 0.09 | — | 4.7 ± 0.7 | 12 ± 1 | 3.47 ± 0.53 | — | 3.6 ± 0.7 | 0.7 |
| F532A/Q536V | 9.1 ± 0.7 | 2.0 ± 0.15 | 2.9 ± 0.3 | 4.5 ± 0.5 | 17 ± 0 | 0.54 ± 0.02 | 3.7 ± 0.5 | 31 ± 1 | 6.8 |
| F532V/Q536A | 11 ± 0.2 | 1.3 ± 0.03 | 1.3 ± 0.0 | 8.3 ± 0.24 | 19 ± 1 | 0.49 ± 0.03 | 3.1 ± 0.4 | 38 ± 2 | 4.6 |
| F385L/Q536V | 5.4 ± 1.1 | 2.4 ± 0.52 | 2.0 ± 0.3 | 2.4 ± 0.7 | 15 ± 1 | 1.46 ± 0.05 | 2.7 ± 0.2 | 10 ± 1 | 4.3 |
| M461L/Q536V | 57 ± 2 | 1.2 ± 0.10 | 1.4 ± 0.1 | 49 ± 5 | 65 ± 5 | 0.72 ± 0.11 | 1.3 ± 0.2 | 92 ± 16 | 1.9 |
| M461A/Q536V[§] | 45 ± 3 | 1.7 ± 0.25 | — | 28 ± 4 | 54 ± 6 | 2.02 ± 0.41 | — | 28 ± 7 | 1.0 |
| M461V/F532V | 12 ± 1.1 | 2.2 ± 0.3 | 1.9 ± 0.2 | 5.6 ± 0.8 | 32 ± 2 | 1.05 ± 0.09 | 1.8 ± 0.2 | 31 ± 3 | 5.4 |
| F465L/Q536V | 25 ± 0.5 | 0.29 ± 0.02 | 2.0 ± 0.2 | 85 ± 5 | 29 ± 1 | 0.18 ± 0.01 | 1.9 ± 0.3 | 164 ± 11 | 1.9 |
| M461L/F532V/Q536V | 65 ± 2 | 0.43 ± 0.03 | 2.1 ± 0.3 | 152 ± 13 | 43 ± 3 | 0.14 ± 0.02 | 2.8 ± 0.8 | 322 ± 47 | 2.1 |
| M380V/M461V/Q536V[§] | 4.9 ± 0.2 | 0.62 ± 0.1 | — | 8.2 ± 1.3 | 25 ± 3 | 3.10 ± 0.73 | — | 8.6 ± 2.3 | 1.1 |
| F385L/M461L/Q536V[§] | 3.4 ± 0.1 | 0.63 ± 0.08 | — | 5.5 ± 0.7 | 15 ± 1 | 2.65 ± 0.49 | — | 6.1 ± 1.2 | 1.1 |

*Initial velocity studies are determined using the HTP coupled assay described in the text. The initial velocities of all the enzymes except those indicated by § are fitted to the Hill equation $\left(v = \dfrac{kcat \cdot s^h}{K_{0.5}^h + s^h}\right)$;

v is the initial velocity at a given substrate concentration, S) using the GraphPad Prism ™ software. $k_{cat}$, $K_{0.5}$, h and $k_{cat}/K_{0.5}$ are the maximal velocity, substrate concentration at half the maximal velocity, Hill coefficient and catalytic efficiency respectively.
Results are the mean ± standard error of 2-3 independent experiments. Specificity of the AbPPDC variant is calculated by taking the ratio of catalytic efficiencies ($k_{cat}/K_{0.5}$) of the variant for 2-KN to that for 2-KO.
[1]The applied naming convention is that the first letter indicates the amino acid residue which has been altered. F = phenylalanine [Phe]; Q = glutamine [Gln]; M = methionine [Met]. The number indicates the position in the amino acid sequence (shown are positions 380, 385, 461, 465, 532, and 536, accordingly). The last letter indicates the amino acid residue that is substituted at that location. G = glycine; A = alanine; I = isoleucine; V = valine; L = leucine.
[§]Initial velocities of these variants are fitted to the classical Michaelis-Menton equation.

EXAMPLE 3

In Vitro Synthesis of C5-C9 Alcohols with the F385L Variant (SEQ ID. 8) of *Azospirillum brasilense* Phenylpyruvate Decarboxylase (AbPPDC)

In vitro synthesis of linear alcohols with the F385L variant is performed by incubating 0.5 mM 2-ketobutyrate (2-KB) with 0.5 mM thiamine diphosphate, 2.5 mM NAD$^+$, 0.2 milligrams per milliliter (0.2 mg/mL) bovine serum albumin (BSA), 5 mM acetyl coenzyme A, 0.036 mg/mL of the H97A/S139G/N167G/P169A/G462D variant of *E. coli* isopropylmalate synthase (reported by Marcheschi, R. J., et al. "A Synthetic Recursive "+1" pathway for carbon chain elongation" *ACS Chem. Biol.* 7:689-697, 2012), 0.16 mg/mL of LeuC subunit of isopropylmalate isomerase (GenBank Accession No. NC 000913.3 Gene ID: 945076) and 0.21 mg/mL of LeuD subunit of isopropylmalate isomerase (GenBank Accession No. NC 000913.3 Gene ID: 945642), 0.264 mg/mL of *E. coli* isopropylmalate dehydrogenase (LeuB; GenBank Accession No. NC_000913.3 Gene ID: 944798), 0.192 mg/mL of L96G/V198A variant of isopropylmalate dehydrogenase (reported in WO2015089127 A1), 0.025 mg/mL of *Saccharomyces cerevisiae* alcohol dehydrogenase (ADH6, GenBank: Accession No. NP_014051.3) and 0.0054 mg/mL of F385L variant (SEQ ID 8) in in vitro synthesis buffer (50 mM 2-[4-(2-hydroxyethyl)piperazin-1-yl]ethanesulfonic acid, pH 7.5, containing 30 mM potassium chloride (KCl) and 5 mM magnesium chloride (MgCl$_2$)).

The reaction is initiated with the addition of 2-ketobutyrate to the rest of the reaction mixture. An equal volume of analytical grade toluene (CHROMOSOLVPlus™ for HPLC, ≥99%, catalog number 650579) is overlaid on top of the reaction mixture and the solution is incubated at 30° C. NADPH is added to the aqueous layer to a final concentration of 1 mM after 2.5 hours of incubation at 30° C. Additional NADPH is added to the aqueous layer to a final concentration of 2 mM after 6 hours of incubation at 30° C. The reaction is incubated an additional 18 hours at 30° C., then stopped by freezing at −20° C. for 30 minutes. Part of the toluene layer is removed and analyzed using a Gas Chromatograph equipped with a Flame Ionization Detector (FID).

In vitro synthesis of branched alcohols with the F385L variant is performed by replacing 2-ketobutyrate with 0.5 mM 2-ketoisovalerate (2-KIV) or 0.5 mM 3-methyl-2-ketopentanoate (3M-2KP) in the above reaction mixture and performing the experiment as described above.

Alcohols are quantified using a Hewlett Packard (HP) 6890 Series Gas Chromatograph equipped with a Flame Ionization Detector (FID), a model G1513A automatic injector, and a GC AutoSampler Controller. The analytes are separated using an Agilent J&W DB-FFAP capillary GC column (30 m×0.320 mm ID×0.25 µM film thickness; catalog number 123-3232, Agilent Technologies, Inc., Wilmington, Del. 19808). The initial GC oven temperature is 40° C., which is held for 1.50 minutes, then is increased to 235° C. with a 40° C./minute gradient. This gradient gives a total run time of 6.38 minutes. The column flow rate is 4.0 mL/minute, with helium as the carrier gas. The injection volume is 1 µL. The temperature settings for the injector and detector are 225° C.

Figure 3:
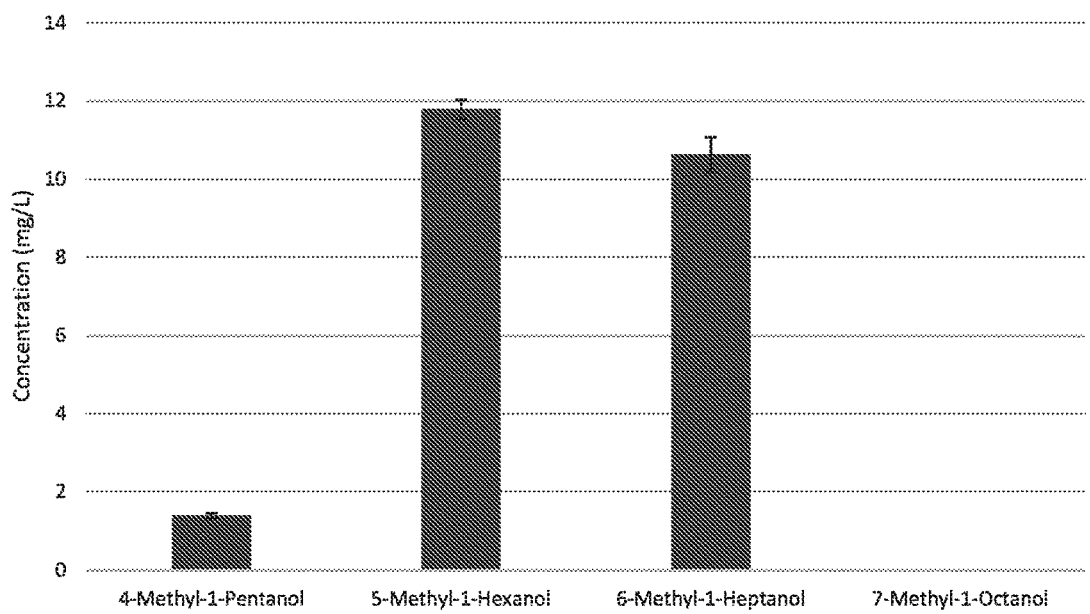
FIG. 3 illustrates branched C5-C8 alcohol production from 2-ketoisovalerate in vitro using a combination of isopropylmalate synthase, isopropylmalate isomerase, isopropylmalate dehydrogenase, and alcohol dehydrogenase (ADH6) in combination with the F385L variant of AbPPDC (SEQ ID 8).
Figure 4:
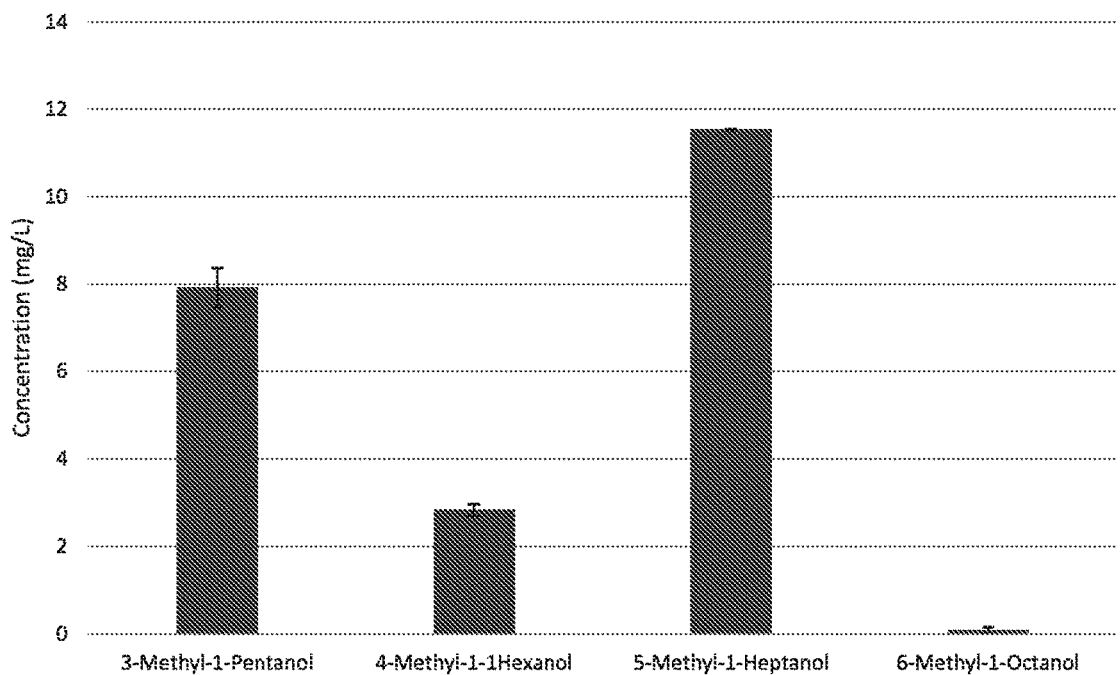
FIG. 4 illustrates branched C5-C8 alcohol production from 3-methyl-2-ketopentanoate in vitro using a combination of isopropylmalate synthase, isopropylmalate isomerase, isopropylmalate dehydrogenase, and alcohol dehydrogenase (ADH6) in combination with the F385L variant of AbPPDC (SEQ ID 8).

The alcohol titers produced from these in vitro synthesis reactions are shown in FIGS. 2, 3 and 4. The results indicate that the F385L variant, in combination with the H97A/ S139G/N167G/-P169A/G462D variant of E. coli isopropylmalate synthase (LeuA), E. coli isopropylmalate isomerase (LeuCD), wild type and modified E. coli isopropylmalate dehydrogenase (LeuB), and alcohol dehydrogenase (ADH6), produces elongated C5-C9 alcohols upon incubation with 2-ketobutyrate, 2-ketoisovalerate, or 3-methyl-2-ketopentanoate. Moreover, the results demonstrate the specificity of the F385L variant for longer linear alcohols, wherein 1-octanol represents approximately 60% of the total alcohols generated upon incubation with 2-ketobutyrate. With branched chain 2-ketoacids (2-ketoisovalerate, KIV, and 3-methyl-2-ketopentanoate, 3M-2-KP), approximately equivalent amounts of 5-methyl-1-hexanol and 6-methyl-1-heptanol are produced upon incubation with 2-ketoisovalerate, and approximately equivalent amounts of 3-methyl-1-pentanol and 5-methyl-1-heptanol are produced upon incubation with 3-methyl-2-ketopentanoate. These results demonstrate that the F385L variant accepts linear as well as branched chain 2-ketoacids as substrates and can produce corresponding linear and branched chain aldehydes which could subsequently be converted to other products such as alcohols, carboxylic acids, or alkanes.

EXAMPLE 4

In Vivo Production of C5-C8 Alcohols in Engineered Strains of E. Con Using Wild Type AbPPDC and its Variants in Combination with the "+1 Pathway" Enzymes

*Escherichia coli* (*E. coli*) MG1655 is engineered to promote long-chain linear alcohol production and to enable gene expression from a T7 promoter. To improve linear alcohol production, ilvBN and ilvIH are inactivated via λRed-mediated homologous recombination as described by Datsenko, K A, Wanner, B L, "One-step inactivation of chromosomal genes in *Escherichia coli* K-12 using PCR products," *Proc. Natl. Acad. Sci. U.S.A.* 2000, 97(12), 6640-6645. The ilvBN and IlvIH genes are involved in branched chain amino acid production, so the inactivation of these genes eliminates the production of branched chain alcohols. The ilvA gene, which is involved in the production of 2-ketobutyrate, is upregulated by replacing its native promoter and ribosome binding site with a strong constitutive promoter and strong ribosome binding site via λRed-mediated homologous recombination as described by Datsenko and Wanner, Ibid. To enable the expression of genes from T7 promoters, the DE3 lysogen is integrated into MG1655 using the ΔDE3 Lysogenization Kit (EMD Millipore Cat #69734). The resulting strain genotype is MG1655(DE3) ΔilvBN ΔilvIH ilvAup.

C5-C8 alcohols are produced in the engineered *E. coli* strain through the expression of eight proteins: (1) *E. coli* isopropylmalate synthase (LeuA); (2) engineered isopropylmalate synthase (described by Marcheschi, et al. *ACS Chem. Biol.* 2012, 7, 689-697); (3) and (4) two subunits of *E. coli* isopropylmalate isomerase (LeuCD); (5) isopropylmalate dehydrogenase (LeuB); (6) L96G/V198A variant of *E. coli* isopropylmalate dehydrogenase (as described in greater detail in co-pending International Patent Application Serial No. PCT/US14/69438, filed Dec. 10, 2014, claiming the benefit of U.S. Provisional Patent Application No. 61/915,040, filed Dec. 12, 2013, both of which are incorporated herein in their entireties by reference); (7) AbPPDC or its variants; and (8) *S. cerevisiae* alcohol dehydrogenase (ADH6). Eleven strains are created in total. One strain is created containing only wild type AbPPDC. As a negative control, a strain with no PPDC is also created. Eight strains containing AbPPDC variants F532V, F358L, F385V, F532V Q536V, M461C, M461V, F385V M461C and F385L M461V are also created. Lastly, a strain containing wild type *Lactococcus lactis* keto-isovalerate decarboxylase (KIVD; Gene Accession No. AJ746364) is created as a comparison, as prior work has shown that KIVD is capable of producing long-chain alcohols in combination with the "+1 pathway" enzymes. See, e.g., Marcheschi, et al. Ibid.

The Novagen Duet Vector system (EMD Millipore Cat #71146, 71341, 71340, and 71147), which allows for the simultaneous expression of eight genes using four compatible plasmids, is used to express the genes mentioned above. Each of the four Duet vectors is cloned with two of the eight genes downstream of T7 promoters, and the four Duet vectors are transformed into the engineered *E. coli* strain. Recombinant strains bearing all of the plasmids are selected for using antibiotics (ampicillin at 25 micrograms per milliliter, μg/mL, chloramphenicol at 17 μg/mL, spectinomycin at 25 μg/mL, and kanamycin at 15 μg/mL) and confirmed with polymerase chain reaction (PCR) using methods known to those skilled in the art. Antibiotics are added at each solid and liquid cultivation step to ensure maintenance of the plasmids. After transformation, plate selection and PCR confirmation, strains are initially cultivated on a Luria-Bertani (LB) agar plate grown at 37° C. A single agar plate colony is used to inoculate 50 mL of LB medium in a 250 mL shake flask which is cultivated aerobically at 37° C. using an incubator shaker set at 200 rpm.

After 12-16 hours of cultivation in the LB shake flasks, serum bottles are inoculated at 1% v/v to evaluate alcohol production. Serum bottle fermentation medium is prepared using deionized water according to the concentrations shown in Table 1. The medium is filter sterilized, and 20 mL of medium is added to butyl rubber-stoppered 125 mL serum bottles. Prior to media addition, serum bottles are pre-sterilized by autoclaving at 125° C. for 30 minutes using a Steris Amsco Century SV-160H Prevac Sterilizer.

TABLE 1

Medium composition used to demonstrate alcohol production from E. coli recombinantly engineered to contain the "+1 pathway" in combination with *Azospirllum brasilense* decarboxylase (AbPPDC) or its variants.

| Component | Concentration (g/L) |
| --- | --- |
| MOPS buffer | 26.2 |
| Glycerol | 20 |
| Tryptone | 10 |
| Yeast Extract | 5 |
| Calcium pantothenate | 1.19 |
| Na2HPO4 | 0.105 |
| (NH4)2SO4 | 0.661 |
| NH4Cl | 1.6 |

After inoculation, serum bottle cultures are cultivated at 37° C. with shaking at 200 rpm in an incubator shaker. Approximately three hours after inoculation, the cultures are induced using 0.1 mM of Isopropyl β-D-1-thiogalactopyranoside (IPTG) to ensure expression of all genes. Fermentations are harvested for analysis 24 hours after induction.

At the end of the fermentation, serum bottles are immediately chilled to 4° C. by placing in a refrigerator for 20-30 minutes. Serum bottles are de-capped, and the fermentation broth is quickly poured into a 50 mL conical tube containing 1 mL of a saturated sodium chloride solution and 2 mL of analytical grade toluene (CHROMOSOLV Plus™ for HPLC, ≥99.9%, catalog number 650579). The broth-sodium chloride-toluene mixture is vortexed for 30 seconds. A 300 µL aliquot of the toluene extract is then submitted for analysis using GC/FID as described in Example 3.

The mean alcohol distributions for the serum bottles are shown in FIG. 5. The results indicate that expression of the wild type *Azospirllum brasilense* decarboxylase (AbPPDC) in combination with the "+1 pathway" genes and ADH6 results in a functional pathway for the production of linear alcohols ranging from pentanol to octanol. No C5-C8 alcohols are detected in strains without AbPPDC, confirming that the presence of this gene is essential for long-chain alcohol production. Furthermore, the results demonstrate that the strain containing wild type AbPPDC accumulated substantially more hexanol, heptanol and octanol than the strain containing KIVD. No hexanol, heptanol or octanol production is detected in the KIVD strain, but the AbPPDC WT strain produces >2 mg/L, >3 mg/L, and >0.1 mg/L of hexanol, heptanol and octanol, respectively. Approximately 50% of alcohol production is heptanol and octanol, which is a significant improvement compared to previous work with other decarboxylases that result primarily in pentanol and hexanol production (Marcheschi, et al. *ACS Chem. Biol.* 2012, 7:689-697). Thus, the use of the AbPPDC decarboxylase appears to shift alcohol production to longer chain lengths, a result which is consistent with the in vitro data contained within Examples 1 and 2.

The additional data in FIG. 5 demonstrates that all of the AbPPDC variants have the ability to produce C5-C8 alcohols. Three of the AbPPDC variants, M461C, M461V and F385L/M461V, demonstrate a significant improvement in C5-C8 alcohol production compared to the wild type AbPPDC. AbPPDC variant M461C produces >3 mg/L of hexanol and >5 mg/L of heptanol, representing more than a 40% improvement compared to the wild type AbPPDC. Most impressively, AbPPDC variant M461V shows more than 2-fold improvements in pentanol, hexanol and heptanol production compared to wild type AbPPDC. The M461V variant also shows a 30% improvement in terms of octanol titer relative to the wild type AbPPDC. This strain containing the M461V variant produces the highest titers with ~9 mg/L of hexanol and ~8.5 mg/L of heptanol. Variants F532V, F385L, F532V Q536V, M461C, M461V and F385L M461V all show improvements in 1-octanol titer compared to KIVD and the AbPPDC wild type gene. Lastly, AbPPDC variant F385L/M461V shows about 60% improvement in hexanol and heptanol production compared to the AbPPDC wild type.

The invention claimed is:

1. A process for genetically modifying a microorganism comprising:
   (A) selecting a microorganism that produces a $C_7$-$C_{11}$ 2-ketoacid; and
   (B) inserting a non-native nucleic acid sequence that encodes at least one of:
   i. an amino acid sequence comprising at least 90 percent homology to SEQ ID NO: 4 and comprising the mutation F385L, and having phenylpyruvate decarboxylase activity;
   ii. an amino acid sequence comprising at least 90 percent homology to SEQ ID NO: 4 and comprising the mutation M461C, and having phenylpyruvate decarboxylase activity;
   iii. an amino acid sequence comprising at least 90 percent homology to SEQ ID NO: 4 and comprising the mutation M461V, and having phenylpyruvate decarboxylase activity;
   iv. an amino acid sequence comprising at least 90 percent homology to SEQ ID NO: 4 and comprising the mutation M461L, and having phenylpyruvate decarboxylase activity;
   v. an amino acid sequence comprising at least 90 percent homology to SEQ ID NO: 4 and comprising the mutation F532V, and having phenylpyruvate decarboxylase activity;
   vi. an amino acid sequence comprising at least 90 percent homology to SEQ ID NO: 4 and comprising the mutation F532L, and having phenylpyruvate decarboxylase activity;
   vii. an amino acid sequence comprising at least 90 percent homology to SEQ ID NO: 4 and comprising the mutation Q536G, and having phenylpyruvate decarboxylase activity;
   viii. an amino acid sequence comprising at least 90 percent homology to SEQ ID NO: 4 and comprising the mutation Q536A, and having phenylpyruvate decarboxylase activity;
   ix. an amino acid sequence comprising at least 90 percent homology to SEQ ID NO: 4 and comprising the mutation Q536L, and having phenylpyruvate decarboxylase activity;
   x. an amino acid sequence comprising at least 90 percent homology to SEQ ID NO: 4 and comprising the mutation Q536I, and having phenylpyruvate decarboxylase activity;
   xi. an amino acid sequence comprising at least 90 percent homology to SEQ ID NO: 4 and comprising the mutation Q536V, and having phenylpyruvate decarboxylase activity;
   xii. an amino acid sequence comprising at least 90 percent homology to SEQ ID NO: 4 and comprising the mutations F532V and Q536V, and having phenylpyruvate decarboxylase activity;
   xiii. an amino acid sequence comprising at least 90 percent homology to SEQ ID NO: 4 and comprising the mutations M380V and M461V, and having phenylpyruvate decarboxylase activity;
   xiv. an amino acid sequence comprising at least 90 percent homology to SEQ ID NO: 4 and comprising the mutations F385L and M461V, and having phenylpyruvate decarboxylase activity;
   xv. an amino acid sequence comprising at least 90 percent homology to SEQ ID NO: 4 and comprising the mutations F532A and Q536V, and having phenylpyruvate decarboxylase activity;
   xvi. an amino acid sequence comprising at least 90 percent homology to SEQ ID NO: 4 and comprising the mutations F532V and Q536A, and having phenylpyruvate decarboxylase activity;
   xvii. an amino acid sequence comprising at least 90 percent homology to SEQ ID NO: 4 and comprising the mutations F385L and Q536V, and having phenylpyruvate decarboxylase activity;
   xviii. an amino acid sequence comprising at least 90 percent homology to SEQ ID NO: 4 and comprising the mutations M461L and Q536V, and having phenylpyruvate decarboxylase activity;
   xix. an amino acid sequence comprising at least 90 percent homology to SEQ ID NO: 4 and comprising the mutations M461A and Q536V, and having phenylpyruvate decarboxylase activity;
   xx. an amino acid sequence comprising at least 90 percent homology to SEQ ID NO: 4 and comprising the mutations M461V and F532V, and having phenylpyruvate decarboxylase activity;
   xxi. an amino acid sequence comprising at least 90 percent homology to SEQ ID NO: 4 and comprising the mutations F465L and Q536V, and having phenylpyruvate decarboxylase activity;
   xxii. an amino acid sequence comprising at least 90 percent homology to SEQ ID NO: 4 and comprising the mutations M461V, F532V, and Q536V, and having phenylpyruvate decarboxylase activity;
   such that a non-native phenylpyruvate decarboxylase is expressed in the microorganism.

2. The process of claim 1 wherein:
   (A) the microorganism is *Escherichia coli*;
   (B) the amino acid sequence of SEQ ID NO: 4 is obtained from *Azospirillum brasilense*; and
   (C) the non-native phenylpyruvate decarboxylase takes part in a metabolic pathway that converts the $C_7$-$C_{11}$ 2-ketoacids to $C_6$-$C_{10}$ aldehydes having one less carbon atom than the $C_7$-$C_{11}$ 2-ketoacid being converted.

3. The process of claim 2, wherein the metabolic pathway proceeds during anaerobic fermentation.

4. A genetically modified microorganism produced by the process of claim 1.

5. The process of claim 1 wherein
   (A) the microorganism is a *Clostridium* species;
   (B) the non-native phenylpyruvate decarboxylase takes part in a metabolic pathway that includes a Wood-Ljungdahl pathway; and
   (C) the amino acid sequence of SEQ ID NO: 4 is obtained from *Azospirillum brasilense*.

6. A process to prepare a $C_6$-$C_{10}$ aldehyde comprising the steps of:
   (A) contacting a $C_4$-$C_{10}$ 2-ketoacid substrate, an isopropylmalate synthase, an isopropylmalate isomerase, and an isopropylmalate dehydrogenase, under conditions that the $C_4$-$C_{10}$ 2-ketoacid substrate is converted to a $C_7$-$C_{11}$ 2-ketoacid through one or more biochemical reactions;
   (B) contacting the $C_7$-$C_{11}$ 2-ketoacid and a phenylpyruvate decarboxylase, the phenylpyruvate decarboxylase comprising at least one of:
   i. an amino acid sequence comprising at least 90 percent homology to SEQ ID NO: 4 and comprising the mutation F385L, and having phenylpyruvate decarboxylase activity;
   ii. an amino acid sequence comprising at least 90 percent homology to SEQ ID NO: 4 and comprising the mutation M461C, and having phenylpyruvate decarboxylase activity;
   iii. an amino acid sequence comprising at least 90 percent homology to SEQ ID NO: 4 and comprising the mutation M461V, and having phenylpyruvate decarboxylase activity;
   iv. an amino acid sequence comprising at least 90 percent homology to SEQ ID NO: 4 and comprising the mutation M461L, and having phenylpyruvate decarboxylase activity;
   v. an amino acid sequence comprising at least 90 percent homology to SEQ ID NO: 4 and comprising the mutation F532V, and having phenylpyruvate decarboxylase activity;
   vi. an amino acid sequence comprising at least 90 percent homology to SEQ ID NO: 4 and comprising the mutation F532L, and having phenylpyruvate decarboxylase activity;
   vii. an amino acid sequence comprising at least 90 percent homology to SEQ ID NO: 4 and comprising the mutation Q536G, and having phenylpyruvate decarboxylase activity;
   viii. an amino acid sequence comprising at least 90 percent homology to SEQ ID NO: 4 and comprising the mutation Q536A, and having phenylpyruvate decarboxylase activity;
   ix. an amino acid sequence comprising at least 90 percent homology to SEQ ID NO: 4 and comprising the mutation Q536L, and having phenylpyruvate decarboxylase activity;
   x. an amino acid sequence comprising at least 90 percent homology to SEQ ID NO: 4 and comprising the mutation Q536I, and having phenylpyruvate decarboxylase activity;
   xi. an amino acid sequence comprising at least 90 percent homology to SEQ ID NO: 4 and comprising the mutation Q536V, and having phenylpyruvate decarboxylase activity;
   xii. an amino acid sequence comprising at least 90 percent homology to SEQ ID NO: 4 and comprising the mutations F532V and Q536V, and having phenylpyruvate decarboxylase activity;
   xiii. an amino acid sequence comprising at least 90 percent homology to SEQ ID NO: 4 and comprising the mutations M380V and M461V, and having phenylpyruvate decarboxylase activity;
   xiv. an amino acid sequence comprising at least 90 percent homology to SEQ ID NO: 4 and comprising the mutations F385L and M461V, and having phenylpyruvate decarboxylase activity;
   xv. an amino acid sequence comprising at least 90 percent homology to SEQ ID NO: 4 and comprising the mutations F532A and Q536V, and having phenylpyruvate decarboxylase activity;
   xvi. an amino acid sequence comprising at least 90 percent homology to SEQ ID NO: 4 and comprising the mutations F532V and Q536A, and having phenylpyruvate decarboxylase activity;
   xvii. an amino acid sequence comprising at least 90 percent homology to SEQ ID NO: 4 and comprising the mutations F385L and Q536V, and having phenylpyruvate decarboxylase activity;
xviii. an amino acid sequence comprising at least 90 percent homology to SEQ ID NO: 4 and comprising the mutations M461L and Q536V, and having phenylpyruvate decarboxylase activity;
xix. an amino acid sequence comprising at least 90 percent homology to SEQ ID NO: 4 and comprising the mutations M461A and Q536V, and having phenylpyruvate decarboxylase activity;
xx. an amino acid sequence comprising at least 90 percent homology to SEQ ID NO: 4 and comprising the mutations M461V and F532V, and having phenylpyruvate decarboxylase activity;
xxi. an amino acid sequence comprising at least 90 percent homology to SEQ ID NO: 4 and comprising the mutations F465L and Q536V, and having phenylpyruvate decarboxylase activity; or
xxii. an amino acid sequence comprising at least 90 percent homology to SEQ ID NO: 4 and comprising the mutations M461V, F532V, and Q536V, and having phenylpyruvate decarboxylase activity;
under conditions such that the $C_7$-$C_{11}$ 2-ketoacid is converted to a $C_6$-$C_{10}$ aldehyde having one less carbon atom than the $C_7$-$C_{11}$ 2-ketoacid being converted.

7. A genetically modified phenylpyruvate decarboxylase polypeptide having phenylpyruvate decarboxylase activity, the polypeptide comprising at least one of:
i. an amino acid sequence comprising at least 90 percent homology to SEQ ID NO: 4 and comprising the mutation F385L;
ii. an amino acid sequence comprising at least 90 percent homology to SEQ ID NO: 4 and comprising the mutation M461C;
iii. an amino acid sequence comprising at least 90 percent homology to SEQ ID NO: 4 and comprising the mutation M461V;
iv. an amino acid sequence comprising at least 90 percent homology to SEQ ID NO: 4 and comprising the mutation M461L;
v. an amino acid sequence comprising at least 90 percent homology to SEQ ID NO: 4 and comprising the mutation F532V;
vi. an amino acid sequence comprising at least 90 percent homology to SEQ ID NO: 4 and comprising the mutation F532L;
vii. an amino acid sequence comprising at least 90 percent homology to SEQ ID NO: 4 and comprising the mutation Q536G;
viii. an amino acid sequence comprising at least 90 percent homology to SEQ ID NO: 4 and comprising the mutation Q536A;
ix. an amino acid sequence comprising at least 90 percent homology to SEQ ID NO: 4 and comprising the mutation Q536L;
x. an amino acid sequence comprising at least 90 percent homology to SEQ ID NO: 4 and comprising the mutation Q536I;
xi. an amino acid sequence comprising at least 90 percent homology to SEQ ID NO: 4 and comprising the mutation Q536V;
xii. an amino acid sequence comprising at least 90 percent homology to SEQ ID NO: 4 and comprising the mutations F532V and Q536V;
xiii. an amino acid sequence comprising at least 90 percent homology to SEQ ID NO: 4 and comprising the mutations M380V and M461V;
xiv. an amino acid sequence comprising at least 90 percent homology to SEQ ID NO: 4 and comprising the mutations F385L and M461V;
xv. an amino acid sequence comprising at least 90 percent homology to SEQ ID NO: 4 and comprising the mutations F532A and Q536V;
xvi. an amino acid sequence comprising at least 90 percent homology to SEQ ID NO: 4 and comprising the mutations F532V and Q536A;
xvii. an amino acid sequence comprising at least 90 percent homology to SEQ ID NO: 4 and comprising the mutations F385L and Q536V;
xviii. an amino acid sequence comprising at least 90 percent homology to SEQ ID NO: 4 and comprising the mutations M461L and Q536V;
xix. an amino acid sequence comprising at least 90 percent homology to SEQ ID NO: 4 and comprising the mutations M461A and Q536V;
xx. an amino acid sequence comprising at least 90 percent homology to SEQ ID NO: 4 and comprising the mutations M461V and F532V;
xxi. an amino acid sequence comprising at least 90 percent homology to SEQ ID NO: 4 and comprising the mutations F465L and Q536V; or
xxii. an amino acid sequence comprising at least 90 percent homology to SEQ ID NO: 4 and comprising the mutations M461V, F532V, and Q536V.

8. The polypeptide of claim 7, wherein the amino acid sequence is at least 95 percent homologous to the amino acid sequence of (i)-(xiii) or (xv)-(xxii).

9. The process according of claim 6, wherein at least one of (A) or (B) independently occurs within a genetically modified microbial organism.

10. The process of claim 6, wherein the at least one of the $C_4$-$C_{10}$ 2-ketoacid substrate comprises 2-ketobutyrate.

11. The process of claim 6, wherein the at least one of the $C_4$-$C_{10}$ 2-ketoacid substrate comprises 2-ketoisovalerate.

12. The process according to claim 6, further comprising: (C) providing the $C_6$-$C_{10}$ aldehyde with an alcohol dehydrogenase having alcohol dehydrogenase activity, under conditions that the $C_6$-$C_{10}$ aldehyde is converted to a corresponding $C_6$-$C_{10}$ alcohol.

13. The process according to claim 6, further comprising: (C) providing the $C_6$-$C_{10}$ aldehyde with an aldehyde dehydrogenase having aldehyde dehydrogenase activity, under conditions that the $C_6$-$C_{10}$ aldehyde is converted to a corresponding $C_6$-$C_{10}$ carboxylic acid.

14. The process according to claim 6, further comprising: (C) providing the $C_6$-$C_{10}$ aldehyde with an aldehyde decarbonylase having fatty aldehyde decarbonylase activity, under conditions that the $C_6$-$C_{10}$ aldehyde is converted to a corresponding $C_{n-1}$ alkane.

15. The process according to claim 6, wherein the process occurs under aerobic or anaerobic conditions.

16. A genetically modified microorganism produced by the process of claim 2.

17. A genetically modified microorganism produced by the process of claim 5.

* * * * *

SEQUENCE LISTING

```
<160> NUMBER OF SEQ ID NOS: 82

<210> SEQ ID NO 1
<211> LENGTH: 39
<212> TYPE: DNA
<213> ORGANISM: Artificial Sequence
<220> FEATURE:
<223> OTHER INFORMATION: 13-Amino acid sequence of the His-tag at the
      N-terminus of the expressed AbPPDC variants
<220> FEATURE:
<221> NAME/KEY: CDS
<222> LOCATION: (1)..(39)

<400> SEQUENCE: 1 atg ggc agc agc cat cat cat cat cat cac agc agc ggc            39
Met Gly Ser Ser His His His His His His Ser Ser Gly
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Met Gly Ser Ser His His His His His His Ser Ser Gly
1               5                   10

<210> SEQ ID NO 3
<211> LENGTH: 1638
<212> TYPE: DNA
<213> ORGANISM: Artificial Sequence
<220> FEATURE:
<223> OTHER INFORMATION: Wild type Azospirillum brasilense
      Phenylpyruvate decarboxylase (AbPPDC)
<220> FEATURE:
<221> NAME/KEY: CDS
<222> LOCATION: (1)..(1638)

<400> SEQUENCE: 3
```

```
atg aag ctg gcc gaa gcc ctg ctg cgc gcg ctg aag gat cgc ggc gca    48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag    96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag   144
Val Ala Glu Glu Thr Gln Ile Leu Pro Leu His Thr Leu Ser His Glu
        35                  40                  45 ccg gcg gtg ggc ttc gcg gcg gac gcg gcg cgt tac agt tcg acg       192
Pro Ala Val Gly Phe Ala Ala Asp Ala Ala Arg Tyr Ser Ser Thr
    50                  55                  60 ctg ggg gtg gcg gcg gtc acc tac gga gcg ggc gcc ttc aac atg gtg   240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc   288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac   336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc   384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag   432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat   480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc   528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg   576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg   624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag   672
Val Cys Val Glu Val Arg Arg Tyr Gly Leu Glu Ala Lys Val Ala Glu
    210                 215                 220 ctg gcg cag cgg ctg ggc gtg ccg gtg gtg acc acc ttc atg ggg cgc   720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc   768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg   816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc   864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg   912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg   960
Val Thr Leu Gly Tyr His Thr Tyr Ala Asp Ile Pro Leu Ala Gly Leu
305                 310                 315                 320
```

```
gtg gac gcc ctc ttg gaa ggg ctg ccg ccg tcc gac cgg acg acc cgc     1008
Val Asp Ala Leu Leu Glu Gly Leu Pro Pro Ser Asp Arg Thr Thr Arg
            325                 330                 335 ggc aag gag ccc cac gcc tac ccg acc ggc ctt cag gcg gac ggc gag     1056
Gly Lys Glu Pro His Ala Tyr Pro Thr Gly Leu Gln Ala Asp Gly Glu
        340                 345                 350 ccg atc gcc ccg atg gac atc gcc cgc gcc gtc aac gac cgc gtc cgc     1104
Pro Ile Ala Pro Met Asp Ile Ala Arg Ala Val Asn Asp Arg Val Arg
    355                 360                 365 gcc ggg cag gaa ccg ctg ctg atc gcg gcg gac atg ggc gac tgc ctg     1152
Ala Gly Gln Glu Pro Leu Leu Ile Ala Ala Asp Met Gly Asp Cys Leu
370                 375                 380 ttc acc gcg atg gac atg atc gac gcc ggg ctg atg gcg ccg ggc tat     1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc     1248
Tyr Ala Gly Met Gly Phe Gly Val Pro Ala Gly Ile Gly Ala Gln Cys
            405                 410                 415 gtg tcg ggc ggc aag cgc atc ctg acc gtg gtc ggc gac ggc gcc ttc     1296
Val Ser Gly Gly Lys Arg Ile Leu Thr Val Val Gly Asp Gly Ala Phe
        420                 425                 430 cag atg acc ggg tgg gag ctt ggc aac tgc cga cgg ctg ggc atc gac     1344
Gln Met Thr Gly Trp Glu Leu Gly Asn Cys Arg Arg Leu Gly Ile Asp
    435                 440                 445 ccc atc gtg atc ctg ttc aac aac gcc agt tgg gag atg ctg cgc acc     1392
Pro Ile Val Ile Leu Phe Asn Asn Ala Ser Trp Glu Met Leu Arg Thr
450                 455                 460 ttc cag ccc gaa tcg gcc ttc aac gac ctg gac gac tgg cgc ttc gcc     1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg     1488
Asp Met Ala Ala Gly Met Gly Gly Asp Gly Val Arg Val Arg Thr Arg
            485                 490                 495 gcg gag ctg aag gcg gcg ctg gac aag gcc ttc gcc acg cgc ggg cgc     1536
Ala Glu Leu Lys Ala Ala Leu Asp Lys Ala Phe Ala Thr Arg Gly Arg
        500                 505                 510 ttc cag ctg atc gag gcg atg atc ccg cgc ggc gtg ctg tcc gac acg     1584
Phe Gln Leu Ile Glu Ala Met Ile Pro Arg Gly Val Leu Ser Asp Thr
    515                 520                 525 ctg gcc cgc ttc gtc cag ggg cag aag cgc ctg cac gcc gcg ccc cgg     1632
Leu Ala Arg Phe Val Gln Gly Gln Lys Arg Leu His Ala Ala Pro Arg
530                 535                 540 gag taa                                                             1638
Glu
545

<210> SEQ ID NO 4
<211> LENGTH: 545
<212> TYPE: PRT
<213> ORGANISM: Artificial Sequence
<220> FEATURE:
<223> OTHER INFORMATION: Synthetic Construct

<400> SEQUENCE: 4

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Thr Gln Ile Leu Pro Leu His Thr Leu Ser His Glu
        35                  40                  45
```

```
Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
                100                 105                 110

His Gln Gly Arg Thr Leu Asp Thr Gln Phe Gln Val Phe Lys Glu Ile
            115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
                180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Leu Gly Thr Tyr Ile Gly
                245                 250                 255

Val Ala Gly Asp Ala Glu Ile Thr Arg Leu Val Glu Glu Ser Asp Gly
                260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
        290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
                340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Met Gly Asp Cys Leu
370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Met Leu Arg Thr
    450                 455                 460
```

```
Phe Gln Pro Glu Ser Ala Phe Asn Asp Leu Asp Trp Arg Phe Ala
465                 470                 475                 480

Asp Met Ala Ala Gly Met Gly Gly Asp Gly Val Arg Val Arg Thr Arg
            485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
            515                 520                 525

Leu Ala Arg Phe Val Gln Gly Gln Lys Arg Leu His Ala Ala Pro Arg
            530                 535                 540

Glu
545

<210> SEQ ID NO 5
<211> LENGTH: 1638
<212> TYPE: DNA
<213> ORGANISM: Artificial Sequence
<220> FEATURE:
<223> OTHER INFORMATION: M380V
<220> FEATURE:
<221> NAME/KEY: CDS
<222> LOCATION: (1)..(1638)

<400> SEQUENCE: 5
```

| | | | | | | | | | | | | | | | | |
|---|---|---|---|---|---|---|---|---|---|---|---|---|---|---|---|---|
| atg | aag | ctg | gcc | gaa | gcc | ctg | ctg | cgc | gcg | ctg | aag | gat | cgc | ggc | gca | 48 |
| Met | Lys | Leu | Ala | Glu | Ala | Leu | Leu | Arg | Ala | Leu | Lys | Asp | Arg | Gly | Ala | |
| 1 | | | | 5 | | | | | 10 | | | | | 15 | | |
| cag | gcc | atg | ttc | ggg | att | ccg | ggt | gat | ttc | gcc | ctg | ccc | ttc | ttc | aag | 96 |
| Gln | Ala | Met | Phe | Gly | Ile | Pro | Gly | Asp | Phe | Ala | Leu | Pro | Phe | Phe | Lys | |
| | | | 20 | | | | | 25 | | | | | 30 | | | |
| gtg | gcg | gag | gaa | acg | cag | atc | ctg | ccg | ctc | cac | acg | ctg | agc | cac | gag | 144 |
| Val | Ala | Glu | Glu | Thr | Gln | Ile | Leu | Pro | Leu | His | Thr | Leu | Ser | His | Glu | |
| | 35 | | | | | 40 | | | | | 45 | | | | | |
| ccg | gcg | gtg | ggc | ttc | gcg | gcg | gac | gcg | gcg | gcg | cgt | tac | agt | tcg | acg | 192 |
| Pro | Ala | Val | Gly | Phe | Ala | Ala | Asp | Ala | Ala | Ala | Arg | Tyr | Ser | Ser | Thr | |
| 50 | | | | | 55 | | | | | 60 | | | | | | |
| ctg | ggg | gtg | gcg | gcg | gtc | acc | tac | gga | gcg | ggc | gcc | ttc | aac | atg | gtg | 240 |
| Leu | Gly | Val | Ala | Ala | Val | Thr | Tyr | Gly | Ala | Gly | Ala | Phe | Asn | Met | Val | |
| 65 | | | | | 70 | | | | | 75 | | | | | 80 | |
| aac | gcg | gtg | gcc | ggc | gcc | tac | gcc | gag | aag | tcg | ccg | gtg | gtc | gtc | atc | 288 |
| Asn | Ala | Val | Ala | Gly | Ala | Tyr | Ala | Glu | Lys | Ser | Pro | Val | Val | Val | Ile | |
| | | | | 85 | | | | | 90 | | | | | 95 | | |
| tcc | ggc | gcg | ccg | ggc | acg | acg | gag | ggc | aac | gcc | ggc | ctg | ctg | ctg | cac | 336 |
| Ser | Gly | Ala | Pro | Gly | Thr | Thr | Glu | Gly | Asn | Ala | Gly | Leu | Leu | Leu | His | |
| | | | 100 | | | | | 105 | | | | | 110 | | | |
| cac | cag | ggc | cgc | acg | ctg | gac | acg | cag | ttc | cag | gtg | ttc | aag | gag | atc | 384 |
| His | Gln | Gly | Arg | Thr | Leu | Asp | Thr | Gln | Phe | Gln | Val | Phe | Lys | Glu | Ile | |
| | 115 | | | | | 120 | | | | | 125 | | | | | |
| acc | gtc | gcc | cag | gcg | cgg | ctg | gac | gac | ccg | gcc | aag | gcc | ccg | gcg | gag | 432 |
| Thr | Val | Ala | Gln | Ala | Arg | Leu | Asp | Asp | Pro | Ala | Lys | Ala | Pro | Ala | Glu | |
| 130 | | | | | 135 | | | | | 140 | | | | | | |
| atc | gcc | cgc | gtg | ctg | ggg | gcc | gcc | cgc | gcc | ctg | tcg | cgc | ccg | gtc | tat | 480 |
| Ile | Ala | Arg | Val | Leu | Gly | Ala | Ala | Arg | Ala | Leu | Ser | Arg | Pro | Val | Tyr | |
| 145 | | | | | 150 | | | | | 155 | | | | | 160 | |
| ctg | gaa | att | ccc | cgc | aac | atg | gtc | aac | gcc | gag | gtc | gag | ccg | gtg | ggc | 528 |
| Leu | Glu | Ile | Pro | Arg | Asn | Met | Val | Asn | Ala | Glu | Val | Glu | Pro | Val | Gly | |
| | | | | 165 | | | | | 170 | | | | | 175 | | |
| gac | gac | ccg | gct | tgg | ccg | gtg | gac | cgc | gac | gcg | ctg | gcc | gcc | tgc | gcg | 576 |
| Asp | Asp | Pro | Ala | Trp | Pro | Val | Asp | Arg | Asp | Ala | Leu | Ala | Ala | Cys | Ala | |
| | | | 180 | | | | | 185 | | | | | 190 | | | |

```
                                             -continued gac gag gtg ctg gcg gcc atg cgc tcg gcc acg tcg ccg gtg ctg atg        624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag        672
Val Cys Val Glu Val Arg Arg Tyr Gly Leu Glu Ala Lys Val Ala Glu
210                 215                 220 ctg gcg cag cgg ctg ggc gtg ccg gtg gtg acc acc ttc atg ggg cgc        720
Leu Ala Gln Arg Leu Gly Val Pro Val Val Thr Thr Phe Met Gly Arg
225                 230                 235                 240 ggc ctg ctg gcc gac gcg ccg acc ccg ctc ggc acc tac atc ggc            768
Gly Leu Leu Ala Asp Ala Pro Thr Pro Leu Gly Thr Tyr Ile Gly
                245                 250                 255 gtc gcc ggc gac gcg gag atc acc cgg ctg gtc gag gag tcg gac ggg        816
Val Ala Gly Asp Ala Glu Ile Thr Arg Leu Val Glu Glu Ser Asp Gly
                260                 265                 270 ctg ttc ctg ctc ggc gcg atc ctc agc gac acc aac ttc gcg gtg tcc        864
Leu Phe Leu Leu Gly Ala Ile Leu Ser Asp Thr Asn Phe Ala Val Ser
            275                 280                 285 cag cgc aag atc gac ctg cgc aag acc atc cac gcc ttc gac cgg gcg        912
Gln Arg Lys Ile Asp Leu Arg Lys Thr Ile His Ala Phe Asp Arg Ala
290                 295                 300 gtg acg ctg ggc tat cac acc tac gcc gac atc ccg ctg gcc ggg ctg        960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc       1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag       1056
Gly Lys Glu Pro His Ala Tyr Pro Thr Gly Leu Gln Ala Asp Gly Glu
                340                 345                 350 ccg atc gcc ccg atg gac atc gcc cgc gcc gtc aac gac cgc gtc cgc       1104
Pro Ile Ala Pro Met Asp Ile Ala Arg Ala Val Asn Asp Arg Val Arg
            355                 360                 365 gcc ggg cag gaa ccg ctg ctg atc gcg gcg gac gtg ggc gac tgc ctg       1152
Ala Gly Gln Glu Pro Leu Leu Ile Ala Ala Asp Val Gly Asp Cys Leu
370                 375                 380 ttc acc gcg atg gac atg atc gac gcc ggg ctg atg gcg ccg ggc tat       1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc       1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc       1296
Val Ser Gly Gly Lys Arg Ile Leu Thr Val Val Gly Asp Gly Ala Phe
                420                 425                 430 cag atg acc ggg tgg gag ctt ggc aac tgc cga cgg ctg ggc atc gac       1344
Gln Met Thr Gly Trp Glu Leu Gly Asn Cys Arg Arg Leu Gly Ile Asp
            435                 440                 445 ccc atc gtg atc ctg ttc aac aac gcc agt tgg gag atg ctg cgc acc       1392
Pro Ile Val Ile Leu Phe Asn Asn Ala Ser Trp Glu Met Leu Arg Thr
450                 455                 460 ttc cag ccc gaa tcg gcc ttc aac gac ctg gac gac tgg cgc ttc gcc       1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg       1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc       1536
Ala Glu Leu Lys Ala Ala Leu Asp Lys Ala Phe Ala Thr Arg Gly Arg
                500                 505                 510
```

-continued

```
ttc cag ctg atc gag gcg atg atc ccg cgc ggc gtg ctg tcc gac acg    1584
Phe Gln Leu Ile Glu Ala Met Ile Pro Arg Gly Val Leu Ser Asp Thr
        515                 520                 525 ctg gcc cgc ttc gtc cag ggg cag aag cgc ctg cac gcc gcg ccc cgg    1632
Leu Ala Arg Phe Val Gln Gly Gln Lys Arg Leu His Ala Ala Pro Arg
530                 535                 540 gag taa                                                             1638
Glu
545

<210> SEQ ID NO 6
<211> LENGTH: 545
<212> TYPE: PRT
<213> ORGANISM: Artificial Sequence
<220> FEATURE:
<223> OTHER INFORMATION: Synthetic Construct

<400> SEQUENCE: 6

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300
```

```
Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Val Gly Asp Cys Leu
    370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
        435                 440                 445

Pro Ile Val Ile Leu Phe Asn Asn Ala Ser Trp Glu Met Leu Arg Thr
    450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Phe Val Gln Gly Gln Lys Arg Leu His Ala Ala Pro Arg
    530                 535                 540

Glu
545

<210> SEQ ID NO 7
<211> LENGTH: 1638
<212> TYPE: DNA
<213> ORGANISM: Artificial Sequence
<220> FEATURE:
<223> OTHER INFORMATION: F385L
<220> FEATURE:
<221> NAME/KEY: CDS
<222> LOCATION: (1)..(1638)

<400> SEQUENCE: 7 atg aag ctg gcc gaa gcc ctg ctg cgc gcg ctg aag gat cgc ggc gca    48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag    96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag   144
Val Ala Glu Glu Thr Gln Ile Leu Pro Leu His Thr Leu Ser His Glu
        35                  40                  45 ccg gcg gtg ggc ttc gcg gcg gac gcg gcg cgt tac agt tcg acg       192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg   240
```

```
Leu Gly Val Ala Ala Val Thr Tyr Gly Ala Gly Ala Phe Asn Met Val
 65                  70                  75                  80 aac gcg gtg gcc ggc gcc tac gcc gag aag tcg ccg gtg gtc gtc atc        288
Asn Ala Val Ala Gly Ala Tyr Ala Glu Lys Ser Pro Val Val Val Ile
                     85                  90                  95 tcc ggc gcg ccg ggc acg acg gag ggc aac gcc ggc ctg ctg ctg cac        336
Ser Gly Ala Pro Gly Thr Thr Glu Gly Asn Ala Gly Leu Leu Leu His
                100                 105                 110 cac cag ggc cgc acg ctg gac acg cag ttc cag gtg ttc aag gag atc        384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag        432
Thr Val Ala Gln Ala Arg Leu Asp Asp Pro Ala Lys Ala Pro Ala Glu
130                 135                 140 atc gcc cgc gtg ctg ggg gcc gcc cgc gcc ctg tcg cgc ccg gtc tat        480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc        528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg        576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg        624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag        672
Val Cys Val Glu Val Arg Arg Tyr Gly Leu Glu Ala Lys Val Ala Glu
210                 215                 220 ctg gcg cag cgg ctg ggc gtg ccg gtg gtg acc acc ttc atg ggg cgc        720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc        768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg        816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc        864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg        912
Gln Arg Lys Ile Asp Leu Arg Lys Thr Ile His Ala Phe Asp Arg Ala
        290                 295                 300 gtg acg ctg ggc tat cac acc tac gcc gac atc ccg ctg gcc ggg ctg        960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc       1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag       1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc       1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg       1152
Ala Gly Gln Glu Pro Leu Leu Ile Ala Ala Asp Met Gly Asp Cys Leu
370                 375                 380
```

```
ctg acc gcg atg gac atg atc gac gcc ggg ctg atg gcg ccg ggc tat       1200
Leu Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc       1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc       1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac       1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc       1392
Pro Ile Val Ile Leu Phe Asn Asn Ala Ser Trp Glu Met Leu Arg Thr
    450                 455                 460 ttc cag ccc gaa tcg gcc ttc aac gac ctg gac gac tgg cgc ttc gcc       1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg       1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc       1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg       1584
Phe Gln Leu Ile Glu Ala Met Ile Pro Arg Gly Val Leu Ser Asp Thr
        515                 520                 525 ctg gcc cgc ttc gtc cag ggg cag aag cgc ctg cac gcc gcg ccc cgg       1632
Leu Ala Arg Phe Val Gln Gly Gln Lys Arg Leu His Ala Ala Pro Arg
    530                 535                 540 gag taa                                                                1638
Glu
545

<210> SEQ ID NO 8
<211> LENGTH: 545
<212> TYPE: PRT
<213> ORGANISM: Artificial Sequence
<220> FEATURE:
<223> OTHER INFORMATION: Synthetic Construct

<400> SEQUENCE: 8

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
```

```
            130                 135                 140
Ile Ala Arg Val Leu Gly Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
                180                 185                 190

Asp Glu Val Leu Ala Ala Met Arg Ser Ala Thr Ser Pro Val Leu Met
                195                 200                 205

Val Cys Val Glu Val Arg Arg Tyr Gly Leu Glu Ala Lys Val Ala Glu
            210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Leu Gly Thr Tyr Ile Gly
                245                 250                 255

Val Ala Gly Asp Ala Glu Ile Thr Arg Leu Val Glu Glu Ser Asp Gly
                260                 265                 270

Leu Phe Leu Leu Gly Ala Ile Leu Ser Asp Thr Asn Phe Ala Val Ser
            275                 280                 285

Gln Arg Lys Ile Asp Leu Arg Lys Thr Ile His Ala Phe Asp Arg Ala
            290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
                340                 345                 350

Pro Ile Ala Pro Met Asp Ile Ala Arg Ala Val Asn Asp Arg Val Arg
                355                 360                 365

Ala Gly Gln Glu Pro Leu Leu Ile Ala Ala Asp Met Gly Asp Cys Leu
            370                 375                 380

Leu Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
                420                 425                 430

Gln Met Thr Gly Trp Glu Leu Gly Asn Cys Arg Arg Leu Gly Ile Asp
                435                 440                 445

Pro Ile Val Ile Leu Phe Asn Asn Ala Ser Trp Glu Met Leu Arg Thr
450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
                500                 505                 510

Phe Gln Leu Ile Glu Ala Met Ile Pro Arg Gly Val Leu Ser Asp Thr
            515                 520                 525

Leu Ala Arg Phe Val Gln Gly Gln Lys Arg Leu His Ala Ala Pro Arg
            530                 535                 540

Glu
545
```

```
<210> SEQ ID NO 9
<211> LENGTH: 1638
<212> TYPE: DNA
<213> ORGANISM: Artificial Sequence
<220> FEATURE:
<223> OTHER INFORMATION: F385V
<220> FEATURE:
<221> NAME/KEY: CDS
<222> LOCATION: (1)..(1638)

<400> SEQUENCE: 9
```

| | | | | | | | | | | | | | | | | |
|---|---|---|---|---|---|---|---|---|---|---|---|---|---|---|---|---|
| atg | aag | ctg | gcc | gaa | gcc | ctg | ctg | cgc | gcg | ctg | aag | gat | cgc | ggc | gca | 48 |
| Met | Lys | Leu | Ala | Glu | Ala | Leu | Leu | Arg | Ala | Leu | Lys | Asp | Arg | Gly | Ala | |
| 1 | | | | 5 | | | | | 10 | | | | | 15 | | |
| cag | gcc | atg | ttc | ggg | att | ccg | ggt | gat | ttc | gcc | ctg | ccc | ttc | ttc | aag | 96 |
| Gln | Ala | Met | Phe | Gly | Ile | Pro | Gly | Asp | Phe | Ala | Leu | Pro | Phe | Phe | Lys | |
| | | | 20 | | | | | 25 | | | | | 30 | | | |
| gtg | gcg | gag | gaa | acg | cag | atc | ctg | ccg | ctc | cac | acg | ctg | agc | cac | gag | 144 |
| Val | Ala | Glu | Glu | Thr | Gln | Ile | Leu | Pro | Leu | His | Thr | Leu | Ser | His | Glu | |
| | 35 | | | | | 40 | | | | | 45 | | | | | |
| ccg | gcg | gtg | ggc | ttc | gcg | gcg | gac | gcg | gcg | gcg | cgt | tac | agt | tcg | acg | 192 |
| Pro | Ala | Val | Gly | Phe | Ala | Ala | Asp | Ala | Ala | Ala | Arg | Tyr | Ser | Ser | Thr | |
| | 50 | | | | | 55 | | | | | 60 | | | | | |
| ctg | ggg | gtg | gcg | gcg | gtc | acc | tac | gga | gcg | ggc | gcc | ttc | aac | atg | gtg | 240 |
| Leu | Gly | Val | Ala | Ala | Val | Thr | Tyr | Gly | Ala | Gly | Ala | Phe | Asn | Met | Val | |
| 65 | | | | | 70 | | | | | 75 | | | | | 80 | |
| aac | gcg | gtg | gcc | ggc | gcc | tac | gcc | gag | aag | tcg | ccg | gtg | gtc | gtc | atc | 288 |
| Asn | Ala | Val | Ala | Gly | Ala | Tyr | Ala | Glu | Lys | Ser | Pro | Val | Val | Val | Ile | |
| | | | | 85 | | | | | 90 | | | | | 95 | | |
| tcc | ggc | gcg | ccg | ggc | acg | acg | gag | ggc | aac | gcc | ggc | ctg | ctg | ctg | cac | 336 |
| Ser | Gly | Ala | Pro | Gly | Thr | Thr | Glu | Gly | Asn | Ala | Gly | Leu | Leu | Leu | His | |
| | | | 100 | | | | | 105 | | | | | 110 | | | |
| cac | cag | ggc | cgc | acg | ctg | gac | acg | cag | ttc | cag | gtg | ttc | aag | gag | atc | 384 |
| His | Gln | Gly | Arg | Thr | Leu | Asp | Thr | Gln | Phe | Gln | Val | Phe | Lys | Glu | Ile | |
| | | 115 | | | | | 120 | | | | | 125 | | | | |
| acc | gtc | gcc | cag | gcg | cgg | ctg | gac | gac | ccg | gcc | aag | gcc | ccg | gcg | gag | 432 |
| Thr | Val | Ala | Gln | Ala | Arg | Leu | Asp | Asp | Pro | Ala | Lys | Ala | Pro | Ala | Glu | |
| | | 130 | | | | | 135 | | | | | 140 | | | | |
| atc | gcc | cgc | gtg | ctg | ggg | gcc | gcc | cgc | gcc | ctg | tcg | cgc | ccg | gtc | tat | 480 |
| Ile | Ala | Arg | Val | Leu | Gly | Ala | Ala | Arg | Ala | Leu | Ser | Arg | Pro | Val | Tyr | |
| 145 | | | | | 150 | | | | | 155 | | | | | 160 | |
| ctg | gaa | att | ccc | cgc | aac | atg | gtc | aac | gcc | gag | gtc | gag | ccg | gtg | ggc | 528 |
| Leu | Glu | Ile | Pro | Arg | Asn | Met | Val | Asn | Ala | Glu | Val | Glu | Pro | Val | Gly | |
| | | | | 165 | | | | | 170 | | | | | 175 | | |
| gac | gac | ccg | gct | tgg | ccg | gtg | gac | cgc | gac | gcg | ctg | gcc | gcc | tgc | gcg | 576 |
| Asp | Asp | Pro | Ala | Trp | Pro | Val | Asp | Arg | Asp | Ala | Leu | Ala | Ala | Cys | Ala | |
| | | | 180 | | | | | 185 | | | | | 190 | | | |
| gac | gag | gtg | ctg | gcg | gcc | atg | cgc | tcg | gcc | acg | tcg | ccg | gtg | ctg | atg | 624 |
| Asp | Glu | Val | Leu | Ala | Ala | Met | Arg | Ser | Ala | Thr | Ser | Pro | Val | Leu | Met | |
| | | 195 | | | | | 200 | | | | | 205 | | | | |
| gtc | tgc | gtc | gag | gtc | cgc | cgc | tac | ggg | ctg | gag | gcc | aag | gtg | gcg | gag | 672 |
| Val | Cys | Val | Glu | Val | Arg | Arg | Tyr | Gly | Leu | Glu | Ala | Lys | Val | Ala | Glu | |
| | | 210 | | | | | 215 | | | | | 220 | | | | |
| ctg | gcg | cag | cgg | ctg | ggc | gtg | ccg | gtg | gtg | acc | acc | ttc | atg | ggg | cgc | 720 |
| Leu | Ala | Gln | Arg | Leu | Gly | Val | Pro | Val | Val | Thr | Thr | Phe | Met | Gly | Arg | |
| 225 | | | | | 230 | | | | | 235 | | | | | 240 | |
| ggc | ctg | ctg | gcc | gac | gcg | ccg | acc | ccg | ccg | ctc | ggc | acc | tac | atc | ggc | 768 |
| Gly | Leu | Leu | Ala | Asp | Ala | Pro | Thr | Pro | Pro | Leu | Gly | Thr | Tyr | Ile | Gly | |
| | | | | 245 | | | | | 250 | | | | | 255 | | |
| gtc | gcc | ggc | gac | gcg | gag | atc | acc | cgg | ctg | gtc | gag | gag | tcg | gac | ggg | 816 |
| | | | | | | | | | | | | | | | | |

```
                Val Ala Gly Asp Ala Glu Ile Thr Arg Leu Val Glu Glu Ser Asp Gly
                            260                 265                 270 ctg ttc ctg ctc ggc gcg atc ctc agc gac acc aac ttc gcg gtg tcc        864
Leu Phe Leu Leu Gly Ala Ile Leu Ser Asp Thr Asn Phe Ala Val Ser
            275                 280                 285 cag cgc aag atc gac ctg cgc aag acc atc cac gcc ttc gac cgg gcg        912
Gln Arg Lys Ile Asp Leu Arg Lys Thr Ile His Ala Phe Asp Arg Ala
290                 295                 300 gtg acg ctg ggc tat cac acc tac gcc gac atc ccg ctg gcc ggg ctg        960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc       1008
Val Asp Ala Leu Leu Glu Gly Leu Pro Pro Ser Asp Arg Thr Thr Arg
            325                 330                 335 ggc aag gag ccc cac gcc tac ccg acc ggc ctt cag gcg gac ggc gag       1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc       1104
Pro Ile Ala Pro Met Asp Ile Ala Arg Ala Val Asn Asp Arg Val Arg
355                 360                 365 gcc ggg cag gaa ccg ctg ctg atc gcg gcg gac atg ggc gac tgc ctg       1152
Ala Gly Gln Glu Pro Leu Leu Ile Ala Ala Asp Met Gly Asp Cys Leu
370                 375                 380 gtt acc gcg atg gac atg atc gac gcc ggg ctg atg gcg ccg ggc tat       1200
Val Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc       1248
Tyr Ala Gly Met Gly Phe Gly Val Pro Ala Gly Ile Gly Ala Gln Cys
            405                 410                 415 gtg tcg ggc ggc aag cgc atc ctg acc gtg gtc ggc gac ggc gcc ttc       1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac       1344
Gln Met Thr Gly Trp Glu Leu Gly Asn Cys Arg Arg Leu Gly Ile Asp
            435                 440                 445 ccc atc gtg atc ctg ttc aac aac gcc agt tgg gag atg ctg cgc acc       1392
Pro Ile Val Ile Leu Phe Asn Asn Ala Ser Trp Glu Met Leu Arg Thr
450                 455                 460 ttc cag ccc gaa tcg gcc ttc aac gac ctg gac gac tgg cgc ttc gcc       1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg       1488
Asp Met Ala Ala Gly Met Gly Gly Asp Gly Val Arg Val Arg Thr Arg
            485                 490                 495 gcg gag ctg aag gcg gcg ctg gac aag gcc ttc gcc acg cgc ggg cgc       1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg       1584
Phe Gln Leu Ile Glu Ala Met Ile Pro Arg Gly Val Leu Ser Asp Thr
            515                 520                 525 ctg gcc cgc ttc gtc cag ggg cag aag cgc ctg cac gcc gcg ccc cgg       1632
Leu Ala Arg Phe Val Gln Gly Gln Lys Arg Leu His Ala Ala Pro Arg
530                 535                 540 gag taa                                                                1638
Glu
545

<210> SEQ ID NO 10
<211> LENGTH: 545
<212> TYPE: PRT
```

<213> ORGANISM: Artificial Sequence
<220> FEATURE:
<223> OTHER INFORMATION: Synthetic Construct

<400> SEQUENCE: 10

```
Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Met Gly Asp Cys Leu
370                 375                 380

Val Thr Ala Met Asp Met Ile Asp Ala Gly Leu Met Ala Pro Gly Tyr
```

```
                385                 390                 395                 400
Tyr Ala Gly Met Gly Phe Gly Val Pro Ala Gly Ile Gly Ala Gln Cys
                    405                 410                 415
Val Ser Gly Gly Lys Arg Ile Leu Thr Val Val Gly Asp Gly Ala Phe
                420                 425                 430
Gln Met Thr Gly Trp Glu Leu Gly Asn Cys Arg Arg Leu Gly Ile Asp
            435                 440                 445
Pro Ile Val Ile Leu Phe Asn Asn Ala Ser Trp Glu Met Leu Arg Thr
    450                 455                 460
Phe Gln Pro Glu Ser Ala Phe Asn Asp Leu Asp Asp Trp Arg Phe Ala
465                 470                 475                 480
Asp Met Ala Ala Gly Met Gly Asp Gly Val Arg Val Arg Thr Arg
                485                 490                 495
Ala Glu Leu Lys Ala Ala Leu Asp Lys Ala Phe Ala Thr Arg Gly Arg
                500                 505                 510
Phe Gln Leu Ile Glu Ala Met Ile Pro Arg Gly Val Leu Ser Asp Thr
            515                 520                 525
Leu Ala Arg Phe Val Gln Gly Gln Lys Arg Leu His Ala Ala Pro Arg
    530                 535                 540
Glu
545

<210> SEQ ID NO 11
<211> LENGTH: 1638
<212> TYPE: DNA
<213> ORGANISM: Artificial Sequence
<220> FEATURE:
<223> OTHER INFORMATION: F385I
<220> FEATURE:
<221> NAME/KEY: CDS
<222> LOCATION: (1)..(1638)

<400> SEQUENCE: 11 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
                20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
            35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
        50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
                100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
```

```
                    130                 135                 140
atc gcc cgc gtg ctg ggg gcc gcc cgc gcc ctg tcg cgc ccg gtc tat         480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtc ggc         528
Leu Glu Ile Pro Arg Asn Met Val Asn Ala Glu Val Glu Pro Val Gly
                    165                 170                 175 gac gac ccg gct tgg ccg gtc gac cgc gac gcg ctg gcc gcc tgc gcg         576
Asp Asp Pro Ala Trp Pro Val Asp Arg Asp Ala Leu Ala Ala Cys Ala
                180                 185                 190 gac gag gtg ctg gcg gcc atg cgc tcg gcc acg tcg ccg gtg ctg atg         624
Asp Glu Val Leu Ala Ala Met Arg Ser Ala Thr Ser Pro Val Leu Met
            195                 200                 205 gtc tgc gtc gag gtc cgc cgc tac ggg ctg gag gcc aag gtg gcg gag         672
Val Cys Val Glu Val Arg Arg Tyr Gly Leu Glu Ala Lys Val Ala Glu
        210                 215                 220 ctg gcg cag cgg ctg ggc gtg ccg gtg gtg acc acc ttc atg ggg cgc         720
Leu Ala Gln Arg Leu Gly Val Pro Val Val Thr Thr Phe Met Gly Arg
225                 230                 235                 240 ggc ctg ctg gcc gac gcg ccg acc ccg ccc ctc ggc acc tac atc ggc         768
Gly Leu Leu Ala Asp Ala Pro Thr Pro Pro Leu Gly Thr Tyr Ile Gly
                    245                 250                 255 gtc gcc ggc gac gcg gag atc acc cgg ctg gtc gag gag tcg gac ggg         816
Val Ala Gly Asp Ala Glu Ile Thr Arg Leu Val Glu Glu Ser Asp Gly
                260                 265                 270 ctg ttc ctg ctc ggc gcg atc ctc agc gac acc aac ttc gcg gtg tcc         864
Leu Phe Leu Leu Gly Ala Ile Leu Ser Asp Thr Asn Phe Ala Val Ser
            275                 280                 285 cag cgc aag atc gac ctg cgc aag acc atc cac gcc ttc gac cgg gcg         912
Gln Arg Lys Ile Asp Leu Arg Lys Thr Ile His Ala Phe Asp Arg Ala
        290                 295                 300 gtg acg ctg ggc tat cac acc tac gcc gac atc ccg ctg gcc ggg ctg         960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc        1008
Val Asp Ala Leu Leu Glu Gly Leu Pro Pro Ser Asp Arg Thr Thr Arg
                    325                 330                 335 ggc aag gag ccc cac gcc tac ccg acc ggc ctt cag gcg gac ggc gag        1056
Gly Lys Glu Pro His Ala Tyr Pro Thr Gly Leu Gln Ala Asp Gly Glu
                340                 345                 350 ccg atc gcc ccg atg gac atc gcc cgc gcc gtc aac gac cgc gtc cgc        1104
Pro Ile Ala Pro Met Asp Ile Ala Arg Ala Val Asn Asp Arg Val Arg
            355                 360                 365 gcc ggg cag gaa ccg ctg ctg atc gcg gcg gac atg ggc gac tgc ctg        1152
Ala Gly Gln Glu Pro Leu Leu Ile Ala Ala Asp Met Gly Asp Cys Leu
        370                 375                 380 att acc gcg atg gac atg atc gac gcc ggg ctg atg gcg ccg ggc tat        1200
Ile Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc        1248
Tyr Ala Gly Met Gly Phe Gly Val Pro Ala Gly Ile Gly Ala Gln Cys
                    405                 410                 415 gtg tcg ggc ggc aag cgc atc ctg acc gtg gtc ggc gac ggc gcc ttc        1296
Val Ser Gly Gly Lys Arg Ile Leu Thr Val Val Gly Asp Gly Ala Phe
                420                 425                 430 cag atg acc ggg tgg gag ctt ggc aac tgc cga cgg ctg ggc atc gac        1344
Gln Met Thr Gly Trp Glu Leu Gly Asn Cys Arg Arg Leu Gly Ile Asp
            435                 440                 445 ccc atc gtg atc ctg ttc aac aac gcc agt tgg gag atg ctg cgc acc        1392
```

```
Pro Ile Val Ile Leu Phe Asn Asn Ala Ser Trp Glu Met Leu Arg Thr
            450                 455                 460 ttc cag ccc gaa tcg gcc ttc aac gac ctg gac gac tgg cgc ttc gcc       1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg       1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc       1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg       1584
Phe Gln Leu Ile Glu Ala Met Ile Pro Arg Gly Val Leu Ser Asp Thr
515                 520                 525 ctg gcc cgc ttc gtc cag ggg cag aag cgc ctg cac gcc gcg ccc cgg       1632
Leu Ala Arg Phe Val Gln Gly Gln Lys Arg Leu His Ala Ala Pro Arg
            530                 535                 540 gag taa                                                               1638
Glu
545

<210> SEQ ID NO 12
<211> LENGTH: 545
<212> TYPE: PRT
<213> ORGANISM: Artificial Sequence
<220> FEATURE:
<223> OTHER INFORMATION: Synthetic Construct

<400> SEQUENCE: 12

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220
```

-continued

```
Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
            245                 250                 255

Val Ala Gly Asp Ala Glu Ile Thr Arg Leu Val Glu Glu Ser Asp Gly
        260                 265                 270

Leu Phe Leu Leu Gly Ala Ile Leu Ser Asp Thr Asn Phe Ala Val Ser
    275                 280                 285

Gln Arg Lys Ile Asp Leu Arg Lys Thr Ile His Ala Phe Asp Arg Ala
290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
            325                 330                 335

Gly Lys Glu Pro His Ala Tyr Pro Thr Gly Leu Gln Ala Asp Gly Glu
        340                 345                 350

Pro Ile Ala Pro Met Asp Ile Ala Arg Ala Val Asn Asp Arg Val Arg
    355                 360                 365

Ala Gly Gln Glu Pro Leu Leu Ile Ala Ala Asp Met Gly Asp Cys Leu
370                 375                 380

Ile Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
        420                 425                 430

Gln Met Thr Gly Trp Glu Leu Gly Asn Cys Arg Arg Leu Gly Ile Asp
    435                 440                 445

Pro Ile Val Ile Leu Phe Asn Asn Ala Ser Trp Glu Met Leu Arg Thr
450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
            485                 490                 495

Ala Glu Leu Lys Ala Ala Leu Asp Lys Ala Phe Ala Thr Arg Gly Arg
        500                 505                 510

Phe Gln Leu Ile Glu Ala Met Ile Pro Arg Gly Val Leu Ser Asp Thr
    515                 520                 525

Leu Ala Arg Phe Val Gln Gly Gln Lys Arg Leu His Ala Ala Pro Arg
530                 535                 540

Glu
545
```

<210> SEQ ID NO 13
<211> LENGTH: 1638
<212> TYPE: DNA
<213> ORGANISM: Artificial Sequence
<220> FEATURE:
<223> OTHER INFORMATION: M461C
<220> FEATURE:
<221> NAME/KEY: CDS
<222> LOCATION: (1)..(1638)

<400> SEQUENCE: 13

```
atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15
```

| | |
|---|---:|
| cag gcc atg ttc ggg att ccg ggt gat ttc gcc ctg ccc ttc ttc aag<br>Gln Ala Met Phe Gly Ile Pro Gly Asp Phe Ala Leu Pro Phe Phe Lys<br>20                          25                      30 | 96 |
| gtg gcg gag gaa acg cag atc ctg ccg ctc cac acg ctg agc cac gag<br>Val Ala Glu Glu Thr Gln Ile Leu Pro Leu His Thr Leu Ser His Glu<br>     35                      40                     45 | 144 |
| ccg gcg gtg ggc ttc gcg gcg gac gcg gcg gcg cgt tac agt tcg acg<br>Pro Ala Val Gly Phe Ala Ala Asp Ala Ala Ala Arg Tyr Ser Ser Thr<br>50                          55                      60 | 192 |
| ctg ggg gtg gcg gcg gtc acc tac gga gcg ggc gcc ttc aac atg gtg<br>Leu Gly Val Ala Ala Val Thr Tyr Gly Ala Gly Ala Phe Asn Met Val<br>65                          70                      75                      80 | 240 |
| aac gcg gtg gcc ggc gcc tac gcc gag aag tcg ccg gtg gtc gtc atc<br>Asn Ala Val Ala Gly Ala Tyr Ala Glu Lys Ser Pro Val Val Val Ile<br>                      85                      90                      95 | 288 |
| tcc ggc gcg ccg ggc acg acg gag ggc aac gcc ggc ctg ctg ctg cac<br>Ser Gly Ala Pro Gly Thr Thr Glu Gly Asn Ala Gly Leu Leu Leu His<br>                    100                    105                  110 | 336 |
| cac cag ggc cgc acg ctg gac acg cag ttc cag gtg ttc aag gag atc<br>His Gln Gly Arg Thr Leu Asp Thr Gln Phe Gln Val Phe Lys Glu Ile<br>     115                      120                    125 | 384 |
| acc gtc gcc cag gcg cgg ctg gac gac ccg gcc aag gcc ccg gcg gag<br>Thr Val Ala Gln Ala Arg Leu Asp Asp Pro Ala Lys Ala Pro Ala Glu<br>130                        135                    140 | 432 |
| atc gcc cgc gtg ctg ggg gcc gcc cgc gcc ctg tcg cgc ccg gtc tat<br>Ile Ala Arg Val Leu Gly Ala Ala Arg Ala Leu Ser Arg Pro Val Tyr<br>145                        150                    155                  160 | 480 |
| ctg gaa att ccc cgc aac atg gtc aac gcc gag gtc gag ccg gtg ggc<br>Leu Glu Ile Pro Arg Asn Met Val Asn Ala Glu Val Glu Pro Val Gly<br>                    165                    170                  175 | 528 |
| gac gac ccg gct tgg ccg gtg gac cgc gac gcg ctg gcc gcc tgc gcg<br>Asp Asp Pro Ala Trp Pro Val Asp Arg Asp Ala Leu Ala Ala Cys Ala<br>           180                      185                    190 | 576 |
| gac gag gtg ctg gcg gcc atg cgc tcg gcc acg tcg ccg gtg ctg atg<br>Asp Glu Val Leu Ala Ala Met Arg Ser Ala Thr Ser Pro Val Leu Met<br>     195                      200                    205 | 624 |
| gtc tgc gtc gag gtc cgc cgc tac ggg ctg gag gcc aag gtg gcg gag<br>Val Cys Val Glu Val Arg Arg Tyr Gly Leu Glu Ala Lys Val Ala Glu<br>210                        215                    220 | 672 |
| ctg gcg cag cgg ctg ggc gtg ccg gtg gtg acc acc ttc atg ggg cgc<br>Leu Ala Gln Arg Leu Gly Val Pro Val Val Thr Thr Phe Met Gly Arg<br>225                        230                    235                  240 | 720 |
| ggc ctg ctg gcc gac gcg ccg acc ccg ccg ctc ggc acc tac atc ggc<br>Gly Leu Leu Ala Asp Ala Pro Thr Pro Pro Leu Gly Thr Tyr Ile Gly<br>                    245                    250                  255 | 768 |
| gtc gcc ggc gac gcg gag atc acc cgg ctg gtc gag gag tcg gac ggg<br>Val Ala Gly Asp Ala Glu Ile Thr Arg Leu Val Glu Glu Ser Asp Gly<br>          260                      265                    270 | 816 |
| ctg ttc ctg ctc ggc gcg atc ctc agc gac acc aac ttc gcg gtg tcc<br>Leu Phe Leu Leu Gly Ala Ile Leu Ser Asp Thr Asn Phe Ala Val Ser<br>     275                      280                    285 | 864 |
| cag cgc aag atc gac ctg cgc aag acc atc cac gcc ttc gac cgg gcg<br>Gln Arg Lys Ile Asp Leu Arg Lys Thr Ile His Ala Phe Asp Arg Ala<br>290                        295                    300 | 912 |
| gtg acg ctg ggc tat cac acc tac gcc gac atc ccg ctg gcc ggg ctg<br>Val Thr Leu Gly Tyr His Thr Tyr Ala Asp Ile Pro Leu Ala Gly Leu<br>305                        310                    315                  320 | 960 |
| gtg gac gcc ctc ttg gaa ggg ctg ccg ccg tcc gac cgg acg acc cgc<br>Val Asp Ala Leu Leu Glu Gly Leu Pro Pro Ser Asp Arg Thr Thr Arg | 1008 |

```
                       325                 330                 335
ggc aag gag ccc cac gcc tac ccg acc ggc ctt cag gcg gac ggc gag      1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc      1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg      1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat      1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag tgt ctg cgc acc      1392
Pro Ile Val Ile Leu Phe Asn Asn Ala Ser Trp Glu Cys Leu Arg Thr
    450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
        515                 520                 525 ctg gcc cgc ttc gtc cag ggg cag aag cgc ctg cac gcc gcg ccc cgg      1632
Leu Ala Arg Phe Val Gln Gly Gln Lys Arg Leu His Ala Ala Pro Arg
    530                 535                 540 gag taa                                                              1638
Glu
545

<210> SEQ ID NO 14
<211> LENGTH: 545
<212> TYPE: PRT
<213> ORGANISM: Artificial Sequence
<220> FEATURE:
<223> OTHER INFORMATION: Synthetic Construct

<400> SEQUENCE: 14

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60
```

```
Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
            115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
            195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
            275                 280                 285

Gln Arg Lys Ile Asp Leu Arg Lys Thr Ile His Ala Phe Asp Arg Ala
290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Met Gly Asp Cys Leu
370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Cys Leu Arg Thr
450                 455                 460

Phe Gln Pro Glu Ser Ala Phe Asn Asp Leu Asp Asp Trp Arg Phe Ala
465                 470                 475                 480
```

-continued

```
Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Phe Val Gln Gly Gln Lys Arg Leu His Ala Ala Pro Arg
    530                 535                 540

Glu
545
```

<210> SEQ ID NO 15
<211> LENGTH: 1638
<212> TYPE: DNA
<213> ORGANISM: Artificial Sequence
<220> FEATURE:
<223> OTHER INFORMATION: M461V
<220> FEATURE:
<221> NAME/KEY: CDS
<222> LOCATION: (1)..(1638)

<400> SEQUENCE: 15

```
atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                  10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
                20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
            35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
        50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
                100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
        130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg     576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg     624
Asp Glu Val Leu Ala Ala Met Arg Ser Ala Thr Ser Pro Val Leu Met
        195                 200                 205
```

-continued

```
gtc tgc gtc gag gtc cgc cgc tac ggg ctg gag gcc aag gtg gcg gag    672
Val Cys Val Glu Val Arg Arg Tyr Gly Leu Glu Ala Lys Val Ala Glu
    210             215                 220 ctg gcg cag cgg ctg ggc gtg ccg gtg gtg acc acc ttc atg ggg cgc    720
Leu Ala Gln Arg Leu Gly Val Pro Val Val Thr Thr Phe Met Gly Arg
225             230                 235                 240 ggc ctg ctg gcc gac gcg ccg acc ccg ccg ctc ggc acc tac atc ggc    768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg    816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc    864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg    912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg    960
Val Thr Leu Gly Tyr His Thr Tyr Ala Asp Ile Pro Leu Ala Gly Leu
305             310                 315                 320 gtg gac gcc ctc ttg gaa ggg ctg ccg ccg tcc gac cgg acg acc cgc   1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag   1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc   1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg   1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat   1200
Phe Thr Ala Met Asp Met Ile Asp Ala Gly Leu Met Ala Pro Gly Tyr
385             390                 395                 400 tac gcg ggc atg ggc ttc ggg gtg ccg gcg ggc atc ggg gcg cag tgc   1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc   1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac   1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag gtg ctg cgc acc   1392
Pro Ile Val Ile Leu Phe Asn Asn Ala Ser Trp Glu Val Leu Arg Thr
    450                 455                 460 ttc cag ccc gaa tcg gcc ttc aac gac ctg gac gac tgg cgc ttc gcc   1440
Phe Gln Pro Glu Ser Ala Phe Asn Asp Leu Asp Asp Trp Arg Phe Ala
465             470                 475                 480 gac atg gcg gcg ggc atg ggc ggc gac ggc gtc cgc gtg cgc aca cgg   1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc   1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg   1584
Phe Gln Leu Ile Glu Ala Met Ile Pro Arg Gly Val Leu Ser Asp Thr
```

```
                    515                 520                 525
ctg gcc cgc ttc gtc cag ggg cag aag cgc ctg cac gcc gcg ccc cgg         1632
Leu Ala Arg Phe Val Gln Gly Gln Lys Arg Leu His Ala Ala Pro Arg
    530                 535                 540 gag taa                                                                 1638
Glu
545

<210> SEQ ID NO 16
<211> LENGTH: 545
<212> TYPE: PRT
<213> ORGANISM: Artificial Sequence
<220> FEATURE:
<223> OTHER INFORMATION: Synthetic Construct

<400> SEQUENCE: 16

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Ser Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300

Val Thr Leu Gly Tyr His Thr Tyr Ala Asp Ile Pro Leu Ala Gly Leu
305                 310                 315                 320
```

```
Val Asp Ala Leu Leu Glu Gly Leu Pro Pro Ser Asp Arg Thr Thr Arg
            325                 330                 335

Gly Lys Glu Pro His Ala Tyr Pro Thr Gly Leu Gln Ala Asp Gly Glu
        340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Met Gly Asp Cys Leu
        370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
        420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Val Leu Arg Thr
        450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
            485                 490                 495

Ala Glu Leu Lys Ala Ala Leu Asp Lys Ala Phe Ala Thr Arg Gly Arg
        500                 505                 510

Phe Gln Leu Ile Glu Ala Met Ile Pro Arg Gly Val Leu Ser Asp Thr
            515                 520                 525

Leu Ala Arg Phe Val Gln Gly Gln Lys Arg Leu His Ala Ala Pro Arg
        530                 535                 540

Glu
545

<210> SEQ ID NO 17
<211> LENGTH: 1638
<212> TYPE: DNA
<213> ORGANISM: Artificial Sequence
<220> FEATURE:
<223> OTHER INFORMATION: M461L
<220> FEATURE:
<221> NAME/KEY: CDS
<222> LOCATION: (1)..(1638)

<400> SEQUENCE: 17 atg aag ctg gcc gaa gcc ctg ctg cgc gcg ctg aag gat cgc ggc gca    48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag    96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag   144
Val Ala Glu Glu Thr Gln Ile Leu Pro Leu His Thr Leu Ser His Glu
        35                  40                  45 ccg gcg gtg ggc ttc gcg gcg gac gcg gcg cgt tac agt tcg acg       192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg   240
Leu Gly Val Ala Ala Val Thr Tyr Gly Ala Gly Ala Phe Asn Met Val
65                  70                  75                  80
```

| | | |
|---|---|---|
| aac gcg gtg gcc ggc gcc tac gcc gag aag tcg ccg gtg gtc gtc atc<br>Asn Ala Val Ala Gly Ala Tyr Ala Glu Lys Ser Pro Val Val Val Ile<br>                        85                    90                  95 | | 288 |
| tcc ggc gcg ccg ggc acg acg gag ggc aac gcc ggc ctg ctg ctg cac<br>Ser Gly Ala Pro Gly Thr Thr Glu Gly Asn Ala Gly Leu Leu Leu His<br>                     100                  105               110 | | 336 |
| cac cag ggc cgc acg ctg gac acg cag ttc cag gtg ttc aag gag atc<br>His Gln Gly Arg Thr Leu Asp Thr Gln Phe Gln Val Phe Lys Glu Ile<br>            115                  120                 125 | | 384 |
| acc gtc gcc cag gcg cgg ctg gac gac ccg gcc aag gcc ccg gcg gag<br>Thr Val Ala Gln Ala Arg Leu Asp Asp Pro Ala Lys Ala Pro Ala Glu<br>130                  135                  140 | | 432 |
| atc gcc cgc gtg ctg ggg gcc gcc cgc gcc ctg tcg cgc ccg gtc tat<br>Ile Ala Arg Val Leu Gly Ala Ala Arg Ala Leu Ser Arg Pro Val Tyr<br>145                  150                  155               160 | | 480 |
| ctg gaa att ccc cgc aac atg gtc aac gcc gag gtc gag ccg gtg ggc<br>Leu Glu Ile Pro Arg Asn Met Val Asn Ala Glu Val Glu Pro Val Gly<br>                   165                  170               175 | | 528 |
| gac gac ccg gct tgg ccg gtg gac cgc gac gcg ctg gcc gcc tgc gcg<br>Asp Asp Pro Ala Trp Pro Val Asp Arg Asp Ala Leu Ala Ala Cys Ala<br>           180                  185               190 | | 576 |
| gac gag gtg ctg gcg gcc atg cgc tcg gcc acg tcg ccg gtg ctg atg<br>Asp Glu Val Leu Ala Ala Met Arg Ser Ala Thr Ser Pro Val Leu Met<br>          195                  200               205 | | 624 |
| gtc tgc gtc gag gtc cgc cgc tac ggg ctg gag gcc aag gtg gcg gag<br>Val Cys Val Glu Val Arg Arg Tyr Gly Leu Glu Ala Lys Val Ala Glu<br>210                  215                  220 | | 672 |
| ctg gcg cag cgg ctg ggc gtg ccg gtg gtg acc acc ttc atg ggg cgc<br>Leu Ala Gln Arg Leu Gly Val Pro Val Val Thr Thr Phe Met Gly Arg<br>225                  230                  235               240 | | 720 |
| ggc ctg ctg gcc gac gcg ccg acc ccg ccg ctc ggc acc tac atc ggc<br>Gly Leu Leu Ala Asp Ala Pro Thr Pro Pro Leu Gly Thr Tyr Ile Gly<br>                   245                  250               255 | | 768 |
| gtc gcc ggc gac gcg gag atc acc cgg ctg gtc gag gag tcg gac ggg<br>Val Ala Gly Asp Ala Glu Ile Thr Arg Leu Val Glu Glu Ser Asp Gly<br>          260                  265               270 | | 816 |
| ctg ttc ctg ctc ggc gcg atc ctc agc gac acc aac ttc gcg gtg tcc<br>Leu Phe Leu Leu Gly Ala Ile Leu Ser Asp Thr Asn Phe Ala Val Ser<br>          275                  280               285 | | 864 |
| cag cgc aag atc gac ctg cgc aag acc atc cac gcc ttc gac cgg gcg<br>Gln Arg Lys Ile Asp Leu Arg Lys Thr Ile His Ala Phe Asp Arg Ala<br>290                  295                  300 | | 912 |
| gtg acg ctg ggc tat cac acc tac gcc gac atc ccg ctg gcc ggg ctg<br>Val Thr Leu Gly Tyr His Thr Tyr Ala Asp Ile Pro Leu Ala Gly Leu<br>305                  310                  315               320 | | 960 |
| gtg gac gcc ctc ttg gaa ggg ctg ccg ccg tcc gac cgg acg acc cgc<br>Val Asp Ala Leu Leu Glu Gly Leu Pro Pro Ser Asp Arg Thr Thr Arg<br>                   325                  330               335 | | 1008 |
| ggc aag gag ccc cac gcc tac ccg acc ggc ctt cag gcg gac ggc gag<br>Gly Lys Glu Pro His Ala Tyr Pro Thr Gly Leu Gln Ala Asp Gly Glu<br>                     340                  345               350 | | 1056 |
| ccg atc gcc ccg atg gac atc gcc cgc gcc gtc aac gac cgc gtc cgc<br>Pro Ile Ala Pro Met Asp Ile Ala Arg Ala Val Asn Asp Arg Val Arg<br>            355                  360               365 | | 1104 |
| gcc ggg cag gaa ccg ctg ctg atc gcg gcg gac atg ggc gac tgc ctg<br>Ala Gly Gln Glu Pro Leu Leu Ile Ala Ala Asp Met Gly Asp Cys Leu<br>370                  375                  380 | | 1152 |
| ttc acc gcg atg gac atg atc gac gcc ggg ctg atg gcg ccg ggc tat<br>Phe Thr Ala Met Asp Met Ile Asp Ala Gly Leu Met Ala Pro Gly Tyr<br>385                  390                  395               400 | | 1200 |

-continued

```
tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag ctg ctg cgc acc      1392
Pro Ile Val Ile Leu Phe Asn Asn Ala Ser Trp Glu Leu Leu Arg Thr
    450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
        515                 520                 525 ctg gcc cgc ttc gtc cag ggg cag aag cgc ctg cac gcc gcg ccc cgg      1632
Leu Ala Arg Phe Val Gln Gly Gln Lys Arg Leu His Ala Ala Pro Arg
    530                 535                 540 gag taa                                                               1638
Glu
545

<210> SEQ ID NO 18
<211> LENGTH: 545
<212> TYPE: PRT
<213> ORGANISM: Artificial Sequence
<220> FEATURE:
<223> OTHER INFORMATION: Synthetic Construct

<400> SEQUENCE: 18

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
```

```
            145                 150                 155                 160
Leu Glu Ile Pro Arg Asn Met Val Asn Ala Glu Val Glu Pro Val Gly
                    165                 170                 175

Asp Asp Pro Ala Trp Pro Val Asp Arg Asp Ala Leu Ala Ala Cys Ala
                    180                 185                 190

Asp Glu Val Leu Ala Ala Met Arg Ser Ala Thr Ser Pro Val Leu Met
                    195                 200                 205

Val Cys Val Glu Val Arg Arg Tyr Gly Leu Glu Ala Lys Val Ala Glu
        210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                    245                 250                 255

Val Ala Gly Asp Ala Glu Ile Thr Arg Leu Val Glu Glu Ser Asp Gly
                    260                 265                 270

Leu Phe Leu Leu Gly Ala Ile Leu Ser Asp Thr Asn Phe Ala Val Ser
                    275                 280                 285

Gln Arg Lys Ile Asp Leu Arg Lys Thr Ile His Ala Phe Asp Arg Ala
            290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                    325                 330                 335

Gly Lys Glu Pro His Ala Tyr Pro Thr Gly Leu Gln Ala Asp Gly Glu
                    340                 345                 350

Pro Ile Ala Pro Met Asp Ile Ala Arg Ala Val Asn Asp Arg Val Arg
                    355                 360                 365

Ala Gly Gln Glu Pro Leu Leu Ile Ala Ala Asp Met Gly Asp Cys Leu
                    370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                    405                 410                 415

Val Ser Gly Gly Lys Arg Ile Leu Thr Val Val Gly Asp Gly Ala Phe
                    420                 425                 430

Gln Met Thr Gly Trp Glu Leu Gly Asn Cys Arg Arg Leu Gly Ile Asp
                    435                 440                 445

Pro Ile Val Ile Leu Phe Asn Asn Ala Ser Trp Glu Leu Leu Arg Thr
        450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                    485                 490                 495

Ala Glu Leu Lys Ala Ala Leu Asp Lys Ala Phe Ala Thr Arg Gly Arg
                    500                 505                 510

Phe Gln Leu Ile Glu Ala Met Ile Pro Arg Gly Val Leu Ser Asp Thr
            515                 520                 525

Leu Ala Arg Phe Val Gln Gly Gln Lys Arg Leu His Ala Ala Pro Arg
        530                 535                 540

Glu
545

<210> SEQ ID NO 19
```

<211> LENGTH: 1638
<212> TYPE: DNA
<213> ORGANISM: Artificial Sequence
<220> FEATURE:
<223> OTHER INFORMATION: M461A
<220> FEATURE:
<221> NAME/KEY: CDS
<222> LOCATION: (1)..(1638)

<400> SEQUENCE: 19

| | | | | | | | | | | | | | | | | |
|---|---|---|---|---|---|---|---|---|---|---|---|---|---|---|---|---|
| atg | aag | ctg | gcc | gaa | gcc | ctg | ctg | cgc | gcg | ctg | aag | gat | cgc | ggc | gca | 48 |
| Met | Lys | Leu | Ala | Glu | Ala | Leu | Leu | Arg | Ala | Leu | Lys | Asp | Arg | Gly | Ala | |
| 1 | | | | 5 | | | | | 10 | | | | | 15 | | |
| cag | gcc | atg | ttc | ggg | att | ccg | ggt | gat | ttc | gcc | ctg | ccc | ttc | ttc | aag | 96 |
| Gln | Ala | Met | Phe | Gly | Ile | Pro | Gly | Asp | Phe | Ala | Leu | Pro | Phe | Phe | Lys | |
| | | | 20 | | | | | 25 | | | | | 30 | | | |
| gtg | gcg | gag | gaa | acg | cag | atc | ctg | ccg | ctc | cac | acg | ctg | agc | cac | gag | 144 |
| Val | Ala | Glu | Glu | Thr | Gln | Ile | Leu | Pro | Leu | His | Thr | Leu | Ser | His | Glu | |
| | | 35 | | | | | 40 | | | | | 45 | | | | |
| ccg | gcg | gtg | ggc | ttc | gcg | gcg | gac | gcg | gcg | gcg | cgt | tac | agt | tcg | acg | 192 |
| Pro | Ala | Val | Gly | Phe | Ala | Ala | Asp | Ala | Ala | Ala | Arg | Tyr | Ser | Ser | Thr | |
| | 50 | | | | | 55 | | | | | 60 | | | | | |
| ctg | ggg | gtg | gcg | gcg | gtc | acc | tac | gga | gcg | ggc | gcc | ttc | aac | atg | gtg | 240 |
| Leu | Gly | Val | Ala | Ala | Val | Thr | Tyr | Gly | Ala | Gly | Ala | Phe | Asn | Met | Val | |
| 65 | | | | | 70 | | | | | 75 | | | | | 80 | |
| aac | gcg | gtg | gcc | ggc | gcc | tac | gcc | gag | aag | tcg | ccg | gtg | gtc | gtc | atc | 288 |
| Asn | Ala | Val | Ala | Gly | Ala | Tyr | Ala | Glu | Lys | Ser | Pro | Val | Val | Val | Ile | |
| | | | | 85 | | | | | 90 | | | | | 95 | | |
| tcc | ggc | gcg | ccg | ggc | acg | acg | gag | ggc | aac | gcc | ggc | ctg | ctg | ctg | cac | 336 |
| Ser | Gly | Ala | Pro | Gly | Thr | Thr | Glu | Gly | Asn | Ala | Gly | Leu | Leu | Leu | His | |
| | | | 100 | | | | | 105 | | | | | 110 | | | |
| cac | cag | ggc | cgc | acg | ctg | gac | acg | cag | ttc | cag | gtg | ttc | aag | gag | atc | 384 |
| His | Gln | Gly | Arg | Thr | Leu | Asp | Thr | Gln | Phe | Gln | Val | Phe | Lys | Glu | Ile | |
| | 115 | | | | | 120 | | | | | 125 | | | | | |
| acc | gtc | gcc | cag | gcg | cgg | ctg | gac | gac | ccg | gcc | aag | gcc | ccg | gcg | gag | 432 |
| Thr | Val | Ala | Gln | Ala | Arg | Leu | Asp | Asp | Pro | Ala | Lys | Ala | Pro | Ala | Glu | |
| 130 | | | | | 135 | | | | | 140 | | | | | | |
| atc | gcc | cgc | gtg | ctg | ggg | gcc | gcc | cgc | gcc | ctg | tcg | cgc | ccg | gtc | tat | 480 |
| Ile | Ala | Arg | Val | Leu | Gly | Ala | Ala | Arg | Ala | Leu | Ser | Arg | Pro | Val | Tyr | |
| 145 | | | | | 150 | | | | | 155 | | | | | 160 | |
| ctg | gaa | att | ccc | cgc | aac | atg | gtc | aac | gcc | gag | gtc | gag | ccg | gtg | ggc | 528 |
| Leu | Glu | Ile | Pro | Arg | Asn | Met | Val | Asn | Ala | Glu | Val | Glu | Pro | Val | Gly | |
| | | | | 165 | | | | | 170 | | | | | 175 | | |
| gac | gac | ccg | gct | tgg | ccg | gtg | gac | cgc | gac | gcg | ctg | gcc | gcc | tgc | gcg | 576 |
| Asp | Asp | Pro | Ala | Trp | Pro | Val | Asp | Arg | Asp | Ala | Leu | Ala | Ala | Cys | Ala | |
| | | | 180 | | | | | 185 | | | | | 190 | | | |
| gac | gag | gtg | ctg | gcg | gcc | atg | cgc | tcg | gcc | acg | tcg | ccg | gtg | ctg | atg | 624 |
| Asp | Glu | Val | Leu | Ala | Ala | Met | Arg | Ser | Ala | Thr | Ser | Pro | Val | Leu | Met | |
| | 195 | | | | | 200 | | | | | 205 | | | | | |
| gtc | tgc | gtc | gag | gtc | cgc | cgc | tac | ggg | ctg | gag | gcc | aag | gtg | gcg | gag | 672 |
| Val | Cys | Val | Glu | Val | Arg | Arg | Tyr | Gly | Leu | Glu | Ala | Lys | Val | Ala | Glu | |
| 210 | | | | | 215 | | | | | 220 | | | | | | |
| ctg | gcg | cag | cgg | ctg | ggc | gtg | ccg | gtg | gtg | acc | acc | ttc | atg | ggg | cgc | 720 |
| Leu | Ala | Gln | Arg | Leu | Gly | Val | Pro | Val | Val | Thr | Thr | Phe | Met | Gly | Arg | |
| 225 | | | | | 230 | | | | | 235 | | | | | 240 | |
| ggc | ctg | ctg | gcc | gac | gcg | ccg | acc | ccg | ctc | ggc | acc | tac | atc | ggc | 768 |
| Gly | Leu | Leu | Ala | Asp | Ala | Pro | Thr | Pro | Pro | Leu | Gly | Thr | Tyr | Ile | Gly | |
| | | | | 245 | | | | | 250 | | | | | 255 | | |
| gtc | gcc | ggc | gac | gcg | gag | atc | acc | cgg | ctg | gtc | gag | gag | tcg | gac | ggg | 816 |
| Val | Ala | Gly | Asp | Ala | Glu | Ile | Thr | Arg | Leu | Val | Glu | Glu | Ser | Asp | Gly | |
| | | | 260 | | | | | 265 | | | | | 270 | | | |

```
ctg ttc ctg ctc ggc gcg atc ctc agc gac acc aac ttc gcg gtg tcc    864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg    912
Gln Arg Lys Ile Asp Leu Arg Lys Thr Ile His Ala Phe Asp Arg Ala
290                 295                 300 gtg acg ctg ggc tat cac acc tac gcc gac atc ccg ctg gcc ggg ctg    960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc   1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag   1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc   1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg   1152
Ala Gly Gln Glu Pro Leu Leu Ile Ala Ala Asp Met Gly Asp Cys Leu
370                 375                 380 ttc acc gcg atg gac atg atc gac gcc ggg ctg atg gcg ccg ggc tat   1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc   1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc   1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac   1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag gcg ctg cgc acc   1392
Pro Ile Val Ile Leu Phe Asn Asn Ala Ser Trp Glu Ala Leu Arg Thr
450                 455                 460 ttc cag ccc gaa tcg gcc ttc aac gac ctg gac gac tgg cgc ttc gcc   1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg   1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc   1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg   1584
Phe Gln Leu Ile Glu Ala Met Ile Pro Arg Gly Val Leu Ser Asp Thr
        515                 520                 525 ctg gcc cgc ttc gtc cag ggg cag aag cgc ctg cac gcc gcg ccc cgg   1632
Leu Ala Arg Phe Val Gln Gly Gln Lys Arg Leu His Ala Ala Pro Arg
530                 535                 540 gag taa                                                            1638
Glu
545

<210> SEQ ID NO 20
<211> LENGTH: 545
<212> TYPE: PRT
<213> ORGANISM: Artificial Sequence
<220> FEATURE:
<223> OTHER INFORMATION: Synthetic Construct
```

<400> SEQUENCE: 20

```
Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Val Thr Tyr Gly Ala Gly Ala Phe Asn Met Val
65              70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
                100                 105                 110

His Gln Gly Arg Thr Leu Asp Thr Gln Phe Gln Val Phe Lys Glu Ile
            115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Met Gly Asp Cys Leu
    370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
```

```
                        405                 410                 415
Val Ser Gly Gly Lys Arg Ile Leu Thr Val Val Gly Asp Gly Ala Phe
                420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Ala Leu Arg Thr
        450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
                500                 505                 510

Phe Gln Leu Ile Glu Ala Met Ile Pro Arg Gly Val Leu Ser Asp Thr
            515                 520                 525

Leu Ala Arg Phe Val Gln Gly Gln Lys Arg Leu His Ala Ala Pro Arg
        530                 535                 540

Glu
545

<210> SEQ ID NO 21
<211> LENGTH: 1638
<212> TYPE: DNA
<213> ORGANISM: Artificial Sequence
<220> FEATURE:
<223> OTHER INFORMATION: F465L
<220> FEATURE:
<221> NAME/KEY: CDS
<222> LOCATION: (1)..(1638)

<400> SEQUENCE: 21 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat     480
```

```
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc    528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg    576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg    624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag    672
Val Cys Val Glu Val Arg Arg Tyr Gly Leu Glu Ala Lys Val Ala Glu
    210                 215                 220 ctg gcg cag cgg ctg ggc gtg ccg gtg gtg acc acc ttc atg ggg cgc    720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc    768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg    816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc    864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg    912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg    960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc   1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag   1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc   1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg   1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat   1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc   1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc   1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac   1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc   1392
Pro Ile Val Ile Leu Phe Asn Asn Ala Ser Trp Glu Met Leu Arg Thr
    450                 455                 460
```

```
ctg cag ccc gaa tcg gcc ttc aac gac ctg gac gac tgg cgc ttc gcc    1440
Leu Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg    1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc    1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg    1584
Phe Gln Leu Ile Glu Ala Met Ile Pro Arg Gly Val Leu Ser Asp Thr
        515                 520                 525 ctg gcc cgc ttc gtc cag ggg cag aag cgc ctg cac gcc gcg ccc cgg    1632
Leu Ala Arg Phe Val Gln Gly Gln Lys Arg Leu His Ala Ala Pro Arg
    530                 535                 540 gag taa                                                            1638
Glu
545

<210> SEQ ID NO 22
<211> LENGTH: 545
<212> TYPE: PRT
<213> ORGANISM: Artificial Sequence
<220> FEATURE:
<223> OTHER INFORMATION: Synthetic Construct

<400> SEQUENCE: 22

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
                100                 105                 110

His Gln Gly Arg Thr Leu Asp Thr Gln Phe Gln Val Phe Lys Glu Ile
            115                 120                 125

Thr Val Ala Gln Ala Arg Leu Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240
```

```
Gly Leu Leu Ala Asp Ala Pro Thr Pro Pro Leu Gly Thr Tyr Ile Gly
            245                 250                 255

Val Ala Gly Asp Ala Glu Ile Thr Arg Leu Val Glu Glu Ser Asp Gly
        260                 265                 270

Leu Phe Leu Leu Gly Ala Ile Leu Ser Asp Thr Asn Phe Ala Val Ser
    275                 280                 285

Gln Arg Lys Ile Asp Leu Arg Lys Thr Ile His Ala Phe Asp Arg Ala
290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
            325                 330                 335

Gly Lys Glu Pro His Ala Tyr Pro Thr Gly Leu Gln Ala Asp Gly Glu
        340                 345                 350

Pro Ile Ala Pro Met Asp Ile Ala Arg Ala Val Asn Asp Arg Val Arg
    355                 360                 365

Ala Gly Gln Glu Pro Leu Leu Ile Ala Ala Asp Met Gly Asp Cys Leu
370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
        420                 425                 430

Gln Met Thr Gly Trp Glu Leu Gly Asn Cys Arg Arg Leu Gly Ile Asp
    435                 440                 445

Pro Ile Val Ile Leu Phe Asn Asn Ala Ser Trp Glu Met Leu Arg Thr
450                 455                 460

Leu Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
            485                 490                 495

Ala Glu Leu Lys Ala Ala Leu Asp Lys Ala Phe Ala Thr Arg Gly Arg
        500                 505                 510

Phe Gln Leu Ile Glu Ala Met Ile Pro Arg Gly Val Leu Ser Asp Thr
    515                 520                 525

Leu Ala Arg Phe Val Gln Gly Gln Lys Arg Leu His Ala Ala Pro Arg
530                 535                 540

Glu
545

<210> SEQ ID NO 23
<211> LENGTH: 1638
<212> TYPE: DNA
<213> ORGANISM: Artificial Sequence
<220> FEATURE:
<223> OTHER INFORMATION: F532A
<220> FEATURE:
<221> NAME/KEY: CDS
<222> LOCATION: (1)..(1638)

<400> SEQUENCE: 23 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
```

```
                        20                      25                      30
gtg gcg gag gaa acg cag atc ctg ccg ctc cac acg ctg agc cac gag       144
Val Ala Glu Glu Thr Gln Ile Leu Pro Leu His Thr Leu Ser His Glu
             35                  40                  45 ccg gcg gtg ggc ttc gcg gcg gac gcg gcg gcg cgt tac agt tcg acg       192
Pro Ala Val Gly Phe Ala Ala Asp Ala Ala Ala Arg Tyr Ser Ser Thr
 50                  55                  60 ctg ggg gtg gcg gcg gtc acc tac gga gcg ggc gcc ttc aac atg gtg       240
Leu Gly Val Ala Ala Val Thr Tyr Gly Ala Gly Ala Phe Asn Met Val
 65                  70                  75                  80 aac gcg gtg gcc ggc gcc tac gcc gag aag tcg ccg gtc gtc atc           288
Asn Ala Val Ala Gly Ala Tyr Ala Glu Lys Ser Pro Val Val Ile
                 85                  90                  95 tcc ggc gcg ccg ggc acg acg gag ggc aac gcc ggc ctg ctg ctg cac       336
Ser Gly Ala Pro Gly Thr Thr Glu Gly Asn Ala Gly Leu Leu Leu His
                100                 105                 110 cac cag ggc cgc acg ctg gac acg cag ttc cag gtg ttc aag gag atc       384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag       432
Thr Val Ala Gln Ala Arg Leu Asp Asp Pro Ala Lys Ala Pro Ala Glu
130                 135                 140 atc gcc cgc gtg ctg ggg gcc gcc cgc gcc ctg tcg cgc ccg gtc tat       480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc       528
Leu Glu Ile Pro Arg Asn Met Val Asn Ala Glu Val Glu Pro Val Gly
                165                 170                 175 gac gac ccg gct tgg ccg gtc gac cgc gac gcg ctg gcc gcc tgc gcg       576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg       624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag       672
Val Cys Val Glu Val Arg Arg Tyr Gly Leu Glu Ala Lys Val Ala Glu
210                 215                 220 ctg gcg cag cgg ctg ggc gtg ccg gtg gtg acc acc ttc atg ggg cgc       720
Leu Ala Gln Arg Leu Gly Val Pro Val Val Thr Thr Phe Met Gly Arg
225                 230                 235                 240 ggc ctg ctg gcc gac gcg ccg acc ccg ctc ggc acc tac atc ggc           768
Gly Leu Leu Ala Asp Ala Pro Thr Pro Leu Gly Thr Tyr Ile Gly
                245                 250                 255 gtc gcc ggc gac gcg gag atc acc cgg ctg gtc gag gag tcg gac ggg       816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc       864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg       912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg       960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc      1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag      1056
```

```
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc      1104
Pro Ile Ala Pro Met Asp Ile Ala Arg Ala Val Asn Asp Arg Val Arg
            355                 360                 365 gcc ggg cag gaa ccg ctg ctg atc gcg gcg gac atg ggc gac tgc ctg      1152
Ala Gly Gln Glu Pro Leu Leu Ile Ala Ala Asp Met Gly Asp Cys Leu
370                 375                 380 ttc acc gcg atg gac atg atc gac gcc ggg ctg atg gcg ccg ggc tat      1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
            405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
            435                 440                 445 ccc atc gtg atc ctg ttc aac aac gcc agt tgg gag atg ctg cgc acc      1392
Pro Ile Val Ile Leu Phe Asn Asn Ala Ser Trp Glu Met Leu Arg Thr
450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
            485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
            515                 520                 525 ctg gcc cgc gcg gtc cag ggg cag aag cgc ctg cac gcc gcg ccc cgg      1632
Leu Ala Arg Ala Val Gln Gly Gln Lys Arg Leu His Ala Ala Pro Arg
530                 535                 540 gag taa                                                               1638
Glu
545

<210> SEQ ID NO 24
<211> LENGTH: 545
<212> TYPE: PRT
<213> ORGANISM: Artificial Sequence
<220> FEATURE:
<223> OTHER INFORMATION: Synthetic Construct

<400> SEQUENCE: 24

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80
```

```
Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
               100                 105                 110

His Gln Gly Arg Thr Leu Asp Thr Gln Phe Gln Val Phe Lys Glu Ile
               115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Val Glu Pro Val Gly
               165                 170                 175

Asp Asp Pro Ala Trp Pro Val Asp Arg Asp Ala Leu Ala Ala Cys Ala
               180                 185                 190

Asp Glu Val Leu Ala Ala Met Arg Ser Ala Thr Ser Pro Val Leu Met
               195                 200                 205

Val Cys Val Glu Val Arg Arg Tyr Gly Leu Glu Ala Lys Val Ala Glu
       210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
               245                 250                 255

Val Ala Gly Asp Ala Glu Ile Thr Arg Leu Val Glu Glu Ser Asp Gly
               260                 265                 270

Leu Phe Leu Leu Gly Ala Ile Leu Ser Asp Thr Asn Phe Ala Val Ser
               275                 280                 285

Gln Arg Lys Ile Asp Leu Arg Lys Thr Ile His Ala Phe Asp Arg Ala
       290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
               325                 330                 335

Gly Lys Glu Pro His Ala Tyr Pro Thr Gly Leu Gln Ala Asp Gly Glu
               340                 345                 350

Pro Ile Ala Pro Met Asp Ile Ala Arg Ala Val Asn Asp Arg Val Arg
               355                 360                 365

Ala Gly Gln Glu Pro Leu Leu Ile Ala Ala Asp Met Gly Asp Cys Leu
370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
               405                 410                 415

Val Ser Gly Gly Lys Arg Ile Leu Thr Val Val Gly Asp Gly Ala Phe
               420                 425                 430

Gln Met Thr Gly Trp Glu Leu Gly Asn Cys Arg Arg Leu Gly Ile Asp
               435                 440                 445

Pro Ile Val Ile Leu Phe Asn Asn Ala Ser Trp Glu Met Leu Arg Thr
               450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
               485                 490                 495
```

```
Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Ala Val Gln Gly Gln Lys Arg Leu His Ala Ala Pro Arg
    530                 535                 540

Glu
545

<210> SEQ ID NO 25
<211> LENGTH: 1638
<212> TYPE: DNA
<213> ORGANISM: Artificial Sequence
<220> FEATURE:
<223> OTHER INFORMATION: F532G
<220> FEATURE:
<221> NAME/KEY: CDS
<222> LOCATION: (1)..(1638)

<400> SEQUENCE: 25
```

| | | | | | | | | | | | | | | | | |
|---|---|---|---|---|---|---|---|---|---|---|---|---|---|---|---|---|
| atg | aag | ctg | gcc | gaa | gcc | ctg | ctg | cgc | gcg | ctg | aag | gat | cgc | ggc | gca | 48 |
| Met | Lys | Leu | Ala | Glu | Ala | Leu | Leu | Arg | Ala | Leu | Lys | Asp | Arg | Gly | Ala | |
| 1 | | | | 5 | | | | | 10 | | | | | 15 | | |
| cag | gcc | atg | ttc | ggg | att | ccg | ggt | gat | ttc | gcc | ctg | ccc | ttc | ttc | aag | 96 |
| Gln | Ala | Met | Phe | Gly | Ile | Pro | Gly | Asp | Phe | Ala | Leu | Pro | Phe | Phe | Lys | |
| | | 20 | | | | | 25 | | | | | 30 | | | | |
| gtg | gcg | gag | gaa | acg | cag | atc | ctg | ccg | ctc | cac | acg | ctg | agc | cac | gag | 144 |
| Val | Ala | Glu | Glu | Thr | Gln | Ile | Leu | Pro | Leu | His | Thr | Leu | Ser | His | Glu | |
| | | | 35 | | | | | 40 | | | | | 45 | | | |
| ccg | gcg | gtg | ggc | ttc | gcg | gcg | gac | gcg | gcg | gcg | cgt | tac | agt | tcg | acg | 192 |
| Pro | Ala | Val | Gly | Phe | Ala | Ala | Asp | Ala | Ala | Ala | Arg | Tyr | Ser | Ser | Thr | |
| | 50 | | | | | 55 | | | | | 60 | | | | | |
| ctg | ggg | gtg | gcg | gcg | gtc | acc | tac | gga | gcg | ggc | gcc | ttc | aac | atg | gtg | 240 |
| Leu | Gly | Val | Ala | Ala | Val | Thr | Tyr | Gly | Ala | Gly | Ala | Phe | Asn | Met | Val | |
| 65 | | | | | 70 | | | | | 75 | | | | | 80 | |
| aac | gcg | gtg | gcc | ggc | gcc | tac | gcc | gag | aag | tcg | ccg | gtg | gtc | gtc | atc | 288 |
| Asn | Ala | Val | Ala | Gly | Ala | Tyr | Ala | Glu | Lys | Ser | Pro | Val | Val | Val | Ile | |
| | | | | 85 | | | | | 90 | | | | | 95 | | |
| tcc | ggc | gcg | ccg | ggc | acg | acg | gag | ggc | aac | gcc | ggc | ctg | ctg | ctg | cac | 336 |
| Ser | Gly | Ala | Pro | Gly | Thr | Thr | Glu | Gly | Asn | Ala | Gly | Leu | Leu | Leu | His | |
| | | | 100 | | | | | 105 | | | | | 110 | | | |
| cac | cag | ggc | cgc | acg | ctg | gac | acg | cag | ttc | cag | gtg | ttc | aag | gag | atc | 384 |
| His | Gln | Gly | Arg | Thr | Leu | Asp | Thr | Gln | Phe | Gln | Val | Phe | Lys | Glu | Ile | |
| | | 115 | | | | | 120 | | | | | 125 | | | | |
| acc | gtc | gcc | cag | gcg | cgg | ctg | gac | gac | ccg | gcc | aag | gcc | ccg | gcg | gag | 432 |
| Thr | Val | Ala | Gln | Ala | Arg | Leu | Asp | Asp | Pro | Ala | Lys | Ala | Pro | Ala | Glu | |
| | | | 130 | | | | | 135 | | | | | 140 | | | |
| atc | gcc | cgc | gtg | ctg | ggg | gcc | gcc | cgc | gcc | ctg | tcg | cgc | ccg | gtc | tat | 480 |
| Ile | Ala | Arg | Val | Leu | Gly | Ala | Ala | Arg | Ala | Leu | Ser | Arg | Pro | Val | Tyr | |
| 145 | | | | | 150 | | | | | 155 | | | | | 160 | |
| ctg | gaa | att | ccc | cgc | aac | atg | gtc | aac | gcc | gag | gtc | gag | ccg | gtg | ggc | 528 |
| Leu | Glu | Ile | Pro | Arg | Asn | Met | Val | Asn | Ala | Glu | Val | Glu | Pro | Val | Gly | |
| | | | | 165 | | | | | 170 | | | | | 175 | | |
| gac | gac | ccg | gct | tgg | ccg | gtg | gac | cgc | gac | gcg | ctg | gcc | gcc | tgc | gcg | 576 |
| Asp | Asp | Pro | Ala | Trp | Pro | Val | Asp | Arg | Asp | Ala | Leu | Ala | Ala | Cys | Ala | |
| | | | 180 | | | | | 185 | | | | | 190 | | | |
| gac | gag | gtg | ctg | gcg | gcc | atg | cgc | tcg | gcc | acg | tcg | ccg | gtg | ctg | atg | 624 |
| Asp | Glu | Val | Leu | Ala | Ala | Met | Arg | Ser | Ala | Thr | Ser | Pro | Val | Leu | Met | |
| | | 195 | | | | | 200 | | | | | 205 | | | | |
| gtc | tgc | gtc | gag | gtc | cgc | cgc | tac | ggg | ctg | gag | gcc | aag | gtg | gcg | gag | 672 |
| Val | Cys | Val | Glu | Val | Arg | Arg | Tyr | Gly | Leu | Glu | Ala | Lys | Val | Ala | Glu | |

```
                210                 215                 220
ctg gcg cag cgg ctg ggc gtg ccg gtg gtg acc acc ttc atg ggg cgc       720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc       768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg       816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc       864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg       912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg       960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc      1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag      1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc      1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg      1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat      1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc      1392
Pro Ile Val Ile Leu Phe Asn Asn Ala Ser Trp Glu Met Leu Arg Thr
    450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
        515                 520                 525 ctg gcc cgc ggt gtc cag ggg cag aag cgc ctg cac gcc gcg ccc cgg      1632
```

```
Leu Ala Arg Gly Val Gln Gly Gln Lys Arg Leu His Ala Ala Pro Arg
            530                 535                 540 gag taa                                                              1638
Glu
545

<210> SEQ ID NO 26
<211> LENGTH: 545
<212> TYPE: PRT
<213> ORGANISM: Artificial Sequence
<220> FEATURE:
<223> OTHER INFORMATION: Synthetic Construct

<400> SEQUENCE: 26

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Leu Gly Thr Tyr Ile Gly Val
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335
```

```
Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Met Gly Asp Cys Leu
        370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Met Leu Arg Thr
        450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
            515                 520                 525

Leu Ala Arg Gly Val Gln Gly Gln Lys Arg Leu His Ala Ala Pro Arg
        530                 535                 540

Glu
545

<210> SEQ ID NO 27
<211> LENGTH: 1638
<212> TYPE: DNA
<213> ORGANISM: Artificial Sequence
<220> FEATURE:
<223> OTHER INFORMATION: F532V
<220> FEATURE:
<221> NAME/KEY: CDS
<222> LOCATION: (1)..(1638)

<400> SEQUENCE: 27 atg aag ctg gcc gaa gcc ctg ctg cgc gcg ctg aag gat cgc ggc gca    48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag    96
Gln Ala Met Phe Gly Ile Pro Gly Asp Phe Ala Leu Pro Phe Phe Lys
                20                  25                  30 gtg gcg gag gaa acg cag atc ctg ccg ctc cac acg ctg agc cac gag   144
Val Ala Glu Glu Thr Gln Ile Leu Pro Leu His Thr Leu Ser His Glu
            35                  40                  45 ccg gcg gtg ggc ttc gcg gcg gac gcg gcg gcg cgt tac agt tcg acg   192
Pro Ala Val Gly Phe Ala Ala Asp Ala Ala Ala Arg Tyr Ser Ser Thr
        50                  55                  60 ctg ggg gtg gcg gcg gtc acc tac gga gcg ggc gcc ttc aac atg gtg   240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc   288
Asn Ala Val Ala Gly Ala Tyr Ala Glu Lys Ser Pro Val Val Val Ile
                85                  90                  95
```

```
tcc ggc gcg ccg ggc acg acg gag ggc aac gcc ggc ctg ctg ctg cac        336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc        384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag        432
Thr Val Ala Gln Ala Arg Leu Asp Asp Pro Ala Lys Ala Pro Ala Glu
130                 135                 140 atc gcc cgc gtg ctg ggg gcc gcc cgc gcc ctg tcg cgc ccg gtc tat        480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc        528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg        576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg        624
Asp Glu Val Leu Ala Ala Met Arg Ser Ala Thr Ser Pro Val Leu Met
            195                 200                 205 gtc tgc gtc gag gtc cgc cgc tac ggg ctg gag gcc aag gtg gcg gag        672
Val Cys Val Glu Val Arg Arg Tyr Gly Leu Glu Ala Lys Val Ala Glu
210                 215                 220 ctg gcg cag cgg ctg ggc gtg ccg gtg gtg acc acc ttc atg ggg cgc        720
Leu Ala Gln Arg Leu Gly Val Pro Val Val Thr Thr Phe Met Gly Arg
225                 230                 235                 240 ggc ctg ctg gcc gac gcg ccg acc ccg ctc ggc acc tac atc ggc            768
Gly Leu Leu Ala Asp Ala Pro Thr Pro Leu Gly Thr Tyr Ile Gly
                245                 250                 255 gtc gcc ggc gac gcg gag atc acc cgg ctg gtc gag gag tcg gac ggg        816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc        864
Leu Phe Leu Leu Gly Ala Ile Leu Ser Asp Thr Asn Phe Ala Val Ser
            275                 280                 285 cag cgc aag atc gac ctg cgc aag acc atc cac gcc ttc gac cgg gcg        912
Gln Arg Lys Ile Asp Leu Arg Lys Thr Ile His Ala Phe Asp Arg Ala
            290                 295                 300 gtg acg ctg ggc tat cac acc tac gcc gac atc ccg ctg gcc ggg ctg        960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc       1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag       1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc       1104
Pro Ile Ala Pro Met Asp Ile Ala Arg Ala Val Asn Asp Arg Val Arg
            355                 360                 365 gcc ggg cag gaa ccg ctg ctg atc gcg gcg gac atg ggc gac tgc ctg       1152
Ala Gly Gln Glu Pro Leu Leu Ile Ala Ala Asp Met Gly Asp Cys Leu
370                 375                 380 ttc acc gcg atg gac atg atc gac gcc ggg ctg atg gcg ccg ggc tat       1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc       1248
Tyr Ala Gly Met Gly Phe Gly Val Pro Ala Gly Ile Gly Ala Gln Cys
```

```
                    405                 410                 415
gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
        420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
            435                 440                 445 ccc atc gtg atc ctg ttc aac aac gcc agt tgg gag atg ctg cgc acc      1392
Pro Ile Val Ile Leu Phe Asn Asn Ala Ser Trp Glu Met Leu Arg Thr
450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
        515                 520                 525 ctg gcc cgc gtg gtc cag ggg cag aag cgc ctg cac gcc gcg ccc cgg      1632
Leu Ala Arg Val Val Gln Gly Gln Lys Arg Leu His Ala Ala Pro Arg
530                 535                 540 gag taa                                                              1638
Glu
545

<210> SEQ ID NO 28
<211> LENGTH: 545
<212> TYPE: PRT
<213> ORGANISM: Artificial Sequence
<220> FEATURE:
<223> OTHER INFORMATION: Synthetic Construct

<400> SEQUENCE: 28

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
```

165                 170                 175
Asp Asp Pro Ala Trp Pro Val Asp Arg Asp Ala Leu Ala Ala Cys Ala
                180                 185                 190

Asp Glu Val Leu Ala Ala Met Arg Ser Ala Thr Ser Pro Val Leu Met
            195                 200                 205

Val Cys Val Glu Val Arg Arg Tyr Gly Leu Glu Ala Lys Val Ala Glu
        210                 215                 220

Leu Ala Gln Arg Leu Gly Val Pro Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
                260                 265                 270

Leu Phe Leu Leu Gly Ala Ile Leu Ser Asp Thr Asn Phe Ala Val Ser
            275                 280                 285

Gln Arg Lys Ile Asp Leu Arg Lys Thr Ile His Ala Phe Asp Arg Ala
        290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
                340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Met Gly Asp Cys Leu
        370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
                420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Met Leu Arg Thr
        450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
                485                 490                 495

Ala Glu Leu Lys Ala Ala Leu Asp Lys Ala Phe Ala Thr Arg Gly Arg
                500                 505                 510

Phe Gln Leu Ile Glu Ala Met Ile Pro Arg Gly Val Leu Ser Asp Thr
            515                 520                 525

Leu Ala Arg Val Val Gln Gly Gln Lys Arg Leu His Ala Ala Pro Arg
        530                 535                 540

Glu
545

<210> SEQ ID NO 29
<211> LENGTH: 1638
<212> TYPE: DNA
<213> ORGANISM: Artificial Sequence

```
<220> FEATURE:
<223> OTHER INFORMATION: F532L
<220> FEATURE:
<221> NAME/KEY: CDS
<222> LOCATION: (1)..(1638)

<400> SEQUENCE: 29 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
                20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
            35                  40                  45 ccg gcg gtg ggc ttc gcg gcg gac gcg gcg cgt tac agt tcg acg         192
Pro Ala Val Gly Phe Ala Ala Asp Ala Ala Arg Tyr Ser Ser Thr
        50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
                100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
        130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg     576
Asp Asp Pro Ala Trp Pro Val Asp Arg Asp Ala Leu Ala Ala Cys Ala
                180                 185                 190 gac gag gtg ctg gcg gcc atg cgc tcg gcc acg tcg ccg gtg ctg atg     624
Asp Glu Val Leu Ala Ala Met Arg Ser Ala Thr Ser Pro Val Leu Met
            195                 200                 205 gtc tgc gtc gag gtc cgc cgc tac ggg ctg gag gcc aag gtg gcg gag     672
Val Cys Val Glu Val Arg Arg Tyr Gly Leu Glu Ala Lys Val Ala Glu
        210                 215                 220 ctg gcg cag cgg ctg ggc gtg ccg gtg gtg acc acc ttc atg ggg cgc     720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc     768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg     816
Val Ala Gly Asp Ala Glu Ile Thr Arg Leu Val Glu Glu Ser Asp Gly
                260                 265                 270 ctg ttc ctg ctc ggc gcg atc ctc agc gac acc aac ttc gcg gtg tcc     864
Leu Phe Leu Leu Gly Ala Ile Leu Ser Asp Thr Asn Phe Ala Val Ser
            275                 280                 285
```

```
cag cgc aag atc gac ctg cgc aag acc atc cac gcg ttc gac cgg gcg       912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg       960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc      1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag      1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc      1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg      1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat      1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc      1392
Pro Ile Val Ile Leu Phe Asn Asn Ala Ser Trp Glu Met Leu Arg Thr
    450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
        515                 520                 525 ctg gcc cgc ctg gtc cag ggg cag aag cgc ctg cac gcc gcg ccc cgg      1632
Leu Ala Arg Leu Val Gln Gly Gln Lys Arg Leu His Ala Ala Pro Arg
    530                 535                 540 gag taa                                                               1638
Glu
545

<210> SEQ ID NO 30
<211> LENGTH: 545
<212> TYPE: PRT
<213> ORGANISM: Artificial Sequence
<220> FEATURE:
<223> OTHER INFORMATION: Synthetic Construct

<400> SEQUENCE: 30
```

```
Met Lys Leu Ala Glu Ala Leu Leu Arg Ala Leu Lys Asp Arg Gly Ala
1               5                   10                  15
Gln Ala Met Phe Gly Ile Pro Gly Asp Phe Ala Leu Pro Phe Phe Lys
            20                  25                  30
Val Ala Glu Glu Thr Gln Ile Leu Pro Leu His Thr Leu Ser His Glu
        35                  40                  45
Pro Ala Val Gly Phe Ala Ala Asp Ala Ala Arg Tyr Ser Ser Thr
    50                  55                  60
Leu Gly Val Ala Ala Val Thr Tyr Gly Ala Gly Ala Phe Asn Met Val
65                  70                  75                  80
Asn Ala Val Ala Gly Ala Tyr Ala Glu Lys Ser Pro Val Val Ile
                85                  90                  95
Ser Gly Ala Pro Gly Thr Thr Glu Gly Asn Ala Gly Leu Leu Leu His
            100                 105                 110
His Gln Gly Arg Thr Leu Asp Thr Gln Phe Gln Val Phe Lys Glu Ile
            115                 120                 125
Thr Val Ala Gln Ala Arg Leu Asp Asp Pro Ala Lys Ala Pro Ala Glu
        130                 135                 140
Ile Ala Arg Val Leu Gly Ala Ala Arg Ala Leu Ser Arg Pro Val Tyr
145                 150                 155                 160
Leu Glu Ile Pro Arg Asn Met Val Asn Ala Glu Val Glu Pro Val Gly
                165                 170                 175
Asp Asp Pro Ala Trp Pro Val Asp Arg Asp Ala Leu Ala Ala Cys Ala
            180                 185                 190
Asp Glu Val Leu Ala Ala Met Arg Ser Ala Thr Ser Pro Val Leu Met
        195                 200                 205
Val Cys Val Glu Val Arg Arg Tyr Gly Leu Glu Ala Lys Val Ala Glu
210                 215                 220
Leu Ala Gln Arg Leu Gly Val Pro Val Val Thr Thr Phe Met Gly Arg
225                 230                 235                 240
Gly Leu Leu Ala Asp Ala Pro Thr Pro Leu Gly Thr Tyr Ile Gly
                245                 250                 255
Val Ala Gly Asp Ala Glu Ile Thr Arg Leu Val Glu Glu Ser Asp Gly
            260                 265                 270
Leu Phe Leu Leu Gly Ala Ile Leu Ser Asp Thr Asn Phe Ala Val Ser
        275                 280                 285
Gln Arg Lys Ile Asp Leu Arg Lys Thr Ile His Ala Phe Asp Arg Ala
        290                 295                 300
Val Thr Leu Gly Tyr His Thr Tyr Ala Asp Ile Pro Leu Ala Gly Leu
305                 310                 315                 320
Val Asp Ala Leu Leu Glu Gly Leu Pro Pro Ser Asp Arg Thr Thr Arg
                325                 330                 335
Gly Lys Glu Pro His Ala Tyr Pro Thr Gly Leu Gln Ala Asp Gly Glu
            340                 345                 350
Pro Ile Ala Pro Met Asp Ile Ala Arg Ala Val Asn Asp Arg Val Arg
        355                 360                 365
Ala Gly Gln Glu Pro Leu Leu Ile Ala Ala Asp Met Gly Asp Cys Leu
    370                 375                 380
Phe Thr Ala Met Asp Met Ile Asp Ala Gly Leu Met Ala Pro Gly Tyr
385                 390                 395                 400
Tyr Ala Gly Met Gly Phe Gly Val Pro Ala Gly Ile Gly Ala Gln Cys
                405                 410                 415
Val Ser Gly Gly Lys Arg Ile Leu Thr Val Val Gly Asp Gly Ala Phe
```

```
              420                 425                 430
Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Met Leu Arg Thr
    450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Leu Val Gln Gly Gln Lys Arg Leu His Ala Ala Pro Arg
    530                 535                 540

Glu
545

<210> SEQ ID NO 31
<211> LENGTH: 1638
<212> TYPE: DNA
<213> ORGANISM: Artificial Sequence
<220> FEATURE:
<223> OTHER INFORMATION: Q536G
<220> FEATURE:
<221> NAME/KEY: CDS
<222> LOCATION: (1)..(1638)

<400> SEQUENCE: 31 atg aag ctg gcc gaa gcc ctg ctg cgc gcg ctg aag gat cgc ggc gca       48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag       96
Gln Ala Met Phe Gly Ile Pro Gly Asp Phe Ala Leu Pro Phe Phe Lys
                20                  25                  30 gtg gcg gag gaa acg cag atc ctg ccg ctc cac acg ctg agc cac gag      144
Val Ala Glu Glu Thr Gln Ile Leu Pro Leu His Thr Leu Ser His Glu
            35                  40                  45 ccg gcg gtg ggc ttc gcg gcg gac gcg gcg gcg cgt tac agt tcg acg      192
Pro Ala Val Gly Phe Ala Ala Asp Ala Ala Ala Arg Tyr Ser Ser Thr
        50                  55                  60 ctg ggg gtg gcg gcg gtc acc tac gga gcg ggc gcc ttc aac atg gtg      240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc      288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac      336
Ser Gly Ala Pro Gly Thr Thr Glu Gly Asn Ala Gly Leu Leu Leu His
                100                 105                 110 cac cag ggc cgc acg ctg gac acg cag ttc cag gtg ttc aag gag atc      384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag      432
Thr Val Ala Gln Ala Arg Leu Asp Asp Pro Ala Lys Ala Pro Ala Glu
        130                 135                 140 atc gcc cgc gtg ctg ggg gcc gcc cgc gcc ctg tcg cgc ccg gtc tat      480
Ile Ala Arg Val Leu Gly Ala Ala Arg Ala Leu Ser Arg Pro Val Tyr
145                 150                 155                 160
```

-continued

| | | |
|---|---|---|
| ctg gaa att ccc cgc aac atg gtc aac gcc gag gtc gag ccg gtg ggc<br>Leu Glu Ile Pro Arg Asn Met Val Asn Ala Glu Val Glu Pro Val Gly<br>                165                    170                  175 | | 528 |
| gac gac ccg gct tgg ccg gtg gac cgc gac gcg ctg gcc gcc tgc gcg<br>Asp Asp Pro Ala Trp Pro Val Asp Arg Asp Ala Leu Ala Ala Cys Ala<br>                180                    185                  190 | | 576 |
| gac gag gtg ctg gcg gcc atg cgc tcg gcc acg tcg ccg gtg ctg atg<br>Asp Glu Val Leu Ala Ala Met Arg Ser Ala Thr Ser Pro Val Leu Met<br>         195                    200                    205 | | 624 |
| gtc tgc gtc gag gtc cgc cgc tac ggg ctg gag gcc aag gtg gcg gag<br>Val Cys Val Glu Val Arg Arg Tyr Gly Leu Glu Ala Lys Val Ala Glu<br>210                    215                    220 | | 672 |
| ctg gcg cag cgg ctg ggc gtg ccg gtg gtg acc acc ttc atg ggg cgc<br>Leu Ala Gln Arg Leu Gly Val Pro Val Val Thr Thr Phe Met Gly Arg<br>225                    230                    235                  240 | | 720 |
| ggc ctg ctg gcc gac gcg ccg acc ccg ctc ggc acc tac atc ggc<br>Gly Leu Leu Ala Asp Ala Pro Thr Pro Pro Leu Gly Thr Tyr Ile Gly<br>                        245                    250                  255 | | 768 |
| gtc gcc ggc gac gcg gag atc acc cgg ctg gtc gag gag tcg gac ggg<br>Val Ala Gly Asp Ala Glu Ile Thr Arg Leu Val Glu Glu Ser Asp Gly<br>                260                    265                  270 | | 816 |
| ctg ttc ctg ctc ggc gcg atc ctc agc gac acc aac ttc gcg gtg tcc<br>Leu Phe Leu Leu Gly Ala Ile Leu Ser Asp Thr Asn Phe Ala Val Ser<br>         275                    280                    285 | | 864 |
| cag cgc aag atc gac ctg cgc aag acc atc cac gcc ttc gac cgg gcg<br>Gln Arg Lys Ile Asp Leu Arg Lys Thr Ile His Ala Phe Asp Arg Ala<br>290                    295                    300 | | 912 |
| gtg acg ctg ggc tat cac acc tac gcc gac atc ccg ctg gcc ggg ctg<br>Val Thr Leu Gly Tyr His Thr Tyr Ala Asp Ile Pro Leu Ala Gly Leu<br>305                    310                    315                  320 | | 960 |
| gtg gac gcc ctc ttg gaa ggg ctg ccg ccg tcc gac cgg acg acc cgc<br>Val Asp Ala Leu Leu Glu Gly Leu Pro Pro Ser Asp Arg Thr Thr Arg<br>                        325                    330                  335 | | 1008 |
| ggc aag gag ccc cac gcc tac ccg acc ggc ctt cag gcg gac ggc gag<br>Gly Lys Glu Pro His Ala Tyr Pro Thr Gly Leu Gln Ala Asp Gly Glu<br>                340                    345                  350 | | 1056 |
| ccg atc gcc ccg atg gac atc gcc cgc gcc gtc aac gac cgc gtc cgc<br>Pro Ile Ala Pro Met Asp Ile Ala Arg Ala Val Asn Asp Arg Val Arg<br>         355                    360                    365 | | 1104 |
| gcc ggg cag gaa ccg ctg ctg atc gcg gcg gac atg ggc gac tgc ctg<br>Ala Gly Gln Glu Pro Leu Leu Ile Ala Ala Asp Met Gly Asp Cys Leu<br>370                    375                    380 | | 1152 |
| ttc acc gcg atg gac atg atc gac gcc ggg ctg atg gcg ccg ggc tat<br>Phe Thr Ala Met Asp Met Ile Asp Ala Gly Leu Met Ala Pro Gly Tyr<br>385                    390                    395                  400 | | 1200 |
| tac gcg ggc atg ggc ttc ggg gtg ccg gcg ggc atc ggg gcg cag tgc<br>Tyr Ala Gly Met Gly Phe Gly Val Pro Ala Gly Ile Gly Ala Gln Cys<br>                        405                    410                  415 | | 1248 |
| gtg tcg ggc ggc aag cgc atc ctg acc gtg gtc ggc gac ggc gcc ttc<br>Val Ser Gly Gly Lys Arg Ile Leu Thr Val Val Gly Asp Gly Ala Phe<br>                    420                    425                  430 | | 1296 |
| cag atg acc ggg tgg gag ctt ggc aac tgc cga cgg ctg ggc atc gac<br>Gln Met Thr Gly Trp Glu Leu Gly Asn Cys Arg Arg Leu Gly Ile Asp<br>                435                    440                  445 | | 1344 |
| ccc atc gtg atc ctg ttc aac aac gcc agt tgg gag atg ctg cgc acc<br>Pro Ile Val Ile Leu Phe Asn Asn Ala Ser Trp Glu Met Leu Arg Thr<br>450                    455                    460 | | 1392 |
| ttc cag ccc gaa tcg gcc ttc aac gac ctg gac gac tgg cgc ttc gcc<br>Phe Gln Pro Glu Ser Ala Phe Asn Asp Leu Asp Asp Trp Arg Phe Ala<br>465                    470                    475                  480 | | 1440 |

-continued

```
gac atg gcg gcg ggc atg ggc ggc gac ggc gtc cgc gtg cgc aca cgg    1488
Asp Met Ala Ala Gly Met Gly Gly Asp Gly Val Arg Val Arg Thr Arg
            485                 490                 495 gcg gag ctg aag gcg gcg ctg gac aag gcc ttc gcc acg cgc ggg cgc    1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg    1584
Phe Gln Leu Ile Glu Ala Met Ile Pro Arg Gly Val Leu Ser Asp Thr
            515                 520                 525 ctg gcc cgc ttc gtc cag ggg ggt aag cgc ctg cac gcc gcg ccc cgg    1632
Leu Ala Arg Phe Val Gln Gly Gly Lys Arg Leu His Ala Ala Pro Arg
            530                 535                 540 gag taa                                                             1638
Glu
545

<210> SEQ ID NO 32
<211> LENGTH: 545
<212> TYPE: PRT
<213> ORGANISM: Artificial Sequence
<220> FEATURE:
<223> OTHER INFORMATION: Synthetic Construct

<400> SEQUENCE: 32

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255
```

```
Val Ala Gly Asp Ala Glu Ile Thr Arg Leu Val Glu Ser Asp Gly
            260                 265                 270

Leu Phe Leu Leu Gly Ala Ile Leu Ser Asp Thr Asn Phe Ala Val Ser
            275                 280                 285

Gln Arg Lys Ile Asp Leu Arg Lys Thr Ile His Ala Phe Asp Arg Ala
        290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Met Gly Asp Cys Leu
    370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
        435                 440                 445

Pro Ile Val Ile Leu Phe Asn Asn Ala Ser Trp Glu Met Leu Arg Thr
    450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Phe Val Gln Gly Gly Lys Arg Leu His Ala Ala Pro Arg
    530                 535                 540

Glu
545

<210> SEQ ID NO 33
<211> LENGTH: 1638
<212> TYPE: DNA
<213> ORGANISM: Artificial Sequence
<220> FEATURE:
<223> OTHER INFORMATION: Q536A
<220> FEATURE:
<221> NAME/KEY: CDS
<222> LOCATION: (1)..(1638)

<400> SEQUENCE: 33 atg aag ctg gcc gaa gcc ctg ctg cgc gcg ctg aag gat cgc ggc gca    48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag    96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag   144
```

```
Val Ala Glu Glu Thr Gln Ile Leu Pro Leu His Thr Leu Ser His Glu
             35                  40                  45 ccg gcg gtg ggc ttc gcg gcg gac gcg gcg gcg cgt tac agt tcg acg        192
Pro Ala Val Gly Phe Ala Ala Asp Ala Ala Ala Arg Tyr Ser Ser Thr
         50                  55                  60 ctg ggg gtg gcg gcg gtc acc tac gga gcg ggc gcc ttc aac atg gtg        240
Leu Gly Val Ala Ala Val Thr Tyr Gly Ala Gly Ala Phe Asn Met Val
 65                  70                  75                  80 aac gcg gtg gcc ggc gcc tac gcc gag aag tcg ccg gtg gtc gtc atc        288
Asn Ala Val Ala Gly Ala Tyr Ala Glu Lys Ser Pro Val Val Val Ile
                 85                  90                  95 tcc ggc gcg ccg ggc acg acg gag ggc aac gcc ggc ctg ctg ctg cac        336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc        384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag        432
Thr Val Ala Gln Ala Arg Leu Asp Asp Pro Ala Lys Ala Pro Ala Glu
            130                 135                 140 atc gcc cgc gtg ctg ggg gcc gcc cgc gcc ctg tcg cgc ccg gtc tat        480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc        528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg        576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg        624
Asp Glu Val Leu Ala Ala Met Arg Ser Ala Thr Ser Pro Val Leu Met
            195                 200                 205 gtc tgc gtc gag gtc cgc cgc tac ggg ctg gag gcc aag gtg gcg gag        672
Val Cys Val Glu Val Arg Arg Tyr Gly Leu Glu Ala Lys Val Ala Glu
            210                 215                 220 ctg gcg cag cgg ctg ggc gtg ccg gtg gtg acc acc ttc atg ggg cgc        720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc        768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg        816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc        864
Leu Phe Leu Leu Gly Ala Ile Leu Ser Asp Thr Asn Phe Ala Val Ser
            275                 280                 285 cag cgc aag atc gac ctg cgc aag acc atc cac gcc ttc gac cgg gcg        912
Gln Arg Lys Ile Asp Leu Arg Lys Thr Ile His Ala Phe Asp Arg Ala
            290                 295                 300 gtg acg ctg ggc tat cac acc tac gcc gac atc ccg ctg gcc ggg ctg        960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc       1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag       1056
Gly Lys Glu Pro His Ala Tyr Pro Thr Gly Leu Gln Ala Asp Gly Glu
            340                 345                 350
```

```
ccg atc gcc ccg atg gac atc gcc cgc gcc gtc aac gac cgc gtc cgc         1104
Pro Ile Ala Pro Met Asp Ile Ala Arg Ala Val Asn Asp Arg Val Arg
            355                 360                 365 gcc ggg cag gaa ccg ctg ctg atc gcg gcg gac atg ggc gac tgc ctg         1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat         1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc         1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc         1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac         1344
Gln Met Thr Gly Trp Glu Leu Gly Asn Cys Arg Arg Leu Gly Ile Asp
    435                 440                 445 ccc atc gtg atc ctg ttc aac aac gcc agt tgg gag atg ctg cgc acc         1392
Pro Ile Val Ile Leu Phe Asn Asn Ala Ser Trp Glu Met Leu Arg Thr
450                 455                 460 ttc cag ccc gaa tcg gcc ttc aac gac ctg gac gac tgg cgc ttc gcc         1440
Phe Gln Pro Glu Ser Ala Phe Asn Asp Leu Asp Asp Trp Arg Phe Ala
                470                 475                 480 gac atg gcg gcg ggc atg ggc ggc gac ggc gtc cgc gtg cgc aca cgg         1488
Asp Met Ala Ala Gly Met Gly Gly Asp Gly Val Arg Val Arg Thr Arg
            485                 490                 495 gcg gag ctg aag gcg gcg ctg gac aag gcc ttc gcc acg cgc ggg cgc         1536
Ala Glu Leu Lys Ala Ala Leu Asp Lys Ala Phe Ala Thr Arg Gly Arg
    500                 505                 510 ttc cag ctg atc gag gcg atg atc ccg cgc ggc gtg ctg tcc gac acg         1584
Phe Gln Leu Ile Glu Ala Met Ile Pro Arg Gly Val Leu Ser Asp Thr
515                 520                 525 ctg gcc cgc ttc gtc cag ggg gcg aag cgc ctg cac gcc gcg ccc cgg         1632
Leu Ala Arg Phe Val Gln Gly Ala Lys Arg Leu His Ala Ala Pro Arg
                535                 540 gag taa                                                                  1638
Glu
545

<210> SEQ ID NO 34
<211> LENGTH: 545
<212> TYPE: PRT
<213> ORGANISM: Artificial Sequence
<220> FEATURE:
<223> OTHER INFORMATION: Synthetic Construct

<400> SEQUENCE: 34

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95
```

```
Ser Gly Ala Pro Gly Thr Thr Glu Gly Asn Ala Gly Leu Leu Leu His
                100                 105                 110
His Gln Gly Arg Thr Leu Asp Thr Gln Phe Gln Val Phe Lys Glu Ile
            115                 120                 125
Thr Val Ala Gln Ala Arg Leu Asp Asp Pro Ala Lys Ala Pro Ala Glu
130                 135                 140
Ile Ala Arg Val Leu Gly Ala Ala Arg Ala Leu Ser Arg Pro Val Tyr
145                 150                 155                 160
Leu Glu Ile Pro Arg Asn Met Val Asn Ala Glu Val Glu Pro Val Gly
                165                 170                 175
Asp Asp Pro Ala Trp Pro Val Asp Arg Asp Ala Leu Ala Ala Cys Ala
            180                 185                 190
Asp Glu Val Leu Ala Ala Met Arg Ser Ala Thr Ser Pro Val Leu Met
            195                 200                 205
Val Cys Val Glu Val Arg Arg Tyr Gly Leu Glu Ala Lys Val Ala Glu
    210                 215                 220
Leu Ala Gln Arg Leu Gly Val Pro Val Val Thr Thr Phe Met Gly Arg
225                 230                 235                 240
Gly Leu Leu Ala Asp Ala Pro Thr Pro Pro Leu Gly Thr Tyr Ile Gly
                245                 250                 255
Val Ala Gly Asp Ala Glu Ile Thr Arg Leu Val Glu Glu Ser Asp Gly
            260                 265                 270
Leu Phe Leu Leu Gly Ala Ile Leu Ser Asp Thr Asn Phe Ala Val Ser
        275                 280                 285
Gln Arg Lys Ile Asp Leu Arg Lys Thr Ile His Ala Phe Asp Arg Ala
    290                 295                 300
Val Thr Leu Gly Tyr His Thr Tyr Ala Asp Ile Pro Leu Ala Gly Leu
305                 310                 315                 320
Val Asp Ala Leu Leu Glu Gly Leu Pro Pro Ser Asp Arg Thr Thr Arg
                325                 330                 335
Gly Lys Glu Pro His Ala Tyr Pro Thr Gly Leu Gln Ala Asp Gly Glu
            340                 345                 350
Pro Ile Ala Pro Met Asp Ile Ala Arg Ala Val Asn Asp Arg Val Arg
        355                 360                 365
Ala Gly Gln Glu Pro Leu Leu Ile Ala Ala Asp Met Gly Asp Cys Leu
    370                 375                 380
Phe Thr Ala Met Asp Met Ile Asp Ala Gly Leu Met Ala Pro Gly Tyr
385                 390                 395                 400
Tyr Ala Gly Met Gly Phe Gly Val Pro Ala Gly Ile Gly Ala Gln Cys
                405                 410                 415
Val Ser Gly Gly Lys Arg Ile Leu Thr Val Val Gly Asp Gly Ala Phe
            420                 425                 430
Gln Met Thr Gly Trp Glu Leu Gly Asn Cys Arg Arg Leu Gly Ile Asp
        435                 440                 445
Pro Ile Val Ile Leu Phe Asn Asn Ala Ser Trp Glu Met Leu Arg Thr
    450                 455                 460
Phe Gln Pro Glu Ser Ala Phe Asn Asp Leu Asp Asp Trp Arg Phe Ala
465                 470                 475                 480
Asp Met Ala Ala Gly Met Gly Asp Gly Val Arg Val Arg Thr Arg
                485                 490                 495
Ala Glu Leu Lys Ala Ala Leu Asp Lys Ala Phe Ala Thr Arg Gly Arg
            500                 505                 510
```

```
Phe Gln Leu Ile Glu Ala Met Ile Pro Arg Gly Val Leu Ser Asp Thr
            515                 520                 525

Leu Ala Arg Phe Val Gln Gly Ala Lys Arg Leu His Ala Ala Pro Arg
    530                 535                 540

Glu
545

<210> SEQ ID NO 35
<211> LENGTH: 1638
<212> TYPE: DNA
<213> ORGANISM: Artificial Sequence
<220> FEATURE:
<223> OTHER INFORMATION: Q536L
<220> FEATURE:
<221> NAME/KEY: CDS
<222> LOCATION: (1)..(1638)

<400> SEQUENCE: 35 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
                20                  25                  30 gtg gcg gag gaa acg cag atc ctc ccg ctc cac acg ctg agc cac gag     144
Val Ala Glu Glu Thr Gln Ile Leu Pro Leu His Thr Leu Ser His Glu
            35                  40                  45 ccg gcg gtg ggc ttc gcg gcc gac gcg gcg cgt tac agt tcg acg         192
Pro Ala Val Gly Phe Ala Ala Asp Ala Ala Arg Tyr Ser Ser Thr
        50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
                100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
        130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg     576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg     624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag     672
Val Cys Val Glu Val Arg Arg Tyr Gly Leu Glu Ala Lys Val Ala Glu
    210                 215                 220 ctg gcg cag cgg ctg ggc gtg ccg gtg gtg acc acc ttc atg ggg cgc     720
```

-continued

| | | | | | | | | | | | | | | |
|---|---|---|---|---|---|---|---|---|---|---|---|---|---|---|
| Leu | Ala | Gln | Arg | Leu | Gly | Val | Pro | Val | Val | Thr | Thr | Phe | Met | Gly | Arg |
| 225 | | | | | 230 | | | | | 235 | | | | | 240 |

| ggc | ctg | ctg | gcc | gac | gcg | ccg | acc | ccg | ccg | ctc | ggc | acc | tac | atc | ggc | 768 |
|---|---|---|---|---|---|---|---|---|---|---|---|---|---|---|---|---|
| Gly | Leu | Leu | Ala | Asp | Ala | Pro | Thr | Pro | Pro | Leu | Gly | Thr | Tyr | Ile | Gly | |
| | | | | 245 | | | | | 250 | | | | | 255 | | |

| gtc | gcc | ggc | gac | gcg | gag | atc | acc | cgg | ctg | gtc | gag | gag | tcg | gac | ggg | 816 |
|---|---|---|---|---|---|---|---|---|---|---|---|---|---|---|---|---|
| Val | Ala | Gly | Asp | Ala | Glu | Ile | Thr | Arg | Leu | Val | Glu | Glu | Ser | Asp | Gly | |
| | | | | 260 | | | | | 265 | | | | | 270 | | |

| ctg | ttc | ctg | ctc | ggc | gcg | atc | ctc | agc | gac | acc | aac | ttc | gcg | gtg | tcc | 864 |
|---|---|---|---|---|---|---|---|---|---|---|---|---|---|---|---|---|
| Leu | Phe | Leu | Leu | Gly | Ala | Ile | Leu | Ser | Asp | Thr | Asn | Phe | Ala | Val | Ser | |
| | | | 275 | | | | | 280 | | | | | 285 | | | |

| cag | cgc | aag | atc | gac | ctg | cgc | aag | acc | atc | cac | gcc | ttc | gac | cgg | gcg | 912 |
|---|---|---|---|---|---|---|---|---|---|---|---|---|---|---|---|---|
| Gln | Arg | Lys | Ile | Asp | Leu | Arg | Lys | Thr | Ile | His | Ala | Phe | Asp | Arg | Ala | |
| | 290 | | | | | 295 | | | | | 300 | | | | | |

| gtg | acg | ctg | ggc | tat | cac | acc | tac | gcc | gac | atc | ccg | ctg | gcc | ggg | ctg | 960 |
|---|---|---|---|---|---|---|---|---|---|---|---|---|---|---|---|---|
| Val | Thr | Leu | Gly | Tyr | His | Thr | Tyr | Ala | Asp | Ile | Pro | Leu | Ala | Gly | Leu | |
| 305 | | | | | 310 | | | | | 315 | | | | | 320 | |

| gtg | gac | gcc | ctc | ttg | gaa | ggg | ctg | ccg | ccg | tcc | gac | cgg | acg | acc | cgc | 1008 |
|---|---|---|---|---|---|---|---|---|---|---|---|---|---|---|---|---|
| Val | Asp | Ala | Leu | Leu | Glu | Gly | Leu | Pro | Pro | Ser | Asp | Arg | Thr | Thr | Arg | |
| | | | | 325 | | | | | 330 | | | | | 335 | | |

| ggc | aag | gag | ccc | cac | gcc | tac | ccg | acc | ggc | ctt | cag | gcg | gac | ggc | gag | 1056 |
|---|---|---|---|---|---|---|---|---|---|---|---|---|---|---|---|---|
| Gly | Lys | Glu | Pro | His | Ala | Tyr | Pro | Thr | Gly | Leu | Gln | Ala | Asp | Gly | Glu | |
| | | | 340 | | | | | 345 | | | | | 350 | | | |

| ccg | atc | gcc | ccg | atg | gac | atc | gcc | cgc | gcc | gtc | aac | gac | cgc | gtc | cgc | 1104 |
|---|---|---|---|---|---|---|---|---|---|---|---|---|---|---|---|---|
| Pro | Ile | Ala | Pro | Met | Asp | Ile | Ala | Arg | Ala | Val | Asn | Asp | Arg | Val | Arg | |
| | | 355 | | | | | 360 | | | | | 365 | | | | |

| gcc | ggg | cag | gaa | ccg | ctg | ctg | atc | gcg | gcg | gac | atg | ggc | gac | tgc | ctg | 1152 |
|---|---|---|---|---|---|---|---|---|---|---|---|---|---|---|---|---|
| Ala | Gly | Gln | Glu | Pro | Leu | Leu | Ile | Ala | Ala | Asp | Met | Gly | Asp | Cys | Leu | |
| | 370 | | | | | 375 | | | | | 380 | | | | | |

| ttc | acc | gcg | atg | gac | atg | atc | gac | gcc | ggg | ctg | atg | gcg | ccg | ggc | tat | 1200 |
|---|---|---|---|---|---|---|---|---|---|---|---|---|---|---|---|---|
| Phe | Thr | Ala | Met | Asp | Met | Ile | Asp | Ala | Gly | Leu | Met | Ala | Pro | Gly | Tyr | |
| 385 | | | | | 390 | | | | | 395 | | | | | 400 | |

| tac | gcg | ggc | atg | ggc | ttc | ggg | gtg | ccg | gcg | ggc | atc | ggg | gcg | cag | tgc | 1248 |
|---|---|---|---|---|---|---|---|---|---|---|---|---|---|---|---|---|
| Tyr | Ala | Gly | Met | Gly | Phe | Gly | Val | Pro | Ala | Gly | Ile | Gly | Ala | Gln | Cys | |
| | | | | 405 | | | | | 410 | | | | | 415 | | |

| gtg | tcg | ggc | ggc | aag | cgc | atc | ctg | acc | gtg | gtc | ggc | gac | ggc | gcc | ttc | 1296 |
|---|---|---|---|---|---|---|---|---|---|---|---|---|---|---|---|---|
| Val | Ser | Gly | Gly | Lys | Arg | Ile | Leu | Thr | Val | Val | Gly | Asp | Gly | Ala | Phe | |
| | | | 420 | | | | | 425 | | | | | 430 | | | |

| cag | atg | acc | ggg | tgg | gag | ctt | ggc | aac | tgc | cga | cgg | ctg | ggc | atc | gac | 1344 |
|---|---|---|---|---|---|---|---|---|---|---|---|---|---|---|---|---|
| Gln | Met | Thr | Gly | Trp | Glu | Leu | Gly | Asn | Cys | Arg | Arg | Leu | Gly | Ile | Asp | |
| | | 435 | | | | | 440 | | | | | 445 | | | | |

| ccc | atc | gtg | atc | ctg | ttc | aac | aac | gcc | agt | tgg | gag | atg | ctg | cgc | acc | 1392 |
|---|---|---|---|---|---|---|---|---|---|---|---|---|---|---|---|---|
| Pro | Ile | Val | Ile | Leu | Phe | Asn | Asn | Ala | Ser | Trp | Glu | Met | Leu | Arg | Thr | |
| 450 | | | | | 455 | | | | | 460 | | | | | | |

| ttc | cag | ccc | gaa | tcg | gcc | ttc | aac | gac | ctg | gac | gac | tgg | cgc | ttc | gcc | 1440 |
|---|---|---|---|---|---|---|---|---|---|---|---|---|---|---|---|---|
| Phe | Gln | Pro | Glu | Ser | Ala | Phe | Asn | Asp | Leu | Asp | Asp | Trp | Arg | Phe | Ala | |
| 465 | | | | | 470 | | | | | 475 | | | | | 480 | |

| gac | atg | gcg | gcg | ggc | atg | ggc | ggc | gac | ggc | gtc | cgg | gtg | cgc | aca | cgg | 1488 |
|---|---|---|---|---|---|---|---|---|---|---|---|---|---|---|---|---|
| Asp | Met | Ala | Ala | Gly | Met | Gly | Gly | Asp | Gly | Val | Arg | Val | Arg | Thr | Arg | |
| | | | | 485 | | | | | 490 | | | | | 495 | | |

| gcg | gag | ctg | aag | gcg | gcg | ctg | gac | aag | gcc | ttc | gcc | acg | cgc | ggg | cgc | 1536 |
|---|---|---|---|---|---|---|---|---|---|---|---|---|---|---|---|---|
| Ala | Glu | Leu | Lys | Ala | Ala | Leu | Asp | Lys | Ala | Phe | Ala | Thr | Arg | Gly | Arg | |
| | | | 500 | | | | | 505 | | | | | 510 | | | |

| ttc | cag | ctg | atc | gag | gcg | atg | atc | ccg | cgc | ggc | gtg | ctg | tcc | gac | acg | 1584 |
|---|---|---|---|---|---|---|---|---|---|---|---|---|---|---|---|---|
| Phe | Gln | Leu | Ile | Glu | Ala | Met | Ile | Pro | Arg | Gly | Val | Leu | Ser | Asp | Thr | |
| | | 515 | | | | | 520 | | | | | 525 | | | | |

| ctg | gcc | cgc | ttc | gtc | cag | ggg | ctg | aag | cgc | ctg | cac | gcc | gcg | ccc | cgg | 1632 |
|---|---|---|---|---|---|---|---|---|---|---|---|---|---|---|---|---|
| Leu | Ala | Arg | Phe | Val | Gln | Gly | Leu | Lys | Arg | Leu | His | Ala | Ala | Pro | Arg | |
| | 530 | | | | | 535 | | | | | 540 | | | | | |

```
gag taa                                                    1638
Glu
545

<210> SEQ ID NO 36
<211> LENGTH: 545
<212> TYPE: PRT
<213> ORGANISM: Artificial Sequence
<220> FEATURE:
<223> OTHER INFORMATION: Synthetic Construct

<400> SEQUENCE: 36

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350
```

```
Pro Ile Ala Pro Met Asp Ile Ala Arg Ala Val Asn Asp Arg Val Arg
            355                 360                 365

Ala Gly Gln Glu Pro Leu Leu Ile Ala Asp Met Gly Asp Cys Leu
    370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Met Leu Arg Thr
            450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
            515                 520                 525

Leu Ala Arg Phe Val Gln Gly Leu Lys Arg Leu His Ala Ala Pro Arg
            530                 535                 540

Glu
545

<210> SEQ ID NO 37
<211> LENGTH: 1638
<212> TYPE: DNA
<213> ORGANISM: Artificial Sequence
<220> FEATURE:
<223> OTHER INFORMATION: Q536I
<220> FEATURE:
<221> NAME/KEY: CDS
<222> LOCATION: (1)..(1638)

<400> SEQUENCE: 37 atg aag ctg gcc gaa gcc ctg ctg cgc gcg ctg aag gat cgc ggc gca    48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag    96
Gln Ala Met Phe Gly Ile Pro Gly Asp Phe Ala Leu Pro Phe Phe Lys
                20                  25                  30 gtg gcg gag gaa acg cag atc ctg ccg ctc cac acg ctg agc cac gag   144
Val Ala Glu Glu Thr Gln Ile Leu Pro Leu His Thr Leu Ser His Glu
            35                  40                  45 ccg gcg gtg ggc ttc gcg gcg gac gcg gcg gcg cgt tac agt tcg acg   192
Pro Ala Val Gly Phe Ala Ala Asp Ala Ala Ala Arg Tyr Ser Ser Thr
        50                  55                  60 ctg ggg gtg gcg gcg gtc acc tac gga gcg ggc gcc ttc aac atg gtg   240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc   288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac   336
Ser Gly Ala Pro Gly Thr Thr Glu Gly Asn Ala Gly Leu Leu Leu His
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 100 |     |     |     |     | 105 |     |     |     |     | 110 |     |     |      |
| cac | cag | ggc | cgc | acg | ctg | gac | acg | cag | ttc | cag | gtg | ttc | aag | gag | atc | 384  |
| His | Gln | Gly | Arg | Thr | Leu | Asp | Thr | Gln | Phe | Gln | Val | Phe | Lys | Glu | Ile |      |
|     |     | 115 |     |     |     |     | 120 |     |     |     |     | 125 |     |     |     |      |
| acc | gtc | gcc | cag | gcg | cgg | ctg | gac | gac | ccg | gcc | aag | gcc | ccg | gcg | gag | 432  |
| Thr | Val | Ala | Gln | Ala | Arg | Leu | Asp | Asp | Pro | Ala | Lys | Ala | Pro | Ala | Glu |      |
|     | 130 |     |     |     |     | 135 |     |     |     |     | 140 |     |     |     |     |      |
| atc | gcc | cgc | gtg | ctg | ggg | gcc | gcc | cgc | gcc | ctg | tcg | cgc | ccg | gtc | tat | 480  |
| Ile | Ala | Arg | Val | Leu | Gly | Ala | Ala | Arg | Ala | Leu | Ser | Arg | Pro | Val | Tyr |      |
| 145 |     |     |     |     | 150 |     |     |     |     | 155 |     |     |     |     | 160 |      |
| ctg | gaa | att | ccc | cgc | aac | atg | gtc | aac | gcc | gag | gtc | gag | ccg | gtg | ggc | 528  |
| Leu | Glu | Ile | Pro | Arg | Asn | Met | Val | Asn | Ala | Glu | Val | Glu | Pro | Val | Gly |      |
|     |     |     |     | 165 |     |     |     |     | 170 |     |     |     |     | 175 |     |      |
| gac | gac | ccg | gct | tgg | ccg | gtg | gac | cgc | gac | gcg | ctg | gcc | gcc | tgc | gcg | 576  |
| Asp | Asp | Pro | Ala | Trp | Pro | Val | Asp | Arg | Asp | Ala | Leu | Ala | Ala | Cys | Ala |      |
|     |     │ 180 |     |     |     |     | 185 |     |     |     |     | 190 |     |     |     |      |
| gac | gag | gtg | ctg | gcg | gcc | atg | cgc | tcg | gcc | acg | tcg | ccg | gtg | ctg | atg | 624  |
| Asp | Glu | Val | Leu | Ala | Ala | Met | Arg | Ser | Ala | Thr | Ser | Pro | Val | Leu | Met |      |
|     |     | 195 |     |     |     |     | 200 |     |     |     |     | 205 |     |     |     |      |
| gtc | tgc | gtc | gag | gtc | cgc | cgc | tac | ggg | ctg | gag | gcc | aag | gtg | gcg | gag | 672  |
| Val | Cys | Val | Glu | Val | Arg | Arg | Tyr | Gly | Leu | Glu | Ala | Lys | Val | Ala | Glu |      |
|     | 210 |     |     |     |     | 215 |     |     |     |     | 220 |     |     |     |     |      |
| ctg | gcg | cag | cgg | ctg | ggc | gtg | ccg | gtg | gtg | acc | acc | ttc | atg | ggg | cgc | 720  |
| Leu | Ala | Gln | Arg | Leu | Gly | Val | Pro | Val | Val | Thr | Thr | Phe | Met | Gly | Arg |      |
| 225 |     |     |     |     | 230 |     |     |     |     | 235 |     |     |     |     | 240 |      |
| ggc | ctg | ctg | gcc | gac | gcg | ccg | acc | ccg | ctc | ggc | acc | tac | atc | ggc | 768 |      |
| Gly | Leu | Leu | Ala | Asp | Ala | Pro | Thr | Pro | Leu | Gly | Thr | Tyr | Ile | Gly |     |      |
|     |     |     |     | 245 |     |     |     |     | 250 |     |     |     |     | 255 |     |      |
| gtc | gcc | ggc | gac | gcg | gag | atc | acc | cgg | ctg | gtc | gag | gag | tcg | gac | ggg | 816  |
| Val | Ala | Gly | Asp | Ala | Glu | Ile | Thr | Arg | Leu | Val | Glu | Glu | Ser | Asp | Gly |      |
|     |     |     | 260 |     |     |     |     | 265 |     |     |     |     | 270 |     |     |      |
| ctg | ttc | ctg | ctc | ggc | gcg | atc | ctc | agc | gac | acc | aac | ttc | gcg | gtg | tcc | 864  |
| Leu | Phe | Leu | Leu | Gly | Ala | Ile | Leu | Ser | Asp | Thr | Asn | Phe | Ala | Val | Ser |      |
|     |     | 275 |     |     |     |     | 280 |     |     |     |     | 285 |     |     |     |      |
| cag | cgc | aag | atc | gac | ctg | cgc | aag | acc | atc | cac | gcc | ttc | gac | cgg | gcg | 912  |
| Gln | Arg | Lys | Ile | Asp | Leu | Arg | Lys | Thr | Ile | His | Ala | Phe | Asp | Arg | Ala |      |
|     | 290 |     |     |     |     | 295 |     |     |     |     | 300 |     |     |     |     |      |
| gtg | acg | ctg | ggc | tat | cac | acc | tac | gcc | gac | atc | ccg | ctg | gcc | ggg | ctg | 960  |
| Val | Thr | Leu | Gly | Tyr | His | Thr | Tyr | Ala | Asp | Ile | Pro | Leu | Ala | Gly | Leu |      |
| 305 |     |     |     |     | 310 |     |     |     |     | 315 |     |     |     |     | 320 |      |
| gtg | gac | gcc | ctc | ttg | gaa | ggg | ctg | ccg | ccg | tcc | gac | cgg | acg | acc | cgc | 1008 |
| Val | Asp | Ala | Leu | Leu | Glu | Gly | Leu | Pro | Pro | Ser | Asp | Arg | Thr | Thr | Arg |      |
|     |     |     |     | 325 |     |     |     |     | 330 |     |     |     |     | 335 |     |      |
| ggc | aag | gag | ccc | cac | gcc | tac | ccg | acc | ggc | ctt | cag | gcg | gac | ggc | gag | 1056 |
| Gly | Lys | Glu | Pro | His | Ala | Tyr | Pro | Thr | Gly | Leu | Gln | Ala | Asp | Gly | Glu |      |
|     |     |     | 340 |     |     |     |     | 345 |     |     |     |     | 350 |     |     |      |
| ccg | atc | gcc | ccg | atg | gac | atc | gcc | cgc | gtc | aac | gac | cgc | gtc | cgc | 1104 |      |
| Pro | Ile | Ala | Pro | Met | Asp | Ile | Ala | Arg | Val | Asn | Asp | Arg | Val | Arg |      |      |
|     |     | 355 |     |     |     |     | 360 |     |     |     |     | 365 |     |     |     |      |
| gcc | ggg | cag | gaa | ccg | ctg | ctg | atc | gcg | gcg | gac | atg | ggc | gac | tgc | ctg | 1152 |
| Ala | Gly | Gln | Glu | Pro | Leu | Leu | Ile | Ala | Ala | Asp | Met | Gly | Asp | Cys | Leu |      |
|     | 370 |     |     |     |     | 375 |     |     |     |     | 380 |     |     |     |     |      |
| ttc | acc | gcg | atg | gac | atg | atc | gac | gcc | ggg | ctg | atg | gcg | ccg | ggc | tat | 1200 |
| Phe | Thr | Ala | Met | Asp | Met | Ile | Asp | Ala | Gly | Leu | Met | Ala | Pro | Gly | Tyr |      |
| 385 |     |     |     |     | 390 |     |     |     |     | 395 |     |     |     |     | 400 |      |
| tac | gcg | ggc | atg | ggc | ttc | ggg | gtg | ccg | gcg | ggc | atc | ggg | gcg | cag | tgc | 1248 |
| Tyr | Ala | Gly | Met | Gly | Phe | Gly | Val | Pro | Ala | Gly | Ile | Gly | Ala | Gln | Cys |      |
|     |     |     |     | 405 |     |     |     |     | 410 |     |     |     |     | 415 |     |      |
| gtg | tcg | ggc | ggc | aag | cgc | atc | ctg | acc | gtg | gtc | ggc | gac | ggc | gcc | ttc | 1296 |

```
              Val Ser Gly Gly Lys Arg Ile Leu Thr Val Val Gly Asp Gly Ala Phe
                              420                 425                 430 cag atg acc ggg tgg gag ctt ggc aac tgc cga cgg ctg ggc atc gac            1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc            1392
Pro Ile Val Ile Leu Phe Asn Asn Ala Ser Trp Glu Met Leu Arg Thr
450                 455                 460 ttc cag ccc gaa tcg gcc ttc aac gac ctg gac gac tgg cgc ttc gcc            1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg            1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc            1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg            1584
Phe Gln Leu Ile Glu Ala Met Ile Pro Arg Gly Val Leu Ser Asp Thr
        515                 520                 525 ctg gcc cgc ttc gtc cag ggg att aag cgc ctg cac gcc gcg ccc cgg            1632
Leu Ala Arg Phe Val Gln Gly Ile Lys Arg Leu His Ala Ala Pro Arg
    530                 535                 540 gag taa                                                                    1638
Glu
545
```

<210> SEQ ID NO 38
<211> LENGTH: 545
<212> TYPE: PRT
<213> ORGANISM: Artificial Sequence
<220> FEATURE:
<223> OTHER INFORMATION: Synthetic Construct

<400> SEQUENCE: 38

```
Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
```

```
                    180                 185                 190
Asp Glu Val Leu Ala Ala Met Arg Ser Ala Thr Ser Pro Val Leu Met
                195                 200                 205

Val Cys Val Glu Val Arg Arg Tyr Gly Leu Glu Ala Lys Val Ala Glu
            210                 215                 220

Leu Ala Gln Arg Leu Gly Val Pro Val Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Met Gly Asp Cys Leu
    370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
        435                 440                 445

Pro Ile Val Ile Leu Phe Asn Asn Ala Ser Trp Glu Met Leu Arg Thr
    450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Phe Val Gln Gly Ile Lys Arg Leu His Ala Ala Pro Arg
    530                 535                 540

Glu
545

<210> SEQ ID NO 39
<211> LENGTH: 1638
<212> TYPE: DNA
<213> ORGANISM: Artificial Sequence
<220> FEATURE:
<223> OTHER INFORMATION: Q536V
<220> FEATURE:
```

```
<221> NAME/KEY: CDS
<222> LOCATION: (1)..(1638)

<400> SEQUENCE: 39 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg     576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg     624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag     672
Val Cys Val Glu Val Arg Arg Tyr Gly Leu Glu Ala Lys Val Ala Glu
    210                 215                 220 ctg gcg cag cgg ctg ggc gtg ccg gtg gtg acc acc ttc atg ggg cgc     720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc     768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg     816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc     864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg     912
Gln Arg Lys Ile Asp Leu Arg Lys Thr Ile His Ala Phe Asp Arg Ala
```

```
gtg acg ctg ggc tat cac acc tac gcc gac atc ccg ctg gcc ggg ctg      960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc     1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag     1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc     1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg     1152
Ala Gly Gln Glu Pro Leu Leu Ile Ala Ala Asp Met Gly Asp Cys Leu
370                 375                 380 ttc acc gcg atg gac atg atc gac gcc ggg ctg atg gcg ccg ggc tat     1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc     1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc     1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac     1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc     1392
Pro Ile Val Ile Leu Phe Asn Asn Ala Ser Trp Glu Met Leu Arg Thr
450                 455                 460 ttc cag ccc gaa tcg gcc ttc aac gac ctg gac gac tgg cgc ttc gcc     1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg     1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc     1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg     1584
Phe Gln Leu Ile Glu Ala Met Ile Pro Arg Gly Val Leu Ser Asp Thr
        515                 520                 525 ctg gcc cgc ttc gtc cag ggg gtt aag cgc ctg cac gcc gcg ccc cgg     1632
Leu Ala Arg Phe Val Gln Gly Val Lys Arg Leu His Ala Ala Pro Arg
530                 535                 540 gag taa                                                              1638
Glu
545

<210> SEQ ID NO 40
<211> LENGTH: 545
<212> TYPE: PRT
<213> ORGANISM: Artificial Sequence
<220> FEATURE:
<223> OTHER INFORMATION: Synthetic Construct

<400> SEQUENCE: 40

Met Lys Leu Ala Glu Ala Leu Leu Arg Ala Leu Lys Asp Arg Gly Ala
1               5                   10                  15
```

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Met Gly Asp Cys Leu
370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp

```
                435                 440                 445
Pro Ile Val Ile Leu Phe Asn Asn Ala Ser Trp Glu Met Leu Arg Thr
450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
                485                 490                 495

Ala Glu Leu Lys Ala Ala Leu Asp Lys Ala Phe Ala Thr Arg Gly Arg
                500                 505                 510

Phe Gln Leu Ile Glu Ala Met Ile Pro Arg Gly Val Leu Ser Asp Thr
            515                 520                 525

Leu Ala Arg Phe Val Gln Gly Val Lys Arg Leu His Ala Ala Pro Arg
        530                 535                 540

Glu
545

<210> SEQ ID NO 41
<211> LENGTH: 1638
<212> TYPE: DNA
<213> ORGANISM: Artificial Sequence
<220> FEATURE:
<223> OTHER INFORMATION: F532V/Q536V
<220> FEATURE:
<221> NAME/KEY: CDS
<222> LOCATION: (1)..(1638)

<400> SEQUENCE: 41 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
    130                 135                 140 atc gcc cgc gtg ctg ggg gcc gcc gcc ctg tcg cgc ccg gtc tat         480
Ile Ala Arg Val Leu Gly Ala Ala Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175
```

```
gac gac ccg gct tgg ccg gtg gac cgc gac gcg ctg gcc gcc tgc gcg      576
Asp Asp Pro Ala Trp Pro Val Asp Arg Asp Ala Leu Ala Ala Cys Ala
        180                 185                 190 gac gag gtg ctg gcg gcc atg cgc tcg gcc acg tcg ccg gtg ctg atg      624
Asp Glu Val Leu Ala Ala Met Arg Ser Ala Thr Ser Pro Val Leu Met
            195                 200                 205 gtc tgc gtc gag gtc cgc cgc tac ggg ctg gag gcc aag gtg gcg gag      672
Val Cys Val Glu Val Arg Arg Tyr Gly Leu Glu Ala Lys Val Ala Glu
        210                 215                 220 ctg gcg cag cgg ctg ggc gtg ccg gtg gtg acc acc ttc atg ggg cgc      720
Leu Ala Gln Arg Leu Gly Val Pro Val Val Thr Thr Phe Met Gly Arg
225                 230                 235                 240 ggc ctg ctg gcc gac gcg ccg acc ccg ccc ctc ggc acc tac atc ggc      768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg      816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc      864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg      912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg      960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc     1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag     1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc     1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg     1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat     1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc     1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc     1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac     1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc     1392
Pro Ile Val Ile Leu Phe Asn Asn Ala Ser Trp Glu Met Leu Arg Thr
    450                 455                 460 ttc cag ccc gaa tcg gcc ttc aac gac ctg gac gac tgg cgc ttc gcc     1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg     1488
Asp Met Ala Ala Gly Met Gly Gly Asp Gly Val Arg Val Arg Thr Arg
```

```
                        485                 490                 495
gcg gag ctg aag gcg gcg ctg gac aag gcc ttc gcc acg cgc ggg cgc    1536
Ala Glu Leu Lys Ala Ala Leu Asp Lys Ala Phe Ala Thr Arg Gly Arg
        500                 505                 510 ttc cag ctg atc gag gcg atg atc ccg cgc ggc gtg ctg tcc gac acg    1584
Phe Gln Leu Ile Glu Ala Met Ile Pro Arg Gly Val Leu Ser Asp Thr
        515                 520                 525 ctg gcc cgc gtg gtc cag ggg gtt aag cgc ctg cac gcc gcg ccc cgg    1632
Leu Ala Arg Val Val Gln Gly Val Lys Arg Leu His Ala Ala Pro Arg
        530                 535                 540 gag taa                                                            1638
Glu
545

<210> SEQ ID NO 42
<211> LENGTH: 545
<212> TYPE: PRT
<213> ORGANISM: Artificial Sequence
<220> FEATURE:
<223> OTHER INFORMATION: Synthetic Construct

<400> SEQUENCE: 42

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Ser Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270
```

```
Leu Phe Leu Leu Gly Ala Ile Leu Ser Asp Thr Asn Phe Ala Val Ser
            275                 280                 285

Gln Arg Lys Ile Asp Leu Arg Lys Thr Ile His Ala Phe Asp Arg Ala
        290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Met Gly Asp Cys Leu
    370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
        435                 440                 445

Pro Ile Val Ile Leu Phe Asn Asn Ala Ser Trp Glu Met Leu Arg Thr
    450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Val Val Gln Gly Val Lys Arg Leu His Ala Ala Pro Arg
    530                 535                 540

Glu
545

<210> SEQ ID NO 43
<211> LENGTH: 1638
<212> TYPE: DNA
<213> ORGANISM: Artificial Sequence
<220> FEATURE:
<223> OTHER INFORMATION: M380L/M461V
<220> FEATURE:
<221> NAME/KEY: CDS
<222> LOCATION: (1)..(1638)

<400> SEQUENCE: 43 atg aag ctg gcc gaa gcc ctg ctg cgc gcg ctg aag gat cgc ggc gca     48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag     96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag    144
Val Ala Glu Glu Thr Gln Ile Leu Pro Leu His Thr Leu Ser His Glu
        35                  40                  45
```

| | | |
|---|---|---|
| ccg gcg gtg ggc ttc gcg gcg gac gcg gcg gcg cgt tac agt tcg acg<br>Pro Ala Val Gly Phe Ala Ala Asp Ala Ala Ala Arg Tyr Ser Ser Thr<br>50                          55                        60 | | 192 |
| ctg ggg gtg gcg gcg gtc acc tac gga gcg ggc gcc ttc aac atg gtg<br>Leu Gly Val Ala Ala Val Thr Tyr Gly Ala Gly Ala Phe Asn Met Val<br>65                        70                        75                        80 | | 240 |
| aac gcg gtg gcc ggc gcc tac gcc gag aag tcg ccg gtc gtc gtc atc<br>Asn Ala Val Ala Gly Ala Tyr Ala Glu Lys Ser Pro Val Val Val Ile<br>                        85                        90                        95 | | 288 |
| tcc ggc gcg ccg ggc acg acg gag ggc aac gcc ggc ctg ctg ctg cac<br>Ser Gly Ala Pro Gly Thr Thr Glu Gly Asn Ala Gly Leu Leu Leu His<br>                      100                      105                      110 | | 336 |
| cac cag ggc cgc acg ctg gac acg cag ttc cag gtg ttc aag gag atc<br>His Gln Gly Arg Thr Leu Asp Thr Gln Phe Gln Val Phe Lys Glu Ile<br>                115                      120                      125 | | 384 |
| acc gtc gcc cag gcg cgg ctg gac gac ccg gcc aag gcc ccg gcg gag<br>Thr Val Ala Gln Ala Arg Leu Asp Asp Pro Ala Lys Ala Pro Ala Glu<br>130                        135                        140 | | 432 |
| atc gcc cgc gtg ctg ggg gcc gcc cgc gcc ctg tcg cgc ccg gtc tat<br>Ile Ala Arg Val Leu Gly Ala Ala Arg Ala Leu Ser Arg Pro Val Tyr<br>145                        150                        155                        160 | | 480 |
| ctg gaa att ccc cgc aac atg gtc aac gcc gag gtc gag ccg gtg ggc<br>Leu Glu Ile Pro Arg Asn Met Val Asn Ala Glu Val Glu Pro Val Gly<br>                        165                      170                      175 | | 528 |
| gac gac ccg gct tgg ccg gtg gac cgc gac gcg ctg gcc gcc tgc gcg<br>Asp Asp Pro Ala Trp Pro Val Asp Arg Asp Ala Leu Ala Ala Cys Ala<br>                180                      185                      190 | | 576 |
| gac gag gtg ctg gcg gcc atg cgc tcg gcc acg tcg ccg gtg ctg atg<br>Asp Glu Val Leu Ala Ala Met Arg Ser Ala Thr Ser Pro Val Leu Met<br>            195                      200                      205 | | 624 |
| gtc tgc gtc gag gtc cgc cgc tac ggg ctg gag gcc aag gtg gcg gag<br>Val Cys Val Glu Val Arg Arg Tyr Gly Leu Glu Ala Lys Val Ala Glu<br>210                        215                        220 | | 672 |
| ctg gcg cag cgg ctg ggc gtg ccg gtg gtg acc acc ttc atg ggg cgc<br>Leu Ala Gln Arg Leu Gly Val Pro Val Val Thr Thr Phe Met Gly Arg<br>225                        230                        235                        240 | | 720 |
| ggc ctg ctg gcc gac gcg ccg acc ccg ccg ctc ggc acc tac atc ggc<br>Gly Leu Leu Ala Asp Ala Pro Thr Pro Pro Leu Gly Thr Tyr Ile Gly<br>                        245                      250                      255 | | 768 |
| gtc gcc ggc gac gcg gag atc acc cgg ctg gtc gag gag tcg gac ggg<br>Val Ala Gly Asp Ala Glu Ile Thr Arg Leu Val Glu Glu Ser Asp Gly<br>                260                      265                      270 | | 816 |
| ctg ttc ctg ctc ggc gcg atc ctc agc gac acc aac ttc gcg gtg tcc<br>Leu Phe Leu Leu Gly Ala Ile Leu Ser Asp Thr Asn Phe Ala Val Ser<br>            275                      280                      285 | | 864 |
| cag cgc aag atc gac ctg cgc aag acc atc cac gcc ttc gac cgg gcg<br>Gln Arg Lys Ile Asp Leu Arg Lys Thr Ile His Ala Phe Asp Arg Ala<br>290                        295                        300 | | 912 |
| gtg acg ctg ggc tat cac acc tac gcc gac atc ccg ctg gcc ggg ctg<br>Val Thr Leu Gly Tyr His Thr Tyr Ala Asp Ile Pro Leu Ala Gly Leu<br>305                        310                        315                        320 | | 960 |
| gtg gac gcc ctc ttg gaa ggg ctg ccg ccg tcc gac cgg acg acc cgc<br>Val Asp Ala Leu Leu Glu Gly Leu Pro Pro Ser Asp Arg Thr Thr Arg<br>                        325                      330                      335 | | 1008 |
| ggc aag gag ccc cac gcc tac ccg acc ggc ctt cag gcg gac ggc gag<br>Gly Lys Glu Pro His Ala Tyr Pro Thr Gly Leu Gln Ala Asp Gly Glu<br>                        340                      345                      350 | | 1056 |
| ccg atc gcc ccg atg gac atc gcc cgc gcc gtc aac gac cgc gtc cgc<br>Pro Ile Ala Pro Met Asp Ile Ala Arg Ala Val Asn Asp Arg Val Arg<br>355                        360                      365 | | 1104 |

```
gcc ggg cag gaa ccg ctg ctg atc gcg gcg gac ctg ggc gac tgc ctg      1152
Ala Gly Gln Glu Pro Leu Leu Ile Ala Ala Asp Leu Gly Asp Cys Leu
    370                 375                 380 ttc acc gcg atg gac atg atc gac gcc ggg ctg atg gcg ccg ggc tat      1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag gtg ctg cgc acc      1392
Pro Ile Val Ile Leu Phe Asn Asn Ala Ser Trp Glu Val Leu Arg Thr
    450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
        515                 520                 525 ctg gcc cgc ttc gtc cag ggg cag aag cgc ctg cac gcc gcg ccc cgg      1632
Leu Ala Arg Phe Val Gln Gly Gln Lys Arg Leu His Ala Ala Pro Arg
    530                 535                 540 gag taa                                                              1638
Glu
545

<210> SEQ ID NO 44
<211> LENGTH: 545
<212> TYPE: PRT
<213> ORGANISM: Artificial Sequence
<220> FEATURE:
<223> OTHER INFORMATION: Synthetic Construct

<400> SEQUENCE: 44

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
                20                  25                  30

Val Ala Glu Glu Thr Gln Ile Leu Pro Leu His Thr Leu Ser His Glu
            35                  40                  45

Pro Ala Val Gly Phe Ala Ala Asp Ala Ala Arg Tyr Ser Ser Thr
        50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110
```

```
His Gln Gly Arg Thr Leu Asp Thr Gln Phe Gln Val Phe Lys Glu Ile
            115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
            165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
            195                 200                 205

Val Cys Val Glu Val Arg Arg Tyr Gly Leu Glu Ala Lys Val Ala Glu
            210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                    245                 250                 255

Val Ala Gly Asp Ala Glu Ile Thr Arg Leu Val Glu Glu Ser Asp Gly
                    260                 265                 270

Leu Phe Leu Leu Gly Ala Ile Leu Ser Asp Thr Asn Phe Ala Val Ser
            275                 280                 285

Gln Arg Lys Ile Asp Leu Arg Lys Thr Ile His Ala Phe Asp Arg Ala
            290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                    325                 330                 335

Gly Lys Glu Pro His Ala Tyr Pro Thr Gly Leu Gln Ala Asp Gly Glu
                    340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Leu Gly Asp Cys Leu
            370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                    405                 410                 415

Val Ser Gly Gly Lys Arg Ile Leu Thr Val Val Gly Asp Gly Ala Phe
                    420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Val Leu Arg Thr
            450                 455                 460

Phe Gln Pro Glu Ser Ala Phe Asn Asp Leu Asp Trp Arg Phe Ala
465                 470                 475                 480

Asp Met Ala Ala Gly Met Gly Gly Asp Gly Val Arg Val Arg Thr Arg
                    485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
            515                 520                 525
```

```
                Leu Ala Arg Phe Val Gln Gly Gln Lys Arg Leu His Ala Ala Pro Arg
                    530                 535                 540

Glu
                545

<210> SEQ ID NO 45
<211> LENGTH: 1638
<212> TYPE: DNA
<213> ORGANISM: Artificial Sequence
<220> FEATURE:
<223> OTHER INFORMATION: M380V/M461V
<220> FEATURE:
<221> NAME/KEY: CDS
<222> LOCATION: (1)..(1638)

<400> SEQUENCE: 45 atg aag ctg gcc gaa gcc ctg ctg cgc gcg ctg aag gat cgc ggc gca       48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag       96
Gln Ala Met Phe Gly Ile Pro Gly Asp Phe Ala Leu Pro Phe Phe Lys
                20                  25                  30 gtg gcg gag gaa acg cag atc ctg ccg ctc cac acg ctg agc cac gag      144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg      192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg      240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc      288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac      336
Ser Gly Ala Pro Gly Thr Thr Glu Gly Asn Ala Gly Leu Leu Leu His
                100                 105                 110 cac cag ggc cgc acg ctg gac acg cag ttc cag gtg ttc aag gag atc      384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag      432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat      480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc      528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg      576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg      624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag      672
Val Cys Val Glu Val Arg Arg Tyr Gly Leu Glu Ala Lys Val Ala Glu
    210                 215                 220 ctg gcg cag cgg ctg ggc gtg ccg gtg gtg acc acc ttc atg ggg cgc      720
Leu Ala Gln Arg Leu Gly Val Pro Val Val Thr Thr Phe Met Gly Arg
225                 230                 235                 240
```

```
ggc ctg ctg gcc gac gcg ccg acc ccg ctc ggc acc tac atc ggc         768
Gly Leu Leu Ala Asp Ala Pro Thr Pro Leu Gly Thr Tyr Ile Gly
            245                 250                 255 gtc gcc ggc gac gcg gag atc acc cgg ctg gtc gag gag tcg gac ggg     816
Val Ala Gly Asp Ala Glu Ile Thr Arg Leu Val Glu Glu Ser Asp Gly
        260                 265                 270 ctg ttc ctg ctc ggc gcg atc ctc agc gac acc aac ttc gcg gtg tcc     864
Leu Phe Leu Leu Gly Ala Ile Leu Ser Asp Thr Asn Phe Ala Val Ser
            275                 280                 285 cag cgc aag atc gac ctg cgc aag acc atc cac gcc ttc gac cgg gcg     912
Gln Arg Lys Ile Asp Leu Arg Lys Thr Ile His Ala Phe Asp Arg Ala
        290                 295                 300 gtg acg ctg ggc tat cac acc tac gcc gac atc ccg ctg gcc ggg ctg     960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc    1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag    1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc    1104
Pro Ile Ala Pro Met Asp Ile Ala Arg Ala Val Asn Asp Arg Val Arg
        355                 360                 365 gcc ggg cag gaa ccg ctg ctg atc gcg gcg gac gtg ggc gac tgc ctg    1152
Ala Gly Gln Glu Pro Leu Leu Ile Ala Ala Asp Val Gly Asp Cys Leu
    370                 375                 380 ttc acc gcg atg gac atg atc gac gcc ggg ctg atg gcg ccg ggc tat    1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc    1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc    1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac    1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag gtg ctg cgc acc    1392
Pro Ile Val Ile Leu Phe Asn Asn Ala Ser Trp Glu Val Leu Arg Thr
    450                 455                 460 ttc cag ccc gaa tcg gcc ttc aac gac ctg gac gac tgg cgc ttc gcc    1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg    1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc    1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg    1584
Phe Gln Leu Ile Glu Ala Met Ile Pro Arg Gly Val Leu Ser Asp Thr
        515                 520                 525 ctg gcc cgc ttc gtc cag ggg cag aag cgc ctg cac gcc gcg ccc cgg    1632
Leu Ala Arg Phe Val Gln Gly Gln Lys Arg Leu His Ala Ala Pro Arg
    530                 535                 540 gag taa                                                             1638
Glu
545
```

<210> SEQ ID NO 46
<211> LENGTH: 545
<212> TYPE: PRT
<213> ORGANISM: Artificial Sequence
<220> FEATURE:
<223> OTHER INFORMATION: Synthetic Construct

<400> SEQUENCE: 46

```
Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
            115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
            195                 200                 205

Val Cys Val Glu Val Arg Arg Tyr Gly Leu Glu Ala Lys Val Ala Glu
        210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365
```

```
Ala Gly Gln Glu Pro Leu Leu Ile Ala Ala Asp Val Gly Asp Cys Leu
    370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
        435                 440                 445

Pro Ile Val Ile Leu Phe Asn Asn Ala Ser Trp Glu Val Leu Arg Thr
    450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Phe Val Gln Gly Gln Lys Arg Leu His Ala Ala Pro Arg
    530                 535                 540

Glu
545

<210> SEQ ID NO 47
<211> LENGTH: 1638
<212> TYPE: DNA
<213> ORGANISM: Artificial Sequence
<220> FEATURE:
<223> OTHER INFORMATION: F385V/M461V
<220> FEATURE:
<221> NAME/KEY: CDS
<222> LOCATION: (1)..(1638)

<400> SEQUENCE: 47 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
```

-continued

```
                His Gln Gly Arg Thr Leu Asp Thr Gln Phe Gln Val Phe Lys Glu Ile
                            115                 120                 125 acc gtc gcc cag gcg cgg ctg gac gac ccg gcc aag gcc ccg gcg gag            432
Thr Val Ala Gln Ala Arg Leu Asp Asp Pro Ala Lys Ala Pro Ala Glu
            130                 135                 140 atc gcc cgc gtg ctg ggg gcc gcc cgc gcc ctg tcg cgc ccg gtc tat            480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc            528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg            576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg            624
Asp Glu Val Leu Ala Ala Met Arg Ser Ala Thr Ser Pro Val Leu Met
            195                 200                 205 gtc tgc gtc gag gtc cgc cgc tac ggg ctg gag gcc aag gtg gcg gag            672
Val Cys Val Glu Val Arg Arg Tyr Gly Leu Glu Ala Lys Val Ala Glu
210                 215                 220 ctg gcg cag cgg ctg ggc gtg ccg gtg gtg acc acc ttc atg ggg cgc            720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc            768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg            816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc            864
Leu Phe Leu Leu Gly Ala Ile Leu Ser Asp Thr Asn Phe Ala Val Ser
            275                 280                 285 cag cgc aag atc gac ctg cgc aag acc atc cac gcc ttc gac cgg gcg            912
Gln Arg Lys Ile Asp Leu Arg Lys Thr Ile His Ala Phe Asp Arg Ala
            290                 295                 300 gtg acg ctg ggc tat cac acc tac gcc gac atc ccg ctg gcc ggg ctg            960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc           1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag           1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc           1104
Pro Ile Ala Pro Met Asp Ile Ala Arg Ala Val Asn Asp Arg Val Arg
            355                 360                 365 gcc ggg cag gaa ccg ctg ctg atc gcg gcg gac atg ggc gac tgc ctg           1152
Ala Gly Gln Glu Pro Leu Leu Ile Ala Ala Asp Met Gly Asp Cys Leu
370                 375                 380 gtg acc gcg atg gac atg atc gac gcc ggg ctg atg gcg ccg ggc tat           1200
Val Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc           1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc           1296
Val Ser Gly Gly Lys Arg Ile Leu Thr Val Val Gly Asp Gly Ala Phe
            420                 425                 430
```

```
cag atg acc ggg tgg gag ctt ggc aac tgc cga cgg ctg ggc atc gac    1344
Gln Met Thr Gly Trp Glu Leu Gly Asn Cys Arg Arg Leu Gly Ile Asp
            435                 440                 445 ccc atc gtg atc ctg ttc aac aac gcc agt tgg gag gtg ctg cgc acc    1392
Pro Ile Val Ile Leu Phe Asn Asn Ala Ser Trp Glu Val Leu Arg Thr
    450                 455                 460 ttc cag ccc gaa tcg gcc ttc aac gac ctg gac gac tgg cgc ttc gcc    1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg    1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc    1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg    1584
Phe Gln Leu Ile Glu Ala Met Ile Pro Arg Gly Val Leu Ser Asp Thr
    515                 520                 525 ctg gcc cgc ttc gtc cag ggg cag aag cgc ctg cac gcc gcg ccc cgg    1632
Leu Ala Arg Phe Val Gln Gly Gln Lys Arg Leu His Ala Ala Pro Arg
530                 535                 540 gag taa                                                            1638
Glu
545

<210> SEQ ID NO 48
<211> LENGTH: 545
<212> TYPE: PRT
<213> ORGANISM: Artificial Sequence
<220> FEATURE:
<223> OTHER INFORMATION: Synthetic Construct

<400> SEQUENCE: 48

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
```

```
                195                 200                 205
Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Met Gly Asp Cys Leu
370                 375                 380

Val Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
        435                 440                 445

Pro Ile Val Ile Leu Phe Asn Asn Ala Ser Trp Glu Val Leu Arg Thr
450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Phe Val Gln Gly Gln Lys Arg Leu His Ala Ala Pro Arg
530                 535                 540

Glu
545

<210> SEQ ID NO 49
<211> LENGTH: 1638
<212> TYPE: DNA
<213> ORGANISM: Artificial Sequence
<220> FEATURE:
<223> OTHER INFORMATION: F385L/M461V
<220> FEATURE:
<221> NAME/KEY: CDS
<222> LOCATION: (1)..(1638)
```

-continued

```
<400> SEQUENCE: 49 atg aag ctg gcc gaa gcc ctg ctg cgc gcg ctg aag gat cgc ggc gca    48
Met Lys Leu Ala Glu Ala Leu Leu Arg Ala Leu Lys Asp Arg Gly Ala
 1               5                  10                  15 cag gcc atg ttc ggg att ccg ggt gat ttc gcc ctg ccc ttc ttc aag    96
Gln Ala Met Phe Gly Ile Pro Gly Asp Phe Ala Leu Pro Phe Phe Lys
             20                  25                  30 gtg gcg gag gaa acg cag atc ctg ccg ctc cac acg ctg agc cac gag   144
Val Ala Glu Glu Thr Gln Ile Leu Pro Leu His Thr Leu Ser His Glu
         35                  40                  45 ccg gcg gtg ggc ttc gcg gcg gac gcg gcg gcg cgt tac agt tcg acg   192
Pro Ala Val Gly Phe Ala Ala Asp Ala Ala Ala Arg Tyr Ser Ser Thr
     50                  55                  60 ctg ggg gtg gcg gcg gtc acc tac gga gcg ggc gcc ttc aac atg gtg   240
Leu Gly Val Ala Ala Val Thr Tyr Gly Ala Gly Ala Phe Asn Met Val
 65                  70                  75                  80 aac gcg gtg gcc ggc gcc tac gcc gag aag tcg ccg gtg gtc gtc atc   288
Asn Ala Val Ala Gly Ala Tyr Ala Glu Lys Ser Pro Val Val Val Ile
                 85                  90                  95 tcc ggc gcg ccg ggc acg acg gag ggc aac gcc ggc ctg ctg ctg cac   336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc   384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag   432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat   480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc   528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg   576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg   624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag   672
Val Cys Val Glu Val Arg Arg Tyr Gly Leu Glu Ala Lys Val Ala Glu
    210                 215                 220 ctg gcg cag cgg ctg ggc gtg ccg gtg gtg acc acc ttc atg ggg cgc   720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc   768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg   816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc   864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg   912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg   960
Val Thr Leu Gly Tyr His Thr Tyr Ala Asp Ile Pro Leu Ala Gly Leu
```

```
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc       1008
Val Asp Ala Leu Leu Glu Gly Leu Pro Pro Ser Asp Arg Thr Thr Arg
                    325                 330                 335 ggc aag gag ccc cac gcc tac ccg acc ggc ctt cag gcg gac ggc gag       1056
Gly Lys Glu Pro His Ala Tyr Pro Thr Gly Leu Gln Ala Asp Gly Glu
                340                 345                 350 ccg atc gcc ccg atg gac atc gcc cgc gcc gtc aac gac cgc gtc cgc       1104
Pro Ile Ala Pro Met Asp Ile Ala Arg Ala Val Asn Asp Arg Val Arg
            355                 360                 365 gcc ggg cag gaa ccg ctg ctg atc gcg gcg gac atg ggc gac tgc ctg       1152
Ala Gly Gln Glu Pro Leu Leu Ile Ala Ala Asp Met Gly Asp Cys Leu
        370                 375                 380 ctg acc gcg atg gac atg atc gac gcc ggg ctg atg gcg ccg ggc tat       1200
Leu Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc       1248
Tyr Ala Gly Met Gly Phe Gly Val Pro Ala Gly Ile Gly Ala Gln Cys
                    405                 410                 415 gtg tcg ggc ggc aag cgc atc ctg acc gtg gtc ggc gac ggc gcc ttc       1296
Val Ser Gly Gly Lys Arg Ile Leu Thr Val Val Gly Asp Gly Ala Phe
                420                 425                 430 cag atg acc ggg tgg gag ctt ggc aac tgc cga cgg ctg ggc atc gac       1344
Gln Met Thr Gly Trp Glu Leu Gly Asn Cys Arg Arg Leu Gly Ile Asp
            435                 440                 445 ccc atc gtg atc ctg ttc aac aac gcc agt tgg gag gtg ctg cgc acc       1392
Pro Ile Val Ile Leu Phe Asn Asn Ala Ser Trp Glu Val Leu Arg Thr
        450                 455                 460 ttc cag ccc gaa tcg gcc ttc aac gac ctg gac gac tgg cgc ttc gcc       1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg       1488
Asp Met Ala Ala Gly Met Gly Gly Asp Gly Val Arg Val Arg Thr Arg
                    485                 490                 495 gcg gag ctg aag gcg gcg ctg gac aag gcc ttc gcc acg cgc ggg cgc       1536
Ala Glu Leu Lys Ala Ala Leu Asp Lys Ala Phe Ala Thr Arg Gly Arg
                500                 505                 510 ttc cag ctg atc gag gcg atg atc ccg cgc ggc gtg ctg tcc gac acg       1584
Phe Gln Leu Ile Glu Ala Met Ile Pro Arg Gly Val Leu Ser Asp Thr
            515                 520                 525 ctg gcc cgc ttc gtc cag ggg cag aag cgc ctg cac gcc gcg ccc cgg       1632
Leu Ala Arg Phe Val Gln Gly Gln Lys Arg Leu His Ala Ala Pro Arg
        530                 535                 540 gag taa                                                                1638
Glu
545

<210> SEQ ID NO 50
<211> LENGTH: 545
<212> TYPE: PRT
<213> ORGANISM: Artificial Sequence
<220> FEATURE:
<223> OTHER INFORMATION: Synthetic Construct

<400> SEQUENCE: 50

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30
```

```
Val Ala Glu Glu Thr Gln Ile Leu Pro Leu His Thr Leu Ser His Glu
     35                  40                  45

Pro Ala Val Gly Phe Ala Ala Asp Ala Ala Arg Tyr Ser Ser Thr
 50                  55                  60

Leu Gly Val Ala Ala Val Thr Tyr Gly Ala Gly Ala Phe Asn Met Val
 65                  70                  75                  80

Asn Ala Val Ala Gly Ala Tyr Ala Glu Lys Ser Pro Val Val Ile
                 85                  90                  95

Ser Gly Ala Pro Gly Thr Thr Glu Gly Asn Ala Gly Leu Leu Leu His
                100                 105                 110

His Gln Gly Arg Thr Leu Asp Thr Gln Phe Gln Val Phe Lys Glu Ile
                115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
                180                 185                 190

Asp Glu Val Leu Ala Ala Met Arg Ser Ala Thr Ser Pro Val Leu Met
                195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
                260                 265                 270

Leu Phe Leu Leu Gly Ala Ile Leu Ser Asp Thr Asn Phe Ala Val Ser
                275                 280                 285

Gln Arg Lys Ile Asp Leu Arg Lys Thr Ile His Ala Phe Asp Arg Ala
290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
                340                 345                 350

Pro Ile Ala Pro Met Asp Ile Ala Arg Ala Val Asn Asp Arg Val Arg
                355                 360                 365

Ala Gly Gln Glu Pro Leu Leu Ile Ala Ala Asp Met Gly Asp Cys Leu
370                 375                 380

Leu Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
                420                 425                 430

Gln Met Thr Gly Trp Glu Leu Gly Asn Cys Arg Arg Leu Gly Ile Asp
                435                 440                 445

Pro Ile Val Ile Leu Phe Asn Asn Ala Ser Trp Glu Val Leu Arg Thr
```

```
                 450               455               460
Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
                500                 505                 510

Phe Gln Leu Ile Glu Ala Met Ile Pro Arg Gly Val Leu Ser Asp Thr
            515                 520                 525

Leu Ala Arg Phe Val Gln Gly Gln Lys Arg Leu His Ala Ala Pro Arg
        530                 535                 540

Glu
545

<210> SEQ ID NO 51
<211> LENGTH: 1638
<212> TYPE: DNA
<213> ORGANISM: Artificial Sequence
<220> FEATURE:
<223> OTHER INFORMATION: F532A/Q536V
<220> FEATURE:
<221> NAME/KEY: CDS
<222> LOCATION: (1)..(1638)

<400> SEQUENCE: 51 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg     576
Asp Asp Pro Ala Trp Pro Val Asp Arg Asp Ala Leu Ala Ala Cys Ala
```

```
                180                 185                 190
gac gag gtg ctg gcg gcc atg cgc tcg gcc acg tcg ccg gtg ctg atg        624
Asp Glu Val Leu Ala Ala Met Arg Ser Ala Thr Ser Pro Val Leu Met
            195                 200                 205 gtc tgc gtc gag gtc cgc cgc tac ggg ctg gag gcc aag gtg gcg gag        672
Val Cys Val Glu Val Arg Arg Tyr Gly Leu Glu Ala Lys Val Ala Glu
210                 215                 220 ctg gcg cag cgg ctg ggc gtg ccg gtg gtg acc acc ttc atg ggg cgc        720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc        768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg        816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc        864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg        912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg        960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc       1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag       1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc       1104
Pro Ile Ala Pro Met Asp Ile Ala Arg Ala Val Asn Asp Arg Val Arg
        355                 360                 365 gcc ggg cag gaa ccg ctg ctc atc gcg gcg gac atg ggc gac tgc ctg       1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat       1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc       1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc       1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac       1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc       1392
Pro Ile Val Ile Leu Phe Asn Asn Ala Ser Trp Glu Met Leu Arg Thr
    450                 455                 460 ttc cag ccc gaa tcg gcc ttc aac gac ctg gac gac tgg cgc ttc gcc       1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg       1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc       1536
```

```
Ala Glu Leu Lys Ala Ala Leu Asp Lys Ala Phe Ala Thr Arg Gly Arg
                500                 505                 510
```

```
ttc cag ctg atc gag gcg atg atc ccg cgc ggc gtg ctg tcc gac acg    1584
Phe Gln Leu Ile Glu Ala Met Ile Pro Arg Gly Val Leu Ser Asp Thr
        515                 520                 525
```

```
ctg gcc cgc gcg gtc cag ggg gtg aag cgc ctg cac gcc gcg ccc cgg    1632
Leu Ala Arg Ala Val Gln Gly Val Lys Arg Leu His Ala Ala Pro Arg
        530                 535                 540
```

```
gag taa                                                             1638
Glu
545
```

<210> SEQ ID NO 52
<211> LENGTH: 545
<212> TYPE: PRT
<213> ORGANISM: Artificial Sequence
<220> FEATURE:
<223> OTHER INFORMATION: Synthetic Construct

<400> SEQUENCE: 52

```
Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
            85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
            115                 120                 125

Thr Val Ala Gln Ala Arg Leu Asp Asp Pro Ala Lys Ala Pro Ala Glu
        130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
            165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
            245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285
```

```
Gln Arg Lys Ile Asp Leu Arg Lys Thr Ile His Ala Phe Asp Arg Ala
    290                 295                 300
Val Thr Leu Gly Tyr His Thr Tyr Ala Asp Ile Pro Leu Ala Gly Leu
305                 310                 315                 320
Val Asp Ala Leu Leu Glu Gly Leu Pro Pro Ser Asp Arg Thr Thr Arg
                325                 330                 335
Gly Lys Glu Pro His Ala Tyr Pro Thr Gly Leu Gln Ala Asp Gly Glu
            340                 345                 350
Pro Ile Ala Pro Met Asp Ile Ala Arg Ala Val Asn Asp Arg Val Arg
        355                 360                 365
Ala Gly Gln Glu Pro Leu Leu Ile Ala Ala Asp Met Gly Asp Cys Leu
370                 375                 380
Phe Thr Ala Met Asp Met Ile Asp Ala Gly Leu Met Ala Pro Gly Tyr
385                 390                 395                 400
Tyr Ala Gly Met Gly Phe Gly Val Pro Ala Gly Ile Gly Ala Gln Cys
                405                 410                 415
Val Ser Gly Gly Lys Arg Ile Leu Thr Val Val Gly Asp Gly Ala Phe
            420                 425                 430
Gln Met Thr Gly Trp Glu Leu Gly Asn Cys Arg Arg Leu Gly Ile Asp
        435                 440                 445
Pro Ile Val Ile Leu Phe Asn Asn Ala Ser Trp Glu Met Leu Arg Thr
    450                 455                 460
Phe Gln Pro Glu Ser Ala Phe Asn Asp Leu Asp Asp Trp Arg Phe Ala
465                 470                 475                 480
Asp Met Ala Ala Gly Met Gly Gly Asp Gly Val Arg Val Arg Thr Arg
                485                 490                 495
Ala Glu Leu Lys Ala Ala Leu Asp Lys Ala Phe Ala Thr Arg Gly Arg
            500                 505                 510
Phe Gln Leu Ile Glu Ala Met Ile Pro Arg Gly Val Leu Ser Asp Thr
        515                 520                 525
Leu Ala Arg Ala Val Gln Gly Val Lys Arg Leu His Ala Ala Pro Arg
    530                 535                 540
Glu
545

<210> SEQ ID NO 53
<211> LENGTH: 1638
<212> TYPE: DNA
<213> ORGANISM: Artificial Sequence
<220> FEATURE:
<223> OTHER INFORMATION: F532V/Q536A
<220> FEATURE:
<221> NAME/KEY: CDS
<222> LOCATION: (1)..(1638)

<400> SEQUENCE: 53 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
    50                  55                  60
```

```
ctg ggg gtg gcg gcg gtc acc tac gga gcg ggc gcc ttc aac atg gtg    240
Leu Gly Val Ala Ala Val Thr Tyr Gly Ala Gly Ala Phe Asn Met Val
 65                  70                  75                  80 aac gcg gtg gcc ggc gcc tac gcc gag aag tcg ccg gtc gtc atc        288
Asn Ala Val Ala Gly Ala Tyr Ala Glu Lys Ser Pro Val Val Val Ile
                     85                  90                  95 tcc ggc gcg ccg ggc acg acg gag ggc aac gcc ggc ctg ctg ctg cac    336
Ser Gly Ala Pro Gly Thr Thr Glu Gly Asn Ala Gly Leu Leu Leu His
                100                 105                 110 cac cag ggc cgc acg ctg gac acg cag ttc cag gtg ttc aag gag atc    384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag    432
Thr Val Ala Gln Ala Arg Leu Asp Asp Pro Ala Lys Ala Pro Ala Glu
130                 135                 140 atc gcc cgc gtg ctg ggg gcc gcc cgc gcc ctg tcg cgc ccg gtc tat    480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc    528
Leu Glu Ile Pro Arg Asn Met Val Asn Ala Glu Val Glu Pro Val Gly
                    165                 170                 175 gac gac ccg gct tgg ccg gtg gac cgc gac gcg ctg gcc gcc tgc gcg    576
Asp Asp Pro Ala Trp Pro Val Asp Arg Asp Ala Leu Ala Ala Cys Ala
                180                 185                 190 gac gag gtg ctg gcg gcc atg cgc tcg gcc acg tcg ccg gtg ctg atg    624
Asp Glu Val Leu Ala Ala Met Arg Ser Ala Thr Ser Pro Val Leu Met
            195                 200                 205 gtc tgc gtc gag gtc cgc cgc tac ggg ctg gag gcc aag gtg gcg gag    672
Val Cys Val Glu Val Arg Arg Tyr Gly Leu Glu Ala Lys Val Ala Glu
        210                 215                 220 ctg gcg cag cgg ctg ggc gtg ccg gtg gtg acc acc ttc atg ggg cgc    720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc    768
Gly Leu Leu Ala Asp Ala Pro Thr Pro Pro Leu Gly Thr Tyr Ile Gly
                    245                 250                 255 gtc gcc ggc gac gcg gag atc acc cgg ctg gtc gag gag tcg gac ggg    816
Val Ala Gly Asp Ala Glu Ile Thr Arg Leu Val Glu Glu Ser Asp Gly
                260                 265                 270 ctg ttc ctg ctc ggc gcg atc ctc agc gac acc aac ttc gcg gtg tcc    864
Leu Phe Leu Leu Gly Ala Ile Leu Ser Asp Thr Asn Phe Ala Val Ser
            275                 280                 285 cag cgc aag atc gac ctg cgc aag acc atc cac gcc ttc gac cgg gcg    912
Gln Arg Lys Ile Asp Leu Arg Lys Thr Ile His Ala Phe Asp Arg Ala
        290                 295                 300 gtg acg ctg ggc tat cac acc tac gcc gac atc ccg ctg gcc ggg ctg    960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc    1008
Val Asp Ala Leu Leu Glu Gly Leu Pro Pro Ser Asp Arg Thr Thr Arg
                    325                 330                 335 ggc aag gag ccc cac gcc tac ccg acc ggc ctt cag gcg gac ggc gag    1056
Gly Lys Glu Pro His Ala Tyr Pro Thr Gly Leu Gln Ala Asp Gly Glu
                340                 345                 350 ccg atc gcc ccg atg gac atc gcc cgc gcc gtc aac gac cgc gtc cgc    1104
Pro Ile Ala Pro Met Asp Ile Ala Arg Ala Val Asn Asp Arg Val Arg
            355                 360                 365 gcc ggg cag gaa ccg ctg ctg atc gcg gcg gac atg ggc gac tgc ctg    1152
Ala Gly Gln Glu Pro Leu Leu Ile Ala Ala Asp Met Gly Asp Cys Leu
```

```
                       370                 375                 380
ttc acc gcg atg gac atg atc gac gcc ggg ctg atg gcg ccg ggc tat      1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc      1392
Pro Ile Val Ile Leu Phe Asn Asn Ala Ser Trp Glu Met Leu Arg Thr
    450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
                500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
            515                 520                 525 ctg gcc cgc gtg gtc cag ggg gcg aag cgc ctg cac gcc gcg ccc cgg      1632
Leu Ala Arg Val Val Gln Gly Ala Lys Arg Leu His Ala Ala Pro Arg
        530                 535                 540 gag taa                                                              1638
Glu
545

<210> SEQ ID NO 54
<211> LENGTH: 545
<212> TYPE: PRT
<213> ORGANISM: Artificial Sequence
<220> FEATURE:
<223> OTHER INFORMATION: Synthetic Construct

<400> SEQUENCE: 54

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
                20                  25                  30

Val Ala Glu Thr Gln Ile Leu Pro Leu His Thr Leu Ser His Glu
            35                  40                  45

Pro Ala Val Gly Phe Ala Ala Asp Ala Ala Ala Arg Tyr Ser Ser Thr
        50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125
```

```
Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Met Gly Asp Cys Leu
    370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
        435                 440                 445

Pro Ile Val Ile Leu Phe Asn Asn Ala Ser Trp Glu Met Leu Arg Thr
    450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Val Val Gln Gly Ala Lys Arg Leu His Ala Ala Pro Arg
    530                 535                 540
```

Glu
545

```
<210> SEQ ID NO 55
<211> LENGTH: 1638
<212> TYPE: DNA
<213> ORGANISM: Artificial Sequence
<220> FEATURE:
<223> OTHER INFORMATION: F385L/Q536V
<220> FEATURE:
<221> NAME/KEY: CDS
<222> LOCATION: (1)..(1638)

<400> SEQUENCE: 55
```

| | | | | | | | | | | | | | | | | |
|---|---|---|---|---|---|---|---|---|---|---|---|---|---|---|---|---|
| atg | aag | ctg | gcc | gaa | gcc | ctg | ctg | cgc | gcg | ctg | aag | gat | cgc | ggc | gca | 48 |
| Met | Lys | Leu | Ala | Glu | Ala | Leu | Leu | Arg | Ala | Leu | Lys | Asp | Arg | Gly | Ala | |
| 1 | | | | 5 | | | | | 10 | | | | | 15 | | |
| cag | gcc | atg | ttc | ggg | att | ccg | ggt | gat | ttc | gcc | ctg | ccc | ttc | ttc | aag | 96 |
| Gln | Ala | Met | Phe | Gly | Ile | Pro | Gly | Asp | Phe | Ala | Leu | Pro | Phe | Phe | Lys | |
| | | | 20 | | | | | 25 | | | | | 30 | | | |
| gtg | gcg | gag | gaa | acg | cag | atc | ctg | ccc | ctc | cac | acg | ctg | agc | cac | gag | 144 |
| Val | Ala | Glu | Glu | Thr | Gln | Ile | Leu | Pro | Leu | His | Thr | Leu | Ser | His | Glu | |
| | | 35 | | | | | 40 | | | | | 45 | | | | |
| ccg | gcg | gtg | ggc | ttc | gcg | gcg | gac | gcg | gcg | cgt | tac | agt | tcg | acg | | 192 |
| Pro | Ala | Val | Gly | Phe | Ala | Ala | Asp | Ala | Ala | Arg | Tyr | Ser | Ser | Thr | | |
| | 50 | | | | | 55 | | | | | 60 | | | | | |
| ctg | ggg | gtg | gcg | gcg | gtc | acc | tac | gga | gcg | ggc | gcc | ttc | aac | atg | gtg | 240 |
| Leu | Gly | Val | Ala | Ala | Val | Thr | Tyr | Gly | Ala | Gly | Ala | Phe | Asn | Met | Val | |
| 65 | | | | | 70 | | | | | 75 | | | | | 80 | |
| aac | gcg | gtg | gcc | ggc | gcc | tac | gcc | gag | aag | tcg | ccg | gtg | gtc | gtc | atc | 288 |
| Asn | Ala | Val | Ala | Gly | Ala | Tyr | Ala | Glu | Lys | Ser | Pro | Val | Val | Val | Ile | |
| | | | | 85 | | | | | 90 | | | | | 95 | | |
| tcc | ggc | gcg | ccg | ggc | acg | acg | gag | ggc | aac | gcc | ggc | ctg | ctg | ctg | cac | 336 |
| Ser | Gly | Ala | Pro | Gly | Thr | Thr | Glu | Gly | Asn | Ala | Gly | Leu | Leu | Leu | His | |
| | | | 100 | | | | | 105 | | | | | 110 | | | |
| cac | cag | ggc | cgc | acg | ctg | gac | acg | cag | ttc | cag | gtg | ttc | aag | gag | atc | 384 |
| His | Gln | Gly | Arg | Thr | Leu | Asp | Thr | Gln | Phe | Gln | Val | Phe | Lys | Glu | Ile | |
| | | 115 | | | | | 120 | | | | | 125 | | | | |
| acc | gtc | gcc | cag | gcg | cgg | ctg | gac | gac | ccg | gcc | aag | gcc | ccg | gcg | gag | 432 |
| Thr | Val | Ala | Gln | Ala | Arg | Leu | Asp | Asp | Pro | Ala | Lys | Ala | Pro | Ala | Glu | |
| | 130 | | | | | 135 | | | | | 140 | | | | | |
| atc | gcc | cgc | gtg | ctg | ggg | gcc | gcc | cgc | gcc | ctg | tcg | cgc | ccg | gtc | tat | 480 |
| Ile | Ala | Arg | Val | Leu | Gly | Ala | Ala | Arg | Ala | Leu | Ser | Arg | Pro | Val | Tyr | |
| 145 | | | | | 150 | | | | | 155 | | | | | 160 | |
| ctg | gaa | att | ccc | cgc | aac | atg | gtc | aac | gcc | gag | gtc | gag | ccg | gtg | ggc | 528 |
| Leu | Glu | Ile | Pro | Arg | Asn | Met | Val | Asn | Ala | Glu | Val | Glu | Pro | Val | Gly | |
| | | | | 165 | | | | | 170 | | | | | 175 | | |
| gac | gac | ccg | gct | tgg | ccg | gtc | gac | cgc | gac | gcg | ctg | gcc | gcc | tgc | gcg | 576 |
| Asp | Asp | Pro | Ala | Trp | Pro | Val | Asp | Arg | Asp | Ala | Leu | Ala | Ala | Cys | Ala | |
| | | | 180 | | | | | 185 | | | | | 190 | | | |
| gac | gag | gtg | ctg | gcg | gcc | atg | cgc | tcg | gcc | acg | tcg | ccg | gtg | ctg | atg | 624 |
| Asp | Glu | Val | Leu | Ala | Ala | Met | Arg | Ser | Ala | Thr | Ser | Pro | Val | Leu | Met | |
| | | 195 | | | | | 200 | | | | | 205 | | | | |
| gtc | tgc | gtc | gag | gtc | cgc | cgc | tac | ggg | ctg | gag | gcc | aag | gtg | gcg | gag | 672 |
| Val | Cys | Val | Glu | Val | Arg | Arg | Tyr | Gly | Leu | Glu | Ala | Lys | Val | Ala | Glu | |
| | 210 | | | | | 215 | | | | | 220 | | | | | |
| ctg | gcg | cag | cgg | ctg | ggc | gtg | ccg | gtg | gtg | acc | acc | ttc | atg | ggg | cgc | 720 |
| Leu | Ala | Gln | Arg | Leu | Gly | Val | Pro | Val | Val | Thr | Thr | Phe | Met | Gly | Arg | |
| 225 | | | | | 230 | | | | | 235 | | | | | 240 | |
| ggc | ctg | ctg | gcc | gac | gcg | ccg | acc | ccg | ccg | ctc | ggc | acc | tac | atc | ggc | 768 |
| Gly | Leu | Leu | Ala | Asp | Ala | Pro | Thr | Pro | Pro | Leu | Gly | Thr | Tyr | Ile | Gly | |
| | | | | 245 | | | | | 250 | | | | | 255 | | |

-continued

| | | |
|---|---|---|
| gtc gcc ggc gac gcg gag atc acc cgg ctg gtc gag gag tcg gac ggg<br>Val Ala Gly Asp Ala Glu Ile Thr Arg Leu Val Glu Glu Ser Asp Gly<br>260                 265                 270 | 816 |
| ctg ttc ctg ctc ggc gcg atc ctc agc gac acc aac ttc gcg gtg tcc<br>Leu Phe Leu Leu Gly Ala Ile Leu Ser Asp Thr Asn Phe Ala Val Ser<br>275                 280                 285 | 864 |
| cag cgc aag atc gac ctg cgc aag acc atc cac gcc ttc gac cgg gcg<br>Gln Arg Lys Ile Asp Leu Arg Lys Thr Ile His Ala Phe Asp Arg Ala<br>290                 295                 300 | 912 |
| gtg acg ctg ggc tat cac acc tac gcc gac atc ccg ctg gcc ggg ctg<br>Val Thr Leu Gly Tyr His Thr Tyr Ala Asp Ile Pro Leu Ala Gly Leu<br>305                 310                 315                 320 | 960 |
| gtg gac gcc ctc ttg gaa ggg ctg ccg ccg tcc gac cgg acg acc cgc<br>Val Asp Ala Leu Leu Glu Gly Leu Pro Pro Ser Asp Arg Thr Thr Arg<br>325                 330                 335 | 1008 |
| ggc aag gag ccc cac gcc tac ccg acc ggc ctt cag gcg gac ggc gag<br>Gly Lys Glu Pro His Ala Tyr Pro Thr Gly Leu Gln Ala Asp Gly Glu<br>340                 345                 350 | 1056 |
| ccg atc gcc ccg atg gac atc gcc cgc gcc gtc aac gac cgc gtc cgc<br>Pro Ile Ala Pro Met Asp Ile Ala Arg Ala Val Asn Asp Arg Val Arg<br>355                 360                 365 | 1104 |
| gcc ggg cag gaa ccg ctg ctg atc gcg gcg gac atg ggc gac tgc ctg<br>Ala Gly Gln Glu Pro Leu Leu Ile Ala Ala Asp Met Gly Asp Cys Leu<br>370                 375                 380 | 1152 |
| ctg acc gcg atg gac atg atc gac gcc ggg ctg atg gcg ccg ggc tat<br>Leu Thr Ala Met Asp Met Ile Asp Ala Gly Leu Met Ala Pro Gly Tyr<br>385                 390                 395                 400 | 1200 |
| tac gcg ggc atg ggc ttc ggg gtg ccg gcg ggc atc ggg gcg cag tgc<br>Tyr Ala Gly Met Gly Phe Gly Val Pro Ala Gly Ile Gly Ala Gln Cys<br>405                 410                 415 | 1248 |
| gtg tcg ggc ggc aag cgc atc ctg acc gtg gtc ggc gac ggc gcc ttc<br>Val Ser Gly Gly Lys Arg Ile Leu Thr Val Val Gly Asp Gly Ala Phe<br>420                 425                 430 | 1296 |
| cag atg acc ggg tgg gag ctt ggc aac tgc cga cgg ctg ggc atc gac<br>Gln Met Thr Gly Trp Glu Leu Gly Asn Cys Arg Arg Leu Gly Ile Asp<br>435                 440                 445 | 1344 |
| ccc atc gtg atc ctg ttc aac aac gcc agt tgg gag atg ctg cgc acc<br>Pro Ile Val Ile Leu Phe Asn Asn Ala Ser Trp Glu Met Leu Arg Thr<br>450                 455                 460 | 1392 |
| ttc cag ccc gaa tcg gcc ttc aac gac ctg gac gac tgg cgc ttc gcc<br>Phe Gln Pro Glu Ser Ala Phe Asn Asp Leu Asp Asp Trp Arg Phe Ala<br>465                 470                 475                 480 | 1440 |
| gac atg gcg gcg ggc atg ggc ggc gac ggc gtc cgc gtg cgc aca cgg<br>Asp Met Ala Ala Gly Met Gly Gly Asp Gly Val Arg Val Arg Thr Arg<br>485                 490                 495 | 1488 |
| gcg gag ctg aag gcg gcg ctg gac aag gcc ttc gcc acg cgc ggg cgc<br>Ala Glu Leu Lys Ala Ala Leu Asp Lys Ala Phe Ala Thr Arg Gly Arg<br>500                 505                 510 | 1536 |
| ttc cag ctg atc gag gcg atg atc ccg cgc ggc gtg ctg tcc gac acg<br>Phe Gln Leu Ile Glu Ala Met Ile Pro Arg Gly Val Leu Ser Asp Thr<br>515                 520                 525 | 1584 |
| ctg gcc cgc ttc gtc cag ggg gtg aag cgc ctg cac gcc gcg ccc cgg<br>Leu Ala Arg Phe Val Gln Gly Val Lys Arg Leu His Ala Ala Pro Arg<br>530                 535                 540 | 1632 |
| gag taa<br>Glu<br>545 | 1638 |

<210> SEQ ID NO 56

<211> LENGTH: 545
<212> TYPE: PRT
<213> ORGANISM: Artificial Sequence
<220> FEATURE:
<223> OTHER INFORMATION: Synthetic Construct

<400> SEQUENCE: 56

| | | | | | | | | | | | | | | |
|---|---|---|---|---|---|---|---|---|---|---|---|---|---|---|
| Met | Lys | Leu | Ala | Glu | Ala | Leu | Leu | Arg | Ala | Leu | Lys | Asp | Arg | Gly | Ala |
| 1 | | | | 5 | | | | | 10 | | | | | 15 | |
| Gln | Ala | Met | Phe | Gly | Ile | Pro | Gly | Asp | Phe | Ala | Leu | Pro | Phe | Phe | Lys |
| | | | 20 | | | | | 25 | | | | | 30 | | |
| Val | Ala | Glu | Glu | Thr | Gln | Ile | Leu | Pro | Leu | His | Thr | Leu | Ser | His | Glu |
| | | | 35 | | | | | 40 | | | | | 45 | | |
| Pro | Ala | Val | Gly | Phe | Ala | Ala | Asp | Ala | Ala | Arg | Tyr | Ser | Ser | Thr | |
| | 50 | | | | | 55 | | | | | 60 | | | | |
| Leu | Gly | Val | Ala | Ala | Val | Thr | Tyr | Gly | Ala | Gly | Ala | Phe | Asn | Met | Val |
| 65 | | | | | 70 | | | | | 75 | | | | | 80 |
| Asn | Ala | Val | Ala | Gly | Ala | Tyr | Ala | Glu | Lys | Ser | Pro | Val | Val | Ile | |
| | | | | 85 | | | | | 90 | | | | | 95 | |
| Ser | Gly | Ala | Pro | Gly | Thr | Thr | Glu | Gly | Asn | Ala | Gly | Leu | Leu | Leu | His |
| | | | 100 | | | | | 105 | | | | | 110 | | |
| His | Gln | Gly | Arg | Thr | Leu | Asp | Thr | Gln | Phe | Gln | Val | Phe | Lys | Glu | Ile |
| | | | 115 | | | | | 120 | | | | | 125 | | |
| Thr | Val | Ala | Gln | Ala | Arg | Leu | Asp | Asp | Pro | Ala | Lys | Ala | Pro | Ala | Glu |
| | 130 | | | | | 135 | | | | | 140 | | | | |
| Ile | Ala | Arg | Val | Leu | Gly | Ala | Ala | Arg | Ala | Leu | Ser | Arg | Pro | Val | Tyr |
| 145 | | | | | 150 | | | | | 155 | | | | | 160 |
| Leu | Glu | Ile | Pro | Arg | Asn | Met | Val | Asn | Ala | Glu | Val | Glu | Pro | Val | Gly |
| | | | | 165 | | | | | 170 | | | | | 175 | |
| Asp | Asp | Pro | Ala | Trp | Pro | Val | Arg | Asp | Ala | Leu | Ala | Ala | Cys | Ala | |
| | | | 180 | | | | | 185 | | | | | 190 | | |
| Asp | Glu | Val | Leu | Ala | Ala | Met | Arg | Ser | Ala | Thr | Ser | Pro | Val | Leu | Met |
| | | | 195 | | | | | 200 | | | | | 205 | | |
| Val | Cys | Val | Glu | Val | Arg | Arg | Tyr | Gly | Leu | Glu | Ala | Lys | Val | Ala | Glu |
| | 210 | | | | | 215 | | | | | 220 | | | | |
| Leu | Ala | Gln | Arg | Leu | Gly | Val | Pro | Val | Val | Thr | Thr | Phe | Met | Gly | Arg |
| 225 | | | | | 230 | | | | | 235 | | | | | 240 |
| Gly | Leu | Leu | Ala | Asp | Ala | Pro | Thr | Pro | Pro | Leu | Gly | Thr | Tyr | Ile | Gly |
| | | | | 245 | | | | | 250 | | | | | 255 | |
| Val | Ala | Gly | Asp | Ala | Glu | Ile | Thr | Arg | Leu | Val | Glu | Glu | Ser | Asp | Gly |
| | | | 260 | | | | | 265 | | | | | 270 | | |
| Leu | Phe | Leu | Leu | Gly | Ala | Ile | Leu | Ser | Asp | Thr | Asn | Phe | Ala | Val | Ser |
| | | | 275 | | | | | 280 | | | | | 285 | | |
| Gln | Arg | Lys | Ile | Asp | Leu | Arg | Lys | Thr | Ile | His | Ala | Phe | Asp | Arg | Ala |
| | 290 | | | | | 295 | | | | | 300 | | | | |
| Val | Thr | Leu | Gly | Tyr | His | Thr | Tyr | Ala | Asp | Ile | Pro | Leu | Ala | Gly | Leu |
| 305 | | | | | 310 | | | | | 315 | | | | | 320 |
| Val | Asp | Ala | Leu | Leu | Glu | Gly | Leu | Pro | Pro | Ser | Asp | Arg | Thr | Thr | Arg |
| | | | | 325 | | | | | 330 | | | | | 335 | |
| Gly | Lys | Glu | Pro | His | Ala | Tyr | Pro | Thr | Gly | Leu | Gln | Ala | Asp | Gly | Glu |
| | | | 340 | | | | | 345 | | | | | 350 | | |
| Pro | Ile | Ala | Pro | Met | Asp | Ile | Ala | Arg | Ala | Val | Asn | Asp | Arg | Val | Arg |
| | | | 355 | | | | | 360 | | | | | 365 | | |
| Ala | Gly | Gln | Glu | Pro | Leu | Leu | Ile | Ala | Ala | Asp | Met | Gly | Asp | Cys | Leu |
| | 370 | | | | | 375 | | | | | 380 | | | | |

```
Leu Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
        420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Met Leu Arg Thr
        450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Phe Val Gln Gly Val Lys Arg Leu His Ala Ala Pro Arg
    530                 535                 540

Glu
545

<210> SEQ ID NO 57
<211> LENGTH: 1638
<212> TYPE: DNA
<213> ORGANISM: Artificial Sequence
<220> FEATURE:
<223> OTHER INFORMATION: F385V/Q536V
<220> FEATURE:
<221> NAME/KEY: CDS
<222> LOCATION: (1)..(1638)

<400> SEQUENCE: 57 atg aag ctg gcc gaa gcc ctg ctg cgc gcg ctg aag gat cgc ggc gca    48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag    96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag   144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg   192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg   240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc   288
Asn Ala Val Ala Gly Ala Tyr Ala Glu Lys Ser Pro Val Val Val Ile
            85                  90                  95 tcc ggc gcg ccg ggc acg acg gag ggc aac gcc ggc ctg ctg ctg cac   336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc   384
His Gln Gly Arg Thr Leu Asp Thr Gln Phe Gln Val Phe Lys Glu Ile
        115                 120                 125
```

-continued

| | | |
|---|---|---|
| acc gtc gcc cag gcg cgg ctg gac gac ccg gcc aag gcc ccg gcg gag<br>Thr Val Ala Gln Ala Arg Leu Asp Asp Pro Ala Lys Ala Pro Ala Glu<br>130                        135                 140 | 432 |
| atc gcc cgc gtg ctg ggg gcc gcc cgc gcc ctg tcg cgc ccg gtc tat<br>Ile Ala Arg Val Leu Gly Ala Ala Arg Ala Leu Ser Arg Pro Val Tyr<br>145                 150                 155               160 | 480 |
| ctg gaa att ccc cgc aac atg gtc aac gcc gag gtc gag ccg gtc ggc<br>Leu Glu Ile Pro Arg Asn Met Val Asn Ala Glu Val Glu Pro Val Gly<br>               165               170               175 | 528 |
| gac gac ccg gct tgg ccg gtc gac cgc gac gcg ctg gcc gcc tgc gcg<br>Asp Asp Pro Ala Trp Pro Val Asp Arg Asp Ala Leu Ala Ala Cys Ala<br>         180                 185               190 | 576 |
| gac gag gtg ctg gcg gcc atg cgc tcg gcc acg tcg ccg gtg ctg atg<br>Asp Glu Val Leu Ala Ala Met Arg Ser Ala Thr Ser Pro Val Leu Met<br>             195               200               205 | 624 |
| gtc tgc gtc gag gtc cgc cgc tac ggg ctg gag gcc aag gtg gcg gag<br>Val Cys Val Glu Val Arg Arg Tyr Gly Leu Glu Ala Lys Val Ala Glu<br>210                        215                 220 | 672 |
| ctg gcg cag cgg ctg ggc gtg ccg gtg gtg acc acc ttc atg ggg cgc<br>Leu Ala Gln Arg Leu Gly Val Pro Val Val Thr Thr Phe Met Gly Arg<br>225                        230                 235               240 | 720 |
| ggc ctg ctg gcc gac gcg ccg acc ccg ctc ggc acc tac atc ggc<br>Gly Leu Leu Ala Asp Ala Pro Thr Pro Pro Leu Gly Thr Tyr Ile Gly<br>                     245               250               255 | 768 |
| gtc gcc ggc gac gcg gag atc acc cgg ctg gtc gag gag tcg gac ggg<br>Val Ala Gly Asp Ala Glu Ile Thr Arg Leu Val Glu Glu Ser Asp Gly<br>         260                 265               270 | 816 |
| ctg ttc ctg ctc ggc gcg atc ctc agc gac acc aac ttc gcg gtg tcc<br>Leu Phe Leu Leu Gly Ala Ile Leu Ser Asp Thr Asn Phe Ala Val Ser<br>             275               280               285 | 864 |
| cag cgc aag atc gac ctg cgc aag acc atc cac gcc ttc gac cgg gcg<br>Gln Arg Lys Ile Asp Leu Arg Lys Thr Ile His Ala Phe Asp Arg Ala<br>290                        295                 300 | 912 |
| gtg acg ctg ggc tat cac acc tac gcc gac atc ccg ctg gcc ggg ctg<br>Val Thr Leu Gly Tyr His Thr Tyr Ala Asp Ile Pro Leu Ala Gly Leu<br>305                        310                 315               320 | 960 |
| gtg gac gcc ctc ttg gaa ggg ctg ccg ccg tcc gac cgg acg acc cgc<br>Val Asp Ala Leu Leu Glu Gly Leu Pro Pro Ser Asp Arg Thr Thr Arg<br>             325               330               335 | 1008 |
| ggc aag gag ccc cac gcc tac ccg acc ggc ctt cag gcg gac ggc gag<br>Gly Lys Glu Pro His Ala Tyr Pro Thr Gly Leu Gln Ala Asp Gly Glu<br>                 340               345               350 | 1056 |
| ccg atc gcc ccg atg gac atc gcc cgc gcc gtc aac gac cgc gtc cgc<br>Pro Ile Ala Pro Met Asp Ile Ala Arg Ala Val Asn Asp Arg Val Arg<br>         355                 360               365 | 1104 |
| gcc ggg cag gaa ccg ctg ctg atc gcg gcg gac atg ggc gac tgc ctg<br>Ala Gly Gln Glu Pro Leu Leu Ile Ala Ala Asp Met Gly Asp Cys Leu<br>370                        375                 380 | 1152 |
| gtg acc gcg atg gac atg atc gac gcc ggg ctg atg gcg ccg ggc tat<br>Val Thr Ala Met Asp Met Ile Asp Ala Gly Leu Met Ala Pro Gly Tyr<br>385                        390                 395               400 | 1200 |
| tac gcg ggc atg ggc ttc ggg gtg ccg gcg ggc atc ggg gcg cag tgc<br>Tyr Ala Gly Met Gly Phe Gly Val Pro Ala Gly Ile Gly Ala Gln Cys<br>                 405               410               415 | 1248 |
| gtg tcg ggc ggc aag cgc atc ctg acc gtg gtc ggc gac ggc gcc ttc<br>Val Ser Gly Gly Lys Arg Ile Leu Thr Val Val Gly Asp Gly Ala Phe<br>         420                 425               430 | 1296 |
| cag atg acc ggg tgg gag ctt ggc aac tgc cga cgg ctg ggc atc gac<br>Gln Met Thr Gly Trp Glu Leu Gly Asn Cys Arg Arg Leu Gly Ile Asp<br>435                        440                 445 | 1344 |

```
ccc atc gtg atc ctg ttc aac aac gcc agt tgg gag atg ctg cgc acc    1392
Pro Ile Val Ile Leu Phe Asn Asn Ala Ser Trp Glu Met Leu Arg Thr
450                 455                 460 ttc cag ccc gaa tcg gcc ttc aac gac ctg gac gac tgg cgc ttc gcc    1440
Phe Gln Pro Glu Ser Ala Phe Asn Asp Leu Asp Asp Trp Arg Phe Ala
465                 470                 475                 480 gac atg gcg gcg ggc atg ggc gac ggc gtc cgc gtg cgc aca cgg        1488
Asp Met Ala Ala Gly Met Gly Asp Gly Val Arg Val Arg Thr Arg
                485                 490                 495 gcg gag ctg aag gcg gcg ctg gac aag gcc ttc gcc acg cgc ggg cgc    1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg    1584
Phe Gln Leu Ile Glu Ala Met Ile Pro Arg Gly Val Leu Ser Asp Thr
            515                 520                 525 ctg gcc cgc ttc gtc cag ggg gtg aag cgc ctg cac gcc gcg ccc cgg    1632
Leu Ala Arg Phe Val Gln Gly Val Lys Arg Leu His Ala Ala Pro Arg
530                 535                 540 gag taa                                                            1638
Glu
545

<210> SEQ ID NO 58
<211> LENGTH: 545
<212> TYPE: PRT
<213> ORGANISM: Artificial Sequence
<220> FEATURE:
<223> OTHER INFORMATION: Synthetic Construct

<400> SEQUENCE: 58

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
```

| | | | | 210 | | | | 215 | | | | 220 | | | |
|---|---|---|---|---|---|---|---|---|---|---|---|---|---|---|---|
Leu Ala Gln Arg Leu Gly Val Pro Val Thr Thr Phe Met Gly Arg
225                 230                 235                 240

Gly Leu Leu Ala Asp Ala Pro Thr Pro Pro Leu Gly Thr Tyr Ile Gly
            245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
            275                 280                 285

Gln Arg Lys Ile Asp Leu Arg Lys Thr Ile His Ala Phe Asp Arg Ala
            290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
            325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Met Gly Asp Cys Leu
370                 375                 380

Val Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Met Leu Arg Thr
            450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
            485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
            515                 520                 525

Leu Ala Arg Phe Val Gln Gly Val Lys Arg Leu His Ala Ala Pro Arg
530                 535                 540

Glu
545

<210> SEQ ID NO 59
<211> LENGTH: 1638
<212> TYPE: DNA
<213> ORGANISM: Artificial Sequence
<220> FEATURE:
<223> OTHER INFORMATION: M461V/Q536V
<220> FEATURE:
<221> NAME/KEY: CDS
<222> LOCATION: (1)..(1638)

<400> SEQUENCE: 59 atg aag ctg gcc gaa gcc ctg ctg cgc gcg ctg aag gat cgc ggc gca        48

-continued

```
                Met Lys Leu Ala Glu Ala Leu Leu Arg Ala Leu Lys Asp Arg Gly Ala
                1               5                   10                  15 cag gcc atg ttc ggg att ccg ggt gat ttc gcc ctg ccc ttc ttc aag              96
Gln Ala Met Phe Gly Ile Pro Gly Asp Phe Ala Leu Pro Phe Phe Lys
                20                  25                  30 gtg gcg gag gaa acg cag atc ctg ccg ctc cac acg ctg agc cac gag            144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg            192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg            240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtc gtc atc                288
Asn Ala Val Ala Gly Ala Tyr Ala Glu Lys Ser Pro Val Val Ile
                85                  90                  95 tcc ggc gcg ccg ggc acg acg gag ggc aac gcc ggc ctg ctg ctg cac            336
Ser Gly Ala Pro Gly Thr Thr Glu Gly Asn Ala Gly Leu Leu Leu His
                100                 105                 110 cac cag ggc cgc acg ctg gac acg cag ttc cag gtg ttc aag gag atc            384
His Gln Gly Arg Thr Leu Asp Thr Gln Phe Gln Val Phe Lys Glu Ile
            115                 120                 125 acc gtc gcc cag gcg cgg ctg gac gac ccg gcc aag gcc ccg gcg gag            432
Thr Val Ala Gln Ala Arg Leu Asp Asp Pro Ala Lys Ala Pro Ala Glu
        130                 135                 140 atc gcc cgc gtg ctg ggg gcc gcc cgc gcc ctg tcg cgc ccg gtc tat            480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc            528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg            576
Asp Asp Pro Ala Trp Pro Val Asp Arg Asp Ala Leu Ala Ala Cys Ala
                180                 185                 190 gac gag gtg ctg gcg gcc atg cgc tcg gcc acg tcg ccg gtg ctg atg            624
Asp Glu Val Leu Ala Ala Met Arg Ser Ala Thr Ser Pro Val Leu Met
            195                 200                 205 gtc tgc gtc gag gtc cgc cgc tac ggg ctg gag gcc aag gtg gcg gag            672
Val Cys Val Glu Val Arg Arg Tyr Gly Leu Glu Ala Lys Val Ala Glu
        210                 215                 220 ctg gcg cag cgg ctg ggc gtg ccg gtg gtg acc acc ttc atg ggg cgc            720
Leu Ala Gln Arg Leu Gly Val Pro Val Val Thr Thr Phe Met Gly Arg
225                 230                 235                 240 ggc ctg ctg gcc gac gcg ccg acc ccg ccc ctc ggc acc tac atc ggc            768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg            816
Val Ala Gly Asp Ala Glu Ile Thr Arg Leu Val Glu Glu Ser Asp Gly
                260                 265                 270 ctg ttc ctg ctc ggc gcg atc ctc agc gac acc aac ttc gcg gtg tcc            864
Leu Phe Leu Leu Gly Ala Ile Leu Ser Asp Thr Asn Phe Ala Val Ser
            275                 280                 285 cag cgc aag atc gac ctg cgc aag acc atc cac gcc ttc gac cgg gcg            912
Gln Arg Lys Ile Asp Leu Arg Lys Thr Ile His Ala Phe Asp Arg Ala
        290                 295                 300 gtg acg ctg ggc tat cac acc tac gcc gac atc ccg ctg gcc ggg ctg            960
Val Thr Leu Gly Tyr His Thr Tyr Ala Asp Ile Pro Leu Ala Gly Leu
305                 310                 315                 320
```

```
gtg gac gcc ctc ttg gaa ggg ctg ccg ccg tcc gac cgg acg acc cgc    1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag    1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc    1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg    1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat    1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc    1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc    1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac    1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag gtg ctg cgc acc    1392
Pro Ile Val Ile Leu Phe Asn Asn Ala Ser Trp Glu Val Leu Arg Thr
    450                 455                 460 ttc cag ccc gaa tcg gcc ttc aac gac ctg gac gac tgg cgc ttc gcc    1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg    1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc    1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg    1584
Phe Gln Leu Ile Glu Ala Met Ile Pro Arg Gly Val Leu Ser Asp Thr
        515                 520                 525 ctg gcc cgc ttc gtc cag ggg gtg aag cgc ctg cac gcc gcg ccc cgg    1632
Leu Ala Arg Phe Val Gln Gly Val Lys Arg Leu His Ala Ala Pro Arg
    530                 535                 540 gag taa                                                              1638
Glu
545

<210> SEQ ID NO 60
<211> LENGTH: 545
<212> TYPE: PRT
<213> ORGANISM: Artificial Sequence
<220> FEATURE:
<223> OTHER INFORMATION: Synthetic Construct

<400> SEQUENCE: 60

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45
```

```
Pro Ala Val Gly Phe Ala Ala Asp Ala Ala Arg Tyr Ser Ser Thr
     50                  55                  60

Leu Gly Val Ala Ala Val Thr Tyr Gly Ala Gly Ala Phe Asn Met Val
 65                  70                  75                  80

Asn Ala Val Ala Gly Ala Tyr Ala Glu Lys Ser Pro Val Val Ile
                 85                  90                  95

Ser Gly Ala Pro Gly Thr Thr Glu Gly Asn Ala Gly Leu Leu Leu His
                100                 105                 110

His Gln Gly Arg Thr Leu Asp Thr Gln Phe Gln Val Phe Lys Glu Ile
                115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
                180                 185                 190

Asp Glu Val Leu Ala Ala Met Arg Ser Ala Thr Ser Pro Val Leu Met
                195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
                260                 265                 270

Leu Phe Leu Leu Gly Ala Ile Leu Ser Asp Thr Asn Phe Ala Val Ser
                275                 280                 285

Gln Arg Lys Ile Asp Leu Arg Lys Thr Ile His Ala Phe Asp Arg Ala
                290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
                340                 345                 350

Pro Ile Ala Pro Met Asp Ile Ala Arg Ala Val Asn Asp Arg Val Arg
                355                 360                 365

Ala Gly Gln Glu Pro Leu Leu Ile Ala Ala Asp Met Gly Asp Cys Leu
370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
                420                 425                 430

Gln Met Thr Gly Trp Glu Leu Gly Asn Cys Arg Arg Leu Gly Ile Asp
                435                 440                 445

Pro Ile Val Ile Leu Phe Asn Asn Ala Ser Trp Glu Val Leu Arg Thr
                450                 455                 460

Phe Gln Pro Glu Ser Ala Phe Asn Asp Leu Asp Asp Trp Arg Phe Ala
```

```
                465                 470                 475                 480
Asp Met Ala Ala Gly Met Gly Gly Asp Gly Val Arg Val Arg Thr Arg
                    485                 490                 495

Ala Glu Leu Lys Ala Ala Leu Asp Lys Ala Phe Ala Thr Arg Gly Arg
                500                 505                 510

Phe Gln Leu Ile Glu Ala Met Ile Pro Arg Gly Val Leu Ser Asp Thr
                515                 520                 525

Leu Ala Arg Phe Val Gln Gly Val Lys Arg Leu His Ala Ala Pro Arg
                530                 535                 540

Glu
545

<210> SEQ ID NO 61
<211> LENGTH: 1638
<212> TYPE: DNA
<213> ORGANISM: Artificial Sequence
<220> FEATURE:
<223> OTHER INFORMATION: M461L/Q536V
<220> FEATURE:
<221> NAME/KEY: CDS
<222> LOCATION: (1)..(1638)

<400> SEQUENCE: 61 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg cgt tac agt tcg acg         192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg     576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg     624
```

-continued

```
                Asp Glu Val Leu Ala Ala Met Arg Ser Ala Thr Ser Pro Val Leu Met
                    195                 200                 205 gtc tgc gtc gag gtc cgc cgc tac ggg ctg gag gcc aag gtg gcg gag        672
Val Cys Val Glu Val Arg Arg Tyr Gly Leu Glu Ala Lys Val Ala Glu
210                 215                 220 ctg gcg cag cgg ctg ggc gtg ccg gtg gtg acc acc ttc atg ggg cgc        720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc        768
Gly Leu Leu Ala Asp Ala Pro Thr Pro Pro Leu Gly Thr Tyr Ile Gly
                    245                 250                 255 gtc gcc ggc gac gcg gag atc acc cgg ctg gtc gag gag tcg gac ggg        816
Val Ala Gly Asp Ala Glu Ile Thr Arg Leu Val Glu Glu Ser Asp Gly
                    260                 265                 270 ctg ttc ctg ctc ggc gcg atc ctc agc gac acc aac ttc gcg gtg tcc        864
Leu Phe Leu Leu Gly Ala Ile Leu Ser Asp Thr Asn Phe Ala Val Ser
                275                 280                 285 cag cgc aag atc gac ctg cgc aag acc atc cac gcc ttc gac cgg gcg        912
Gln Arg Lys Ile Asp Leu Arg Lys Thr Ile His Ala Phe Asp Arg Ala
            290                 295                 300 gtg acg ctg ggc tat cac acc tac gcc gac atc ccg ctg gcc ggg ctg        960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc       1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag       1056
Gly Lys Glu Pro His Ala Tyr Pro Thr Gly Leu Gln Ala Asp Gly Glu
                340                 345                 350 ccg atc gcc ccg atg gac atc gcc cgc gcc gtc aac gac cgc gtc cgc       1104
Pro Ile Ala Pro Met Asp Ile Ala Arg Ala Val Asn Asp Arg Val Arg
            355                 360                 365 gcc ggg cag gaa ccg ctg ctg atc gcg gcg gac atg ggc gac tgc ctg       1152
Ala Gly Gln Glu Pro Leu Leu Ile Ala Ala Asp Met Gly Asp Cys Leu
370                 375                 380 ttc acc gcg atg gac atg atc gac gcc ggg ctg atg gcg ccg ggc tat       1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc       1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc       1296
Val Ser Gly Gly Lys Arg Ile Leu Thr Val Val Gly Asp Gly Ala Phe
                420                 425                 430 cag atg acc ggg tgg gag ctt ggc aac tgc cga cgg ctg ggc atc gac       1344
Gln Met Thr Gly Trp Glu Leu Gly Asn Cys Arg Arg Leu Gly Ile Asp
            435                 440                 445 ccc atc gtg atc ctg ttc aac aac gcc agt tgg gag ctg ctg cgc acc       1392
Pro Ile Val Ile Leu Phe Asn Asn Ala Ser Trp Glu Leu Leu Arg Thr
450                 455                 460 ttc cag ccc gaa tcg gcc ttc aac gac ctg gac gac tgg cgc ttc gcc       1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg       1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc       1536
Ala Glu Leu Lys Ala Ala Leu Asp Lys Ala Phe Ala Thr Arg Gly Arg
                500                 505                 510
```

-continued

```
ttc cag ctg atc gag gcg atg atc ccg cgc ggc gtg ctg tcc gac acg    1584
Phe Gln Leu Ile Glu Ala Met Ile Pro Arg Gly Val Leu Ser Asp Thr
        515                 520                 525 ctg gcc cgc ttc gtc cag ggg gtg aag cgc ctg cac gcc gcg ccc cgg    1632
Leu Ala Arg Phe Val Gln Gly Val Lys Arg Leu His Ala Ala Pro Arg
530                 535                 540 gag taa                                                            1638
Glu
545
```

<210> SEQ ID NO 62
<211> LENGTH: 545
<212> TYPE: PRT
<213> ORGANISM: Artificial Sequence
<220> FEATURE:
<223> OTHER INFORMATION: Synthetic Construct

<400> SEQUENCE: 62

```
Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300
```

```
Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
            325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Met Gly Asp Cys Leu
370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Leu Leu Arg Thr
450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
            485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
515                 520                 525

Leu Ala Arg Phe Val Gln Gly Val Lys Arg Leu His Ala Ala Pro Arg
            530                 535                 540

Glu
545

<210> SEQ ID NO 63
<211> LENGTH: 1638
<212> TYPE: DNA
<213> ORGANISM: Artificial Sequence
<220> FEATURE:
<223> OTHER INFORMATION: M461A/Q536V
<220> FEATURE:
<221> NAME/KEY: CDS
<222> LOCATION: (1)..(1638)

<400> SEQUENCE: 63 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80
```

-continued

| | | | | | | | | | | | | | | | | |
|---|---|---|---|---|---|---|---|---|---|---|---|---|---|---|---|---|
| | 65 | | | | 70 | | | | 75 | | | | 80 | | | |
| aac | gcg | gtg | gcc | ggc | gcc | tac | gcc | gag | aag | tcg | ccg | gtg | gtc | gtc | atc | 288 |
| Asn | Ala | Val | Ala | Gly | Ala | Tyr | Ala | Glu | Lys | Ser | Pro | Val | Val | Val | Ile | |
| | | | | 85 | | | | | 90 | | | | | 95 | | |
| tcc | ggc | gcg | ccg | ggc | acg | acg | gag | ggc | aac | gcc | ggc | ctg | ctg | ctg | cac | 336 |
| Ser | Gly | Ala | Pro | Gly | Thr | Thr | Glu | Gly | Asn | Ala | Gly | Leu | Leu | Leu | His | |
| | | | | 100 | | | | | 105 | | | | | 110 | | |
| cac | cag | ggc | cgc | acg | ctg | gac | acg | cag | ttc | cag | gtg | ttc | aag | gag | atc | 384 |
| His | Gln | Gly | Arg | Thr | Leu | Asp | Thr | Gln | Phe | Gln | Val | Phe | Lys | Glu | Ile | |
| | | | | 115 | | | | | 120 | | | | | 125 | | |
| acc | gtc | gcc | cag | gcg | cgg | ctg | gac | gac | ccg | gcc | aag | gcc | ccg | gcg | gag | 432 |
| Thr | Val | Ala | Gln | Ala | Arg | Leu | Asp | Asp | Pro | Ala | Lys | Ala | Pro | Ala | Glu | |
| | 130 | | | | | 135 | | | | | 140 | | | | | |
| atc | gcc | cgc | gtg | ctg | ggg | gcc | gcc | cgc | gcc | ctg | tcg | cgc | ccg | gtc | tat | 480 |
| Ile | Ala | Arg | Val | Leu | Gly | Ala | Ala | Arg | Ala | Leu | Ser | Arg | Pro | Val | Tyr | |
| 145 | | | | | 150 | | | | | 155 | | | | | 160 | |
| ctg | gaa | att | ccc | cgc | aac | atg | gtc | aac | gcc | gag | gtc | gag | ccg | gtg | ggc | 528 |
| Leu | Glu | Ile | Pro | Arg | Asn | Met | Val | Asn | Ala | Glu | Val | Glu | Pro | Val | Gly | |
| | | | | 165 | | | | | 170 | | | | | 175 | | |
| gac | gac | ccg | gct | tgg | ccg | gtg | gac | cgc | gac | gcg | ctg | gcc | gcc | tgc | gcg | 576 |
| Asp | Asp | Pro | Ala | Trp | Pro | Val | Asp | Arg | Asp | Ala | Leu | Ala | Ala | Cys | Ala | |
| | | | 180 | | | | | 185 | | | | | 190 | | | |
| gac | gag | gtg | ctg | gcg | gcc | atg | cgc | tcg | gcc | acg | tcg | ccg | gtg | ctg | atg | 624 |
| Asp | Glu | Val | Leu | Ala | Ala | Met | Arg | Ser | Ala | Thr | Ser | Pro | Val | Leu | Met | |
| | | 195 | | | | | 200 | | | | | 205 | | | | |
| gtc | tgc | gtc | gag | gtc | cgc | cgc | tac | ggg | ctg | gag | gcc | aag | gtg | gcg | gag | 672 |
| Val | Cys | Val | Glu | Val | Arg | Arg | Tyr | Gly | Leu | Glu | Ala | Lys | Val | Ala | Glu | |
| | 210 | | | | | 215 | | | | | 220 | | | | | |
| ctg | gcg | cag | cgg | ctg | ggc | gtg | ccg | gtg | gtg | acc | acc | ttc | atg | ggg | cgc | 720 |
| Leu | Ala | Gln | Arg | Leu | Gly | Val | Pro | Val | Val | Thr | Thr | Phe | Met | Gly | Arg | |
| 225 | | | | | 230 | | | | | 235 | | | | | 240 | |
| ggc | ctg | ctg | gcc | gac | gcg | ccg | acc | ccg | ctc | ggc | acc | tac | atc | ggc | | 768 |
| Gly | Leu | Leu | Ala | Asp | Ala | Pro | Thr | Pro | Leu | Gly | Thr | Tyr | Ile | Gly | | |
| | | | | 245 | | | | | 250 | | | | | 255 | | |
| gtc | gcc | ggc | gac | gcg | gag | atc | acc | cgg | ctg | gtc | gag | gag | tcg | gac | ggg | 816 |
| Val | Ala | Gly | Asp | Ala | Glu | Ile | Thr | Arg | Leu | Val | Glu | Glu | Ser | Asp | Gly | |
| | | | | 260 | | | | | 265 | | | | | 270 | | |
| ctg | ttc | ctg | ctc | ggc | gcg | atc | ctc | agc | gac | acc | aac | ttc | gcg | gtg | tcc | 864 |
| Leu | Phe | Leu | Leu | Gly | Ala | Ile | Leu | Ser | Asp | Thr | Asn | Phe | Ala | Val | Ser | |
| | | 275 | | | | | 280 | | | | | 285 | | | | |
| cag | cgc | aag | atc | gac | ctg | cgc | aag | acc | atc | cac | gcc | ttc | gac | cgg | gcg | 912 |
| Gln | Arg | Lys | Ile | Asp | Leu | Arg | Lys | Thr | Ile | His | Ala | Phe | Asp | Arg | Ala | |
| | 290 | | | | | 295 | | | | | 300 | | | | | |
| gtg | acg | ctg | ggc | tat | cac | acc | tac | gcc | gac | atc | ccg | ctg | gcc | ggg | ctg | 960 |
| Val | Thr | Leu | Gly | Tyr | His | Thr | Tyr | Ala | Asp | Ile | Pro | Leu | Ala | Gly | Leu | |
| 305 | | | | | 310 | | | | | 315 | | | | | 320 | |
| gtg | gac | gcc | ctc | ttg | gaa | ggg | ctg | ccg | ccg | tcc | gac | cgg | acg | acc | cgc | 1008 |
| Val | Asp | Ala | Leu | Leu | Glu | Gly | Leu | Pro | Pro | Ser | Asp | Arg | Thr | Thr | Arg | |
| | | | | 325 | | | | | 330 | | | | | 335 | | |
| ggc | aag | gag | ccc | cac | gcc | tac | ccg | acc | ggc | ctt | cag | gcg | gac | ggc | gag | 1056 |
| Gly | Lys | Glu | Pro | His | Ala | Tyr | Pro | Thr | Gly | Leu | Gln | Ala | Asp | Gly | Glu | |
| | | | | 340 | | | | | 345 | | | | | 350 | | |
| ccg | atc | gcc | ccg | atg | gac | atc | gcc | cgc | gcc | gtc | aac | gac | cgc | gtc | cgc | 1104 |
| Pro | Ile | Ala | Pro | Met | Asp | Ile | Ala | Arg | Ala | Val | Asn | Asp | Arg | Val | Arg | |
| | | | 355 | | | | | 360 | | | | | 365 | | | |
| gcc | ggg | cag | gaa | ccg | ctg | ctg | atc | gcg | gcg | gac | atg | ggc | gac | tgc | ctg | 1152 |
| Ala | Gly | Gln | Glu | Pro | Leu | Leu | Ile | Ala | Ala | Asp | Met | Gly | Asp | Cys | Leu | |
| | 370 | | | | | 375 | | | | | 380 | | | | | |
| ttc | acc | gcg | atg | gac | atg | atc | gac | gcc | ggg | ctg | atg | gcg | ccg | ggc | tat | 1200 |

```
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag gcg ctg cgc acc      1392
Pro Ile Val Ile Leu Phe Asn Asn Ala Ser Trp Glu Ala Leu Arg Thr
    450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
        515                 520                 525 ctg gcc cgc ttc gtc cag ggg gtg aag cgc ctg cac gcc gcg ccc cgg      1632
Leu Ala Arg Phe Val Gln Gly Val Lys Arg Leu His Ala Ala Pro Arg
    530                 535                 540 gag taa                                                                1638
Glu
545

<210> SEQ ID NO 64
<211> LENGTH: 545
<212> TYPE: PRT
<213> ORGANISM: Artificial Sequence
<220> FEATURE:
<223> OTHER INFORMATION: Synthetic Construct

<400> SEQUENCE: 64

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
                20                  25                  30

Val Ala Glu Glu Thr Gln Ile Leu Pro Leu His Thr Leu Ser His Glu
            35                  40                  45

Pro Ala Val Gly Phe Ala Ala Asp Ala Ala Ala Arg Tyr Ser Ser Thr
        50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140
```

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
            165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
            195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
            245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
            275                 280                 285

Gln Arg Lys Ile Asp Leu Arg Lys Thr Ile His Ala Phe Asp Arg Ala
290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
            325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Met Gly Asp Cys Leu
370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Ala Leu Arg Thr
450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
            485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
            515                 520                 525

Leu Ala Arg Phe Val Gln Gly Val Lys Arg Leu His Ala Ala Pro Arg
530                 535                 540

Glu
545

<210> SEQ ID NO 65
<211> LENGTH: 1638
<212> TYPE: DNA
<213> ORGANISM: Artificial Sequence
<220> FEATURE:
<223> OTHER INFORMATION: M461V/F532V
<220> FEATURE:
<221> NAME/KEY: CDS
<222> LOCATION: (1)..(1638)

<400> SEQUENCE: 65

| | | | | | | | | | | | | | | | | |
|---|---|---|---|---|---|---|---|---|---|---|---|---|---|---|---|---|
| atg | aag | ctg | gcc | gaa | gcc | ctg | ctg | cgc | gcg | ctg | aag | gat | cgc | ggc | gca | 48 |
| Met | Lys | Leu | Ala | Glu | Ala | Leu | Leu | Arg | Ala | Leu | Lys | Asp | Arg | Gly | Ala | |
| 1 | | | | 5 | | | | | 10 | | | | | 15 | | |
| cag | gcc | atg | ttc | ggg | att | ccg | ggt | gat | ttc | gcc | ctg | ccc | ttc | ttc | aag | 96 |
| Gln | Ala | Met | Phe | Gly | Ile | Pro | Gly | Asp | Phe | Ala | Leu | Pro | Phe | Phe | Lys | |
| | | | 20 | | | | | 25 | | | | | 30 | | | |
| gtg | gcg | gag | gaa | acg | cag | atc | ctg | ccg | ctc | acg | ctg | agc | cac | gag | | 144 |
| Val | Ala | Glu | Glu | Thr | Gln | Ile | Leu | Pro | Leu | His | Thr | Leu | Ser | His | Glu | |
| | | | 35 | | | | 40 | | | | | 45 | | | | |
| ccg | gcg | gtg | ggc | ttc | gcg | gcg | gac | gcg | gcg | gcg | cgt | tac | agt | tcg | acg | 192 |
| Pro | Ala | Val | Gly | Phe | Ala | Ala | Asp | Ala | Ala | Ala | Arg | Tyr | Ser | Ser | Thr | |
| | 50 | | | | | 55 | | | | | 60 | | | | | |
| ctg | ggg | gtg | gcg | gcg | gtc | acc | tac | gga | gcg | ggc | gcc | ttc | aac | atg | gtg | 240 |
| Leu | Gly | Val | Ala | Ala | Val | Thr | Tyr | Gly | Ala | Gly | Ala | Phe | Asn | Met | Val | |
| 65 | | | | | 70 | | | | | 75 | | | | | 80 | |
| aac | gcg | gtg | gcc | ggc | gcc | tac | gcc | gag | aag | tcg | ccg | gtg | gtc | gtc | atc | 288 |
| Asn | Ala | Val | Ala | Gly | Ala | Tyr | Ala | Glu | Lys | Ser | Pro | Val | Val | Val | Ile | |
| | | | | 85 | | | | | 90 | | | | | 95 | | |
| tcc | ggc | gcg | ccg | ggc | acg | acg | gag | ggc | aac | gcc | ggc | ctg | ctg | ctg | cac | 336 |
| Ser | Gly | Ala | Pro | Gly | Thr | Thr | Glu | Gly | Asn | Ala | Gly | Leu | Leu | Leu | His | |
| | | | 100 | | | | | 105 | | | | | 110 | | | |
| cac | cag | ggc | cgc | acg | ctg | gac | acg | cag | ttc | cag | gtg | ttc | aag | gag | atc | 384 |
| His | Gln | Gly | Arg | Thr | Leu | Asp | Thr | Gln | Phe | Gln | Val | Phe | Lys | Glu | Ile | |
| | | 115 | | | | | 120 | | | | | 125 | | | | |
| acc | gtc | gcc | cag | gcg | cgg | ctg | gac | gac | ccg | gcc | aag | gcc | ccg | gcg | gag | 432 |
| Thr | Val | Ala | Gln | Ala | Arg | Leu | Asp | Asp | Pro | Ala | Lys | Ala | Pro | Ala | Glu | |
| | 130 | | | | | 135 | | | | | 140 | | | | | |
| atc | gcc | cgc | gtg | ctg | ggg | gcc | gcc | cgc | gcc | ctg | tcg | cgc | ccg | gtc | tat | 480 |
| Ile | Ala | Arg | Val | Leu | Gly | Ala | Ala | Arg | Ala | Leu | Ser | Arg | Pro | Val | Tyr | |
| 145 | | | | | 150 | | | | | 155 | | | | | 160 | |
| ctg | gaa | att | ccc | cgc | aac | atg | gtc | aac | gcc | gag | gtc | gag | ccg | gtg | ggc | 528 |
| Leu | Glu | Ile | Pro | Arg | Asn | Met | Val | Asn | Ala | Glu | Val | Glu | Pro | Val | Gly | |
| | | | | 165 | | | | | 170 | | | | | 175 | | |
| gac | gac | ccg | gct | tgg | ccg | gtg | gac | cgc | gac | gcg | ctg | gcc | gcc | tgc | gcg | 576 |
| Asp | Asp | Pro | Ala | Trp | Pro | Val | Asp | Arg | Asp | Ala | Leu | Ala | Ala | Cys | Ala | |
| | | | 180 | | | | | 185 | | | | | 190 | | | |
| gac | gag | gtg | ctg | gcg | gcc | atg | cgc | tcg | gcc | acg | tcg | ccg | gtg | ctg | atg | 624 |
| Asp | Glu | Val | Leu | Ala | Ala | Met | Arg | Ser | Ala | Thr | Ser | Pro | Val | Leu | Met | |
| | | 195 | | | | | 200 | | | | | 205 | | | | |
| gtc | tgc | gtc | gag | gtc | cgc | cgc | tac | ggg | ctg | gag | gcc | aag | gtg | gcg | gag | 672 |
| Val | Cys | Val | Glu | Val | Arg | Arg | Tyr | Gly | Leu | Glu | Ala | Lys | Val | Ala | Glu | |
| | 210 | | | | | 215 | | | | | 220 | | | | | |
| ctg | gcg | cag | cgg | ctg | ggc | gtg | ccg | gtg | gtg | acc | acc | ttc | atg | ggg | cgc | 720 |
| Leu | Ala | Gln | Arg | Leu | Gly | Val | Pro | Val | Val | Thr | Thr | Phe | Met | Gly | Arg | |
| 225 | | | | | 230 | | | | | 235 | | | | | 240 | |
| ggc | ctg | ctg | gcc | gac | gcg | ccg | acc | ccg | ccg | ctc | ggc | acc | tac | atc | ggc | 768 |
| Gly | Leu | Leu | Ala | Asp | Ala | Pro | Thr | Pro | Pro | Leu | Gly | Thr | Tyr | Ile | Gly | |
| | | | | 245 | | | | | 250 | | | | | 255 | | |
| gtc | gcc | ggc | gac | gcg | gag | atc | acc | cgg | ctg | gtc | gag | gag | tcg | gac | ggg | 816 |
| Val | Ala | Gly | Asp | Ala | Glu | Ile | Thr | Arg | Leu | Val | Glu | Glu | Ser | Asp | Gly | |

```
                     260                 265                 270
ctg ttc ctg ctc ggc gcg atc ctc agc gac acc aac ttc gcg gtg tcc        864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg        912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg        960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc       1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag       1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc       1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg       1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat       1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc       1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc       1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac       1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag gtg ctg cgc acc       1392
Pro Ile Val Ile Leu Phe Asn Asn Ala Ser Trp Glu Val Leu Arg Thr
    450                 455                 460 ttc cag ccc gaa tcg gcc ttc aac gac ctg gac gac tgg cgc ttc gcc       1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg       1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc       1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg       1584
Phe Gln Leu Ile Glu Ala Met Ile Pro Arg Gly Val Leu Ser Asp Thr
        515                 520                 525 ctg gcc cgc gtg gtc cag ggg cag aag cgc ctg cac gcc gcg ccc cgg       1632
Leu Ala Arg Val Val Gln Gly Gln Lys Arg Leu His Ala Ala Pro Arg
    530                 535                 540 gag taa                                                                1638
Glu
545

<210> SEQ ID NO 66
<211> LENGTH: 545
<212> TYPE: PRT
<213> ORGANISM: Artificial Sequence
```

<220> FEATURE:
<223> OTHER INFORMATION: Synthetic Construct

<400> SEQUENCE: 66

```
Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
                100                 105                 110

His Gln Gly Arg Thr Leu Asp Thr Gln Phe Gln Val Phe Lys Glu Ile
            115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Met Gly Asp Cys Leu
    370                 375                 380

Phe Thr Ala Met Asp Met Ile Asp Ala Gly Leu Met Ala Pro Gly Tyr
385                 390                 395                 400
```

```
Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
        420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Val Leu Arg Thr
    450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
                500                 505                 510

Phe Gln Leu Ile Glu Ala Met Ile Pro Arg Gly Val Leu Ser Asp Thr
        515                 520                 525

Leu Ala Arg Val Val Gln Gly Gln Lys Arg Leu His Ala Ala Pro Arg
    530                 535                 540

Glu
545

<210> SEQ ID NO 67
<211> LENGTH: 1638
<212> TYPE: DNA
<213> ORGANISM: Artificial Sequence
<220> FEATURE:
<223> OTHER INFORMATION: F465L/Q536V
<220> FEATURE:
<221> NAME/KEY: CDS
<222> LOCATION: (1)..(1638)

<400> SEQUENCE: 67 atg aag ctg gcc gaa gcc ctg ctg cgc gcg ctg aag gat cgc ggc gca     48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag     96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag    144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg    192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg    240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc    288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac    336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc    384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag    432
Thr Val Ala Gln Ala Arg Leu Asp Asp Pro Ala Lys Ala Pro Ala Glu
    130                 135                 140
```

-continued

| | |
|---|---|
| atc gcc cgc gtg ctg ggg gcc gcc cgc gcc ctg tcg cgc ccg gtc tat<br>Ile Ala Arg Val Leu Gly Ala Ala Arg Ala Leu Ser Arg Pro Val Tyr<br>145                                 150                       155                       160 | 480 |
| ctg gaa att ccc cgc aac atg gtc aac gcc gag gtc gag ccg gtc ggc<br>Leu Glu Ile Pro Arg Asn Met Val Asn Ala Glu Val Glu Pro Val Gly<br>                         165                     170                     175 | 528 |
| gac gac ccg gct tgg ccg gtg gac cgc gac gcg ctg gcc gcc tgc gcg<br>Asp Asp Pro Ala Trp Pro Val Asp Arg Asp Ala Leu Ala Ala Cys Ala<br>          180                     185                     190 | 576 |
| gac gag gtg ctg gcg gcc atg cgc tcg gcc acg tcg ccg gtg ctg atg<br>Asp Glu Val Leu Ala Ala Met Arg Ser Ala Thr Ser Pro Val Leu Met<br>195                               200                     205 | 624 |
| gtc tgc gtc gag gtc cgc cgc tac ggg ctg gag gcc aag gtg gcg gag<br>Val Cys Val Glu Val Arg Arg Tyr Gly Leu Glu Ala Lys Val Ala Glu<br>     210                     215                     220 | 672 |
| ctg gcg cag cgg ctg ggc gtg ccg gtg gtg acc acc ttc atg ggg cgc<br>Leu Ala Gln Arg Leu Gly Val Pro Val Val Thr Thr Phe Met Gly Arg<br>225                           230                     235                   240 | 720 |
| ggc ctg ctg gcc gac gcg ccg acc ccg ctc ggc acc tac atc ggc<br>Gly Leu Leu Ala Asp Ala Pro Thr Pro Leu Gly Thr Tyr Ile Gly<br>                       245                     250                     255 | 768 |
| gtc gcc ggc gac gcg gag atc acc cgg ctg gtc gag gag tcg gac ggg<br>Val Ala Gly Asp Ala Glu Ile Thr Arg Leu Val Glu Glu Ser Asp Gly<br>          260                     265                     270 | 816 |
| ctg ttc ctg ctc ggc gcg atc ctc agc gac acc aac ttc gcg gtg tcc<br>Leu Phe Leu Leu Gly Ala Ile Leu Ser Asp Thr Asn Phe Ala Val Ser<br>              275                     280                     285 | 864 |
| cag cgc aag atc gac ctg cgc aag acc atc cac gcc ttc gac cgg gcg<br>Gln Arg Lys Ile Asp Leu Arg Lys Thr Ile His Ala Phe Asp Arg Ala<br>290                               295                     300 | 912 |
| gtg acg ctg ggc tat cac acc tac gcc gac atc ccg ctg gcc ggg ctg<br>Val Thr Leu Gly Tyr His Thr Tyr Ala Asp Ile Pro Leu Ala Gly Leu<br>305                               310                     315                   320 | 960 |
| gtg gac gcc ctc ttg gaa ggg ctg ccg ccg tcc gac cgg acg acc cgc<br>Val Asp Ala Leu Leu Glu Gly Leu Pro Pro Ser Asp Arg Thr Thr Arg<br>                       325                     330                     335 | 1008 |
| ggc aag gag ccc cac gcc tac ccg acc ggc ctt cag gcg gac ggc gag<br>Gly Lys Glu Pro His Ala Tyr Pro Thr Gly Leu Gln Ala Asp Gly Glu<br>                     340                     345                     350 | 1056 |
| ccg atc gcc ccg atg gac atc gcc cgc gcc gtc aac gac cgc gtc cgc<br>Pro Ile Ala Pro Met Asp Ile Ala Arg Ala Val Asn Asp Arg Val Arg<br>               355                     360                     365 | 1104 |
| gcc ggg cag gaa ccg ctg ctg atc gcg gcg gac atg ggc gac tgc ctg<br>Ala Gly Gln Glu Pro Leu Leu Ile Ala Ala Asp Met Gly Asp Cys Leu<br>370                               375                     380 | 1152 |
| ttc acc gcg atg gac atg atc gac gcc ggg ctg atg gcg ccg ggc tat<br>Phe Thr Ala Met Asp Met Ile Asp Ala Gly Leu Met Ala Pro Gly Tyr<br>385                               390                     395                   400 | 1200 |
| tac gcg ggc atg ggc ttc ggg gtg ccg gcg ggc atc ggg gcg cag tgc<br>Tyr Ala Gly Met Gly Phe Gly Val Pro Ala Gly Ile Gly Ala Gln Cys<br>                     405                     410                     415 | 1248 |
| gtg tcg ggc ggc aag cgc atc ctg acc gtg gtc ggc gac ggc gcc ttc<br>Val Ser Gly Gly Lys Arg Ile Leu Thr Val Val Gly Asp Gly Ala Phe<br>                     420                     425                     430 | 1296 |
| cag atg acc ggg tgg gag ctt ggc aac tgc cga cgg ctg ggc atc gac<br>Gln Met Thr Gly Trp Glu Leu Gly Asn Cys Arg Arg Leu Gly Ile Asp<br>               435                     440                     445 | 1344 |
| ccc atc gtg atc ctg ttc aac aac gcc agt tgg gag atg ctg cgc acc<br>Pro Ile Val Ile Leu Phe Asn Asn Ala Ser Trp Glu Met Leu Arg Thr | 1392 |

```
                  450                 455                 460
ctg cag ccc gaa tcg gcc ttc aac gac ctg gac gac tgg cgc ttc gcc        1440
Leu Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg        1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgg ggg cgc        1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg        1584
Phe Gln Leu Ile Glu Ala Met Ile Pro Arg Gly Val Leu Ser Asp Thr
        515                 520                 525 ctg gcc cgc ttc gtc cag ggg gtg aag cgc ctg cac gcc gcg ccc cgg        1632
Leu Ala Arg Phe Val Gln Gly Val Lys Arg Leu His Ala Ala Pro Arg
    530                 535                 540 gag taa                                                                1638
Glu
545

<210> SEQ ID NO 68
<211> LENGTH: 545
<212> TYPE: PRT
<213> ORGANISM: Artificial Sequence
<220> FEATURE:
<223> OTHER INFORMATION: Synthetic Construct

<400> SEQUENCE: 68

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
```

```
              225                 230                 235                 240
        Gly Leu Leu Ala Asp Ala Pro Thr Pro Pro Leu Gly Thr Tyr Ile Gly
                        245                 250                 255

Val Ala Gly Asp Ala Glu Ile Thr Arg Leu Val Glu Glu Ser Asp Gly
                        260                 265                 270

Leu Phe Leu Leu Gly Ala Ile Leu Ser Asp Thr Asn Phe Ala Val Ser
                        275                 280                 285

Gln Arg Lys Ile Asp Leu Arg Lys Thr Ile His Ala Phe Asp Arg Ala
                        290                 295                 300

Val Thr Leu Gly Tyr His Thr Tyr Ala Asp Ile Pro Leu Ala Gly Leu
        305                 310                 315                 320

Val Asp Ala Leu Leu Glu Gly Leu Pro Pro Ser Asp Arg Thr Thr Arg
                        325                 330                 335

Gly Lys Glu Pro His Ala Tyr Pro Thr Gly Leu Gln Ala Asp Gly Glu
                        340                 345                 350

Pro Ile Ala Pro Met Asp Ile Ala Arg Ala Val Asn Asp Arg Val Arg
                        355                 360                 365

Ala Gly Gln Glu Pro Leu Leu Ile Ala Ala Asp Met Gly Asp Cys Leu
                        370                 375                 380

Phe Thr Ala Met Asp Met Ile Asp Ala Gly Leu Met Ala Pro Gly Tyr
        385                 390                 395                 400

Tyr Ala Gly Met Gly Phe Gly Val Pro Ala Gly Ile Gly Ala Gln Cys
                        405                 410                 415

Val Ser Gly Gly Lys Arg Ile Leu Thr Val Val Gly Asp Gly Ala Phe
                        420                 425                 430

Gln Met Thr Gly Trp Glu Leu Gly Asn Cys Arg Arg Leu Gly Ile Asp
                        435                 440                 445

Pro Ile Val Ile Leu Phe Asn Asn Ala Ser Trp Glu Met Leu Arg Thr
                        450                 455                 460

Leu Gln Pro Glu Ser Ala Phe Asn Asp Leu Asp Asp Trp Arg Phe Ala
        465                 470                 475                 480

Asp Met Ala Ala Gly Met Gly Gly Asp Gly Val Arg Val Arg Thr Arg
                        485                 490                 495

Ala Glu Leu Lys Ala Ala Leu Asp Lys Ala Phe Ala Thr Arg Gly Arg
                        500                 505                 510

Phe Gln Leu Ile Glu Ala Met Ile Pro Arg Gly Val Leu Ser Asp Thr
                        515                 520                 525

Leu Ala Arg Phe Val Gln Gly Val Lys Arg Leu His Ala Ala Pro Arg
        530                 535                 540

Glu
        545

<210> SEQ ID NO 69
<211> LENGTH: 1638
<212> TYPE: DNA
<213> ORGANISM: Artificial Sequence
<220> FEATURE:
<223> OTHER INFORMATION: F465V/Q536V
<220> FEATURE:
<221> NAME/KEY: CDS
<222> LOCATION: (1)..(1638)

<400> SEQUENCE: 69 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15
```

```
cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
         20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
 35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
     50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
 65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                 85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg     576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg     624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag     672
Val Cys Val Glu Val Arg Arg Tyr Gly Leu Glu Ala Lys Val Ala Glu
    210                 215                 220 ctg gcg cag cgg ctg ggc gtg ccg gtg gtg acc acc ttc atg ggg cgc     720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc     768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg     816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc     864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg     912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg     960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc    1008
Val Asp Ala Leu Leu Glu Gly Leu Pro Pro Ser Asp Arg Thr Thr Arg
                325                 330                 335
```

```
ggc aag gag ccc cac gcc tac ccg acc ggc ctt cag gcg gac ggc gag      1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc      1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg      1152
Ala Gly Gln Glu Pro Leu Leu Ile Ala Ala Asp Met Gly Asp Cys Leu
370                 375                 380 ttc acc gcg atg gac atg atc gac gcc ggg ctg atg gcg ccg ggc tat      1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc      1392
Pro Ile Val Ile Leu Phe Asn Asn Ala Ser Trp Glu Met Leu Arg Thr
    450                 455                 460 gtg cag ccc gaa tcg gcc ttc aac gac ctg gac gac tgg cgc ttc gcc      1440
Val Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
        515                 520                 525 ctg gcc cgc ttc gtc cag ggg gtg aag cgc ctg cac gcc gcg ccc cgg      1632
Leu Ala Arg Phe Val Gln Gly Val Lys Arg Leu His Ala Ala Pro Arg
    530                 535                 540 gag taa                                                              1638
Glu
545

<210> SEQ ID NO 70
<211> LENGTH: 545
<212> TYPE: PRT
<213> ORGANISM: Artificial Sequence
<220> FEATURE:
<223> OTHER INFORMATION: Synthetic Construct

<400> SEQUENCE: 70

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60
```

-continued

```
Leu Gly Val Ala Ala Val Thr Tyr Gly Ala Gly Ala Phe Asn Met Val
 65                  70                  75                  80

Asn Ala Val Ala Gly Ala Tyr Ala Glu Lys Ser Pro Val Val Ile
                 85                  90                  95

Ser Gly Ala Pro Gly Thr Thr Glu Gly Asn Ala Gly Leu Leu Leu His
                100                 105                 110

His Gln Gly Arg Thr Leu Asp Thr Gln Phe Gln Val Phe Lys Glu Ile
                115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
                180                 185                 190

Asp Glu Val Leu Ala Ala Met Arg Ser Ala Thr Ser Pro Val Leu Met
                195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Leu Gly Thr Tyr Ile Gly
                245                 250                 255

Val Ala Gly Asp Ala Glu Ile Thr Arg Leu Val Glu Glu Ser Asp Gly
                260                 265                 270

Leu Phe Leu Leu Gly Ala Ile Leu Ser Asp Thr Asn Phe Ala Val Ser
                275                 280                 285

Gln Arg Lys Ile Asp Leu Arg Lys Thr Ile His Ala Phe Asp Arg Ala
                290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
                340                 345                 350

Pro Ile Ala Pro Met Asp Ile Ala Arg Ala Val Asn Asp Arg Val Arg
                355                 360                 365

Ala Gly Gln Glu Pro Leu Leu Ile Ala Ala Asp Met Gly Asp Cys Leu
                370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415

Val Ser Gly Gly Lys Arg Ile Leu Thr Val Val Gly Asp Gly Ala Phe
                420                 425                 430

Gln Met Thr Gly Trp Glu Leu Gly Asn Cys Arg Arg Leu Gly Ile Asp
                435                 440                 445

Pro Ile Val Ile Leu Phe Asn Asn Ala Ser Trp Glu Met Leu Arg Thr
                450                 455                 460

Val Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
```

|     |     | 485 |     |     |     | 490 |     |     |     | 495 |     |     |
| --- | --- | --- | --- | --- | --- | --- | --- | --- | --- | --- | --- | --- |
| Ala | Glu | Leu | Lys | Ala | Ala | Leu | Asp | Lys | Ala | Phe | Ala | Thr | Arg | Gly | Arg |
|     |     |     | 500 |     |     |     |     | 505 |     |     |     |     | 510 |     |     |

Phe Gln Leu Ile Glu Ala Met Ile Pro Arg Gly Val Leu Ser Asp Thr
            515                 520                 525

Leu Ala Arg Phe Val Gln Gly Val Lys Arg Leu His Ala Ala Pro Arg
    530                 535                 540

Glu
545

<210> SEQ ID NO 71
<211> LENGTH: 1638
<212> TYPE: DNA
<213> ORGANISM: Artificial Sequence
<220> FEATURE:
<223> OTHER INFORMATION: F465L/Q532V
<220> FEATURE:
<221> NAME/KEY: CDS
<222> LOCATION: (1)..(1638)

<400> SEQUENCE: 71

```
atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                  10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg     576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg     624
Asp Glu Val Leu Ala Ala Met Arg Ser Ala Thr Ser Pro Val Leu Met
        195                 200                 205
```

```
gtc tgc gtc gag gtc cgc cgc tac ggg ctg gag gcc aag gtg gcg gag      672
Val Cys Val Glu Val Arg Arg Tyr Gly Leu Glu Ala Lys Val Ala Glu
210             215                 220 ctg gcg cag cgg ctg ggc gtg ccg gtg gtg acc acc ttc atg ggg cgc      720
Leu Ala Gln Arg Leu Gly Val Pro Val Val Thr Thr Phe Met Gly Arg
225                 230                 235                 240 ggc ctg ctg gcc gac gcg ccg acc ccg ctc ggc acc tac atc ggc          768
Gly Leu Leu Ala Asp Ala Pro Thr Pro Leu Gly Thr Tyr Ile Gly
                245                 250                 255 gtc gcc ggc gac gcg gag atc acc cgg ctg gtc gag gag tcg gac ggg      816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc      864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg      912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg      960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc     1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag     1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc     1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg     1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat     1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc     1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc     1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac     1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag atg ctg cgc acc     1392
Pro Ile Val Ile Leu Phe Asn Asn Ala Ser Trp Glu Met Leu Arg Thr
    450                 455                 460 ctg cag ccc gaa tcg gcc ttc aac gac ctg gac gac tgg cgc ttc gcc     1440
Leu Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg     1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc     1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg     1584
Phe Gln Leu Ile Glu Ala Met Ile Pro Arg Gly Val Leu Ser Asp Thr
        515                 520                 525
```

```
ctg gcc cgc gtg gtc cag ggg cag aag cgc ctg cac gcc gcg ccc cgg    1632
Leu Ala Arg Val Val Gln Gly Gln Lys Arg Leu His Ala Ala Pro Arg
    530                 535                 540 gag taa                                                            1638
Glu
545

<210> SEQ ID NO 72
<211> LENGTH: 545
<212> TYPE: PRT
<213> ORGANISM: Artificial Sequence
<220> FEATURE:
<223> OTHER INFORMATION: Synthetic Construct

<400> SEQUENCE: 72

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
    130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
    210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300

Val Thr Leu Gly Tyr His Thr Tyr Ala Asp Ile Pro Leu Ala Gly Leu
305                 310                 315                 320
```

-continued

```
Val Asp Ala Leu Leu Glu Gly Leu Pro Pro Ser Asp Arg Thr Thr Arg
            325                 330                 335

Gly Lys Glu Pro His Ala Tyr Pro Thr Gly Leu Gln Ala Asp Gly Glu
        340                 345                 350

Pro Ile Ala Pro Met Asp Ile Ala Arg Ala Val Asn Asp Arg Val Arg
    355                 360                 365

Ala Gly Gln Glu Pro Leu Leu Ile Ala Ala Asp Met Gly Asp Cys Leu
370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
        420                 425                 430

Gln Met Thr Gly Trp Glu Leu Gly Asn Cys Arg Arg Leu Gly Ile Asp
    435                 440                 445

Pro Ile Val Ile Leu Phe Asn Asn Ala Ser Trp Glu Met Leu Arg Thr
450                 455                 460

Leu Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
            485                 490                 495

Ala Glu Leu Lys Ala Ala Leu Asp Lys Ala Phe Ala Thr Arg Gly Arg
        500                 505                 510

Phe Gln Leu Ile Glu Ala Met Ile Pro Arg Gly Val Leu Ser Asp Thr
    515                 520                 525

Leu Ala Arg Val Val Gln Gly Gln Lys Arg Leu His Ala Ala Pro Arg
530                 535                 540

Glu
545

<210> SEQ ID NO 73
<211> LENGTH: 1638
<212> TYPE: DNA
<213> ORGANISM: Artificial Sequence
<220> FEATURE:
<223> OTHER INFORMATION: F532A/Q536A
<220> FEATURE:
<221> NAME/KEY: CDS
<222> LOCATION: (1)..(1638)

<400> SEQUENCE: 73 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
```

-continued

```
           Asn Ala Val Ala Gly Ala Tyr Ala Glu Lys Ser Pro Val Val Ile
                           85                  90                  95 tcc ggc gcg ccg ggc acg acg gag ggc aac gcc ggc ctg ctg ctg cac        336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc        384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag        432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat        480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtc ggc        528
Leu Glu Ile Pro Arg Asn Met Val Asn Ala Glu Val Glu Pro Val Gly
                165                 170                 175 gac gac ccg gct tgg ccg gtc gac cgc gac gcg ctg gcc gcc tgc gcg        576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg        624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag        672
Val Cys Val Glu Val Arg Arg Tyr Gly Leu Glu Ala Lys Val Ala Glu
    210                 215                 220 ctg gcg cag cgg ctg ggc gtg ccg gtg gtg acc acc ttc atg ggg cgc        720
Leu Ala Gln Arg Leu Gly Val Pro Val Val Thr Thr Phe Met Gly Arg
225                 230                 235                 240 ggc ctg ctg gcc gac gcg ccg acc ccg ccc ctc ggc acc tac atc ggc        768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg        816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc        864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg        912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg        960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc       1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag       1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc       1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg       1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat       1200
Phe Thr Ala Met Asp Met Ile Asp Ala Gly Leu Met Ala Pro Gly Tyr
385                 390                 395                 400
```

```
tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                    405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
                420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
            435                 440                 445 ccc atc gtg atc ctg ttc aac aac gcc agt tgg gag atg ctg cgc acc      1392
Pro Ile Val Ile Leu Phe Asn Asn Ala Ser Trp Glu Met Leu Arg Thr
        450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
                500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
            515                 520                 525 ctg gcc cgc gcg gtc cag ggg gcg aag cgc ctg cac gcc gcg ccc cgg      1632
Leu Ala Arg Ala Val Gln Gly Ala Lys Arg Leu His Ala Ala Pro Arg
        530                 535                 540 gag taa                                                               1638
Glu
545

<210> SEQ ID NO 74
<211> LENGTH: 545
<212> TYPE: PRT
<213> ORGANISM: Artificial Sequence
<220> FEATURE:
<223> OTHER INFORMATION: Synthetic Construct

<400> SEQUENCE: 74

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
                100                 105                 110

His Gln Gly Arg Thr Leu Asp Thr Gln Phe Gln Val Phe Lys Glu Ile
            115                 120                 125

Thr Val Ala Gln Ala Arg Leu Asp Asp Pro Ala Lys Ala Pro Ala Glu
        130                 135                 140

Ile Ala Arg Val Leu Gly Ala Ala Arg Ala Leu Ser Arg Pro Val Tyr
145                 150                 155                 160
```

```
Leu Glu Ile Pro Arg Asn Met Val Asn Ala Glu Val Glu Pro Val Gly
            165                 170                 175

Asp Asp Pro Ala Trp Pro Val Asp Arg Asp Ala Leu Ala Ala Cys Ala
        180                 185                 190

Asp Glu Val Leu Ala Ala Met Arg Ser Ala Thr Ser Pro Val Leu Met
            195                 200                 205

Val Cys Val Glu Val Arg Arg Tyr Gly Leu Glu Ala Lys Val Ala Glu
        210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
            245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
        290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
            325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
        355                 360                 365

Ala Gly Gln Glu Pro Leu Leu Ile Ala Ala Asp Met Gly Asp Cys Leu
        370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
            420                 425                 430

Gln Met Thr Gly Trp Glu Leu Gly Asn Cys Arg Arg Leu Gly Ile Asp
        435                 440                 445

Pro Ile Val Ile Leu Phe Asn Asn Ala Ser Trp Glu Met Leu Arg Thr
        450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
            485                 490                 495

Ala Glu Leu Lys Ala Ala Leu Asp Lys Ala Phe Ala Thr Arg Gly Arg
        500                 505                 510

Phe Gln Leu Ile Glu Ala Met Ile Pro Arg Gly Val Leu Ser Asp Thr
        515                 520                 525

Leu Ala Arg Ala Val Gln Gly Ala Lys Arg Leu His Ala Ala Pro Arg
530                 535                 540

Glu
545

<210> SEQ ID NO 75
<211> LENGTH: 1638
```

```
<212> TYPE: DNA
<213> ORGANISM: Artificial Sequence
<220> FEATURE:
<223> OTHER INFORMATION: M461V/F532V/Q536V
<220> FEATURE:
<221> NAME/KEY: CDS
<222> LOCATION: (1)..(1638)

<400> SEQUENCE: 75 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
                20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
            35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
        50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg     576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg     624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag     672
Val Cys Val Glu Val Arg Arg Tyr Gly Leu Glu Ala Lys Val Ala Glu
    210                 215                 220 ctg gcg cag cgg ctg ggc gtg ccg gtg gtg acc acc ttc atg ggg cgc     720
Leu Ala Gln Arg Leu Gly Val Pro Val Val Thr Thr Phe Met Gly Arg
225                 230                 235                 240 ggc ctg ctg gcc gac gcg ccg acc ccg ccg ctc ggc acc tac atc ggc     768
Gly Leu Leu Ala Asp Ala Pro Thr Pro Pro Leu Gly Thr Tyr Ile Gly
                245                 250                 255 gtc gcc ggc gac gcg gag atc acc cgg ctg gtc gag gag tcg gac ggg     816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc     864
```

```
                Leu Phe Leu Leu Gly Ala Ile Leu Ser Asp Thr Asn Phe Ala Val Ser
                        275                 280                 285 cag cgc aag atc gac ctg cgc aag acc atc cac gcc ttc gac cgg gcg             912
Gln Arg Lys Ile Asp Leu Arg Lys Thr Ile His Ala Phe Asp Arg Ala
    290                 295                 300 gtg acg ctg ggc tat cac acc tac gcc gac atc ccg ctg gcc ggg ctg             960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc            1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag            1056
Gly Lys Glu Pro His Ala Tyr Pro Thr Gly Leu Gln Ala Asp Gly Glu
            340                 345                 350 ccg atc gcc ccg atg gac atc gcc cgc gcc gtc aac gac cgc gtc cgc            1104
Pro Ile Ala Pro Met Asp Ile Ala Arg Ala Val Asn Asp Arg Val Arg
        355                 360                 365 gcc ggg cag gaa ccg ctg ctg atc gcg gcg gac atg ggc gac tgc ctg            1152
Ala Gly Gln Glu Pro Leu Leu Ile Ala Ala Asp Met Gly Asp Cys Leu
    370                 375                 380 ttc acc gcg atg gac atg atc gac gcc ggg ctg atg gcg ccg ggc tat            1200
Phe Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc            1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc            1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac            1344
Gln Met Thr Gly Trp Glu Leu Gly Asn Cys Arg Arg Leu Gly Ile Asp
        435                 440                 445 ccc atc gtg atc ctg ttc aac aac gcc agt tgg gag gtg ctg cgc acc            1392
Pro Ile Val Ile Leu Phe Asn Asn Ala Ser Trp Glu Val Leu Arg Thr
    450                 455                 460 ttc cag ccc gaa tcg gcc ttc aac gac ctg gac gac tgg cgc ttc gcc            1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg            1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc            1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg            1584
Phe Gln Leu Ile Glu Ala Met Ile Pro Arg Gly Val Leu Ser Asp Thr
        515                 520                 525 ctg gcc cgc gtg gtc cag ggg gtg aag cgc ctg cac gcc gcg ccc cgg            1632
Leu Ala Arg Val Val Gln Gly Val Lys Arg Leu His Ala Ala Pro Arg
    530                 535                 540 gag taa                                                                    1638
Glu
545

<210> SEQ ID NO 76
<211> LENGTH: 545
<212> TYPE: PRT
<213> ORGANISM: Artificial Sequence
<220> FEATURE:
<223> OTHER INFORMATION: Synthetic Construct
```

```
<400> SEQUENCE: 76

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
            115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
            195                 200                 205

Val Cys Val Glu Val Arg Arg Tyr Gly Leu Glu Ala Lys Val Ala Glu
210                 215                 220

Leu Ala Gln Arg Leu Gly Val Pro Val Thr Thr Phe Met Gly Arg
225                 230                 235                 240

Gly Leu Leu Ala Asp Ala Pro Thr Pro Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
            275                 280                 285

Gln Arg Lys Ile Asp Leu Arg Lys Thr Ile His Ala Phe Asp Arg Ala
            290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335

Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Met Gly Asp Cys Leu
        370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                405                 410                 415
```

```
Val Ser Gly Gly Lys Arg Ile Leu Thr Val Gly Asp Gly Ala Phe
            420                 425                 430

Gln Met Thr Gly Trp Glu Leu Gly Asn Cys Arg Arg Leu Gly Ile Asp
        435                 440                 445

Pro Ile Val Ile Leu Phe Asn Asn Ala Ser Trp Glu Val Leu Arg Thr
450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
        515                 520                 525

Leu Ala Arg Val Val Gln Gly Val Lys Arg Leu His Ala Ala Pro Arg
    530                 535                 540

Glu
545

<210> SEQ ID NO 77
<211> LENGTH: 1638
<212> TYPE: DNA
<213> ORGANISM: Artificial Sequence
<220> FEATURE:
<223> OTHER INFORMATION: M380V/M461V/Q536V
<220> FEATURE:
<221> NAME/KEY: CDS
<222> LOCATION: (1)..(1638)

<400> SEQUENCE: 77 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
            20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
        35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
    50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
```

```
                145               150               155               160
ctg gaa att ccc cgc aac atg gtc aac gcc gag gtc gag ccg gtg ggc       528
Leu Glu Ile Pro Arg Asn Met Val Asn Ala Glu Val Glu Pro Val Gly
                    165               170               175 gac gac ccg gct tgg ccg gtg gac cgc gac gcg ctg gcc gcc tgc gcg       576
Asp Asp Pro Ala Trp Pro Val Asp Arg Asp Ala Leu Ala Ala Cys Ala
            180               185               190 gac gag gtg ctg gcg gcc atg cgc tcg gcc acg tcg ccg gtg ctg atg       624
Asp Glu Val Leu Ala Ala Met Arg Ser Ala Thr Ser Pro Val Leu Met
                    195               200               205 gtc tgc gtc gag gtc cgc cgc tac ggg ctg gag gcc aag gtg gcg gag       672
Val Cys Val Glu Val Arg Arg Tyr Gly Leu Glu Ala Lys Val Ala Glu
        210               215               220 ctg gcg cag cgg ctg ggc gtg ccg gtg gtg acc acc ttc atg ggg cgc       720
Leu Ala Gln Arg Leu Gly Val Pro Val Val Thr Thr Phe Met Gly Arg
225               230               235               240 ggc ctg ctg gcc gac gcg ccg acc ccg ccc ctc ggc acc tac atc ggc       768
Gly Leu Leu Ala Asp Ala Pro Thr Pro Pro Leu Gly Thr Tyr Ile Gly
                245               250               255 gtc gcc ggc gac gcg gag atc acc cgg ctg gtc gag gag tcg gac ggg       816
Val Ala Gly Asp Ala Glu Ile Thr Arg Leu Val Glu Glu Ser Asp Gly
            260               265               270 ctg ttc ctg ctc ggc gcg atc ctc agc gac acc aac ttc gcg gtg tcc       864
Leu Phe Leu Leu Gly Ala Ile Leu Ser Asp Thr Asn Phe Ala Val Ser
                275               280               285 cag cgc aag atc gac ctg cgc aag acc atc cac gcc ttc gac cgg gcg       912
Gln Arg Lys Ile Asp Leu Arg Lys Thr Ile His Ala Phe Asp Arg Ala
        290               295               300 gtg acg ctg ggc tat cac acc tac gcc gac atc ccg ctg gcc ggg ctg       960
Val Thr Leu Gly Tyr His Thr Tyr Ala Asp Ile Pro Leu Ala Gly Leu
305               310               315               320 gtg gac gcc ctc ttg gaa ggg ctg ccg ccg tcc gac cgg acg acc cgc      1008
Val Asp Ala Leu Leu Glu Gly Leu Pro Pro Ser Asp Arg Thr Thr Arg
                325               330               335 ggc aag gag ccc cac gcc tac ccg acc ggc ctt cag gcg gac ggc gag      1056
Gly Lys Glu Pro His Ala Tyr Pro Thr Gly Leu Gln Ala Asp Gly Glu
            340               345               350 ccg atc gcc ccg atg gac atc gcc cgc gcc gtc aac gac cgc gtc cgc      1104
Pro Ile Ala Pro Met Asp Ile Ala Arg Ala Val Asn Asp Arg Val Arg
                355               360               365 gcc ggg cag gaa ccg ctg ctg atc gcg gcg gac gtg ggc gac tgc ctg      1152
Ala Gly Gln Glu Pro Leu Leu Ile Ala Ala Asp Val Gly Asp Cys Leu
        370               375               380 ttc acc gcg atg gac atg atc gac gcc ggg ctg atg gcg ccg ggc tat      1200
Phe Thr Ala Met Asp Met Ile Asp Ala Gly Leu Met Ala Pro Gly Tyr
385               390               395               400 tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                405               410               415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420               425               430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
                435               440               445 ccc atc gtg atc ctg ttc aac aac gcc agt tgg gag gtg ctg cgc acc      1392
Pro Ile Val Ile Leu Phe Asn Asn Ala Ser Trp Glu Val Leu Arg Thr
        450               455               460 ttc cag ccc gaa tcg gcc ttc aac gac ctg gac gac tgg cgc ttc gcc      1440
```

```
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                    485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
        515                 520                 525 ctg gcc cgc ttc gtc cag ggg gtg aag cgc ctg cac gcc gcg ccc cgg      1632
Leu Ala Arg Phe Val Gln Gly Val Lys Arg Leu His Ala Ala Pro Arg
    530                 535                 540 gag taa                                                              1638
Glu
545

<210> SEQ ID NO 78
<211> LENGTH: 545
<212> TYPE: PRT
<213> ORGANISM: Artificial Sequence
<220> FEATURE:
<223> OTHER INFORMATION: Synthetic Construct

<400> SEQUENCE: 78

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
            85                  90                  95

Ser Gly Ala Pro Gly Thr Thr Glu Gly Asn Ala Gly Leu Leu Leu His
        100                 105                 110

His Gln Gly Arg Thr Leu Asp Thr Gln Phe Gln Val Phe Lys Glu Ile
    115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
            165                 170                 175

Asp Asp Pro Ala Trp Pro Val Arg Asp Ala Leu Ala Ala Cys Ala
        180                 185                 190

Asp Glu Val Leu Ala Ala Met Arg Ser Ala Thr Ser Pro Val Leu Met
    195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
```

```
                  245                 250                 255
Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
    290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
            325                 330                 335

Gly Lys Glu Pro His Ala Tyr Pro Thr Gly Leu Gln Ala Asp Gly Glu
        340                 345                 350

Pro Ile Ala Pro Met Asp Ile Ala Arg Ala Val Asn Asp Arg Val Arg
    355                 360                 365

Ala Gly Gln Glu Pro Leu Leu Ile Ala Ala Asp Val Gly Asp Cys Leu
370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
            405                 410                 415

Val Ser Gly Gly Lys Arg Ile Leu Thr Val Val Gly Asp Gly Ala Phe
        420                 425                 430

Gln Met Thr Gly Trp Glu Leu Gly Asn Cys Arg Arg Leu Gly Ile Asp
    435                 440                 445

Pro Ile Val Ile Leu Phe Asn Asn Ala Ser Trp Glu Val Leu Arg Thr
    450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
            485                 490                 495

Ala Glu Leu Lys Ala Ala Leu Asp Lys Ala Phe Ala Thr Arg Gly Arg
        500                 505                 510

Phe Gln Leu Ile Glu Ala Met Ile Pro Arg Gly Val Leu Ser Asp Thr
    515                 520                 525

Leu Ala Arg Phe Val Gln Gly Val Lys Arg Leu His Ala Ala Pro Arg
    530                 535                 540

Glu
545

<210> SEQ ID NO 79
<211> LENGTH: 1638
<212> TYPE: DNA
<213> ORGANISM: Artificial Sequence
<220> FEATURE:
<223> OTHER INFORMATION: F385L/M461L/Q536V
<220> FEATURE:
<221> NAME/KEY: CDS
<222> LOCATION: (1)..(1638)

<400> SEQUENCE: 79 atg aag ctg gcc gaa gcc ctg ctg cgc gcg ctg aag gat cgc ggc gca    48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag    96
Gln Ala Met Phe Gly Ile Pro Gly Asp Phe Ala Leu Pro Phe Phe Lys
            20                  25                  30
```

```
gtg gcg gag gaa acg cag atc ctg ccg ctc cac acg ctg agc cac gag      144
Val Ala Glu Glu Thr Gln Ile Leu Pro Leu His Thr Leu Ser His Glu
         35                  40                  45 ccg gcg gtg ggc ttc gcg gcg gac gcg gcg gcg cgt tac agt tcg acg      192
Pro Ala Val Gly Phe Ala Ala Asp Ala Ala Ala Arg Tyr Ser Ser Thr
 50                  55                  60 ctg ggg gtg gcg gcg gtc acc tac gga gcg ggc gcc ttc aac atg gtg      240
Leu Gly Val Ala Ala Val Thr Tyr Gly Ala Gly Ala Phe Asn Met Val
 65                  70                  75                  80 aac gcg gtg gcc ggc gcc tac gcc gag aag tcg ccg gtg gtc gtc atc      288
Asn Ala Val Ala Gly Ala Tyr Ala Glu Lys Ser Pro Val Val Val Ile
                 85                  90                  95 tcc ggc gcg ccg ggc acg acg gag ggc aac gcc ggc ctg ctg ctg cac      336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc      384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag      432
Thr Val Ala Gln Ala Arg Leu Asp Asp Pro Ala Lys Ala Pro Ala Glu
130                 135                 140 atc gcc cgc gtg ctg ggg gcc gcc cgc gcc ctg tcg cgc ccg gtc tat      480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc      528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg      576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg      624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag      672
Val Cys Val Glu Val Arg Arg Tyr Gly Leu Glu Ala Lys Val Ala Glu
210                 215                 220 ctg gcg cag cgg ctg ggc gtg ccg gtg gtg acc acc ttc atg ggg cgc      720
Leu Ala Gln Arg Leu Gly Val Pro Val Val Thr Thr Phe Met Gly Arg
225                 230                 235                 240 ggc ctg ctg gcc gac gcg ccg acc ccg ctc ggc acc tac atc ggc          768
Gly Leu Leu Ala Asp Ala Pro Thr Pro Leu Gly Thr Tyr Ile Gly
                245                 250                 255 gtc gcc ggc gac gcg gag atc acc cgg ctg gtc gag gag tcg gac ggg      816
Val Ala Gly Asp Ala Glu Ile Thr Arg Leu Val Glu Glu Ser Asp Gly
            260                 265                 270 ctg ttc ctg ctc ggc gcg atc ctc agc gac acc aac ttc gcg gtg tcc      864
Leu Phe Leu Leu Gly Ala Ile Leu Ser Asp Thr Asn Phe Ala Val Ser
        275                 280                 285 cag cgc aag atc gac ctg cgc aag acc atc cac gcc ttc gac cgg gcg      912
Gln Arg Lys Ile Asp Leu Arg Lys Thr Ile His Ala Phe Asp Arg Ala
290                 295                 300 gtg acg ctg ggc tat cac acc tac gcc gac atc ccg ctg gcc ggg ctg      960
Val Thr Leu Gly Tyr His Thr Tyr Ala Asp Ile Pro Leu Ala Gly Leu
305                 310                 315                 320 gtg gac gcc ctc ttg gaa ggg ctg ccg ccg tcc gac cgg acg acc cgc      1008
Val Asp Ala Leu Leu Glu Gly Leu Pro Pro Ser Asp Arg Thr Thr Arg
                325                 330                 335 ggc aag gag ccc cac gcc tac ccg acc ggc ctt cag gcg gac ggc gag      1056
Gly Lys Glu Pro His Ala Tyr Pro Thr Gly Leu Gln Ala Asp Gly Glu
```

```
                    340             345             350
ccg atc gcc ccg atg gac atc gcc cgc gcc gtc aac gac cgc gtc cgc      1104
Pro Ile Ala Pro Met Asp Ile Ala Arg Ala Val Asn Asp Arg Val Arg
            355                 360                 365 gcc ggg cag gaa ccg ctg ctg atc gcg gcg gac atg ggc gac tgc ctg      1152
Ala Gly Gln Glu Pro Leu Leu Ile Ala Ala Asp Met Gly Asp Cys Leu
    370                 375                 380 ctg acc gcg atg gac atg atc gac gcc ggg ctg atg gcg ccg ggc tat      1200
Leu Thr Ala Met Asp Met Ile Asp Ala Gly Leu Met Ala Pro Gly Tyr
385                 390                 395                 400 tac gcg ggc atg ggc ttc ggg gtg ccg gcg ggc atc ggg gcg cag tgc      1248
Tyr Ala Gly Met Gly Phe Gly Val Pro Ala Gly Ile Gly Ala Gln Cys
                405                 410                 415 gtg tcg ggc ggc aag cgc atc ctg acc gtg gtc ggc gac ggc gcc ttc      1296
Val Ser Gly Gly Lys Arg Ile Leu Thr Val Val Gly Asp Gly Ala Phe
            420                 425                 430 cag atg acc ggg tgg gag ctt ggc aac tgc cga cgg ctg ggc atc gac      1344
Gln Met Thr Gly Trp Glu Leu Gly Asn Cys Arg Arg Leu Gly Ile Asp
    435                 440                 445 ccc atc gtg atc ctg ttc aac aac gcc agt tgg gag ctg ctg cgc acc      1392
Pro Ile Val Ile Leu Phe Asn Asn Ala Ser Trp Glu Leu Leu Arg Thr
450                 455                 460 ttc cag ccc gaa tcg gcc ttc aac gac ctg gac gac tgg cgc ttc gcc      1440
Phe Gln Pro Glu Ser Ala Phe Asn Asp Leu Asp Asp Trp Arg Phe Ala
465                 470                 475                 480 gac atg gcg gcg ggc atg ggc ggc gac ggc gtc cgc gtg cgc aca cgg      1488
Asp Met Ala Ala Gly Met Gly Gly Asp Gly Val Arg Val Arg Thr Arg
                485                 490                 495 gcg gag ctg aag gcg gcg ctg gac aag gcc ttc gcc acg cgc ggg cgc      1536
Ala Glu Leu Lys Ala Ala Leu Asp Lys Ala Phe Ala Thr Arg Gly Arg
            500                 505                 510 ttc cag ctg atc gag gcg atg atc ccg cgc ggc gtg ctg tcc gac acg      1584
Phe Gln Leu Ile Glu Ala Met Ile Pro Arg Gly Val Leu Ser Asp Thr
    515                 520                 525 ctg gcc cgc ttc gtc cag ggg gtg aag cgc ctg cac gcc gcg ccc cgg      1632
Leu Ala Arg Phe Val Gln Gly Val Lys Arg Leu His Ala Ala Pro Arg
530                 535                 540 gag taa                                                               1638
Glu
545

<210> SEQ ID NO 80
<211> LENGTH: 545
<212> TYPE: PRT
<213> ORGANISM: Artificial Sequence
<220> FEATURE:
<223> OTHER INFORMATION: Synthetic Construct

<400> SEQUENCE: 80

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80
```

```
Asn Ala Val Ala Gly Ala Tyr Ala Glu Lys Ser Pro Val Val Ile
             85                  90                  95
Ser Gly Ala Pro Gly Thr Thr Glu Gly Asn Ala Gly Leu Leu His
            100                 105                 110
His Gln Gly Arg Thr Leu Asp Thr Gln Phe Gln Val Phe Lys Glu Ile
            115                 120                 125
Thr Val Ala Gln Ala Arg Leu Asp Asp Pro Ala Lys Ala Pro Ala Glu
130                 135                 140
Ile Ala Arg Val Leu Gly Ala Ala Arg Ala Leu Ser Arg Pro Val Tyr
145                 150                 155                 160
Leu Glu Ile Pro Arg Asn Met Val Asn Ala Glu Val Glu Pro Val Gly
                    165                 170                 175
Asp Asp Pro Ala Trp Pro Val Asp Arg Asp Ala Leu Ala Ala Cys Ala
                180                 185                 190
Asp Glu Val Leu Ala Ala Met Arg Ser Ala Thr Ser Pro Val Leu Met
            195                 200                 205
Val Cys Val Glu Val Arg Arg Tyr Gly Leu Glu Ala Lys Val Ala Glu
            210                 215                 220
Leu Ala Gln Arg Leu Gly Val Pro Val Val Thr Thr Phe Met Gly Arg
225                 230                 235                 240
Gly Leu Leu Ala Asp Ala Pro Thr Pro Pro Leu Gly Thr Tyr Ile Gly
                    245                 250                 255
Val Ala Gly Asp Ala Glu Ile Thr Arg Leu Val Glu Glu Ser Asp Gly
                260                 265                 270
Leu Phe Leu Leu Gly Ala Ile Leu Ser Asp Thr Asn Phe Ala Val Ser
            275                 280                 285
Gln Arg Lys Ile Asp Leu Arg Lys Thr Ile His Ala Phe Asp Arg Ala
            290                 295                 300
Val Thr Leu Gly Tyr His Thr Tyr Ala Asp Ile Pro Leu Ala Gly Leu
305                 310                 315                 320
Val Asp Ala Leu Leu Glu Gly Leu Pro Pro Ser Asp Arg Thr Thr Arg
                    325                 330                 335
Gly Lys Glu Pro His Ala Tyr Pro Thr Gly Leu Gln Ala Asp Gly Glu
                340                 345                 350
Pro Ile Ala Pro Met Asp Ile Ala Arg Ala Val Asn Asp Arg Val Arg
            355                 360                 365
Ala Gly Gln Glu Pro Leu Leu Ile Ala Ala Asp Met Gly Asp Cys Leu
            370                 375                 380
Leu Thr Ala Met Asp Met Ile Asp Ala Gly Leu Met Ala Pro Gly Tyr
385                 390                 395                 400
Tyr Ala Gly Met Gly Phe Gly Val Pro Ala Gly Ile Gly Ala Gln Cys
                    405                 410                 415
Val Ser Gly Gly Lys Arg Ile Leu Thr Val Val Gly Asp Gly Ala Phe
                420                 425                 430
Gln Met Thr Gly Trp Glu Leu Gly Asn Cys Arg Arg Leu Gly Ile Asp
            435                 440                 445
Pro Ile Val Ile Leu Phe Asn Asn Ala Ser Trp Glu Leu Leu Arg Thr
450                 455                 460
Phe Gln Pro Glu Ser Ala Phe Asn Asp Leu Asp Asp Trp Arg Phe Ala
465                 470                 475                 480
Asp Met Ala Ala Gly Met Gly Gly Asp Gly Val Arg Val Arg Thr Arg
                    485                 490                 495
Ala Glu Leu Lys Ala Ala Leu Asp Lys Ala Phe Ala Thr Arg Gly Arg
```

```
                  500               505               510
Phe Gln Leu Ile Glu Ala Met Ile Pro Arg Gly Val Leu Ser Asp Thr
          515               520               525

Leu Ala Arg Phe Val Gln Gly Val Lys Arg Leu His Ala Ala Pro Arg
        530               535               540

Glu
545

<210> SEQ ID NO 81
<211> LENGTH: 1638
<212> TYPE: DNA
<213> ORGANISM: Artificial Sequence
<220> FEATURE:
<223> OTHER INFORMATION: M380V/F385V/M461V
<220> FEATURE:
<221> NAME/KEY: CDS
<222> LOCATION: (1)..(1638)

<400> SEQUENCE: 81 atg aag ctg gcc gaa gcc ctg ctg cgc gcg ctg aag gat cgc ggc gca      48
Met Lys Leu Ala Glu Ala Leu Leu Arg Ala Leu Lys Asp Arg Gly Ala
1               5                   10                  15 cag gcc atg ttc ggg att ccg ggt gat ttc gcc ctg ccc ttc ttc aag      96
Gln Ala Met Phe Gly Ile Pro Gly Asp Phe Ala Leu Pro Phe Phe Lys
                20                  25                  30 gtg gcg gag gaa acg cag atc ctg ccg ctc cac acg ctg agc cac gag     144
Val Ala Glu Glu Thr Gln Ile Leu Pro Leu His Thr Leu Ser His Glu
            35                  40                  45 ccg gcg gtg ggc ttc gcg gcg gac gcg gcg gcg cgt tac agt tcg acg     192
Pro Ala Val Gly Phe Ala Ala Asp Ala Ala Ala Arg Tyr Ser Ser Thr
        50                  55                  60 ctg ggg gtg gcg gcg gtc acc tac gga gcg ggc gcc ttc aac atg gtg     240
Leu Gly Val Ala Ala Val Thr Tyr Gly Ala Gly Ala Phe Asn Met Val
65                  70                  75                  80 aac gcg gtg gcc ggc gcc tac gcc gag aag tcg ccg gtg gtc gtc atc     288
Asn Ala Val Ala Gly Ala Tyr Ala Glu Lys Ser Pro Val Val Val Ile
                85                  90                  95 tcc ggc gcg ccg ggc acg acg gag ggc aac gcc ggc ctg ctg ctg cac     336
Ser Gly Ala Pro Gly Thr Thr Glu Gly Asn Ala Gly Leu Leu Leu His
            100                 105                 110 cac cag ggc cgc acg ctg gac acg cag ttc cag gtg ttc aag gag atc     384
His Gln Gly Arg Thr Leu Asp Thr Gln Phe Gln Val Phe Lys Glu Ile
        115                 120                 125 acc gtc gcc cag gcg cgg ctg gac gac ccg gcc aag gcc ccg gcg gag     432
Thr Val Ala Gln Ala Arg Leu Asp Asp Pro Ala Lys Ala Pro Ala Glu
    130                 135                 140 atc gcc cgc gtg ctg ggg gcc gcc cgc gcc ctg tcg cgc ccg gtc tat     480
Ile Ala Arg Val Leu Gly Ala Ala Arg Ala Leu Ser Arg Pro Val Tyr
145                 150                 155                 160 ctg gaa att ccc cgc aac atg gtc aac gcc gag gtc gag ccg gtg ggc     528
Leu Glu Ile Pro Arg Asn Met Val Asn Ala Glu Val Glu Pro Val Gly
                165                 170                 175 gac gac ccg gct tgg ccg gtg gac cgc gac gcg ctg gcc gcc tgc gcg     576
Asp Asp Pro Ala Trp Pro Val Asp Arg Asp Ala Leu Ala Ala Cys Ala
            180                 185                 190 gac gag gtg ctg gcg gcc atg cgc tcg gcc acg tcg ccg gtg ctg atg     624
Asp Glu Val Leu Ala Ala Met Arg Ser Ala Thr Ser Pro Val Leu Met
        195                 200                 205 gtc tgc gtc gag gtc cgc cgc tac ggg ctg gag gcc aag gtg gcg gag     672
Val Cys Val Glu Val Arg Arg Tyr Gly Leu Glu Ala Lys Val Ala Glu
    210                 215                 220
```

-continued

| | | |
|---|---|---|
| ctg gcg cag cgg ctg ggc gtg ccg gtg gtg acc acc ttc atg ggg cgc<br>Leu Ala Gln Arg Leu Gly Val Pro Val Val Thr Thr Phe Met Gly Arg<br>225                           230                             235                        240 | 720 |
| ggc ctg ctg gcc gac gcg ccg acc ccg ccg ctc ggc acc tac atc ggc<br>Gly Leu Leu Ala Asp Ala Pro Thr Pro Pro Leu Gly Thr Tyr Ile Gly<br>                        245                             250                         255 | 768 |
| gtc gcc ggc gac gcg gag atc acc cgg ctg gtc gag gag tcg gac ggg<br>Val Ala Gly Asp Ala Glu Ile Thr Arg Leu Val Glu Glu Ser Asp Gly<br>                        260                             265                        270 | 816 |
| ctg ttc ctg ctc ggc gcg atc ctc agc gac acc aac ttc gcg gtg tcc<br>Leu Phe Leu Leu Gly Ala Ile Leu Ser Asp Thr Asn Phe Ala Val Ser<br>        275                         280                             285 | 864 |
| cag cgc aag atc gac ctg cgc aag acc atc cac gcc ttc gac cgg gcg<br>Gln Arg Lys Ile Asp Leu Arg Lys Thr Ile His Ala Phe Asp Arg Ala<br>290                           295                             300 | 912 |
| gtg acg ctg ggc tat cac acc tac gcc gac atc ccg ctg gcc ggg ctg<br>Val Thr Leu Gly Tyr His Thr Tyr Ala Asp Ile Pro Leu Ala Gly Leu<br>305                           310                             315                        320 | 960 |
| gtg gac gcc ctc ttg gaa ggg ctg ccg ccg tcc gac cgg acg acc cgc<br>Val Asp Ala Leu Leu Glu Gly Leu Pro Pro Ser Asp Arg Thr Thr Arg<br>                        325                             330                         335 | 1008 |
| ggc aag gag ccc cac gcc tac ccg acc ggc ctt cag gcg gac ggc gag<br>Gly Lys Glu Pro His Ala Tyr Pro Thr Gly Leu Gln Ala Asp Gly Glu<br>                        340                             345                        350 | 1056 |
| ccg atc gcc ccg atg gac atc gcc cgc gcc gtc aac gac cgc gtc cgc<br>Pro Ile Ala Pro Met Asp Ile Ala Arg Ala Val Asn Asp Arg Val Arg<br>        355                         360                             365 | 1104 |
| gcc ggg cag gaa ccg ctg ctg atc gcg gcg gac gtg ggc gac tgc ctg<br>Ala Gly Gln Glu Pro Leu Leu Ile Ala Ala Asp Val Gly Asp Cys Leu<br>370                           375                             380 | 1152 |
| gtg acc gcg atg gac atg atc gac gcc ggg ctg atg gcg ccg ggc tat<br>Val Thr Ala Met Asp Met Ile Asp Ala Gly Leu Met Ala Pro Gly Tyr<br>385                           390                             395                        400 | 1200 |
| tac gcg ggc atg ggc ttc ggg gtg ccg gcg ggc atc ggg gcg cag tgc<br>Tyr Ala Gly Met Gly Phe Gly Val Pro Ala Gly Ile Gly Ala Gln Cys<br>                        405                             410                        415 | 1248 |
| gtg tcg ggc ggc aag cgc atc ctg acc gtg gtc ggc gac ggc gcc ttc<br>Val Ser Gly Gly Lys Arg Ile Leu Thr Val Val Gly Asp Gly Ala Phe<br>                        420                             425                        430 | 1296 |
| cag atg acc ggg tgg gag ctt ggc aac tgc cga cgg ctg ggc atc gac<br>Gln Met Thr Gly Trp Glu Leu Gly Asn Cys Arg Arg Leu Gly Ile Asp<br>                        435                             440                        445 | 1344 |
| ccc atc gtg atc ctg ttc aac aac gcc agt tgg gag gtg ctg cgc acc<br>Pro Ile Val Ile Leu Phe Asn Asn Ala Ser Trp Glu Val Leu Arg Thr<br>450                           455                             460 | 1392 |
| ttc cag ccc gaa tcg gcc ttc aac gac ctg gac gac tgg cgc ttc gcc<br>Phe Gln Pro Glu Ser Ala Phe Asn Asp Leu Asp Asp Trp Arg Phe Ala<br>465                           470                             475                        480 | 1440 |
| gac atg gcg gcg ggc atg ggc ggc gac ggc gtc cgc gtg cgc aca cgg<br>Asp Met Ala Ala Gly Met Gly Gly Asp Gly Val Arg Val Arg Thr Arg<br>                        485                             490                        495 | 1488 |
| gcg gag ctg aag gcg gcg ctg gac aag gcc ttc gcc acg cgc ggg cgc<br>Ala Glu Leu Lys Ala Ala Leu Asp Lys Ala Phe Ala Thr Arg Gly Arg<br>                        500                             505                        510 | 1536 |
| ttc cag ctg atc gag gcg atg atc ccg cgc ggc gtg ctg tcc gac acg<br>Phe Gln Leu Ile Glu Ala Met Ile Pro Arg Gly Val Leu Ser Asp Thr<br>        515                         520                             525 | 1584 |
| ctg gcc cgc ttc gtc cag ggg cag aag cgc ctg cac gcc gcg ccc cgg<br>Leu Ala Arg Phe Val Gln Gly Gln Lys Arg Leu His Ala Ala Pro Arg | 1632 |

```
               530                 535                 540
gag taa                                                                    1638
Glu
545

<210> SEQ ID NO 82
<211> LENGTH: 545
<212> TYPE: PRT
<213> ORGANISM: Artificial Sequence
<220> FEATURE:
<223> OTHER INFORMATION: Synthetic Construct

<400> SEQUENCE: 82

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Thr Gln Ile Leu Pro Leu His Thr Leu Ser His Glu
        35                  40                  45

Pro Ala Val Gly Phe Ala Ala Asp Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Ile
                85                  90                  95

Ser Gly Ala Pro Gly Thr Thr Glu Gly Asn Ala Gly Leu Leu Leu His
            100                 105                 110

His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
130                 135                 140

Ile Ala Arg Val Leu Gly Ala Ala Arg Ala Leu Ser Arg Pro Val Tyr
145                 150                 155                 160

Leu Glu Ile Pro Arg Asn Met Val Asn Ala Glu Val Glu Pro Val Gly
                165                 170                 175

Asp Asp Pro Ala Trp Pro Val Asp Arg Asp Ala Leu Ala Ala Cys Ala
            180                 185                 190

Asp Glu Val Leu Ala Ala Met Arg Ser Ala Thr Ser Pro Val Leu Met
        195                 200                 205

Val Cys Val Glu Val Arg Arg Tyr Gly Leu Glu Ala Lys Val Ala Glu
210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Leu Gly Thr Tyr Ile Gly
                245                 250                 255

Val Ala Gly Asp Ala Glu Ile Thr Arg Leu Val Glu Glu Ser Asp Gly
            260                 265                 270

Leu Phe Leu Leu Gly Ala Ile Leu Ser Asp Thr Asn Phe Ala Val Ser
        275                 280                 285

Gln Arg Lys Ile Asp Leu Arg Lys Thr Ile His Ala Phe Asp Arg Ala
290                 295                 300

Val Thr Leu Gly Tyr His Thr Tyr Ala Asp Ile Pro Leu Ala Gly Leu
305                 310                 315                 320

Val Asp Ala Leu Leu Glu Gly Leu Pro Pro Ser Asp Arg Thr Thr Arg
                325                 330                 335
```

```
Gly Lys Glu Pro His Ala Tyr Pro Thr Gly Leu Gln Ala Asp Gly Glu
            340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Val Gly Asp Cys Leu
            370                 375                 380

Val Thr Ala Met Asp Met Ile Asp Ala Gly Leu Met Ala Pro Gly Tyr
385                     390                 395                 400

Tyr Ala Gly Met Gly Phe Gly Val Pro Ala Gly Ile Gly Ala Gln Cys
                    405                 410                 415

Val Ser Gly Gly Lys Arg Ile Leu Thr Val Val Gly Asp Gly Ala Phe
                420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Val Leu Arg Thr
            450                 455                 460

Phe Gln Pro Glu Ser Ala Phe Asn Asp Leu Asp Asp Trp Arg Phe Ala
465                 470                 475                 480

Asp Met Ala Ala Gly Met Gly Gly Asp Gly Val Arg Val Arg Thr Arg
                485                 490                 495

Ala Glu Leu Lys Ala Ala Leu Asp Lys Ala Phe Ala Thr Arg Gly Arg
            500                 505                 510

Phe Gln Leu Ile Glu Ala Met Ile Pro Arg Gly Val Leu Ser Asp Thr
            515                 520                 525

Leu Ala Arg Phe Val Gln Gly Gln Lys Arg Leu His Ala Ala Pro Arg
            530                 535                 540

Glu
545
```